(12) United States Patent
Rajagopal et al.

(10) Patent No.: US 12,331,319 B2
(45) Date of Patent: Jun. 17, 2025

(54) RESPIRATORY AND SWEAT GLAND IONOCYTES

(71) Applicants: The Broad Institute, Inc., Cambridge, MA (US); The General Hospital Corporation, Boston, MA (US); Massachusetts Institute of Technology, Cambridge, MA (US)

(72) Inventors: Jayaraj Rajagopal, Boston, MA (US); Aviv Regev, Cambridge, MA (US); Moshe Biton, Cambridge, MA (US); Adam Haber, Cambridge, MA (US); Daniel Montoro, Boston, MA (US); Orit Rozenblatt-Rosen, Cambridge, MA (US)

(73) Assignees: THE BROAD INSTITUTE, INC., Cambridge, MA (US); THE GENERAL HOSPITAL CORPORATION, Boston, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1055 days.

(21) Appl. No.: 16/604,596

(22) PCT Filed: Apr. 12, 2018

(86) PCT No.: PCT/US2018/027337
§ 371 (c)(1),
(2) Date: Oct. 11, 2019

(87) PCT Pub. No.: WO2018/191520
PCT Pub. Date: Oct. 18, 2018

(65) Prior Publication Data
US 2021/0115407 A1   Apr. 22, 2021

Related U.S. Application Data

(60) Provisional application No. 62/484,782, filed on Apr. 12, 2017.

(51) Int. Cl.
| | | |
|---|---|---|
| *C12N 5/071* | (2010.01) | |
| *A61K 35/42* | (2015.01) | |
| *A61P 11/00* | (2006.01) | |
| *G01N 33/50* | (2006.01) | |

(52) U.S. Cl.
CPC ............ *C12N 5/0688* (2013.01); *A61K 35/42* (2013.01); *A61P 11/00* (2018.01); *G01N 33/5044* (2013.01); *C12N 2501/42* (2013.01); *C12N 2506/27* (2013.01)

(58) Field of Classification Search
CPC .............. C12N 5/0688; C12N 2501/42; C12N 2506/27; A61K 35/42; A61P 11/00; G01N 33/5044

USPC ........................ 424/93.7, 557, 574
See application file for complete search history.

(56) References Cited

U.S. PATENT DOCUMENTS

| | | |
|---|---|---|
| 1,995,970 A | 3/1935 | Dorough |
| 2,676,945 A | 4/1954 | Higgins |
| 2,683,136 A | 7/1954 | Higgins |
| 2,703,316 A | 3/1955 | Schneider |
| 2,758,987 A | 8/1956 | Salzberg |
| 2,951,828 A | 9/1960 | Zeile et al. |
| 3,531,561 A | 9/1970 | Trehu |
| 4,816,567 A | 3/1989 | Cabilly et al. |
| 5,270,163 A | 12/1993 | Gold et al. |
| 6,479,626 B1 | 11/2002 | Kim et al. |
| 6,534,261 B1 | 3/2003 | Co et al. |
| 6,607,882 B1 | 8/2003 | Co et al. |
| 6,746,838 B1 | 6/2004 | Choo et al. |
| 6,794,136 B1 | 9/2004 | Eisenberg et al. |
| 6,824,978 B1 | 11/2004 | Co et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Co et al. |
| 7,013,219 B2 | 3/2006 | Case et al. |
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |

(Continued)

FOREIGN PATENT DOCUMENTS

| | | |
|---|---|---|
| EP | 2 764 103 A2 | 8/2014 |
| EP | 2 771 468 A1 | 9/2014 |

(Continued)

OTHER PUBLICATIONS

Saint-Criq et al.: "Role of CFTR in epithelial physiology", Cellular and Molecular Life Sciences, Oct. 6, 2016, (74):1, 93-115 (Year: 2016).*
Hans et al., "Pax8 and Pax2a function synergistically in otic specification, downstream of the Foxi1 and Dlx3b transcription factors". Development. Oct. 2004;131(20):5091-5102. (Year: 2004).*
Kurth et al., "The forkhead transcription factor Foxi1 directly activates the AE4 promoter". Biochem. J. Jan. 1, 2006; 393(Pt 1): 277-283. (Year: 2006).*
UniPort. "Foxi1—Forkhead box protein 11—Mus musculus (Mouse)". Jul. 26, 2007. Retrieved from https://www.uniprot.org/uniprotkb/Q92215/entry (Year: 2007).*

(Continued)

*Primary Examiner* — Allison M Fox
*Assistant Examiner* — Hanan Isam Abuzeineh
(74) *Attorney, Agent, or Firm* — FOLEY & LARDNER LLP

(57) ABSTRACT

Provided herein are methods and compositions for identifying ionocytes from respiratory epithelial cells, and uses of such cells for treatment of inflammatory lung disease. Also provided herein are methods and compositions for modulating respiratory tract epithelial cell proliferation, differentiation, maintenance, and/or function.

8 Claims, 58 Drawing Sheets

Specification includes a Sequence Listing.

(56) References Cited

U.S. PATENT DOCUMENTS

| | | |
|---|---|---|
| 7,595,376 B2 | 9/2009 | Kim et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,507,272 B2 | 8/2013 | Zhang et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2014/0342456 A1 | 11/2014 | Mali et al. |
| 2014/0356959 A1 | 12/2014 | Church et al. |
| 2015/0031132 A1 | 1/2015 | Church et al. |
| 2015/0184139 A1 | 7/2015 | Zhang et al. |

FOREIGN PATENT DOCUMENTS

| | | |
|---|---|---|
| EP | 2 784 162 A1 | 10/2014 |
| WO | 00/25226 A1 | 5/2000 |
| WO | 2011/005306 A2 | 1/2011 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093713 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2016/004925 A1 | 1/2016 |
| WO | 2016/049258 A2 | 3/2016 |
| WO | 2016/094867 A1 | 6/2016 |
| WO | 2016/094872 A1 | 6/2016 |
| WO | 2016/094874 A1 | 6/2016 |
| WO | 2016/106244 A1 | 6/2016 |
| WO | 2018/191520 A1 | 10/2018 |

OTHER PUBLICATIONS

Rosenecker et al., "Gene therapy for cystic fibrosis lung disease: Current status and future perspectives". Current Opinion in Molecular Therapeutics. Oct. 2006; 439-445. (Year: 2006).*

Rajagopal "International Search Report and Written Opinion issued in International Application No. PCT/US2018/027337", mailed on Aug. 10, 2018, 13 pages.

Adappa, et al., "Genetics of The Taste Receptor T2R38 Correlates With Chronic Rhinosinusitis Necessitating Surgical Intervention", International Forum of Allergy & Rhinology, vol. 3, No. 3, Mar. 2013, 184-187.

Ardini-Poleske, et al., "LungMAP: The Molecular Atlas of Lung Development Program", The American Journal of Physiology-Lung Cellular and Molecular Physiology, vol. 313, No. 5, Nov. 1, 2017, L733-L740.

Bansal, et al., "Suppression of Immunoglobulin E-mediated Allergic Responses by Regulator of G Protein Signaling 13", Nature Immunology, vol. 9, No. 1, Jan. 2008, 73-80.

Bergstrom, et al., "Gram-Positive Bacteria are Held at a Distance In The Colon Mucus by The Lectin-like Protein Zg16", Proceedings of the National Academy of Sciences, vol. 113, No. 48, Nov. 29, 2016, 13833-13838.

Birket, et al., "A Functional Anatomic Defect of The Cystic Fibrosis Airway", American Journal of Respiratory and Critical Care Medicine, vol. 190, No. 4, Aug. 15, 2014, 421-432.

Birket, et al., "Combination Therapy with Cystic Fibrosis Transmembrane Conductance Regulator Modulators Augment the Airway Functional Microanatomy", The American Journal of Physiology-Lung Cellular and Molecular Physiology, vol. 310, No. 10, May 15, 2016, L 928-L 939.

Birket, et al., "Development of an Airway Mucus Defect in The Cystic Fibrosis Rat", JCI Insight, vol. 3, No. 1, Jan. 11, 2018, 14 pages.

Blomqvist, et al., "Epididymal Expression of The Forkhead Transcription Factor Foxi1 is Required for Male Fertility", The EMBO Journal, vol. 25, No. 17, Sep. 6, 2006, 4131-4141.

Blume, et al., "Temporal Monitoring of Differentiated Human Airway Epithelial Cells Using Microfluidics", PLoS One, vol. 10, No. 10, Oct. 5, 2015, 13 pages.

Bochkov, et al., "Cadherin-Related Family Member 3, a Childhood Asthma Susceptibility Gene Product, Mediates Rhinovirus C Binding and Replication", Proceedings of the National Academy of Sciences of the United States of America, vol. 112, No. 17, Apr. 28, 2015, 5485-5490.

Bonnelykke, et al., "A Genome-Wide Association Study Identifies Cdhr3 as A Susceptibility Locus For Early Childhood Asthma With Severe Exacerbations", Nature Genetics, vol. 46, No., 1, Jan. 2014, 51-55.

Chan, I., "The Role Of Extracellular Matrix Protein 1 In Human Skin", Clinical and Experimental Dermatology, vol. 29, No. 1, Jan. 2004, 52-56.

Chen, et al., "In Silico Cloning of Mouse Muc5B Gene and Upregulation of Its Expression in Mouse Asthma Model", American Journal of Respiratory and Critical Care Medicine, vol. 164, No. 6, Sep. 15, 2001, 1059-1066.

(56) References Cited

OTHER PUBLICATIONS

Chintagari, et al., "Vacuolar ATPase Regulates Surfactant Secretion in Rat Alveolar Type II Cells by Modulating Lamellar Body Calcium", PLoS One, vol. 5, No. 2, Feb. 16, 2010, 14 pages.
D'Acquisto, et al., "Annexin-1 Modulates T-Cell Activation and Differentiation", Blood, vol. 109, No. 3, Feb. 1, 2007, 1095-1102.
Danahay, et al., "Notch2 is Required for Inflammatory Cytokine-driven Goblet Cell Metaplasia In The Lung", Cell Reports, vol. 10, No. 2, Jan. 13, 2015, 239-252.
Davies, et al., "Targeted Deletion of The Epididymal Receptor HE6 Results in Fluid Dysregulation and Male Infertility", Molecular and Cellular Biology, vol. 24, No. 19, Oct. 2004, 8642-8648.
Del-Sol, et al., "Big-Data-Driven Stem Cell Science and Tissue Engineering: Vision and Unique Opportunities", Cell Stem Cell, vol. 20, No. 2, Feb. 2, 2017, 157-160.
Dixon, et al., "Requirement of a 5-Lipoxygenase-Activating Protein for Leukotriene Synthesis", Nature, vol. 343, No. 6255, Jan. 18, 1990, 282-284.
Du, et al., "Lung Gene Expression Analysis (Lgea): An Integrative Web Portal For Comprehensive Gene Expression Data Analysis In Lung Development", Thorax, vol. 72, No. 5, Jan. 9, 2017, 4 pages.
Engelhardt, et al., "Submucosal Glands are The Predominant Site of Cftr Expression in The Human Bronchus", Nature Genetics, vol. 2, No. 3, Nov. 1992, 240-248.
Esaki, et al., "Mechanism Of Development Of Ionocytes Rich In Vacuolar-type H(+)-atpase In The Skin Of Zebrafish Larvae", Developmental Biology, vol. 329, No. 1, May 1, 2009, 116-129.
Gerbe, et al., "Intestinal Epithelial Tuft Cells Initiate Type 2 Mucosal Immunity to Helminth Parasites", Nature, vol. 529, No. 7585, Jan. 14, 2016, 226-230.
von Moltke, et al., "Tuft-Cell-Derived Il-25 Regulates an Intestinal Ilc2-Epithelial Response Circuit", Nature, vol. 529, No. 7585, Jan. 14, 2016, 221-225.
Ghaleb, et al., "Krüppel-like Factors 4 And 5: The Yin And Yang Regulators Of Cellular Proliferation", Cell Research, vol. 15, No. 2, Feb. 2005, 92-96.
Ghio, et al., "Growth of Human Bronchial Epithelial Cells at an Air-Liquid Interface Alters the Response to Particle Exposure", Particle and Fibre Toxicology, vol. 10, No. 25, 2013, 8 pages.
Ghio, et al., "Metal-dependent Expression Of Ferritin And Lactoferrin By Respiratory Epithelial Cells", American Journal of Physiology-Lung Cellular and Molecular Physiology, vol. 274, Issue 5, May 1998, L728-L736.
Grubb, et al., "Anomalies in Ion Transport In CF Mouse Tracheal Epithelium", American Journal of Physiology, vol. 267, Jul. 1994, C 293-C 300.
Haber, et al., "A Single-cell Survey of The Small Intestinal Epithelium", Nature, vol. 551, No. 7680, Nov. 16, 2017, 333-339.
Hase, et al., "Uptake Through Glycoprotein 2 of FimH(+) Bacteria by M Cells Initiates Mucosal Immune Response", Nature, vol. 462, No. 7270, Nov. 12, 2009, 226-230.
Heitzmann, et al., "The in Vivo Respiratory Phenotype of the Adenosine A1 Receptor Knockout Mouse", Respiratory Physiology and Neurobiology Journal Elsevier, vol. 222, Feb. 1, 2016, 16-28.
Hoegger, et al., "Impaired Mucus Detachment Disrupts Mucociliary Transport in a Piglet Model of Cystic Fibrosis", Science, vol. 345, No. 6198, Aug. 15, 2014, 818-822.
Howitt, et al., "Tuft Cells Taste-Chemosensory Cells, Orchestrate Parasite Type 2 Immunity in the Gut", Science, vol. 351, No. 6279, Mar. 18, 2016, 1329-1333.
Jakobsson, et al., "Identification and Characterization of A Novel Microsomal Enzyme With Glutathione-Dependent Transferase and Peroxidase Activities", Journal of Biological Chemistry, vol. 272, No. 36, Sep. 5, 1997, 22934-22939.
Janicke, et al., "Foxi3 Transcription Factors And Notch Signaling Control The Formation Of Skin Ionocytes From Epidermal Precursors Of The Zebrafish Embryo", Developmental Biology, vol. 307, No. 2, Jul. 15, 2007, 258-271.

Jonz, et al., "Epithelial Mitochondria-Rich Cells and Associated Innervation in Adult and Developing Zebrafish", The Journal of Comparative Neurology, vol. 497, No. 5, Aug. 10, 2006, 817-832.
Krasteva, et al., "Cholinergic Brush Cells In The Trachea Mediate Respiratory Responses To Quorum Sensing Molecules", Life Sciences, vol. 91, No. (21-22), Nov. 27, 2012, 992-996.
Krasteva, et al., "Cholinergic Chemosensory Cells In The Trachea Regulate Breathing", Proceedings of the National Academy of Sciences of the United States of America, vol. 108, No. 23, Jun. 7, 2011, 9478-9483.
Lee, et al., "T2R38 Taste Receptor Polymorphisms Underlie Susceptibility to Upper Respiratory Infection", Journal of Clinical Investigation, vol. 122, No. 11, Nov. 2012, 4145-4159.
Li, et al., "Gwasdb V2: An Update Database for Human Genetic Variants Identified by Genome-wide Association Studies", Nucleic Acids Research, vol. 44, Jan. 4, 2016, D869-D876.
Li, et al., "The Cellular Localization Of Na(+)/H(+) Exchanger 1, Cystic Fibrosis Transmembrane Conductance Regulator, Potassium Channel, Epithelial Sodium Channel γ And Vacuolar-type H+-atpase In Human Eccrine Sweat Glands", Acta Histochemica, vol. 116, No. 8, Oct. 2014, 1237-1243.
Liu, et al., "An Autoregulatory Mechanism Governing Mucociliary Transport is Sensitive to Mucus Load", American Journal of Respiratory Cell and Molecular Biology, vol. 51, No. 4, Oct. 2014, 485-493.
Liu, et al., "Method for Quantitative Study of Airway Functional Microanatomy Using Micro-Optical Coherence Tomography", Plos One, vol. 8, Issue 1, Jan. 2013, 8 pages.
Lopezjimenez, et al., "Two Novel Genes, Gpr113, which Encodes a Family 2 G-protein-coupled Receptor, and Trcg1, are Selectively Expressed In Taste Receptor Cells", Genomics, vol. 85, No. 4, Apr. 2005, 472-482.
Moriyama, et al., "Multiple Roles of Notch Signaling in The Regulation of Epidermal Development", Developmental Cell, vol. 14, No. 4, Apr. 2008, 594-604.
Mullins, et al., "Identification of A Human Ortholog of The Mouse Dcpp Gene Locus, Encoding A Novel Member of The Csp-1/Dcpp Salivary Protein Family", Physiological Genomics—American Journal of Physiology, vol. 28, No. 1, Dec. 2006, 129-140.
Munitz, et al., "Distinct Roles for IL-13 and IL-4 Via IL-13 Receptor Alpha1 and the Type II IL-4 Receptor in Asthma Pathogenesis", Proceedings of the National Academy of Sciences of the United States of America, vol. 105, No. 20, May 20, 2008, 7240-8211.
Ng, et al., "Annexin-1-Deficient Mice Exhibit Spontaneous Airway Hyperresponsiveness and Exacerbated Allergen-Specific Antibody Responses in a Mouse Model Of Asthma", Clinical and Experimental Allergy, vol. 41, No. 12, Dec. 2011, 1793-1803.
Overdier, et al., "The Winged Helix Transcriptional Activator Hfh-3 is Expressed in The Distal Tubules of Embryonic and Adult Mouse Kidney", Journal of Biological Chemistry, vol. 272, No. 21, May 23, 1997, 13725-13730.
Pardo-Saganta, et al., "Parent Stem Cells Can Serve as Niches for their Daughter Cells", Nature, vol. 523, No. 7562, Jul. 30, 2015, 597-601.
Py, et al., "Cochlin Produced by Follicular Dendritic Cells Promotes Antibacterial Innate Immunity", Immunity, vol. 38, No. 5, May 23, 2013, 1063-1072.
Quigley, et al., "Specification of Ion Transport Cells in The Xenopus Larval Skin", Development, vol. 138, No. 4, Feb. 2011, 705-714.
Rawlins, et al., "The Role of Scgb1A1+ Clara Cells in the Long-term Maintenance and Repair of Lung Airway, but not Alveolar, Epithelium", Cell Stem Cell, vol. 4, No. 6, Jun. 5, 2009, 525-534.
Regev, et al., "Science Forum: The Human Cell Atlas", eLife, vol. 6, Dec. 5, 2017, 30 pages.
Rock, et al., "Basal Cells As Stem Cells Of The Mouse Trachea And Human Airway Epithelium", Proceedings of the National Academy of Sciences of the United States of America, vol. 106, No. 31, Aug. 4, 2009, 12771-12775.
Ross, et al., "Transcriptional Profiling Of Mucociliary Differentiation In Human Airway Epithelial Cells", American Journal of Respiratory Cell and Molecular Biology, vol. 37, No. 2, Aug. 2007, 169-185.

(56) References Cited

OTHER PUBLICATIONS

Rosvall, et al., "Maps of Random Walks on Complex Networks Reveal Community Structure", Proceedings of the National Academy of Sciences of the United States of America, vol. 105, No. 4, Jan. 29, 2008, 1118-1123.
Roy, et al., "Muc5B is Required for Airway Defence", Nature, vol. 505, No. 7483, Jan. 16, 2014, 412-416.
Saint-Criq, et al., "Role of CFTR In Epithelial Physiology", Cellular and Molecular Life Sciences, vol. 74, No. 1, Oct. 6, 2016, 93-115.
Sakaguchi, et al., "S100A11, A Dual Growth Regulator of Epidermal Keratinocytes", Amino Acids, vol. 41, No. 4, Oct. 2011, 797-807.
Saunders, et al., "Chemosensory Brush Cells of the Trachea. A Stable Population in a Dynamic Epithelium", American Journal of Respiratory Cell and Molecular Biology, vol. 49, No. 2, Aug. 2013, 190-196.
Shah, et al., "Airway Acidification Initiates Host Defense Abnormalities in Cystic Fibrosis Mice", Science, vol. 351, No. 6272, Jan. 29, 2016, 503-507.
Shekhar, et al., "Comprehensive Classification of Retinal Bipolar Neurons by Single-Cell Transcriptomics", Cell, vol. 166, No. 5, Aug. 25, 2016, 1308-1323.
Shindo, et al., "Fxyd6, a Na,K-ATPase Regulator, is Expressed in Type II Taste Cells", Bioscience, Biotechnology and Biochemistry, vol. 75, No. 6, 2011, 1061-1066.
Sriuranpong, et al., "Notch Signaling Induces Rapid Degradation of Achaete-Scute Homolog 1", Molecular and Cellular Biology, vol. 22, No. 9, May 2002, 3129-3139.
Sun, et al., "Disease Phenotype of A Ferret Cftr-Knockout Model of Cystic Fibrosis", Journal of Clinical Investigation, vol. 120, No. 9, Sep. 2010, 3149-3160.
Sun, et al., "Lung Phenotype of Juvenile and Adult Cystic Fibrosis Transmembrane Conductance Regulator-Knockout Ferrets", American Journal of Respiratory Cell and Molecular Biology, vol. 50, No. 3, Mar. 2014, 502-512.
Tang, et al., "Acidic Ph Increases Airway Surface Liquid Viscosity in Cystic Fibrosis", Journal of Clinical Investigation, vol. 126, No. 3, Mar. 1, 2016, 879-891.
Tarran, et al., "Regulation of Murine Airway Surface Liquid Volume by Cftr and Ca2+-activated Cl-Conductances", The Journal of General Physiology, vol. 120, No. 3, Sep. 2002, 407-418.
Tata, et al., "Dedifferentiation of Committed Epithelial Cells into Stem Cells in Vivo", Nature, vol. 503, No. 7475, Nov. 14, 2013, 218-223.
Treutlein, et al., "Reconstructing Lineage Hierarchies of The Distal Lung Epithelium Using Single-cell Rna-seq", Nature, vol. 509, No. 7500, May 15, 2014, 371-375.
Troy, et al., "Claudin Immunolocalization in Neonatal Mouse Epithelial Tissues", Cell and Tissue Research, vol. 330, No. 2, Nov. 2007, 381-388.
Verzi, et al., "Transcription Factor Foxq1 Controls Mucin Gene Expression And Granule Content in Mouse Stomach Surface Mucous Cells", Gastroenterology, vol. 135, No. 2, Aug. 2008, 591-600.
Vidarsson, et al., "The Forkhead Transcription Factor Foxi1 is A Master Regulator of Vacuolar H-atpase Proton Pump Subunits In The Inner Ear, Kidney and Epididymis", PLoS One, vol. 4, No. 2, 2009, 11 pages.
Warburton, et al., "The Molecular Basis Of Lung Morphogenesis", Mechanisms of Development, vol. 92, No. 1, Mar. 15, 2000, 55-81.
Watson, et al., "Clonal Dynamics Reveal Two Distinct Populations of Basal Cells in Slow-Turnover Airway Epithelium", Cell Reports, vol. 12, No. 1, Jul. 7, 2015, 90-101.
Wong, et al., "Directed Differentiation Of Human Pluripotent Stem Cells Into Mature Airway Epithelia Expressing Functional CFTR Protein", Nature Biotechnology, vol. 30, No. 9, Sep. 2012, 876-882.
Yan, et al., "Single-cell Rna Sequencing Identifies Diverse Roles Of Epithelial Cells In Idiopathic Pulmonary Fibrosis", JCI Insight, vol. 1, No. 20, Dec. 8, 2016, 19 pages.

Yoon, et al., "Association between Polymorphisms in Bitter Taste Receptor Genes and Clinical Features in Korean Asthmatics", Respiration, vol. 91, No. 2, 2016, 141-150.
Zuberi, et al., "Critical Role For Galectin-3 in Airway Inflammation and Bronchial Hyperresponsiveness in a Murine Model Of Asthma", The American Journal of Pathology, vol. 165, No. 6, Dec. 2004, 2045-2053.
Kabadi, A., et al., "Epigenome editing of the CFTR-locus for treatment of Cystic Fibrosis", J Cyst Fibros. Jan. 2022; 21(1): 164-171.
Kerschner, J., et al., "An ectopic enhancer restores CFTR expression through de novo chromatin looping", Gene Therapy (2023) 30:478-486.
Lei, L., et al., "CFTR-rich ionocytes mediate chloride absorption across airway epithelia", J Clin Invest. 2023;133(20): e171268, 11 pages.
Lei, L., et al., "CFTR-rich ionocytes mediate chloride absorption across airway epithelia", 2023, Supplementary Materials, 14 pages.
Elborn, Stuart, "Cystic fibrosis", The Lancet, 388 (2016), pp. 2519-2531.
Amir et al., "viSNE Enables Visualization of High Dimensional Single-Cell Data and Reveals Phenotypic Heterogeneity of Leukemia," Nature Biotechnology, Jun. 2013, vol. 31, No. 6 (25 pages).
Banaszynski et al., "A rapid, reversible, and tunable method to regulate protein function in living cells using synthetic small molecules," Cell, Sep. 8, 2006 Vol. 126, No. 5 (pp. 995-1004).
Banaszynski et al., "Chemical control of protein stability and function in living mice," Nature Medicine, Oct. 2008, vol. 14, No. 10 (pp. 1123-1127).
Baron et al., "An overview of the Notch signalling pathway," Seminars in Cell & Developmental Biology, 2003, vol. 14 (pp. 113-119).
Bartel et al., "MicroRNAs: Genomics, Biogenesis, Mechanism, and Function," Cell, Jan. 23, 2004, vol. 116, No. 2 (pp. 281-297).
Bendall et al., "Single-cell Trajectory Detection Uncovers Progression and Regulatory Coordination in Human B Cell Development", Cell, Apr. 24, 2014, vol. 157, No. 3 (pp. 714-725).
Benjamini et al., "Controlling the False Discovery Rate - A practical and powerful approach to multiple testing," Journal of the Royal Statistical Society, 1995, vol. 57, No. 1 (pp. 289-300).
Boch et al., "Breaking the Code of DNA Binding Specificity of TAL-Type III Effectors," Science, Dec. 11, 2009, vol. 326 (pp. 1509-1512).
Bray, S., "Notch signalling: a simple pathway becomes complex," Nature reviews Molecular cell biology, 2006, vol. 7 (pp. 678-689).
Brennecke et al., "Accounting for Technical Noise in Single-Cell RNA-seq Experiments," Nature Methods, Sep. 22, 2013, vol. 10, No. 11 (pp. 1093-1095).
Buettner et al., "Computational analysis of cell-to-cell heterogeneity in single-cell RNA-sequencing data reveals hidden subpopulations of cells," Nature Biotechnology, Feb. 2015, vol. 33, No. 2 (pp. 155-160).
Buja et al., "Remarks on Parallel Analysis," published in: Multivariate Behavioral Research, 1992, vol. 27, No. 4 (26 pages).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Clackson et al., "Making antibody fragments using phage display libraries," Nature, Aug. 1991, vol. 352 (pp. 624-628).
Coifman et al., "Geometric diffusions as a tool for harmonic analysis and structure definition of data: diffusion maps," Proceedings of the National Academy of Sciences, USA, May 24, 2005, vol. 102, No. 21 (pp. 7426-7431).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].

(56) References Cited

OTHER PUBLICATIONS

Doyon et al., "Enhancing zinc-finger-nuclease activity with improved obligate heterodimeric architectures," Nature Methods, Jan. 2011, vol. 8, No. 1 (pp. 74-79).
Ellington et al., "In vitro selection of RNA molecules that bind specific ligands," Nature, 1990, vol. 346, No. 6287 (pp. 818-822).
Ester et al., "KDD'96: Proceedings of the Second International Conference on Knowledge Discovery and Data Mining," 1996 KDD-96 Proceedings-Preface (pp. 1-2).
Fiuza et al., "Cell and molecular biology of Notch," Journal of Endocrinology, 2007, vol. 194 (pp. 459-474).
Forgac, M., "Structure and properties of the vacuolar (H+)-ATPases," Journal of Biological Chemistry, May 7, 1999, vol. 274, No. 19 (pp. 12951-12954).
Fortini, M., "Notch signaling: the core pathway and its post-translational regulation," Developmental Cell, 2009, vol. 16 (pp. 633-647).
Graham et al., "Functional genomics identifies negative regulatory nodes controlling phagocyte oxidative burst," Nature Communications, 2015, vol. 6, No. 7838 (pp. 1-12).
Grubb et al., "Pathophysiology of Gene-Targeted Mouse Models for Cystic Fibrosis," Physiological Reviews, Jan. 1999, vol. 79, Suppl. 1 (pp. S193-S214).
Haghverdi et al., "Diffusion maps for high-dimensional single-cell analysis of differentiation data," Bioinformatics, 2015, vol. 31, No. 18 (pp. 2989-2998).
Heinz et al., "The selection and function of cell type-specific enhancers," Nature Reviews Molecular Cell Biology, Mar. 2015, vol. 16, No. 3 (pp. 144-154).
Hicke et al., "Escort aptamers: a delivery service for diagnosis and therapy," The Journal of Clinical Investigation, Oct. 2000, vol. 106, No. 8 (pp. 923-928).
Horwell et al., "The 'peptoid' approach to the design of non-peptide, small molecule agonists and antagonists of neuropeptides," Trends in Biotechnology, Apr. 1995, vol. 13, No. 4 (pp. 132-134).
Hoymann, H.G., "Invasive and noninvasive lung function measurements in rodents," Journal of Pharmacological and Toxicological Methods, 2007, vol. 55, No. 1 (pp. 16-26).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases," Nature Biotechnology, Sep. 2013, vol. 31, No. 9 (pp. 827-832).
Huangfu et al., "Induction of pluripotent stem cells by defined factors is greatly improved by small-molecule compounds," Nature Biotechnology, Jul. 2008, vol. 26 (pp. 795-1797).
Ianowski et al., "Mucus secretion by single tracheal submucosal glands from normal and cystic fibrosis transmembrane conductance regulator knockout mice," The Journal of Physiology, Mar. 21, 2007, vol. 580, No. 1 (pp. 301-314).
Inokuchi et al., "Prolactin 177, prolactin 188, and extracellular osmolality independently regulate the gene expression of ion transport effectors in gill of Mozambique tilapia," American Journal of Physiology-Regulatory, Integrative and Comparative Physiology, Nov. 2015, vol. 309 (pp. R1251-R1263).
Jaenisch et al., "Stem cells, the molecular circuitry of pluripotency and nuclear reprogramming," Cell, Feb. 22, 2008, vol. 132, No. 4 (pp. 567-582).
Jiang et al., "RNA-guided editing of bacterial genomes using CRISPR-Cas systems," Nature Biotechnology, Mar. 2013, vol. 31 [30 p. including supplementary information] (pp. 233-239).
Johnson et al., "Adjusting batch effects in microarray expression data using empirical Bayes methods," Biostatistics, Jan. 2007, vol. 8, No. 1 (pp. 118-127).
Keefe et al., "Aptamers as therapeutics," Nature Reviews, Jul. 2010, vol. 9 (pp. 537-550).
Khatodia et al., "The CRISPR/Cas genome-editing tool: application in improvement of crops," Frontiers in Plant Science, Apr. 19, 2016, vol. 7, No. 506 (pp. 1-13).

Kim et al., "Chimeric restriction endonuclease," Proceedings of the National Academy of Sciences, USA, Biochemistry, Feb. 1994, vol. 91 (pp. 883-887).
Kim et al., "Hybrid restriction enzymes: Zinc finger fusions to Fok I cleavage domain," Proceedings of the National Academy of Science, USA, Feb. 1996, vol. 93, No. 3 (pp. 1156-1160).
Klein et al., "Droplet Barcoding for Single-Cell Transcriptomics Applied to Embryonic Stem Cells," Cell, 2015, vol. 161, No. 5 (pp. 1187-1201).
Kleinstiver et al., "Engineered CRISPR-Cas9 nucleases with altered PAM specificities," Nature, Jul. 23, 2015, vol. 523, No. 7561 (pp. 481-485).
Koch et al., "Notch and cancer: a double-edged sword," Cellular and Molecular Life Sciences, Aug. 11, 2007, vol. 64 (pp. 2746-2762).
Kochurani et al., "Live detection and purification of cells based on the expression of a histone chaperone, HIRA, using a binding peptide," Scientific Reports, Nov. 24, 2015, vol. 5, No. 17218 (pp. 1-8).
Koenker et al., "Quantile Regression," The Journal of Economic Perspectives, Fall 2001, vol. 15, No. 4 (pp. 143-156).
Kohler et al., "Continuous cultures of fused cells secreting antibody of predefined specificity," Nature, 1975, vol. 256 (pp. 495-497).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Kopan et al., "The canonical Notch signaling pathway: unfolding the activation mechanism," Cell, Apr. 17, 2009, vol. 137 (pp. 216-233).
Kowalczyk et al., "Single Cell RNA-Seq Reveals Changes in Cell Cycle and Differentiation Programs Upon Aging of Hematopoietic Stem Cell," Genome Research, Dec. 2015, vol. 25, No. 12 (pp. 1860-1872).
Kuhn et al., "Quantification of C-reactive protein in the serum of patients with rheumatoid arthritis using multiple reaction monitoring mass spectrometry and 13C-labeled peptide standards," Proteomics, Apr. 2004, vol. 4, No. 4 (pp. 1175-1186).
Kumar et al., "Modeling allergic asthma in mice: pitfalls and opportunities," American Journal of Respiratory Cell and Molecular Biology, 2002, vol. 27 (pp. 267-272).
Lagos-Quintana et al., "Identification of Novel Genes Coding for Small Expressed RNAs," Science, Oct. 26, 2001, vol. 294 (pp. 853-858).
Lagos-Quintana et al., "Identification of tissue-specific microRNAs from mouse," Current Biology, Apr. 30, 2002, vol. 12, (pp. 735-739).
Lagos-Quintana et al., "New microRNAs from mouse and human," RNA, 2003, vol. 9 (pp. 175-179).
Langmead et al., "Ultrafast and memory-efficient alignment of short DNA sequences to the human genome", Genome Biology, Mar. 4, 2009, vol. 10, No. 3 (pp. 1-10).
Lau et al., "An Abundant Class of Tiny RNAs with Probably Regulatory Roles in Caenorhabditis elegans," Science, Oct. 26, 2001, vol. 294 (pp. 858-861).
Le Borgne et al., "Regulation of Notch signalling by endocytosis and endosomal sorting," Current Opinion in Cell Biology, 2006, vol. 18 (pp. 213-222).
Lee et al., "An Extensive Class of Small RNAs in Caenorhabditis elegans," Science, Oct. 26, 2001, vol. 294 (pp. 862-864).
Leek et al., "The sva package for removing batch effects and other unwanted variation in high-throughput experiments," Bioinformatics, Mar. 15, 2012, vol. 28, No. 6 (pp. 882-883).
Levine et al., "Data-Driven Phenotypic Dissection of AML Reveals Progenitor-like Cells that Correlate with Prognosis," Cell, 2015, vol. 162, No. 1 (pp. 184-197).
Levy-Nissenbaum et al., Nanotechnology and aptamers: applications in drug delivery, Trends in Biotechnology, Aug. 2008, vol. 26, No. 8 (pp. 442-449).

(56) References Cited

OTHER PUBLICATIONS

Li et al., "RSEM: accurate transcript quantification from RNA-Seq data with or without a reference genome," BMC Bioinformatics, 2011, vol. 12 No. 323 (16 pages).
Liberzon et al., "Molecular signatures database (MSigDB) 3.0," Bioinformatics Jun. 15, 2011, vol. 27, No. 12 (pp. 1739-1740).
Lim et al., "The microRNAs of Caenorhabditis elegans," Genes & Development, Apr. 15, 2003, vol. 17, No. 8 (pp. 991-1008).
Lim et al., "Vertebrate microRNA genes," Science, Mar. 7, 2003, vol. 299, No. 5612 (p. 1540).
Longhin et al., "Cell cycle alterations induced by urban PM2.5 in bronchial epithelial cells: characterization of the process and possible mechanisms involved," Particle and Fibre Toxicology, 2013, vol. 10, No. 63 (pp. 1-19).
Lu et al., "Sweat gland progenitors in development, homeostasis, and wound repair," Cold Spring Harbor Perspectives in Medicine, Feb. 1, 2014, vol. 4, No. 2 (pp. 1-18).
Luo et al., "Isolation and functional analysis of a cDNA for human Jagged2, a gene encoding a ligand for the Notch1 receptor," Molecular and Cellular Biology, 1997, vol. 17 (pp. 6057-6067).
Ma et al., "Genome modification by CRISPR/Cas9," FEBS Journal, Dec. 2014, vol. 281, No. 23 (pp. 5186-5193).
Macosko et al., "Highly Parallel Genome-wide Expression Profiling of Individual Cells Using Nanoliter Droplets," Cell, May 21, 2015, vol. 161 (pp. 1202-1214).
Mali et al. "RNA-Guided Human Genome Engineering Via Cas9," Science, dated Feb. 15, 2013, vol. 339 (pp. 823-826).
Mangelsdorf et al., "The nuclear receptor superfamily: the second decade," Cell, 1995, vol. 83 (pp. 835-839).
Mangelsdorf et al., "The RXR heterodimers and orphan receptors," Cell, Dec. 15, 1995, vol. 83 (pp. 841-850).
Marks et al., "By-passing immunization: Human antibodies from V-gene libraries displayed on phage," Journal of Molecular Biology, Dec. 1991, vol. 222, No. 3 (pp. 581-597).
Marson et al., "Wnt Signaling Promotes Reprogramming of Somatic Cells to Pluripotency," Cell Stem Cell, Aug. 7, 2008, vol. 3 (pp. 132-135).
Maynard et al., "A directed approach for engineering conditional protein stability using biologically silent small molecules," Journal of Biological Chemistry, Sep. 2007, vol. 282, No. 34 (p. 24866-24872).
Miyazaki et al., "Destabilizing Domains Derived from the Human Estrogen Receptor," Journal of the American Chemical Society, Mar. 7, 2012, vol. 134 (pp. 3942-3945).
Moscou et al., "A Simple Cipher Governs DNA Recognition by TAL Effectors", Science, Dec. 11, 2009, vol. 326 (p. 1501).
Mou et al., "Dual SMAD Signaling Inhibition Enables Long-Term Expansion of Diverse Epithelial Basal Cells," Cell Stem Cell, 2016, vol. 19 (pp. 217-231).
Nakamura et al., "Codon usage tabulated from the international DNA sequence databases: status for the year 2000," Nucleic Acids Research, 2000, vol. 28, No. 1 (p. 292).
Ng et al., "Leucine-rich repeat (LRR) proteins: integrators of pattern recognition and signaling in immunity," Autophagy, Sep. 2011, vol. 7, No. 9 (pp. 1082-1084).
Nials et al., "Mouse models of allergic asthma: acute and chronic allergen challenge," Disease Models and Mechanisms, Nov. 21, 2008, vol. 1, Nos. 4-5 (pp. 213-220).
Nishi et al., "The vacuolar (H+ )-ATPases-nature's most versatile proton pumps," Nature reviews Molecular cell biology, 2002, vol. 3, No. 2 (pp. 94-103).
Nishimasu et al., "Crystal Structure of Cas9 in Complex with Guide RNA and Target DNA," Cell, Feb. 27, 2014, vol. 156 (pp. 935-949).
Paige et al., "RNA mimics of green fluorescent protein," Science, Jul. 29, 2011, vol. 333, No. 6042 (pp. 642-646).
Pershadsing, H., "Pharmacological peroxisome proliferator-activated receptor-gamma ligands: emerging clinical indications beyond diabetes," Expert Opinion on Investigational Drugs, 1999, vol. 8, No. 11 (pp. 1859-1872).
Picelli et al. "Full-length RNA-seq from single cells using Smart-seq2," Nature Protocols, Jan. 2014, vol. 9, No. 1 (pp. 171-181).
Pilewski et al., "Role of CFTR in Airway Disease," Physiological Reviews, Jan. 1, 1999, vol. 79 (Suppl.: S215-S255).
Platt et al., "CRISPR-Cas9 Knockin Mice for Genome Editing and Cancer Modeling," Cell, 2014, vol. 159 (pp. 440-455).
Pujana et al., "Network modeling links breast cancer susceptibility and centrosome dysfunction," Nature Genetics, 2007, vol. 39 (pp. 1338-1349).
Ran et al., "Double Nicking by RNA-guided CRISPR Cas9 for enhanced genome editing specificity," Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Robertson et al., "Mutations in a novel cochlear gene cause DFNA9, a human nonsyndromic deafness with vestibular dysfunction," Nature Genetics, Nov. 1998, vol. 20, No. 3 (pp. 299-303).
Salic et al., "A chemical method for fast and sensitive detection of DNA synthesis in vivo," Proceedings of the National Academy of Sciences, USA, 2008, vol. 105 (pp. 2415-2420).
Schneider et al., "NIH Image to ImageJ: 25 years of image analysis," Nature Methods, Jul. 2012, vol. 9, No. 7 (pp. 671-675).
Shalem et al., "Genome-Scale CRISPR-Cas9 Knockout Screening in Human Cells," Science, Jan. 3, 2014, vol. 343 (pp. 84-87).
Shi et al., "A Combined Chemical and Genetic Approach for the Generation of Induced Pluripotent Stem Cells," Cell Stem Cell, Jun. 2008, vol. 2, No. 6 (pp. 525-528).
Shields et al., "Microfluidic cell sorting: a review of the advances in the separation of cells from debulking to rare cell isolation," Lab Chip, Mar. 7, 2015 Vol. 15, No. 5 (pp. 1230-1249).
Shmakov et al., "Discovery and Functional Characterization of Diverse Class 2 CRISPR-Cas Systems," Molecular Cell, Nov. 1, 2015, vol. 60, No. 3 (pp. 385-397).
Slaymaker et al., "Rationally engineered Cas9 nucleases with improved specificity," Science, Jan. 1, 2016, vol. 351, No. 6268 (pp. 84-88).
Smith et al., "Adenoviral constructs encoding phosphorylation-competent full-length and truncated forms of the human retinoblastoma protein inhibit myocyte proliferation and neointima formation," Circulation, Sep. 16, 1997, vol. 96, No. 6 (pp. 1899-1905).
Stijnen et al., "Random effects meta-analysis of event outcome in the framework of the generalized linear mixed model with applications in sparse data," Statistics in Medicine, Jun. 25, 2010, vol. 29 (pp. 3046-3067).
Sun-Wada et al., "Diversity of mouse proton-translocating ATPase: presence of multiple isoforms of the C, d and G subunits," Gene, 2003, vol. 302 (pp. 147-153).
Swiech et al., "In vivo interrogation of gene function in the mammalian brain using CRISPR-Cas9," Nature Biotechnology, 2014, vol. 33 (pp. 102-106) [Including Supplemental information, 4 pages].
Takahashi et al., "Induction of Pluripotent Stem Cells from Adult Human Fibroblasts by Defined Factors," Cell, Nov. 30, 2007, vol. 131, No. 5 (pp. 861-872).
Takahashi et al., Induction of Pluripotent Stem Cells from Mouse Embryonic and Adult Fibroblast Cultures by Defined Factors, Cell, Aug. 2006, vol. 126 (pp. 663-676).
Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).
Tuerk et al., "Systematic evolution of ligands by exponential enrichment: RNA ligands to bacteriophage T4 Dna polymerase," Science, Aug. 3, 1990, vol. 249, No. 4968 (pp. 505-510).
Van Der Maaten et al., "Visualizing Data Using t-SNE," Journal of Machine Learning Research, Nov. 2008, vol. 9 (pp. 2579-2605).
Van Der Maaten, "Accelerating t-SNE using Tree-Based Algorithms", Journal of Machine Learning Research, Oct. 2014, vol. 15, No. 1 (pp. 3221-3245).
Van Keymeulen et al., "Distinct stem cells contribute to mammary gland development and maintenance," Nature, 2011, vol. 479 (pp. 189-193).
Wang et al., "Genetic screens in human cells using the CRISPR/Cas9 system," Science, Jan. 3, 2014, vol. 343 No. 6166 (pp. 80-84).

(56) References Cited

OTHER PUBLICATIONS

Wang et al., "One-Step Generation Of Mice Carrying Mutations In Multiple Genes By CRISPR/Cas- Mediated Genome Engineering," Cell, May 9, 2013, vol. 153 (pp. 910-918).

Warren et al., "Highly efficient reprogramming to pluripotency and directed differentiation of human cells with synthetic modified mRNA," Cell Stem Cell, Nov. 5, 2010, vol. 7, No. 5 (pp. 618-630).

Wills et al., "Development and characterization of recombinant adenoviruses encoding human p53 for gene therapy of cancer," Human Gene Therapy, 1994, vol. 5 (pp. 1079-1088).

Willson et al., "The PPARs: from orphan receptors to drug discovery," Journal of Medicinal Chemistry, Feb. 24, 2000, vol. 43, No. 4 (pp. 527-550).

Wong, P. Y.D., "Cftr gene and male fertility," Molecular Human Reproduction, Feb. 1, 1998, vol. 4, No. 2 (pp. 107-110).

Wu et al., "Genome-wide binding of the CRISPR endonuclease Cas9 in mammalian cells," Nature Biotechnology, 2014, Including Supplemental information, 2 p. (pp. 1-9).

Young et al., "Gene ontology analysis for RNA-seq: accounting for selection bias," Genome Biology, 2010, vol. 11, No. R14 (pp. 1-12).

Zeisel et al., Brain Strcuture: "Cell Types in The Mouse Cortex and Hippocampus Revealed by Single-cell RNA-seq," Science, Mar. 6, 2015, vol. 347, No. 6226 (pp. 1138-1142).

Zetsche at el., "Cpf1 Is a Single RNA-Guided Endonuclease of a Class 2 CRISPR-Cas System," Cell, Oct. 22, 2015, vol. 163, No. 3 (pp. 759-771).

Zetsche et al., "A split-Cas9 architecture for inducible genome editing and transcription modulation," Nature Biotechnology, Feb. 2015, vol. 33, No. 2 (pp. 139-142).

Zhang et al., "AnimalTFDB: a comprehensive animal transcription factor database," Nucleic Acids Research, 2012, vol. 40 (pp. 1-6).

Zhang et al., "Efficient Construction of Sequence-Specific TAL Effectors for Modulating Mammalian Transcription," Nature Biotechnology, Feb. 2011, vol. 29, No. 2 (pp. 149-154).

Zheng et al., "Massively parallel digital transcriptional profiling of single cells," Nature Communications, Jan. 16, 2017, vol. 8, No. 14049 (12 pages).

Zhou et al., "Aptamer-targeted cell-specific RNA interference," Silence, Feb. 1, 2010, vol. 1, No. 4 (10 pages).

Zosky et al., "Animal models of asthma," Clinical & Experimental Allergy, 2007, vol. 37, No. 7 (pp. 973-988).

\* cited by examiner

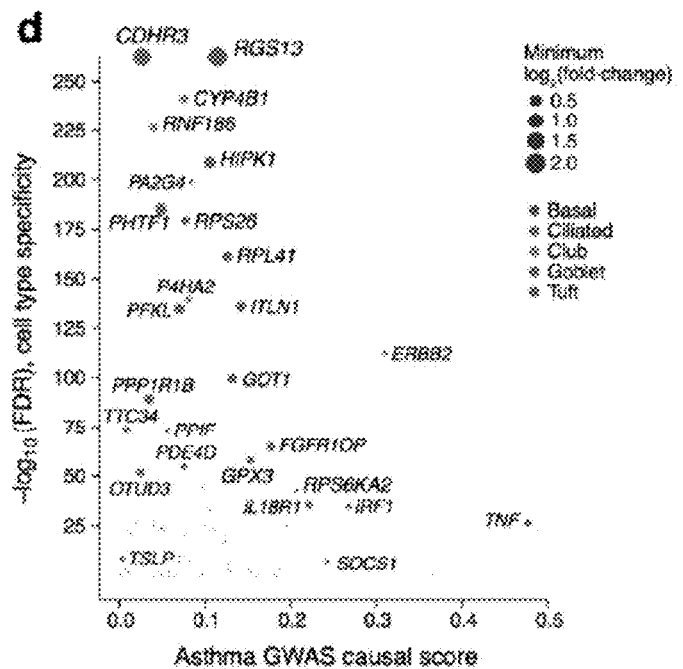
FIG. 25D
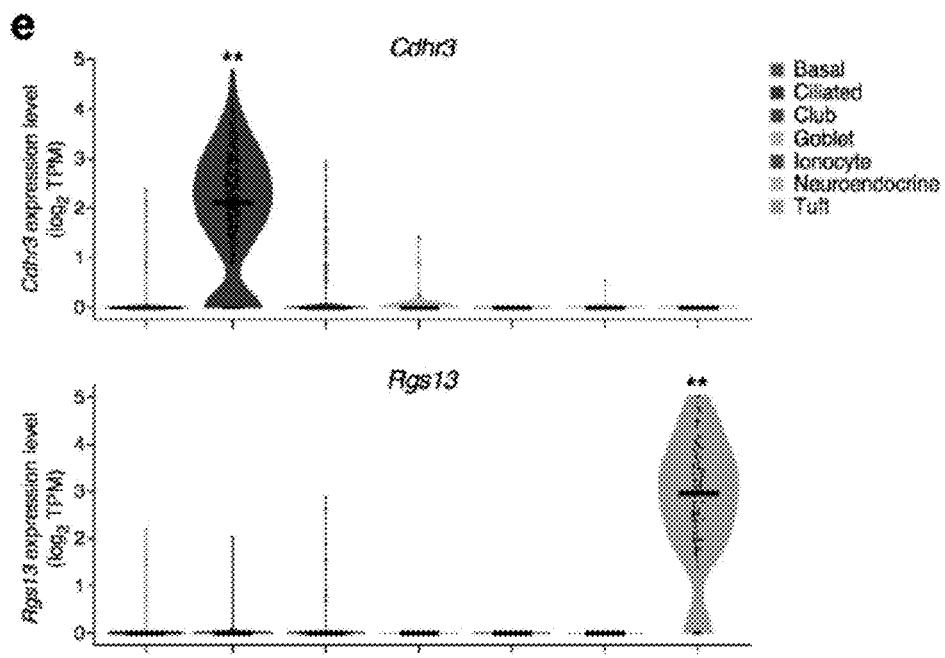
FIGRUE 25E

RESPIRATORY AND SWEAT GLAND IONOCYTES

REFERENCE TO AN ELECTRONIC SEQUENCE LISTING

The contents of the electronic sequence listing (BROD-2055_ST25.txt; size is 9,527 bytes and it was created on Sep. 20, 2019) is herein incorporated by reference in its entirety.

This application is a U.S. National Stage of International Application No. PCT/US2018/027337, filed Apr. 12, 2018. Reference is made to U.S. provisional application Ser. No. 62/484,782 filed on Apr. 12, 2017. The entire content of the above-identified application is hereby fully incorporated herein by reference.

Citation or identification of any document in this application is not an admission that such document is available as prior art to the present invention. All applications, and all documents cited herein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates generally to compositions and methods for identifying ionocytes in respiratory epithelial cells and/or sweat gland cells. This invention also relates generally to modulating, controlling or otherwise influencing respiratory epithelial cell and/or sweat gland cell proliferation, differentiation, maintenance and function by using the ionocyte thereof. The invention further relates to methods for treating inflammatory lung diseases by using pulmonary ionocytes and treating diseases associated with sweat gland disorder by using sweat gland ionocytes.

BACKGROUND

Lung diseases, including respiratory diseases, are a major cause of mortality and morbidity worldwide. Inflammatory lung diseases, which affect the respiratory system to varying degrees, have been greatly increasing for several decades, in particular in industrialized countries. The number of worldwide deaths related to these diseases is estimated at more than 3 million per year.

A common symptom of inflammatory lung disease is fluid build-up in the lung, which is caused by an imbalance between fluid extravasation and fluid resorption. Oftentimes, the permeability of the lung tissue is damaged in patients with inflammatory lung disease, causing an increased fluid supply in tissues or organs (e.g., in the lungs). As a result, of the increased fluid accumulation, gas exchange in the tissue or organ is impeded or restricted, thus preventing or inhibiting oxygen from reaching the organism's blood.

Current treatments are directed to reducing symptoms of lung disease and offer little to no prospect of cure or complete disease reversal. There is a need for a therapy that prevents, delays or reverses the progression of inflammatory lung diseases, for example by reversing the fluid build-up in the lung.

SUMMARY

The inventors have identified novel ionocytes from respiratory epithelial cells, and novel markers and networks driving the regulation and differentiation of lung stem cells and respiratory epithelial cells, have identified markers capable of identifying new subpopulations of cells, and identified the crucial role of ionocytes in controlling respiratory epithelial cell function.

In some embodiments, the invention provides a method for modulating respiratory epithelial cell proliferation, differentiation, maintenance, and/or function, the method comprising contacting a respiratory epithelial ionocyte cell or a population of respiratory epithelial ionocyte cells with an ionocyte modulating agent in an amount sufficient to modify proliferation, differentiation, maintenance, and/or function of the respiratory epithelial ionocyte cell or population of respiratory epithelial ionocyte cells.

In some embodiments, the respiratory epithelial cell is a laryngeal epithelial cell, a tracheal epithelial cell, a bronchial epithelial cell, or a submucosal gland cell.

In some embodiments, the invention provides a method for modulating sweat gland cell proliferation, differentiation, maintenance, and/or function, the method comprising contacting a sweat gland ionocyte cell or a population of sweat gland ionocyte cells with an ionocyte modulating agent in an amount sufficient to modify proliferation, differentiation, maintenance, and/or function of the respiratory epithelial ionocyte cell or population of respiratory epithelial ionocyte cells.

In some embodiments, such modulation of the respiratory epithelial cell proliferation, differentiation, maintenance, and/or function modulates inflammation of the respiratory system.

In some embodiments, the modulating agent modulates expression and/or activity of one or more of FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2. In some embodiments, the expression and/or activity of FOXI2 is modulated. In some embodiments, the expression and/or activity of one or more of FOXI1, FOXI2, ASCL3, V-Type Proton ATPases, CFTR, PPARG, Cochlin, STAP1, P2RY14, MOXD1, GM933, ATP6V1C2, ATP6V0D2, ASGR1, and ASGR2 is upregulated. In some embodiments, the expression and/or activity of FOXI2 is upregulated. In other embodiments, the expression and/or activity of one or more of FOXI1, FOXI2, ASCL3, V-Type Proton ATPases, CFTR, PPARG, Cochlin, STAP1, P2RY14, MOXD1, GM933, ATP6V1C2, ATP6V0D2, ASGR1, and ASGR2 is downregulated. In some embodiments, the expression and/or activity of FOXI2 is downregulated.

In some embodiments, the upregulation or downregulation of one or more of these genes alters Notch signaling pathway function in the cell. In some embodiments, the upregulation or downregulation of one or more of these changes induces a change in one or more genes or proteins, which are the effectors of ionocyte specification. In some embodiments, the effectors are one or more gene and/or protein in the Notch signaling pathway. In some embodiments, the effector is one or more of Notch1, Notch2, Jag2, Dll1, Dll2, and Jag2.

In a specific embodiment, the modulating agent is a small molecule, a protein, a polypeptide, an antibody or an antigen binding fragment thereof, or a nucleic acid. In some embodiment, the modulating agent is an agonist of one or more of FOXI1, FOXI2, ASCL3, V-Type Proton ATPases, CFTR, PPARG, Cochlin, STAP1, P2RY14, MOXD1, GM933, ATP6V1C2, ATP6V0D2, ASGR1, and ASGR2. Preferably said agonist increases expression of one or more of FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2. In some embodiments, the modulating agent is an agonist of FOXI1. Preferably, said agonist increases expression of FOXI1.

In some embodiments, the modulating agent modulates expression and/or activity of one or more genes and/or proteins that regulate ion transport and/or ion homeostasis.

In some embodiments, the ion is one or more of H+, Na+, K+, Cu2+, Ca2+, HCO3−, Cl−, and a combination of two or more thereof.

In some embodiments, the ionocyte extracts ions from or secretes ions to its external environment. In some embodiments, the ionocyte changes the osmolality of its external environment. In some embodiments, the ionocyte changes epithelial surface physiology, including the amount and viscosity of mucus in the airway surface liquid (ASL) and ciliary beat frequency.

In some embodiments, the foregoing method is useful for the modulation of respiratory function and in the related treatment of an inflammatory lung disease. In some embodiments, such diseases include asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, α-1-anti-trypsin deficiency, or congestive heart failure. In some embodiments, the methods are useful for the treatment or preventing of a lung injury or a lung disease or disorder in a subject in need thereof.

In some embodiments, a modulating agent as disclosed herein is provided for use in the treatment of an inflammatory lung disease. Also provided in the use of a modulating agent as disclosed herein in the manufacture of a medicament for the treatment of an inflammatory lung disease.

In some embodiments, the foregoing method is useful for the modulation of function and in the related treatment of a disease or condition associated with sweat gland disorders. In some embodiments, such diseases include hyperhidrosis, hidradenitis suppurativa, miliaria, pompholyx, bromhidrosis, fox-fordyce disease, or anhidrosis.

In a preferred embodiment, a modulating agent as disclosed herein is provided for use in the treatment of a disease or condition associated with sweat gland disorders. Also provided in the use of a modulating agent as disclosed herein in the manufacture of a medicament for a disease or condition associated with sweat gland disorders.

In another aspect, the present invention provides a method for identifying an ionocyte in a respiratory epithelial cell sample, comprising detecting expression of one or more genes that regulate ion transport and/or ion homeostasis, wherein an expression level above or below a pre-determined threshold indicates the presence of an ionocyte.

In another aspect, the present invention provides a method for identifying an ionocyte from a respiratory epithelial cell sample, comprising detecting expression of one or more genes selected from FOXI1, FOXI2, ASCL3, V-Type Proton A TPase, CFTR, PPARG, Cochlin, STAP1, P2RY14, MOXD1, GM933, ATP6V1C2, ATP6V0D2, ASGR1, and ASGR2, wherein an expression level above a pre-determined threshold indicates the presence of an ionocyte. In some embodiments, the method comprises detecting expression of FOXI1, wherein an expression level of FOXI1 above a pre-determined threshold indicates the presence of an ionocyte.

In another aspect, the present invention provides a method for isolating an ionocyte from a respiratory epithelial cell sample, comprising detecting expression of one or more genes that regulate ion transport and/or ion homeostasis in said cell sample, wherein an expression level above or below a pre-determined threshold indicates the presence of an ionocyte. Preferably, the method further comprises isolating a cell that is above or below the pre-determined threshold thereby isolating an ionocyte from said sample.

In some embodiments, these genes includes, but are not limited to FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2 wherein elevated expression of one or more of these genes indicates ionocytes. In some embodiments, the gene is FOXII1, and elevated expression of FOXI1 indicates ionocytes.

In another aspect, the present invention provides a method for isolating an ionocyte from a respiratory epithelial cell sample, comprising detecting expression of one or more genes selected from FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2, wherein an expression level above a pre-determined threshold indicates the presence of an ionocyte. Preferably, the method further comprises isolating a cell that is above the pre-determined threshold thereby isolating an ionocyte from said sample. In some embodiments, the method for isolating an ionocyte from a respiratory epithelial cell sample, comprising detecting expression of FOXI1, wherein an expression level of FOXI1 above a pre-determined threshold indicates the presence of an ionocyte.

In some embodiments, the respiratory epithelial cell is laryngeal epithelial cell, a tracheal epithelial cell, a bronchial epithelial cell or a submucosal gland cell.

In another aspect, the present invention provides a method for identifying an ionocyte in a sweat gland cell sample, comprising detecting expression of one or more genes that regulate ion transport and/or ion homeostasis, wherein an expression level above or below a pre-determined threshold indicates the presence of an ionocyte.

In another aspect, the present invention provides a method for identifying an ionocyte from a sweat gland cell sample, comprising detecting expression of one or more genes selected from FOXI1, FOXI2, ASCL3, V-Type Proton ATPase, CFTR, PPARG, Cochlin, and STAP1, wherein an expression level above a pre-determined threshold indicates the presence of an ionocyte.

In another aspect, the present invention provides a method for isolating an ionocyte from a sweat gland cell sample, comprising detecting expression of one or more genes selected from FOXI1, FOXI2, ASCL3, V-Type Proton ATPase, CFTR, PPARG, Cochlin, STAP1 P2RY4, MOXD1, GM933, ATP6V1C2, ATP6V0D2 ASGR1, and ASGR2, in said cell sample, wherein an expression level above a pre-determined threshold indicates the presence of an ionocyte. Preferably, the method further comprises isolating a cell that is above the pre-determined threshold thereby isolating an ionocyte from said sample.

In another aspect, the present invention provides a method for isolating an ionocyte from a sweat gland cell sample, comprising detecting expression of one or more genes that regulate ion transport and/or ion homeostasis in said cell sample, wherein an expression level above or below a pre-determined threshold indicates the presence of an ionocyte. Preferably, the method further comprises isolating a cell that is above or below the pre-determined threshold thereby isolating an ionocyte from said sample.

In some embodiments, these genes include, but are not limited to FOXI1, FOXI2, ASCL3, V-Type Proton ATPases, CFTR, PPARG, Cochlin, STAP1, P2RY14, MOXD1, GM933, ATP6V1C2, ATP6V0D2, ASGR1, and ASGR2 wherein elevated expression of one or more of these genes indicates an ionocyte.

In some embodiments, the present invention provides a method of generating an ionocyte from a lung stem cell, comprising a) differentiating the lung stem cell, and b) detecting expression of one or more genes that regulate ion transport and/or ion homeostasis, wherein an expression level above or below a pre-determined threshold indicates the presence of an ionocytes.

Preferably, wherein step b) comprises detecting expression of one or more genes selected from FOXI1, FOXI2, ASCL3, V-Type Proton ATPase, CTR, PPARG, Cochlin, STAP1, P2RY14, MOXD1, GM933, ATP6V1C2, ATP6V0D2, ASGR1, and ASGR2 and expression level above a pre-determined threshed indicates the presence of an ionocyte. In some embodiments, step b) comprises detecting expression of FOXI1 and expression level of FOXI1 above pre-determined threshold indicates the presence of an ionocyte. Preferably, wherein said method comprises reprogramming lung stem cells. Preferably, the method further comprises isolating a cell that is above or below the pre-determined threshold thereby isolating an ionocyte from said sample.

In another aspect, the present invention provides a method of treating an inflammatory lung disease (or for the treatment or prevention of a lung injury or a lung disease or disorder), the method comprising administering to a subject in need thereof a therapeutically effective amount of respiratory epithelial ionocytes or their progenitor cells.

In some embodiments, the respiratory epithelial ionocytes or their progenitor cells are implanted in the respiratory tract of a subject in need thereof. In another embodiment of this aspect, the cell is autologous to the subject into which the composition is being implanted. In some embodiments, the cell is allogenic to the subject into which the composition is being implanted. In some embodiments, the cell is engineered by CRISPR system to correct any mutation in the CFTR gene that are associated with cystic fibrosis. In some embodiments, the mutation is selected from the group consisting of G542X, W1282X, R553X, F508del, N1303k, I507del, G551d, S549N, D1152H, R347P, R117H, 3849+10kbC→T, 2789+5G→A, and A455E.

In some embodiments, the ionocytes or their progenitor cells are implanted in the subject as part of a composition further comprising a scaffold. In some embodiments, the scaffold is biodegradable.

In some embodiments, the scaffold comprises a natural fiber, a synthetic fiber, decellularized lung tissue, or a combination thereof.

In some embodiments, the natural fiber is selected from the group consisting of collagen, fibrin, silk, thrombin, chitosan, chitin, alginic acid, hyaluronic acid, and gelatin.

In some embodiments, the synthetic fiber is selected from the group consisting of: representative biodegradable aliphatic polyesters such as polylactic acid (PLA), polyglycolic acid (PGA), poly(D,L-lactide-co-glycolide) (PLGA), poly (caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), and poly(hydroxyl valerate).

In some embodiments of this aspect, the inflammatory lung disease is asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, or α-1-anti-trypsin deficiency.

In another aspect, the present invention provides a method for treating a disease or condition associated with sweat gland disorders, the method comprises administering to a subject in need thereof a therapeutically effective amount of sweat gland ionocytes or their progenitor cells. In some embodiments, the disease or condition is hyperhidrosis, hidradenitis suppurativa, *miliaria*, pompholyx, bromhidrosis, fox-fordyce disease, or anhidrosis.

In another aspect, the present invention provides a method for identifying an agent for treating defective respiratory epithelial ion transport in a subject, the method comprising contacting the agent with a respiratory epithelial ionocyte or its progenitor cell, and comparing the proliferation of the respiratory epithelial ionocyte with and without contacting the agent, wherein an increased proliferation indicates the agent is effective for treating defective ion transport in the subject.

In a related aspect, the present invention provides a method for identifying an agent for treating defective respiratory epithelial ion transport in a subject, the method comprising contacting the agent with a respiratory epithelial ionocyte or its progenitor cell, and comparing the activity of the respiratory epithelial ionocyte with and without contacting the agent, wherein an increased activity of ionocytes indicates the agent is effective for treating defective ion transport in the subject.

In another aspect, the present invention provides a method for identifying an agent for treating an inflammatory lung disease (or for the treatment or prevention of a lung injury or a lung disease or disorder), the method comprising contacting the agent with a respiratory epithelial ionocyte or its progenitor cell, and comparing the proliferation of the respiratory epithelial ionocyte, wherein an increased proliferation of the respiratory epithelial ionocyte indicates the agent is effective for treating the inflammatory lung disease.

In another aspect, the present invention provides a method for identifying an agent for treating defective respiratory epithelial ion transport in a subject, the method comprising contacting the agent with a respiratory epithelial ionocyte or its progenitor cell, and comparing the activity of the respiratory epithelial ionocyte, wherein an increased activity of the ionocyte indicates the agent is effective for treating defective ion transport in the subject.

In some embodiments, the inflammatory lung disease is asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, or α-1-anti-trypsin deficiency.

In another aspect, the present invention provides a method for identifying an agent for treating defective sweat gland ion transport in a subject, comprising contacting the agent with a sweat gland ionocyte or its progenitor cell, wherein increased proliferation of the sweat gland ionocyte indicates the agent is effective for treating defective ion transport in the subject.

In another aspect, the present invention provides a method for identifying an agent for treating a disease or condition associated with a sweat gland disorder, comprising contacting the agent with a sweat gland ionocyte or its progenitor cell, wherein increased proliferation of the sweat gland ionocyte indicates the agent is effective for treating the disease or condition. In some embodiments, the disease or condition is hyperhidrosis, hidradenitis suppurativa, *miliaria*, pompholyx, bromhidrosis, fox-fordyce disease, or anhidrosis.

In accordance with any of the aspects, the candidate agent preferably comprises a small molecule, a protein, a polypeptide, an antibody or an antigen binding fragment thereof, or a nucleic acid.

In another aspect, the present invention provides a composition comprising an isolated ionocyte cell or its precursor and a scaffold. In some embodiments, the scaffold is implantable in a subject. In some embodiments, the cell is autologous to the subject into which the composition is being implanted. In other embodiments, the cell is allogenic to the subject into which the composition is being implanted, and preferably wherein the cell has been engineered so that it is not rejected by the immune system of the subject being implanted. In some embodiments, the scaffold is biodegradable. In some embodiments, the scaffold comprises a natural fiber, a synthetic fiber, decellularized lung tissue, or a combination thereof.

In some embodiments, the natural fiber is selected from the group consisting of collagen, fibrin, silk, thrombin, chitosan, chitin, alginic acid, hyaluronic acid, and gelatin.

In some embodiments, the synthetic fiber is selected from the group consisting of: biodegradable aliphatic polyesters, such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), poly(hydroxyl valerate), and combinations of two or more thereof.

In some embodiments, the ionocyte cell is isolated from respiratory tract epithelial cells or sweat gland cells.

In some embodiments, the present invention provides a method of treating an inflammatory lung disease, comprising administering such composition, and optionally a pharmaceutically acceptable carrier to a subject in need thereof. Preferably, said compositions are provided for use in the treatment of an inflammatory lung disease. In some embodiments, the inflammatory lung disease is one or more of asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, or α-1-anti-trypsin deficiency.

In some embodiments, the present invention provides a method of treating a disease or condition associated with sweat gland disorder, the method comprising administering the composition of the present invention, and optionally a pharmaceutically acceptable carrier to a subject in need thereof. Preferably, said compositions are provided for use in the treatment of a disease or condition associated with sweat gland disorder. In some embodiments, the disease or condition is hyperhidrosis, hidradenitis suppurativa, *miliaria*, pompholyx, bromhidrosis, fox-fordyce disease, or anhidrosis.

In another aspect, the present invention provides a kit for treating an inflammatory lung disease, comprising the composition of the present invention and an instruction for treating the inflammatory lung disease. In some embodiments, the inflammatory lung disease is asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, or α-1-anti-trypsin deficiency.

In another aspect, the present invention provides a kit for treating a disease or condition associated with sweat gland disorder, comprising the composition of present invention and an instruction for treating the disease or condition. In some embodiments, the disease or condition is hyperhidrosis, hidradenitis suppurativa, *miliaria*, pompholyx, bromhidrosis, fox-fordyce disease, or anhidrosis.

In another aspect, the present invention provides a method for identifying the developmental lineage of ionocyte, comprising measuring the expression of mRNA or protein of any one or more of FOXI1, FOXI2, ASCL3, V-Type Proton ATPases, CFTR, PPARG, Cochlin, STAP1, P2RY14, MOXD1, GM933, ATP6V1C2, ATP6V0D2, ASGR1, and ASGR2.

These and other embodiments are disclosed and encompassed by the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 25A-25E show high-confidence consensus cell type markers, and cell-type specific expression of asthma-associated genes. A. Cell type clusters in full-length plate-based scRNA-seq data. Cell-cell Pearson correlation coefficient (r, color bar), between all 301 cells (individual rows and columns) ordered by cluster assignment (color bar, as in FIG. 24D). Right: zoomed in view of 17 cells (black border on left) from the rare types. B. High confidence consensus markers. Relative expression level (row-wise Z-score of mean log₂(TPM+1), color bar at bottom) of consensus marker genes (rows, FDR<0.01 in both 3'-droplet and full-length plate-based scRNA-seq datasets, likelihood-ratio test) for each cell type (flanking color bar) across 7,193 cells in the 3' droplet data (columns, left) and the 301 cells in the plate-based dataset (columns, right). C-E. Cell-type specific expression of genes associated with asthma by GWAS. c. Relative expression (Z-score of mean log₂(TPM+1), color bar bottom right) of genes (rows) that are associated with asthma in GWAS and enriched (FDR<0.01, likelihood-ratio test) for cell type (columns) specific expression in our 3' scRNA-seq data. D. For each gene from (C) shown is the significance ($-\log_{10}$(FDR), Fisher's combined p-value, likelihood-ratio test, y axis) and effect size (point size, mean $\log_2$(fold-change)) of cell type specific expression in the relevant cell (color legend) and its genetic association strength from GWAS[15] (x axis). E. Distribution of expression levels (y axis, $\log_2$(TPM+1)) in the cells in each cluster (x axis, color legend) for two asthma GWAS genes: Cdhr3 (left; specific to ciliated cells) and Rgs13 (right; specific to tuft cells). **FDR<0.0001, likelihood-ratio test.

DETAILED DESCRIPTION

General Definitions

Figure 1:
FIG. 1 shows single-molecule fluorescence in situ hybridization (smFISH) with immunofluorescence assay (IFA) of ionocytes co-staining of FOXI1-GFP (green) and FOXI1 (pink).

As used herein, the singular forms "a", "an", and "the" include both singular and plural reference unless the context clearly dictates otherwise.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more members or at least one member of a group of members, is clear per se, by means of further exemplification, the term encompasses inter alia a reference to any one of the members, or to any two or more of the members, such as, e.g., any ≥3, ≥4, ≥5, ≥6 or ≥7 etc. of the members, and up to all members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and from different embodiments, as would be understood by those in the art. For example, in the appended claims, any of the claimed embodiments can be used in any combination.

The term "isolated" as used throughout this specification with reference to a particular component generally denotes that such component exists in separation from—for example, has been separated from or prepared and/or maintained in separation from—one or more other components of its natural environment. More particularly, the term "isolated" as used herein in relation to a cell or cell population denotes that such cell or cell population does not form part of an animal or human body.

As used herein the term "human stem cell" refers to a human cell that can self-renew and differentiate to at least one cell type. The term "human stem cell" encompasses human stem cell lines, human-derived iPS cells, human embryonic stem cells, human pluripotent cells, human multipotent stem cells or human adult stem cells.

As used herein the term "precursor cell" refers to a cell having the capability to differentiate into a mature cell. Thus, a precursor cell specifies a cell which is partially or fully undifferentiated. With regard to the present invention, the precursor cell is a partially differentiated cell or a fully undifferentiated cell and has the capability to differentiate into a cell having a mature cell phenotype. Precursor cells, in accordance with the present invention, thus encompass stem cells, such as e.g. embryonic stem cells, adult stem cells, germline-derived stem cells or induced pluripotent stem cells but also partially reprogrammed cells.

As used herein, the term "multipotent" refers to the ability of a cell to differentiate into a plurality of different phenotypes. Multipotent cells can generally only differentiate into cells of a single germ layer lineage. This is in contrast to pluripotent cells which can, by definition, differentiate into cells of all three germ layers. Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. A pluripotent cell typically has the potential to divide in vitro for a long period of time, e.g., greater than one year or more than 30 passages.

By the term "differentiated cell" is meant any primary cell that is not, in its native form, pluripotent as that term is defined herein. Those of ordinary skill in the art recognize that there is a spectrum of differentiation from totipotent or pluripotent cells at one end to fully differentiated cells that do not have the normal capacity to naturally differentiate to any other phenotype. Thus, a pluripotent cell is differentiated relative to a totipotent cell, and a multipotent cell is differentiated relative to a pluripotent cell. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "positive for" when referring to a cell positive for a marker means that a cell surface marker is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control for that marker.

As used herein, the phrase "cell is proliferative" refers to the ability of a stem cell to self-renew. Self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

As used herein, the term "capacity to differentiate" refers to the ability of a stem cell, progenitor cell, pluripotent cell, or multipotent cell to differentiate into a subset of more differentiated cells. The term "capacity to differentiate" does not encompass moving backwards along the differentiation spectrum such that a cell is produced that comprises a greater differentiation capacity than the parent cell. That is, the term "capacity to differentiate" does not encompass re-programming methods to shift cells to a less differentiated state.

In the context of cell ontogeny, the term "differentiate", or "differentiating" is a relative term that indicates a "differentiated cell" is a cell that has progressed further down the developmental pathway than its precursor cell. Thus in some embodiments, a reprogrammed cell as this term is defined herein, can differentiate to lineage-restricted precursor cells (such as a human lung progenitor cell), which in turn can differentiate into other types of precursor cells further down the pathway (such as a tissue specific precursor, for example, a proximal airway multipotent progenitor cell), and then to an end-stage differentiated cell, which plays a characteristic role in a certain tissue type, and may or may not retain the capacity to proliferate further.

As used herein, the term "induced to differentiate" refers to a chemical/biological treatment, a physical environment or a genetic modification that is conducive to the formation of more differentiated cells (e.g., ionocytes) from pluripotent or multipotent stem cells (e.g., lung stem cells). Differentiation can be assessed by the appearance of distinct cell-type specific markers or by the loss of stem cell-specific markers, or both.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a multipotent cell can be dedifferentiated to a pluripotent cell. That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Every cell type in the mammalian body—apart from the sperm and ova, the cells from which they are made (gametocytes) and undifferentiated stem cells—is a somatic cell: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

As used herein, the term "adult cell" refers to a cell found throughout the body after embryonic development.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human lung progenitor cells, e.g., a substantially pure population of human lung progenitor cells as compared to a heterogeneous population of cells comprising human lung progenitor cells and cells from which the human lung progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of lung progenitor cells, refers to a population of cells that contain fewer than about 25%, more preferably fewer than about 15%, 10%, 8%, 7%, most preferably fewer than about 5%, 4%, 3%, 2%, 1%, or less than 1%, of cells that are not lung progenitor cells as defined by the terms herein.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation can also be promoted by release from the actions of intra- or extracellular signals and mechanisms that block or negatively affect cell proliferation.

The terms "renewal" or "self-renewal" or "proliferation" are used interchangeably herein, and refers to a process of a cell making more copies of itself (e.g. duplication) of the cell. In some embodiments, lung progenitor cells are capable of renewal of themselves by dividing into the same undifferentiated cells (e.g. as determined by measuring the presence of absence of one or more cell surface markers) over long periods, and/or many months to years. In some instances, proliferation refers to the expansion of lung progenitor cells by the repeated division of single cells into two identical daughter cells.

The term "separation" or "selection" as used herein refers to isolating different cell types into one or more populations and collecting the isolated population as a target cell population which is enriched in a specific target stem cell population. Selection can be performed using positive selection, whereby a target enriched cell population is retained, or negative selection, whereby non-target cell types are discarded (thereby enriching for desired target cell types in the remaining cell population).

The terms "enriching" or "enriched" are used interchangeably herein and mean that the yield (fraction) of cells of one type, such as human lung progenitor cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

The term "positive selection" as used herein refers to selection of a desired cell type by retaining the cells of interest. In some embodiments, positive selection involves the use of an agent to assist in retaining the cells of interest, e.g., use of a positive selection agent such as an antibody which has specific binding affinity for a surface antigen on the desired or target cell. In some embodiments, positive selection can occur in the absence of a positive selection agent, e.g., in a "touch-free" or closed system, for example, where positive selection of a target cell type is based on any of cell size, density and/or morphology of the target cell type.

The term "negative selection" as used herein refers to selection of undesired or non-target stem cells for depletion or discarding, thereby retaining (and thus enriching) the desired target cell type. In some embodiments, negative selection involves the use of an agent to assist in selecting undesirable cells for discarding, e.g., use of a negative selection agent such as a monoclonal antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired (non-target) cell type to be discarded is based on any of cell size, density and/or morphology of the undesired (non-target) cell type.

The term "marker" as used herein is used to describe the characteristics and/or phenotype of a cell. Markers can be used for selection of cells comprising characteristics of interest and can vary with specific cells. Markers are characteristics, whether morphological, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological characteristics.

In one embodiment, the marker is a cell surface marker. In some embodiments, the absence of a cell surface marker can be used to distinguish ionocyte from another type of cell. One of skill in the art will recognize that a cell surface marker can be present at a particular point in development or in a particular ionocyte cell type. Thus, a cell surface marker can be used in combination with a positive or negative selection strategy for ionocytes.

As used herein, the term "scaffold" refers to a structure, comprising a biocompatible material, that provides a surface suitable for adherence and proliferation of cells. A scaffold can further provide mechanical stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the term "implantable in a subject" refers to any non-living (e.g., acellular) implantable structure that upon implantation does not generate an appreciable immune response in the host organism. Thus, an implantable structure should not for example, be or contain an irritant, or contain LPS, etc.

As used herein, the term "biodegradable" refers to the ability of a scaffold to degrade under physiological conditions, for example under conditions that do not adversely affect cell viability of the delivered cells or cells in vivo. Such biodegradable scaffolds will preferably not be or contain an irritant or an allergen that can cause a systemic reaction in the subject to which the composition has been implanted. In some embodiments, biodegradable means that the scaffold can be metabolized and the metabolites cleared from the subject by physiological excretion mechanisms (e.g., urine, feces, liver detoxification etc.).

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of lung progenitor cells so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a lung disorder, a lung disease (e.g., an inflammatory lung disease) as referred to herein refers to therapeutic intervention that stabilizes or improves the function of the lung or the airway. That is, "treatment" is oriented to the function of the respiratory tract. A therapeutic approach that stabilizes or improves the function of the lung or the airway by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the lung disease or disorder to be considered effective treatment.

As used herein, "prevention" or "preventing," when used in reference to a disease, disorder or symptoms thereof, refers to a reduction in the likelihood that an individual will develop a disease or disorder, e.g., a lung disorder. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The terms "sample" or "biological sample" as used throughout this specification include any biological specimen obtained from a subject. Particularly preferred are samples from respiratory tissue, but may also include samples from sweat glands. The term "tissue" as used throughout this specification refers to any animal tissue types, but particularly preferred is respiratory tissue. The tissue may be healthy or affected by pathological alterations. The tissue may be from a living subject or may be cadaveric tissue. The tissue may be autologous tissue or syngeneic tissue or may be allograft or xenograft tissue.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein.

Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition, and can be determined by standard clinical techniques.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used herein, "transport" refers to the movement of an ion or other species across a membrane boundary.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having the disease or condition. For example, a prediction of a disease or condition in a subject may indicate a probability, chance or risk that the subject will develop the disease or condition, for example within a certain time period or by a certain age. The probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The terms "disease" or "disorder" are used interchangeably throughout this specification, and refer to any alternation in state of the body or of some of the organs, interrupting or disturbing the performance of the functions and/or causing symptoms such as inflammation, discomfort, dysfunction, distress, or even death to the person afflicted or those in contact with a person. A disease or disorder can also be related to a distemper, ailing, ailment, malady, disorder, sickness, illness, complaint, indisposition, or affliction.

In certain embodiments, the pathological condition may be an infection, inflammation, proliferative disease, autoimmune disease, or allergy.

The term "inflammation" generally refers to a response in vasculated tissues to cellular or tissue injury usually caused by physical, chemical and/or biological agents, that is marked in the acute form by the classical sequences of pain, heat, redness, swelling, and loss of function, and serves as a mechanism initiating the elimination, dilution or walling-off of noxious agents and/or of damaged tissue. Inflammation histologically involves a complex series of events, including dilation of the arterioles, capillaries, and venules with increased permeability and blood flow, exudation of fluids including plasma proteins, and leukocyte migration into the inflammatory focus.

Further, the term encompasses inflammation caused by extraneous physical or chemical injury or by biological agents, e.g., viruses, bacteria, fungi, protozoan or metazoan parasite infections, as well as inflammation which is seemingly unprovoked, e.g., which occurs in the absence of demonstrable injury or infection, inflammation responses to self-antigens (auto-immune inflammation), inflammation responses to engrafted xenogeneic or allogeneic cells, tissues or organs, inflammation responses to allergens, etc. The term covers both acute inflammation and chronic inflammation. Also, the term includes both local or localised inflammation, as well as systemic inflammation, i.e., where one or more inflammatory processes are not confined to a particular tissue but occur generally in the endothelium and/or other organ systems.

Systemic inflammatory conditions may particularly encompass systemic inflammatory response syndrome (SIRS) or sepsis. "SIRS" is a systemic inflammatory response syndrome with no signs of infection. It can be characterised by the presence of at least two of the four following clinical criteria: fever or hypothermia (temperature of 38.0° C.) or more, or temperature of 36.0° C. or less); tachycardia (at least 90 beats per minute); tachypnea (at least 20 breaths per minute or PaCO2 less than 4.3 kPa (32.0 mm Hg) or the need for mechanical ventilation); and an altered white blood cell (WBC) count of 12×106 cells/mL or more, or an altered WBC count of 4×106 cells/mL or less, or the presence of more than 10% band forms. "Sepsis" can generally be defined as SIRS with a documented infection, such as for example a bacterial infection. Infection can be diagnosed by standard textbook criteria or, in case of uncertainty, by an infectious disease specialist. Bacteraemia is defined as sepsis where bacteria can be cultured from blood. Sepsis may be characterised or staged as mild sepsis, severe sepsis (sepsis with acute organ dysfunction), septic shock (sepsis with refractory arterial hypotension), organ failure, multiple organ dysfunction syndrome and death.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

Respiratory Tract

Many diseases affect the human respiratory tract. For example, cystic fibrosis, which is the most common lethal inherited disease affecting the Caucasian population, has been linked to the production of a defective protein which appears to affect electrolyte transport across respiratory epithelial tissues.

The respiratory tract comprise a large and complex collection of organs, that encompasses all of the tissues having surfaces exposed to the passage of air during normal breathing through either the nose or mouth. The respiratory tract includes the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

The nose and nasal cavity constitute the main external opening of the respiratory system. They represent the entryway to the respiratory tract—a passage through the body which air uses for travel in order to reach the lungs. The nose is made out of bone, muscle, cartilage and skin, while the nasal cavity is, more or less, hollow space. Although the nose is typically credited as being the main external breathing apparatus, its role is actually to provide support and protection to the nasal cavity. The cavity is lined with mucus membranes and hairs that can filter the air before it goes into the respiratory tract. They can trap all harmful particles such as dust, mold and pollen and prevent them from reaching any of the internal components. At the same time, the cold outside air is warmed up and moisturized before going through the respiratory tract. During exhalation, the warm air that is eliminated returns the heat and moisture back to the nasal cavity, so this forms a continuous process.

The oral cavity, more commonly referred to as the mouth, is the only other external component that is part of the respiratory system. The oral cavity can supplement the air inhaled through the nose or act as an alternative when breathing through the nasal cavity is not possible or exceedingly difficult. Normally, breathing through nose is preferable to breathing through the mouth. The pathway leading from the mouth is shorter and the diameter is wider, which means that more air can enter the body at the same speed.

The pharynx is the next component of the respiratory tract, even though most people refer to it simply as the throat. It resembles a funnel made out of muscles that acts as an intermediary between the nasal cavity and the larynx and esophagus. It is divided into three separate sections: nasopharynx, oropharynx and laryngopharynx. The nasopharynx is the upper region of the structure, which begins at the posterior of the nasal cavity and simply allows air to travel through it and reach the lower sections. The oropharynx does something similar, except it is located at the posterior of the oral cavity. Once the air reaches the laryngopharynx, the epiglottis (a flap that switches access between the esophagus and trachea) diverts it to the larynx. The epiglottis ensures that air will travel through the trachea, but that food which is swallowed and travels through the pharynx is diverted to the esophagus.

The larynx is the next component, but represents only a small section of the respiratory tract that connects the laryngopharynx to the trachea. It is commonly referred to as the voice box, and it is located near the anterior section of the neck, just below the hyoid bone. The aforementioned epiglottis is part of the larynx, as are the thyroid cartilage, the cricoid cartilage and the vocal folds. Both cartilages offer support and protection to other components, such as the vocal folds and the larynx itself. The thyroid cartilage also goes by a more common name—the Adam's apple. The vocal folds comprise mucous membranes that tense up and vibrate to create sound. The pitch and volume of these sounds can be controlled by modifying the tension and speed of the vocal folds.

The trachea is a longer section of the respiratory tract, shaped like a tube and approximately 5 inches in length. It has several C-shaped hyaline cartilage rings which are lined with pseudostratified ciliated columnar epithelium. The rings keep the trachea open for air all the time. The rings are C-shaped in order to allow the open end to face the esophagus, which allows the esophagus to expand into the area normally occupied by the trachea in order to permit larger chunks of food to pass through. The trachea, more commonly referred to as the windpipe, connects the larynx to the bronchi and also has the role of filtering the air prior to it entering the lungs. The epithelium which lines the cartilage rings produces mucus which traps harmful particles. The cilia then move the mucus upward towards the pharynx, where it is redirected towards the gastrointestinal tract in order for it to be digested.

The lower end of the trachea splits the respiratory tract into two branches termed the primary bronchi. These first run into each of the lungs before further branching off into smaller bronchi. These secondary bronchi continue carrying the air to the lobes of the lungs, then further split into tertiary bronchi. The tertiary bronchi then split into even smaller sections that are spread out throughout the lungs called bronchioles. Each one of these bronchioles continues to split into even smaller parts called terminal bronchioles. At this stage, these tiny bronchioles number in the millions, are less than a millimeter in length, and work to conduct the air to the lungs' alveoli. The larger bronchi contain C-shaped cartilage rings similar to the ones used in the trachea to keep the airway open. As the bronchi get smaller, so do the rings that become progressively more widely spaced. The tiny bronchioles do not have any kind of cartilage and instead rely on muscles and elastin.

This system creates a tree-like pattern, with smaller branches growing from the bigger ones. At the same time, it also ensures that air from the trachea reaches all the regions of the lungs. Besides simply carrying the air, the bronchi and bronchioles also possess mucus and cilia that further refine the air and get rid of any leftover environmental contaminants. The walls of the bronchi and bronchioles are also lined with muscle tissue, which can control the flow of air going into the lungs. In certain instances, such as during physical activity, the muscles relax and allow more air to go into the lungs.

The lungs are two organs located inside the thorax on the left and right sides. They are surrounded by a membrane that provides them with enough space to expand when filled with air. Because the left lung is located lateral to the heart, the organs are not identical: the left lung is smaller and has only 2 lobes while the right lung has 3. Inside, the lungs resemble a sponge made of millions and millions of small sacs that are named alveoli. These alveoli are found at the ends of terminal bronchioles and are surrounded by capillaries through which blood passes. Thanks to an epithelium layer covering the alveoli, the air that goes inside them is free to exchange gasses with the blood that goes through the capillaries.

Respiratory tract epithelial cells are a type of epithelium found lining the entire respiratory tract comprising the airways and the alveoli. The respiratory tract functions, inter alia, to conduct air, form a barrier to potential pathogens and foreign particles, prevent infection and tissue injury (e.g., by action of the mucociliary escalator), and to exchange oxygen and carbon dioxide. There are four main types of cells of the respiratory epithelium, including tracheal epithelial cells, bronchial epithelial cells, alveolar epithelial type 2 cells and alveolar epithelial type 1 cells. Development of effective pulmonary gas exchange structures and production of surfactant are helpful for successful adaptation to extrauterine life. These key processes in lung maturation require differentiation of epithelium into type 2 cells, which produce surfactant, and further differentiation into type 1 cells, which establishes the thin alveolar-capillary membrane for efficient gas exchange. Morphologically, type 2 cell differentiation is marked by the disappearance of glycogen stores, a resource for surfactant phospholipid, by formation of lamellar bodies, the intracellular storage site and secreted form of surfactant, and expansion of the apical cell surface in the form of microvilli.

Tracheal epithelial cells line the trachea (or windpipe) while bronchial epithelial cells play an important role as they constitute the surface epithelium of normal bronchi. In mice, Clara cells are the predominant cell type in the tracheo-bronchial and bronchiolar epithelium of the conducting airways. In humans, Clara cells only reside in the bronchiolar epithelium while the predominant cell type of the conducting airways are the ciliated cells. Precursor cells for ciliated cells are basal cells as well as Clara cells. Clara cells thus have a progenitor cell function as well as additional lung protective functions like detoxifying xenobiotics. Ciliated cells are crucial for the mucociliary clearance of the airways.

"Bronchial epithelial cells", such as for example Clara cells are characterised by the expression of the marker proteins clara cell secretory protein (CCSP), surfactant protein B (SP-B) and/or cytochrome P450 enzymes and/or morphological characteristics including a dome-shape, the presence of microvilli and/or smooth endoplasmic reticulum.

Ciliated cells are an example of "tracheal epithelial cells", and also "bronchial epithelial cells", that are characterised by the expression of the marker proteins β-tubulin 4 and/or Foxj1 (also referred to as HFH-4 in the literature) and/or the presence of cilia as evident by microscopic analysis.

Submucosal glands line the cartilaginous airways and produce most of the antimicrobial mucus that keeps the airways sterile. It secretes mucus when stimulated by secretagogues such as acetylcholine (ACh) or vasoactive intestinal peptide (VIP). Airway submucosal glands are complex structures that normally produce mucus in response to a wide range of different stimuli. Electrical stimulation of the superior laryngeal nerves elicits tracheal mucus secretion, and this provided early evidence for neuronal control of mucus secretion. Submucosal gland secretion is controlled by parasympathetic and possibly sympathetic innervation as well as by local release of stimulatory signals from nociceptive sensory nerves comprising C- and Aδ-fibres. Lanowski et al., *J. Physiol.* (2007) 581:301-314. There is evidence that airway submucosal glands play an important role in the pathophysiology of cystic fibrosis (CF). Submucosal glands from CF patients have altered responses to secretagogues when compared to normal glands. Non-CF submucosal glands secrete fluid when stimulated with Ca2+-elevating agents (e.g. ACh or carbachol) and/or cAMP agonists whereas those from CF patients do not respond to VIP or forskolin and produce a mucus during stimulation with carbachol that is thicker and more acidic. Lanowski et al., *J. Physiol.* (2007) 581:301-314.

It is understood by the person skilled in the art that the above described morphological factors vary dependent on the culture surroundings of the cells. Thus, when grown in vitro the shape of the cells might be similar but not identical to cells grown in the context of a physiological environment including naturally occurring neighbouring cells. Thus, when characterising the differentiated respiratory epithelial cells of the present invention, the expression of marker proteins serves as a primary characteristic while the morphological characteristics serve as secondary markers. The skilled person knows how to compare the shape of a cell obtained by the method of the present invention with a naturally occurring respiratory epithelial cells, for example by isolating respiratory epithelial cells obtained from a biopsy and/or by culturing said cells in vitro for comparison.

Lung Stem Cell and Epidermal Stem Cell

As used herein, the term "lung stem cell" is a general term that refers to any progenitor cell that is committed to the pulmonary lineage and also retains the ability to self-renew. In some embodiments, the human lung stem cells are differentiated into an airway basal stem cell, a ciliated cell, a Clara cell, a mucin secreting goblet cell, a type I pneumocyte, a type II pneumocyte or a neuroendocrine cell when placed under selected differentiation conditions. In some embodiments, the human lung stem cells are differentiated into ionocytes when placed under selected differentiation conditions. A human lung stem cell is not a tumor cell or a cancer cell. In one aspect, a human lung stem cell is not derived from an embryo or from an embryonic stem cell or other cell derived in culture from an embryo. In some embodiments, the human lung stem cells are differentiated from an autologous cell or from a non-autologous cell. In one embodiment, the human lung stem cell is not genetically modified or derived from a genetically modified cell.

As used herein, the term "epidermal stem cell (ESC)" is a general term that refers to any progenitor cell that is committed to the epithelial lineage and also retains the ability to self-renew. The epidermal stem cell (ESC) is located in the basal layer of the epidermis and can differentiate into sweat gland cells under selected differentiation conditions. In some embodiments, the epidermal stem cells (ESC) are differentiated into ionocytes when placed under selected differentiation conditions. An epidermal stem cell is not a tumor cell or a cancer cell. In one aspect, an epidermal stem cell is not derived from an embryo or from an embryonic stem cell or other cell derived in culture from an embryo. In some embodiments, the epidermal stem cells are differentiated from an autologous cell or from a non-autologous cell. In one embodiment, the epidermal stem cell is not genetically modified or derived from a genetically modified cell.

Reprogramming Cells from Patients for Generating Human Lung Stem Cells and Epidermal Stem Cells In some embodiments, the ionocytes of the present invention are generated from human lung stem cells, which can be obtained by reprogramming cells derived from the same subject to which the ionocytes are to be administered. In some embodiments, the ionocytes of the present invention are generated from epidermal stem cells, which can be obtained by reprogramming cells derived from the same subject to which the ionocytes are to be administered.

In some embodiments, the human lung stem cells and epidermal stem cells described herein are derived from isolated pluripotent stem cells (iPSCs). An advantage of using iPSCs is that the cells can be derived from the same subject to which the ionocytes are to be administered. That is, a somatic cell can be obtained from a subject, reprogrammed to an induced pluripotent stem cell, and then re-differentiated into a human lung stem cell, and which is then induced to differentiate into ionocytes to be administered to the subject (e.g., autologous cells). Since the ionocytes are essentially derived from an autologous source, the risk of engraftment rejection or allergic responses is reduced compared to the use of cells from another subject or group of subjects. In some embodiments, the ionocytes are derived from non-autologous sources, in which case the ionocytes are engineered before administration so that it will not be rejected by the immune system of the subject being administered. In addition, the use of iPSCs negates the need for cells obtained from an embryonic source. Thus, in one embodiment, the stem cells used in the disclosed methods are not embryonic stem cells.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Although differentiation is generally irreversible under physiological contexts, several methods have been recently developed to reprogram somatic cells to induced pluripotent stem cells. Exemplary methods are known to those of skill in the art and are described briefly herein below.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc (Takahashi and Yamanaka, (2006) *Cell,* 126(4):663-76). iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission, and tetraploid complementation.

Subsequent studies have shown that human iPS cells can be obtained using similar transduction methods, and the transcription factor trio, OCT4, SOX2, and NANOG, has been established as the core set of transcription factors that govern pluripotency (Jaenisch and Young (2008) *Cell* 132 (4):567-582. The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., *Cell Stem Cell,* 2010 Nov. 5; 7(5):618-30).

Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) *Cell-Stem Cell,* 2:525-528, Huangfu, D., et al (2008) *Nature Biotechnology* 26(7):795-797, and Marson, A., et al (2008) *Cell-Stem Cell* 3: 132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include:

Suberoylanilide Hydroxamic Acid (SAHA (e.g., MK0683, vorinostat) and other hydroxamic acids), BML-210, Depudecin (e.g., (–)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnamic acid bishydroxamic acid), JNJ16241199, Tubacin, A-161906, proxamide, oxamflatin, 3-Cl-UCHA (e.g., 6-(3-chlorophenylureido)caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering A G, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecatl, Esgl, Eras, Gdf3, Fgf4, Cripto, Daxl, Zpf296, Slc2a3, Rexl, Utfl, and Natl. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for reprogramming: Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of human ionocytes to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; oc-smooth muscle actin (oc-SMA); fibroblast growth factor 4 (Fgf4), Cripto, Daxl; zinc finger protein 296 (Zfp296); N-acetyltransferase-1 (Natl); (ES cell associated transcript 1 (ECAT1); ESG1/DPPA5/ECAT2; ECAT3; ECAT6; ECAT7; EC AT 8; ECAT9; ECAT10; ECAT15-1; ECAT15-2; Fthll7; Sall4; undifferentiated embryonic cell transcription factor (Utf1); Rexl; p53; G3PDH; telomerase, including TERT; silent X chromosome genes; Dnmt3a; Dnmt3b; TRIM28; F-box containing protein 15 (Fbxl5); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tell); DPPA3/Stella; DPPA4; other general markers for pluripotency, etc. Other markers can include Dnmt3L; Soxl5; Stat3; Grb2; β-catenin, and Bmil. Such cells can also be characterized by the down-regulation of markers characteristic of the somatic cell from which the induced pluripotent stem cell is derived.

Sweat Gland and Disorder Associated Thereof

Sweating plays an important role in the regulation of human body temperature through dissipating thermal energy from the skin surface when water in the sweat evaporates. Sweat counteracts heat stress after we exercise and allows us to survive in extreme climates. Hypohidrosis (also referred to as anhidrosis) is a condition in which patients have deficient or absent sweating. On heat stress, body temperature in these patients can increase to dangerous levels leading to hyperthermia, heat exhaustion, heat stroke, and potentially death. Conversely, hyperhidrotic patients generate excessive sweat that can cause various levels of discomfort and stress, ranging from dehydration and skin infections to social embarrassment.

Human skin has two major types of sweat glands: eccrine and apocrine. In eccrine glands, the duct opens onto the skin surface enabling the gland to secrete a water- and salt-based liquid. In contrast, the apocrine sweat gland is an appendage of the hair follicle and releases fluid through the follicle orifice. Moreover, apocrine sweat glands release an oily substance by shearing off cell parts as necrobiotic secretions. A third type of sweat gland, termed apoeccrine sweat gland, has been reported to exist in axillae areas of the human body. Lu et al., (2014) *Cold Spring Harb Perspect Med.,* 4(2): a015222.

In humans, eccrine sweat glands are distributed widely on the body surface with as many as ~700/cm$^2$ in adult skin from the palms and soles. In contrast, apocrine glands are restricted to very hairy body regions, such as axillae and perineum. The density of apocrine glands is much less compared to eccrine glands with ~50/cm$^2$ (or less).

Most domestic mammals lack eccrine glands over most of their body surface, and yet for many, sweating is still essential for their thermal regulation in withstanding climate and stress extremes. Horses and camels are among the best examples of working animals whose sweating function is critical for their survival and performance; they use apocrine secretion to dissipate heat. Mouse, as the most commonly used laboratory animal, has eccrine sweat glands exclusively present in the pads of their paws, and its trunk skin lacks sweat glands altogether. Animals such as this are sensitive to extremes in climate.

The duct of the eccrine gland is a straight channel, which distinguishes it from the branched duct of the more extensively studied mammary gland. The secretory portion of the eccrine gland also contrasts with that of the mammary gland in its distinctive, coiled tubular structure, narrow center (lumen), and secretion of sweat rather than milk. These differences aside, the overall tissue architecture is a classical bilayered gland consisting of a hollow center surrounded by an inner layer of secretory (luminal) cells, and an outer layer of myoepithelial cells encased by a basement membrane.

Myoepithelial cells are enriched in myofilaments and actins, suggesting that their role may be to provide contractile support to facilitate sweat secretion. Within the single luminal layer, there are two types of cells, clear cells and dark cells, which can be distinguished by different affinities to basic dyes and their granule contents. The clear cells are larger and without secretory granules, and the dark cells are smaller and rich in Schiff-reactive granules. Both are responsible for producing sweat and its ingredients. Based on their histochemistry, it is thought that clear cells are mainly responsible for generating water, electrolytes, and inorganic substances in the sweat, and dark cells contribute to the secretion of macromolecules such as glycoproteins. There are also various proteolytic enzymes and active interleukin-1 present in the eccrine sweat, which are considered to contribute to the barrier function of the skin.

Electrolytes in the primary sweat are reabsorbed in the duct to generate hypotonic fluid before being released to the skin surface. Importantly, elevated NaCl levels in sweat, caused by defective reabsorption, is a diagnostic criterion for cystic fibrosis (CF). CF patients have mutations in the gene encoding the CF transmembrane regulator, which is abundantly expressed not only in lungs, but also in eccrine sweat ducts and is critical for proper electrolyte absorption. Abnormal electrolyte transport across the epithelium results in thicker secretions, which in lungs, may result in lung infections and difficulty to breath.

Sweating disorders can be categorized by the amount of sweat produced: anhidrosis (absent sweating), hypohidrosis (decreased sweating), and hyperhidrosis (excessive sweating). Hypohidrotic/anhidrotic ectodermal dysplasia (HED) is a rare hereditary genetic disease caused by defects in the development of ectodermal appendages and characterized by little or no sweat that can be produced by patients. Hypohidrosis and anhidrosis can also occur when sweat glands are damaged and undergo necrosis if they fail to repair. Common causes are burns, irradiation, inflammation, chemical treatment, and wounds. Various systemic dermatological diseases, such as psoriasis, scleroderma, erythroderma, ichthyosis, can also affect sweat gland integrity and function. In psoriatic skin, for instance, the sweat duct becomes blocked, most likely caused by hyperplasia obstructing the orifice. *Miliaria* (also called sweat rash or prickly heat), on the other hand, is a disease specific to eccrine sweat ducts and sweat glands. It can be caused by friction, overheating, or blockage of sweat ducts by skin and bacterial debris. Environmental factors, such as excessive exposure to heat and humidity, often trigger the disease onset. Based on the level of sweat retention and tissue obstruction, *miliaria* is classified into three types: *miliaria* crystalline, with ductal obstruction in the superficial stratum corneum; *Miliaria rubra*, with obstruction deeper within the sweat duct and causing local inflammation and skin redness; and *Miliaria profunda*, with damage deep in the sweat gland and most severe in phenotype. When a significant portion of the body surface is affected, these patients risk heat exhaustion caused by ineffective sweating.

Ionocyte

Without being bound by theory, it is believed that osmoregulation is essential to maintaining homeostasis, which, in turn, is essential to optimal cell function. In most vertebrates, plasma osmolality and specific ion concentrations are maintained within narrow physiological ranges. Ionocytes regulate osmolality by regulating ion transport and/or ion homeostasis. Ionocytes—which are traditionally found in fish—are also referred to as chloride cells or mitochondrion-rich cells, which are responsible for ion uptake in fresh water and ion secretion in seawater. Inokuchi et al., *Am. J. Physiol. Regul. Integr. Comp. Physiol.* (2015) 309(10):L R1251-R1263. The present inventors discovered ionocytes from the respiratory tract and sweat glands. It is previously unknown that ionocytes exist in respiratory tract and sweat glands. The ionocyte identified from respiratory tract is termed pulmonary ionocyte, and it has a conserved expression pattern with known ionocytes from freshwater fish skin and gill epithelia, *Xenopus* skin, and the mammalian kidney and epididymis. They are specialized cells that function to regulate ion transport and pH. Based on their expression signature, pulmonary ionocytes resemble evolutionarily conserved V-ATPase-rich ionocytes in other organisms, where Foxi1 orthologs specify cell identity and regulate V-ATPase expression. Mammalian Foxi1 regulates V-ATPase in specialized cells of the inner ear, kidney, and epididymis that regulate ion transport and fluid pH. Pulmonary ionocytes are similarly enriched in the expression of V-ATPase subunits Atp6v1c2 and Atp6v0d2. The present inventors also found that pulmonary ionocytes extend lateral processes about 10 μm-20 μm away from their cell bodies, contacting several additional epithelial cells beyond their immediate neighbors, as well as the basement membrane. Without bring bound by theory, it is believed that pulmonary ionocytes may be involved in chemosensation and cell-to-cell communication.

The present inventors also discovered that pulmonary ionocyte is specifically enriched for the expression of cystic fibrosis transmembrane conductance regulator (Cftr) mRNA, and is the major source of CFTR in the airway epithelium. Pulmonary ionocytes also specifically express Cochlin (Coch), a secreted protein that promotes antibacterial innate immunity against *Pseudomonas aeruginosa* and *Staphylococcus aureus*, the two most prominent pathogens in CF lung disease.

Both the amount and viscosity of mucus in the airway surface liquid (ASL) is tightly regulated and this process is necessary for effective mucociliary clearance of debris and pathogens and is disturbed in diseases such as cystic fibrosis. The present inventors discovered that modulating Foxi1 expression in airway epithelium alters physiologic parameters that govern mucus clearance, such as ASL depth, mucus viscosity, and ciliary beat frequency. Therefore, the pulmonary ionocytes discovered by the present inventors are as a novel rare airway epithelial cell type with unique morphology, expression profile, and role in regulating airway epithelial surface physiology.

According to the present invention, the secretion of ion and/or uptake of ion by the ionocytes can be mediated by one or more of FOXI1, FOXI2, ASCL3, V-Type Proton ATPases, CFTR, PPARG, Cochlin, and STAP1 or their respective downstream signaling pathway.

Forkhead Box I1 (FOXI1) and Forkhead Box 12 (FOXI2) are transcription factors belong to the forkhead family, which is characterized by a distinct forkhead domain. The specific function of these has not yet been determined;

however, it is possible that this gene plays an important role in the development of the cochlea and vestibulum, as well as embryogenesis.

Achaete-Scute Family BHLH Transcription Factor 3 (ASCL3) is basic helix-loop-helix transcription factors, which are essential for the determination of cell fate and the development and differentiation of numerous tissues.

Vacuolar-type H+-ATPase (V-Type Proton ATPases, or V-ATPase) is a protein for acidifying a wide array of intracellular organelles and pump protons across the plasma membranes of numerous cell types. V-ATPases couple the energy of ATP hydrolysis to proton transport across intracellular and plasma membranes of eukaryotic cells. It is generally seen as the polar opposite of ATP synthase because ATP synthase is a proton channel that uses the energy from a proton gradient to produce ATP. V-ATPase however, is a proton pump that uses the energy from ATP hydrolysis to produce a proton gradient, acidify the late endosome by pumping protons across the endosomal membrane. V-ATPases are multisubunit molecular motors consisting of a cytosolic Vi domain and a transmembrane Vo domain. The Vi domain consists of eight different subunits while the Vo domain consists of five subunits (Forgac et al., *J. Biol. Chem.* (1999) 274(19):12951-12954). The V-ATPase is also referred to as ATP6; with the V1 subunits referred to as ATP6V1A (A-subunit), ATP6V1B (B-subunit). ATP6V1C (C-subunit), ATP6V1D (D-subunit), ATP6V1E (E-subunit), ATP6V1F (F-subunit), ATP6V1G (G-subunit), and ATP6V1H (I-subunit) and the V0 domains as A1TP6V0a (a-subunit), A-TP6V0b (c"-subunit), ATP6V0c (c-subunit), ATP6V0d (d-subunit), and ATP6V0e (e-subunit). Various tissue specific isoforms of certain subunits have been described (Sun-Wada et al, *Gene* (2003) 302:147-153). V-ATPases are found on membranes of different intracellular organelles as well as in cytoplasmic membranes and are involved in multiple cellular processes that require pH regulation, including intracellular membrane transport, prohormone processing or transport of neurotransmitters (reviewed in Nishi et al, *Nat. Rev. Mol. Cell Biol.* (2002) 3(2):94-103)).

The term V-ATPase refers to any one or more of the 13 different subunits. In some embodiments, all 13 subunits are upregulated or downregulated. However, a skilled person will also appreciate that upregulation in a cell of one of the subunits over a pre-determined threshold may indicate that the cell is an ionocyte. This is particularly relevant for subunits that are concertation limiting. Preferably, upregulation of the density of functional V-ATPases at the cell surface indicates the that the cell is an ionocyte. In addition, in some embodiments the expression and/or activity of one of the subunits is increased by a modulating agent. More preferably, the expression and/or activity of all of the subunits is increased. Preferably, the modulating agent increases the expression of functional V-ATPase, e.g., increasing the density of functional V-ATPases at the cell surface.

Cystic fibrosis transmembrane conductance regulator (CFTR) is a cAMP-activated chloride (Cf) channel expressed in epithelial cells in mammalian airways, intestine, pancreas and testis. CFTR is the chloride-channel responsible for CAMP-mediated Cl- secretion. Hormones, such as a 3-adrenergic agonist, or a toxin, such as cholera toxin, leads to an increase in CAMP, activation of cAMP-dependent proteinase, and phosphorylation of the CFTR Cl− channel, which causes the channel to open. An increase in cell Ca2+ can also activate different apical membrane channels. Phosphorylation by protein kinase C can either open or shut Cl− channels in the apical membrane. CFTR is predominantly located in epithelia where it provides a pathway for the movement of Cl− ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea. The hereditary lethal disease cystic fibrosis (CF) is caused by mutations in CFTR. Observations in human cystic fibrosis (CF) patients and CF mouse models indicate the functional importance of CFTR in intestinal and pancreatic fluid transport, as well as in male fertility (Grubb et al. *Physiol. Rev.* (1999) 79:5193-5214; Wong, P. Y., *Mol. Hum. Reprod.* (1997) 4:107-110). However, the mechanisms remain unclear by which defective CFTR produces airway disease, which is the principal cause of morbidity and mortality in CF (Pilewslci et al., *Physiol. Rev.* (1999) 79:5215-5255). All people have two copies of the CFTR gene, and there must be mutations in both copies to cause CF. More than 1,700 mutations of the CFTR gene have been identified. Although some are common, others are rare and found in only a few people. CFTR mutations are grouped into classes based on the way the mutations affect the CFTR protein. Certain types of CFTR mutations are associated with different disease complications. For example, some mutations are more likely to affect the pancreas than others. However, this correlation is not perfect, and knowing an individual's CFTR mutations cannot always tell you how severe that person's CF symptoms will be. Class I CFTR mutations are also called "production mutations," which causes no production of functional CFTR, and include nonsense mutations, some splice mutations and deletions. For example, G542X, W1282X and R552X are Class I CFTR mutations. Class II CFTR mutations are also called "processing mutations," which causes CFTR protein to misfold and thus being kept from moving to the cell surface. Class II mutations include F508del, N1303K, and I507del. Class III CFTR mutations are also called "gating mutations," because the protein containing these mutations are created and moves to the cell surface but the channel gate does not open properly. Exemplary mutations in this class include G551D and S549N. Class IV CFTR mutations are also called "conduction mutations," because the protein containing these mutations is created and moves to the cell surface, but the function of the channel is faulty. Exemplary mutations of this class include D1152H, R347P, and R117H. Class V CFTR mutations leads to normal CFTR protein being created and can move to the cell surface, but in insufficient quantities. In some embodiments of the present invention, a CRISPR system is introduced to the ionocyte that contains one or more CFTR mutations associated with cystic fibrosis, and wherein the CRISPR system corrects the mutation.

Peroxisome Proliferator Activated Receptor Gamma (PPARG) is a member of the Peroxisome Proliferator Activated Receptor family, which belongs to the nuclear receptor superfamily of ligand-activated transcription factors. Three subtypes of PPARs have been cloned from the mouse and human: i.e., PPARalpha, PPARgamma and PPARdelta. In humans PPARgamma and PPARalpha are differentially expressed in organs and tissues. Willson et al. *J. Med. Chem.* (2000) 43:527-50. Nuclear receptors like PPAR possess DNA-binding domains (DBDs) that recognized specific DNA sequences (called response elements) located in the regulatory regions of their target genes Mangelsdorf et al, *Cell* (1995) 83:835-839. Activation of PPARs modulates the expression of genes containing the appropriate respective peroxisome proliferator response elements (PPRE) in its promoter region. PCT WO/25226. PPARgamma consists of three forms, PPARgamma1 which is broadly expressed in most tissues, PPARgamma2, is more restricted to adipose (white fat and brown fat) tissue, and PPARgamma3. PPARgamma3 is confined to adipose tissue, macrophages and colonic epithelium in rodent and human tissues. Mangelsdorf and Evans *Cell* (1995) 83:841-850; Spiegehnan, *Diabetes* (1998) 47:507-514; Willson et al., *J. Med Chem.* (2000) 43:527-550. The distribution of the other PPARs also varies in different tissues. Throughout this writing PPAR refers to any of these isoforms, subtypes or combination thereof. PPARgamma is functionally involved in intermediary metabolism of cells and tissues that express this nuclear receptor.

PPARgamma and PPARalpha and PPARdelta are differentially expressed in different organs and tissues. Activation of PPARgamma and/or PPARalpha and/or PPARdelta modulates the expression of genes involved in: 1) glucose and lipid metabolism, 2) the regulation of cell growth, differentiation and regulation of the mitotic cycle, 3) the inflammatory response in cells of the immune system, 4) suppression of components of the immune system that become activated in pathological situations, and 5) regulation of apoptosis (programmed cell death) in a variety of cell types. Impairment in these processes lead to pathophysiological conditions involving metabolic (endocrine) dysfunction, proliferative diseases, inflammatory diseases and degenerative diseases. Pershadsingh, *Expert Opin. Investig. Drugs* 8(11): 1859-1872 (1999).

Cochlin is a protein in humans encoded by the COCH gene. Hybridization to this gene was detected in spindle-shaped cells located along nerve fibers between the auditory ganglion and sensory epithelium It is identified as a gene responsible for non-symptomatic hereditary deafness DFNA9. The amino acid sequence of human Cochlin is described in *Nature Genet.*, (1998) 20, 299-303.

Signal Transducing Adaptor Family Member 1 (STAP1) is a substrate of tyrosine-protein kinase Tec, and its interaction with tyrosine-protein kinase Tec is phosphorylation-dependent. This protein is thought to participate in a positive feedback loop by upregulating the activity of tyrosine-protein kinase Tec.

The upregulation or down regulation of one or more of these genes induces changes in the expression of one or more genes and/or protein in the Notch signaling pathway, including but is not limited to, Notch1, Notch2, Jag2, Dll1, or Dll2.

Notch signaling pathway regulates multiple aspects of invertebrate and vertebrate development in a number of cell types including cardiac, endocrine and immune cells. Fortini et al. *Dev. Cell.* (2009) 16:633-647. Notch signaling remains active in the adult where it is involved in processes ranging from the maintenance of stem cell populations and differentiation to synaptic plasticity and memory formation Kopan and Llagan, *Cell* (2009) 137:216-233. Perturbations in Notch signaling have been implicated in cancer biology and in neurological disease.

There are four mammalian Notch receptors (Notch 1, Notch2, Notch3, and Notch4). Notch receptors are large single pass, glycosylated, transmembrane proteins that are characterized by numerous (over thirty) extracellular epidermal growth factor (EGF)-like repeats, which are involved in ligand interactions Baron et al., *Sem. Cell Dev. Biol.* (2003) 14: 113-119. Notch receptors also contain three juxtamembrane repeats known as Lin-12-Notch (LN) repeats that mediate interactions between the extracellular domain and the membrane tethered intracellular domain. The intracellular region of Notch comprises seven ankyrin repeats flanked by nuclear localization signals, a proline, glutamine, serine, threonine-rich (PEST) domain and a transactivation domain (TAD).

Notch receptors expressed on the 'signal receiving cell' undergo a series of sequential proteolytic cleavages to yield an intracellular fragment that directly mediates transcriptional regulation of Notch target genes. Kadesch et al., *Cell. Mol. Life Sci.* (2000) 64:2746-2762; Fiúza and Arias, *J. Endocrinol.* (2007) 194:459-474; Kopan and Llagan (2009) *Cell* 137:216-233. Notch ligands belonging to the Delta and Serrate families, known as delta-like and Jagged, expressed on the signal sending cell. Notch ligands are also transmembrane proteins and therefore cell-to-cell contact is an important prerequisite to trigger Notch signaling.

A central concept in Notch signaling is the 'lateral inhibition' model that explains how Notch can suppress differentiation and promote the maintenance of a pool of progenitor cells. Bray et al., *Nat. Rev. Mol. Cell Biol.* (2006) 7:678-689; Fortini et al. *Dev. Cell.* (2009) 16:633-647. Expression of Notch ligands by the signal sending cell results in the activation of Notch signaling in neighboring signal receiving cells. Notch ligands induce the liberation of the Notch intracellular domain (NICD) in the signal receiving cell. The NICD subsequently translocates to the nucleus and induces the expression of Notch target genes. Notch target genes in turn suppress differentiation by antagonizing the expression and/or function of lineage specifying genes; for example in neurogenesis members of the Mammalian achaete scute homolog (Mash) and neurogenin families. The expression of Notch target genes also reduces the expression of Notch ligands on the cell surface consequently precluding Notch signaling in neighboring cells, which promotes their differentiation. In its purest form lateral inhibition results in a random 'salt and pepper' pattern of differentiated cell types within a population of progenitor cells and is reliant on small differences in the expression of Notch and its ligands on the surface of neighboring cells.

Notch signaling is inhibited by the membrane associated protein Numb (Numb and Numb-like in mammals), which consequently promotes differentiation and cell fate assignment. Le Borgne et al., *Curr. Opin. Cell Biol.* (2006) 18:213-222; Fortini et al. *Dev. Cell.* (2009) 16:633-647. Numb inhibits Notch directly and is also thought to target Notch for ubiquitination and degradation through a mechanism involving alpha-adaptin and endocytosis. Furthermore, evidence suggests that Numb can antagonize Notch signaling through endocytosis of the plasma membrane pool of Sandopo, a multipass transmembrane protein, which normally serves to enhance Notch signaling. The asymmetrical inheritance of Notch regulators such as Numb during mitosis results in two daughter cells adopting different fates. Such regulatory mechanisms of Notch signaling allow for a more complex pattern of Notch activation than the purely random pattern of mosaic differentiation predicted using the lateral inhibition model. Notch signaling is also involved in boundary formation (inductive signaling) between two layers of adjacent cells and is due to the differential expression of Notch ligands or other Notch regulatory proteins in the signal sending cells along the boundary.

Jag2 (or Jagged 2) is a protein in the Notch signaling pathway, in particular, a Notch Ligand. Jag 2 appears to mediate control of differentiation events in mammalian muscle and to be involved in positive feedback control of expression of a group of genes encoding Notch1, Notch3 and Jagged 1. Luo et al., *Mol. Cell Biol.*, 1997, 17, 6057-6067.

Delta like canonical Notch Ligand 1 (Dll1) and Delta like canonical Notch Ligand 2 (Dll2) are Notch ligands in the Notch signaling pathway. Dll1 It plays a role in mediating cell fate decisions during hematopoiesis.

The ionocytes according to the present invention regulate ion transport and/or ion homeostasis. In some embodiments, the ionocytes express specific ion transporters or enzymes, and are responsible for the transport of ions, including but not limited to H+, Na+, K+, Cu2+, Ca2+, HCO3−, Cl−, or a combination of two or more thereof.

In some embodiments, the ionocyte uptake or extracts from its external environment of one or more of such ions. In some embodiments, such external environment is the respiratory tract, such as the lung. In some embodiments, such external environment is the skin or area of skin with sweat gland. In some embodiments, the ionocyte secretes to its external environment of one or more of such ions. In some embodiments, the ionocytes are $H^+$-ATPase-rich (HR) cells. In some embodiments, the ionocytes are $Na^+$—$K^+$-ATPase-rich (NaR) cells. In some embodiments, the ionocytes are $Na^+$—$Cl^-$ cotransporter-expressing (NCC) cells. In some embodiments, the ionocytes are solute carrier family 26 (SLC26) expressing cells. In some embodiments, the ionocytes are $K^+$-secreting (KS) cells. In some embodiments, the ionocytes express different sets of ion transporters which allows them to conduct secretion or uptake of one or more of the ions of H+, Na+, K+, Cu2+, Ca2+, HCO3− and Cl−.

Identifying and Isolating Ionocytes

In preferred embodiments, an ionocyte is defined herein as a cell having an expression level of one or more of FOXI1, FOXI2, ASCL3, a V-Type Proton ATPase, CFTR, PPARG, Cochlin, STAP1, P2RY14, MOXD1, GM933, ATP6V1C2, ATP6V0D2, ASGR1, and ASGR2, above a pre-determined threshold. Preferably, the methods include determining the expression level of one or more of FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2. Preferably, the methods include determining the expression level of FOXI1, FOXI2, ASCL3, V-Type Proton ATPase, CFTR, PPARG, Cochlin, and STAP1. Preferably, the expression of FOXI1 and CFTR above a pre-determined threshold indicates that the cell is an ionocyte. Preferably, the expression of FOXI1 above a pre-determined threshold indicates that the cell is an ionocyte. Preferably, the expression of FOXI1, FOXI2, ASCL3, an V-Type Proton ATPase subunit, CFTR, PPARG, Cochlin, STAP1, P2RY14, MOXD1, GM933, ATP6V1C2, ATP6V0D2, ASGR1, and ASGR2 above a pre-determined threshold indicates that the cell is an ionocyte. Preferably, the expression of at least two, at least 3, at least 4, at least 5, at least 6, at least 7, at least 8, at least 9, at least 10, at least 11, at least 12, at least 13, at least 14 or at least 15 genes selected from FOXI1, FOXI2, ASCL3, an V-Type Proton ATPase subunit, CFTR, PPARG, Cochlin, STAP1, P2RY14, MOXD1, GM933, ATP6V1C2, ATP6V0D2, ASGR1, and ASGR2 above a pre-determined threshold indicates that the cell is an ionocyte.

Preferably the pre-determined threshold is the average expression level of the relevant tissue. For example, a pre-determined threshold for a respiratory ionocyte may be based on the expression levels from a population of airway epithelium cells. The population of cells may be a random population or a specific subset such as basal stem cells. A skilled person can readily determine the amount of increase above a pre-determined threshold which is considered significant. As is known to a skilled person many factors will effect the significance including the variation in expression of a particular gene.

In some aspects the present disclosure refers to a method of identifying a cell or cell marker, comprising: a) isolating target cells based on a marker specifically expressed in or on the cell or by label-free imaging flow cytometry; b) quantifying gene expression in the target cells by single cell sequencing, and c) clustering the target cells based on the gene expression by application of one or more algorithms, d) optionally determining a transcription signature for each cluster based at least in part on identifying differentially expressed genes between two or more clusters and between each cluster and the remaining cells as background, and e) optionally validating gene expression against cellular morphology.

In some examples of the present disclosure identifying differentially expressed transcripts comprises application of a supervised or unsupervised machine learning model. A supervised machine learning model is for example selected from the group consisting of an analytical learning model, an artificial neural network model, a back propagation model, a boosting model, a Bayesian statistics model, a case-based model, a decision tree learning model, an inductive logic programming model, a Gaussian process regression model, a group method of data handling model, a kernel estimator model, a learning automata model, a minimum message length model, a multilinear subspace learning, a naïve bayes classifier model, a nearest neighbor model, a probably approximately correct (PAC) learning model, a ripple down rules model, a symbolic machine learning model, a subsymbolic machine learning model, a support vector machine learning model, a minimum complexity machine model, a random forest model, an ensemble of classifiers model, an ordinal classification model, a data pre-processing model, a handling imbalanced datasets model, a statistical relational learning model, a Proaftn model. An unsupervised machine learning model is for example selected from the group consisting of a k-means model, a mixture model, a hierarchical clustering model, an anomaly detection model, a neural network model, an expectation-maximization (EM) model, a method of moments model, or a blind signal separation technique.

These models are used separately or in combination with each other or in combination with any other machine learning model, wherein a supervised model is combined with a supervised model, or an unsupervised model is combined with an unsupervised model or a supervised model is combined with an unsupervised model.

Some embodiments comprise validating gene expression against cellular morphology comprises sparse labeling the cell to enhance the expression of a fluorescent protein in the cell and combining the sparse labeling with fluorescent in situ hybridization (FISH) to validate the marker against cellular morphology in step e). In examples of the previous aspects FISH is for example combined with a specific antibody, double FISH or a transgenic reporter mouse line directed to a previously identified marker in the cell. For example an enhancer element is inserted into a lentivirus or an adeno-associated virus (AAV) vector upstream of the fluorescent protein to enhance its expression.

In one aspect, the present invention provides a method for isolating or purifying ionocytes from a biological sample, preferably from respiratory epithelial cells or sweat gland cells. The terms "isolating" or "purifying" as used throughout this specification with reference to a particular component of a composition or mixture (e.g., the biological sample) encompass processes or techniques whereby such component is separated from one or more or (substantially) all other components of the composition or mixture (e.g., the biological sample). The terms do not require absolute purity. In some embodiments, isolating or purifying the component will produce a discrete environment in which the abundance of the component relative to one or more or all other components is greater than in the starting composition or mixture (e.g., the biological sample). A discrete environment may denote a single medium, such as for example a single solution, dispersion, gel, precipitate, etc.

Isolating or purifying ionocytes from the biological sample may increase the abundance of the specified cells relative to all other cells comprised in the biological sample, or relative to other cells of a select subset of the cells comprised in the biological sample.

By means of example, isolating or purifying ionocytes from the biological sample may yield a cell population, in which the specified cells constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The ionocytes disclosed herein are generally described or characterised with reference to certain marker(s) or combination(s) of markers (such as genes or gene products, e.g., peptides, polypeptides, proteins, or nucleic acids) expressed or not expressed by the cells, or with reference to certain gene or gene product signature(s) comprised by the cells. Accordingly, the present methods for detecting, quantifying or isolating the specified cells may be marker-based or gene or gene product signature-based, i.e., may involve detection, quantification or isolation of cells expressing or not expressing marker(s) or combination(s) of markers the expression or lack of expression of which is taught herein as typifying or characterising the specified cells, or may involve detection, quantification or isolation of cells comprising gene or gene product signature(s) taught herein as typifying or characterising the specified cells.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the ionocytes in, or to isolate the ionocytes from, a biological sample (e.g., a cell population, tissue, organ, organism, or other biological sample of a subject). Such methods allow to detect, quantify or isolate the ionocytes in or from the tested object (e.g., a cell population, tissue, organ, organism, or other biological sample of a subject) substantially to the exclusion of other cells comprised in the tested object.

Such methods may allow to detect, quantify or isolate the ionocytes with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified cells.

In some embodiments, methods for detecting, quantifying or isolating the specified cells may comprise treatment(s) or step(s) which diminish or eliminate the viability of the cells. For example, methods which comprise measuring intracellular marker(s) typically necessitate permeabilisation of the cell membrane and possibly fixation of the cells; and methods which comprise measuring nucleic acid marker(s) may typically necessitate obtaining nucleic acids (such as particularly RNA, more particularly mRNA) from the cells. In certain other embodiments, methods for detecting, quantifying or isolating the specified cells may substantially preserve the viability of the cells. For example, methods which comprise measuring extracellular or cell surface marker(s) need not disturb the integrity of the cell membrane and may not require fixation/permeabilisation of the cells. In addition, new detection methods including those described by Kochuranie et al. Sci Rep. (2015) 5: 17218 also allow for the isolation of viable cells using intracellular markers. By means of an example, methods for detecting, quantifying or isolating the specified cells may be configured such that at least 40% (by number), for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of the detected, quantified or isolated cells remain viable. The term "viable cells" as used throughout this specification refers to cells that can be qualified as viable by tests and assays known per se. For instance, the viability of cells may be measured using conventional dye exclusion assays, such as Trypan Blue exclusion assay or propidium iodide exclusion assay. In such assays, viable cells exclude the dye and hence remain unstained, while non-viable cells take up the dye and are stained. The cells and their uptake of the dye can be visualised and revealed by suitable techniques (e.g., conventional light microscopy, fluorescence microscopy, or flow cytometry), and viable (unstained) and non-viable (stained) cells in the tested sample can be counted.

In certain embodiments, methods for detecting, quantifying or isolating the ionocytes may be single-cell-based, i.e., may allow to discretely detect, quantify or isolate the specified cells as individual cells. In other embodiments, methods for detecting, quantifying or isolating the ionocytes may be cell population-based, i.e., may only allow to detect, quantify or isolate the ionocytes as a group or collection of cells, without providing information on or allowing to isolate individual cells.

Methods for detecting, quantifying or isolating the ionocytes, the respiratory epithelial cells, respiratory epithelial stem cells, respiratory immune cells (preferably respiratory epithelial cells), or sweat gland cells may employ any of the above-described techniques for measuring markers, insofar the separation or the qualitative and/or quantitative measurement of the marker(s) can be correlated with or translated into detection, quantification or isolation of the specified cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the ionocytes.

In certain embodiments, the ionocytes are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analysed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyse cells by replacing fluorochrome-labelled binding reagents with mass tagged binding reagents, i.e., tagged with an element or isotope having a defined mass. In these methods, labelled particles are introduced into a mass cytometer, where they are individually atomised and ionised. The individual particles are then subjected to elemental analysis, which identifies and measures the abundance of the mass tags used. The identities and the amounts of the isotopic elements associated with each particle are then stored and analysed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analysed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 µm, more preferably less than 400 µm, more preferably less than 300 µm, more preferably less than 200 µm, e.g., 100 µm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

In certain embodiments, the aforementioned methods and techniques may employ agent(s) capable of specifically binding to one or more gene products, e.g., peptides, polypeptides, proteins, or nucleic acids, expressed or not expressed by the ionocytes, respiratory epithelial cells, respiratory epithelial stem cells, respiratory immune cells (preferably respiratory epithelial cells), or sweat gland cells as taught herein. Preferably, the gene products, e.g., peptides, polypeptides, or proteins, may be expressed on the cell surface (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridisation probes or amplification or sequencing primers and primer pairs), small molecules, or combinations thereof.

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^8$ M$^{-1}$, even more preferably $K_A \geq 1 \times 10^9$ M$^{-1}$, and still more preferably $K_A \geq 1 \times 10^{10}$ M$^{-1}$ or $K_A \geq 1 \times 10^{11}$ M$^{-1}$ or $K_A \geq 1 \times 10^{12}$ M$^{-1}$, wherein $K_A$=[SBA_T]/[SBA][T], SBA denotes the specific-binding agent, T denotes the intended target. Determination of $K_A$ can be carried out by methods known in the art, such as for example, using equilibrium dialysis and Scatchard plot analysis.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse. An antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., $K_A$ in the order $1\times10^9 \text{ M}^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "oligonucleotide" as used throughout this specification refers to a nucleic acid (including nucleic acid analogues and mimetics) oligomer or polymer as defined herein. Preferably, an oligonucleotide, such as more particularly an antisense oligonucleotide, is (substantially) single-stranded. Oligonucleotides as intended herein may be preferably between about 10 and about 100 nucleoside units (i.e., nucleotides or nucleotide analogues) in length, preferably between about 15 and about 50, more preferably between about 20 and about 40, also preferably between about 20 and about 30. Oligonucleotides as intended herein may comprise one or more or all non-naturally occurring heterocyclic bases and/or one or more or all non-naturally occurring sugar groups and/or one or more or all non-naturally occurring inter-nucleoside linkages, the inclusion of which may improve properties such as, for example, increased stability in the presence of nucleases and increased hybridization affinity, increased tolerance for mismatches, etc. The reference to oligonucleotides may in particular but without limitation include hybridisation probes and/or amplification primers and/or sequencing primers, etc., as commonly used in nucleic acid detection technologies.

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to the target nucleic acid sequence. Antisense agents suitable for use herein, such as hybridisation probes or amplification or sequencing primers and primer pairs) may typically be capable of annealing with (hybridising to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In certain embodiments, the one or more binding agents may be one or more antibodies. In other embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., $Ni^{2+}$), maltose:maltose binding protein, etc. In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof. In certain embodiments, the one or more binding agents are one or more antibodies.

A marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

Modulate Ionocyte

In some aspects, the present invention provides a method for modulating respiratory epithelial cell proliferation, differentiation, maintenance and/or function, by contacting a respiratory epithelial ionocyte cell or a population of respiratory epithelial ionocyte cells with an ionocyte modulating agent in an amount sufficient to modify proliferation, differentiation, maintenance, and/or function of the respiratory epithelial ionocyte cell or population of respiratory epithelial ionocyte cells. In another aspect, the present invention provides a method for modulating sweat gland cell proliferation, differentiation, maintenance and/or function, by contacting a sweat gland ionocyte cell or a population of sweat gland ionocyte cells with an ionocyte modulating agent in an amount sufficient to modify proliferation, differentiation, maintenance, and/or function of the sweat gland ionocyte cell or population of sweat gland ionocyte cells. In some embodiments, the modulating agent modulates expression and/or activity of one or more genes and/or proteins that regulate ion transport and/or ion homeostasis. In some embodiments, the modulating agent modulates expression and/or activity of one or more of FOXI1, FOXI2, ASCL3, V-Type Proton ATPase, CFTR, PPARG, Cochlin, STAP1, P2RY14, MOXD1, GM933, ATP6V1C2, ATP6V0D2, ASGR1, and ASGR2. In some embodiments, the modulating agent modulates expression and/or activity of FOXI1. In some embodiments, the modulating agent is an agonist of one or more of such genes. In some embodiments, the modulating agent is an antagonist of one or more such genes. In some embodiments, the modulating agent is a small molecule, a protein, a polypeptide, an antibody or an antigen binding fragment thereof, or a nucleic acid.

As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products. The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without the modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without the modulation. Preferably, modulation may be specific or selective, hence, one or more desired phenotypic aspects of a cell or cell population may be modulated without substantially altering other (unintended, undesired) phenotypic aspect(s).

In certain embodiments, a modulating agent may comprise altering expression and/or activity of one or more endogenous genes of the cell. The term "altered expression" denotes that the modification of the cell alters, i.e., changes or modulates, the expression of the recited gene(s) or polypeptides(s). The term "altered expression" encompasses any direction and any extent of the alteration. Hence, "altered expression" may reflect qualitative and/or quantitative change(s) of expression, and specifically encompasses both increase (e.g., activation or stimulation) or decrease (e.g., inhibition) of expression.

Marker

The term "marker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification.

Preferably, markers as intended herein may be peptide-, polypeptide- and/or protein-based, or may be nucleic acid-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or copy DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilisation of the cells. However, as intracellular markers can also be detected in viable cells, such intracellular markers may also be used.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "nucleic acid" as used throughout this specification typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoroarabinose, etc.).

Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borane, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof.

A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

Unless otherwise apparent from the context, reference herein to any marker, such as a peptide, polypeptide, protein, or nucleic acid, may generally also encompass modified forms of the marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

Orthologs and Homologs

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Thus, when reference is made to mouse genes and proteins, it is understood that the same is believed to apply to the corresponding ortholog in humans or other species.

Likewise, when referencing Cas9 and other proteins, it is understood to also apply to orthologs and homologs.

The CRISPR-CRISPR associated (Cas) systems of bacterial and archaeal adaptive immunity are some such systems that show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multisubunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The effector protein may comprise a chimeric effector protein comprising a first fragment from a first effector protein ortholog and a second fragment from a second effector protein ortholog, and wherein the first and second effector protein orthologs are different. At least one of the first and second effector protein orthologs may comprise an effector protein from an organism comprising *Bergeyella, Prevotella, Porphyromonas, Bacteroides, Alistipes, Riemerella, Myroides, Flavobacterium, Capnocytophaga, Chryseobacterium, Paludibacter, Phaeodactylibacter* or *Psychroflexus*.

In certain embodiments, the effector protein, particularly a Group 29 or Group 30 effector protein effector protein may be at least 700 amino acids long. In preferred embodiments, the effector protein may be about 1100 to about 1500 amino acids long, e.g., about 1100 to about 1200 amino acids long, or about 1200 to about 1300 amino acids long, or about 1300 to about 1400 amino acids long, or about 1400 to about 1500 amino acids long, e.g., about 900, about 1000, about 1100, about 1200, about 1300, about 1400, about 1500, about 1600, about 1700, or about 1800 amino acids long.

In certain embodiments, the Group 29 or Group 30 effector proteins as intended herein may be associated with a locus comprising short CRISPR repeats between 30 and 40 bp long, more typically between 34 and 38 bp long, even more typically between 36 and 37 bp long, e.g., 30, 31, 32, 33, 34, 35, 36, 37, 38, 39, or 40 bp long. In certain embodiments the CRISPR repeats are long or dual repeats between 80 and 350 bp long such as between 80 and 200 bp long, even more typically between 86 and 88 bp long, e.g., 80, 81, 82, 83, 84, 85, 86, 87, 88, 89, or 90 bp long.

Orthologous proteins may but need not be structurally related, or are only partially structurally related. In particular embodiments, the homologue or orthologue of a Group 29 or Group 30 protein as referred to herein has a sequence homology or identity of at least 80%, more preferably at least 85%, even more preferably at least 90%, such as for instance at least 95% with the Group 29 or Group 30 effector protein. In a preferred embodiment, the Group 29 or Group 30 effector protein may be an ortholog of an organism of a genus which includes but is not limited to *Bergeyella, Prevotella, Porphyromonas, Bacteroides, Alistipes, Riemerella, Myroides, Flavobacterium, Capnocytophaga, Chryseobacterium, Phaeodactylibacter, Paludibacter* or *Psychroflexus*. Some methods of identifying orthologs of CRISPR system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Bergeyella, Prevotella, Porphyromonas, Bacteroides, Alistipes, Rienerella, Myroides, Flavobacterium, Capnocytophaga, Chryseobacterium, Phaeodactylibacter, Paludibacter* or *Psychroflexus*. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species.

TABLE 1

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Paludibacter propionicigenes* WB4 (NC_014734.1) | WP_013446107.1 | NA | 8 | N | N | N | 1155 |
| *Prevotella* sp. P5-60 (NZ_JXQJ01000080.1) | WP_044074780.1 | NA | 5 | Y | ? | ? | 1091 |
| *Prevotella* sp. P4-76 (NZ_JXQI01000021.1) | WP_044072147.1 | NA | 0 | ? | ? | ? | 1091 |
| *Prevotella* sp. P5-125 (NZ_JXQL01000055.1) | WP_044065294.1 | NA | 11 | ? | ? | ? | 1091 |
| *Prevotella* sp. P5-119 (NZ_JXQK01000043.1) | WP_042518169.1 | NA | 11 | ? | ? | ? | 1091 |
| *Capnocytophaga canimorsus* Cc5 (NC_015846.1) | WP_013997271.1 | WP_013997274.1 | 51 | Y | Y | Y | 1200 |
| *Phaeodactylibacter xiamenensis* (NZ_JPOS01000018.1) | WP_044218239.1 | WP_044218241.1 | 19 | ? | ? | ? | 1132 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Porphyromonas gingivalis* W83 (NC_002950.2) | WP_005873511.1 | WP_005873518.1 | 7 | Y | Y | Y | 1136 |
| *Porphyromonas gingivalis* F0570 (NZ_KI259168.1) | WP_021665475.1 | WP_021665476.1 | 3 | ? | ? | ? | 1136 |
| *Porphyromonas gingivalis* ATCC 33277 (NC_010729.1) | WP_012458151.1 | WP_012458152.1 | 12 | Y | Y | Y | 1136 |
| *Porphyromonas gingivalis* F0185 (AWVC01000122.1) | ERJ81987.1 | ERJ81988.1 | 0 | ? | ? | ? | 1136 |
| *Porphyromonas gingivalis* F0185 (NZ_KI259960.1) | WP_021677657.1 | WP_021677658.1 | 6 | ? | ? | ? | 1136 |
| *Porphyromonas gingivalis* SJD2 (NZ_KI629875.1) | WP_023846767.1 | WP_005873518.1 | 4 | ? | ? | ? | 1136 |
| *Porphyromonas gingivalis* F0568 (AWUU01000145.1) | ERJ65637.1 | ERJ65638.1 | 3 | ? | ? | ? | 1136 |
| *Porphyromonas gingivalis* W4087 (AWVE01000130.1) | ERJ87335.1 | ERJ87336.1 | 2 | ? | ? | ? | 1136 |
| *Porphyromonas gingivalis* W4087 (NZ_KI260263.1) | WP_021680012.1 | WP_005873518.1 | 4 | ? | ? | ? | 1136 |
| *Porphyromonas gingivalis* F0568 (NZ_KI258981.1) | WP_021663197.1 | WP_021663198.1 | 6 | ? | ? | ? | 1136 |
| *Porphyromonas gingivalis* (NZ_LOEL01000010.1) | WP_061156637.1 | WP_005873518.1 | 11 | ? | ? | ? | 1136 |
| *Porphyromonas gulae* (NZ_JRAQ01000019.1) | WP_039445055.1 | WP_039445052.1 | 10 | ? | ? | ? | 1136 |
| *Bacteroides pyogenes* F0041 (KE993153.1) | ERI81700.1 | ERI81699.1 | 5 | ? | ? | ? | 1116 |
| *Bacteroides pyogenes* JCM 10003 (NZ_BAIU01000001.1) | WP_034542281.1 | WP_034542279.1 | 18 | ? | ? | ? | 1116 |
| *Alistipes* sp. ZOR0009 (NZ_JTLD01000029.1) | WP_047447901.1 | NA | 7 | ? | ? | ? | 954 |
| *Flavobacterium branchiophilum* FL-15 (NC_016001.1) | WP_014084666.1 | WP_014084665.1 | 19 | Y | N | Y | 1151 |
| *Prevotella* sp. MA2016 (NZ_JHUW01000010.1) | WP_036929175.1 | NA | 7 | ? | ? | ? | 1323 |
| *Myroides odoratimimus* CCUG 10230 (AGEC02000017.1) | EHO06562.1 | EHO06560.1 | 2 | ? | ? | ? | 1160 |
| *Myroides odoratimimus* CCUG 3837 (AGZK01000016.1) | EKB06014.1 | EKB06015.1 | 0 | ? | ? | ? | 1158 |
| *Myroides odoratimimus* CCUG 3837 (NZ_JH815535.1) | WP_006265509.1 | WP_006265510.1 | 0 | ? | ? | ? | 1158 |
| *Myroides odoratimimus* CCUG 12901 (NZ_JH590834.1) | WP_006261414.1 | WP_006261415.1 | 0 | ? | ? | ? | 1158 |
| *Myroides odoratimimus* CCUG 12901 (AGED01000033.1) | EHO08761.1 | EHO08762.1 | 0 | ? | ? | ? | 1158 |
| *Myroides odoratimimus* (NZ_CP013690.1) | WP_058700060.1 | WP_006261415.1 | 10 | Y | Y | Y | 1160 |
| *Bergeyella zoohelcum* ATCC 43767 (AGYA01000037.1) | EKB54193.1 | EKB54194.1 | 9 | ? | ? | ? | 1225 |
| *Capnocytophaga cynodegmi* (NZ_CDOD01000002.1) | WP_041989581.1 | WP_041989578.1 | 7 | ? | ? | ? | 1219 |
| *Bergeyella zoohelcum* ATCC 43767 (NZ_JH932293.1) | WP_002664492.1 | WP_034985946.1 | 8 | Y | Y | Y | 1225 |
| *Flavobacterium* sp. 316 (NZ_JYGZ01000003.1) | WP_045968377.1 | NA | 0 | ? | ? | ? | 1156 |
| *Psychroflexus torquis* ATCC 700755 (NC_018721.1) | WP_015024765.1 | NA | 16 | Y | Y | Y | 1146 |
| *Flavobacterium columnare* ATCC 49512 (NC_016510.2) | WP_014165541.1 | NA | 7 | Y | Y | Y | 1180 |
| *Flavobacterium columnare* (NZ_CP013992.1) | WP_060381855.1 | NA | 5 | Y | Y | Y | 1214 |
| *Flavobacterium columnare* (NZ_CP015107.1) | WP_063744070.1 | NA | 3 | Y | Y | Y | 1214 |
| *Flavobacterium columnare* (NZ_CP016277.1) | WP_065213424.1 | NA | 14 | Y | Y | Y | 1215 |
| *Chryseobacterium* sp. YR477 (NZ_KN549099.1) | WP_047431796.1 | NA | 0 | ? | ? | ? | 1146 |
| *Riemerella anatipestifer* ATCC 11845 = DSM 15868 (NC_014738.1) | WP_004919755.1 | WP_004919758.1 | 12 | Y | Y | Y | 1096 |
| *Riemerella anatipestifer* RA-CH-2 (NC_020125.1) | WP_015345620.1 | WP_004919758.1 | 12 | Y | Y | Y | 949 |
| *Riemerella anatipestifer* (NZ_CP007504.1) | WP_049354263.1 | WP_004919758.1 | 11 | Y | Y | Y | 949 |
| *Riemerella anatipestifer* (NZ_LUDU01000012.1) | WP_061710138.1 | WP_061710139.1 | 13 | ? | ? | ? | 951 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Riemerella anatipestifer* (NZ_LUDI01000010.1) | WP_064970887.1 | WP_064970885.1 | 4 | ? | ? | ? | 1096 |
| *Prevotella saccharolytica* F0055 (AMEP01000091.1) | EKY00089.1 | EKY00090.1 | 0 | ? | ? | ? | 1151 |
| *Prevotella saccharolytica* JCM 17484 (NZ_BAKN01000001.1) | WP_051522484.1 | NA | 5 | Y | Y | Y | 1152 |
| *Prevotella buccae* ATCC 33574 (AEPD01000005.1) | EFU31981.1 | EFU31982.1 | 16 | ? | ? | ? | 1128 |
| *Prevotella buccae* ATCC 33574 (NZ_GL586311.1) | WP_004343973.1 | WP_004343974.1 | 16 | Y | Y | Y | 1128 |
| *Prevotella buccae* D17 (NZ_GG739967.1) | WP_004343581.1 | WP_004343582.1 | 8 | ? | ? | ? | 1128 |
| *Prevotella* sp. MSX73 (NZ_ALJQ01000043.1) | WP_007412163.1 | WP_036927782.1 | 13 | ? | ? | ? | 1128 |
| *Prevotella pallens* ATCC 700821 (AFPY01000052.1) | EGQ18444.1 | EGQ18443.1 | 4 | ? | ? | ? | 1126 |
| *Prevotella pallens* ATCC 700821 (NZ_GL982513.1) | WP_006044833.1 | WP_050795200.1 | 4 | ? | ? | ? | 1126 |
| *Prevotella intermedia* ATCC 25611 = DSM 20706 (NZ_JAEZ01000017.1) | WP_036860899.1 | WP_050795200.1 | 11 | ? | ? | ? | 1127 |
| *Prevotella intermedia* (NZ_LBGT01000010.1) | WP_061868553.1 | NA | 27 | ? | ? | ? | 1121 |
| *Prevotella intermedia* 17 (CP003502.1) | AFJ07523.1 | AFJ07898.1 | 16 | N | N | N | 1135 |
| *Prevotella intermedia* (NZ_AP014926.1) | WP_050955369.1 | WP_014708440.1 | 16 | N | N | N | 1133 |
| *Prevotella intermedia* (AP014598.1) | BAU18623.1 | BAU18624.1 | 6 | N | N | N | 1134 |
| *Prevotella intermedia* ZT (ATMK01000017.1) | KJJ86756.1 | KJJ86755.1 | 2 | ? | ? | ? | 1126 |
| *Prevotella aurantiaca* JCM 15754 (NZ_BAKF01000019.1) | WP_025000926.1 | WP_036889078.1 | 5 | ? | ? | ? | 1125 |
| *Prevotella pleuritidis* F0068 (NZ_AWET01000045.1) | WP_021584635.1 | WP_021584705.1 | 6 | ? | ? | ? | 1140 |
| *Prevotella pleuritidis* JCM 14110 (NZ_BAJN01000005.1) | WP_036931485.1 | WP_024991772.1 | 7 | ? | ? | ? | 1117 |
| *Prevotella falsenii* DSM 22864 = JCM 15124 (NZ_BAJY01000004.1) | WP_036884929.1 | WP_051527348.1 | 10 | ? | ? | ? | 1134 |
| *Porphyromonas gulae* (NZ_JRAT01000012.1) | WP_039418912.1 | WP_052073447.1 | 11 | Y | Y | Y | 1176 |
| *Porphyromonas* sp. COT-052 OH4946 (NZ_JQZY01000014.1) | WP_039428968.1 | WP_050563578.1 | 12 | ? | ? | ? | 1176 |
| *Porphyromonas gulae* (NZ_JRFD01000046.1) | WP_039442171.1 | WP_050563578.1 | 9 | ? | ? | ? | 1175 |
| *Porphyromonas gulae* (NZ_JRAJ01000010.1) | WP_039431778.1 | WP_046201041.1 | 2 | ? | ? | ? | 1176 |
| *Porphyromonas gulae* (NZ_KQ040500.1) | WP_046201018.1 | WP_046201041.1 | 4 | ? | ? | ? | 1176 |
| *Porphyromonas gulae* (NZ_JRAL01000022.1) | WP_039434803.1 | WP_039434800.1 | 20 | ? | ? | ? | 1176 |
| *Porphyromonas gulae* (NZ_JRAI01000002.1) | WP_039419792.1 | WP_052078041.1 | 9 | ? | ? | ? | 1120 |
| *Porphyromonas gulae* (NZ_JRAK01000129.1) | WP_039426176.1 | WP_039426172.1 | 6 | ? | ? | ? | 1120 |
| *Porphyromonas gulae* (NZ_KN294104.1) | WP_039437199.1 | WP_052102013.1 | 0 | ? | ? | ? | 1120 |
| *Porphyromonas gingivalis* TDC60 (NC_015571.1) | WP_013816155.1 | WP_043890185.1 | 2 | Y | Y | Y | 1120 |
| *Porphyromonas gingivalis* ATCC 33277 (NC_010729.1) | WP_012458414.1 | WP_012458413.1 | 4 | Y | Y | Y | 1120 |
| *Porphyromonas gingivalis* A7A1-28 (NZ_CP013131.1) | WP_058019250.1 | WP_043898408.1 | 6 | Y | Y | Y | 1176 |
| *Porphyromonas gingivalis* JCVI SC001 (APMB01000175.1) | EOA10535.1 | EOA10563.1 | 5 | ? | ? | ? | 1176 |
| *Porphyromonas gingivalis* W50 (NZ_AJZS01000051.1) | WP_005874195.1 | WP_010955981.1 | 2 | ? | ? | ? | 1176 |
| *Porphyromonas gingivalis* (NZ_CP011995.1) | WP_052912312.1 | WP_010955981.1 | 7 | Y | Y | Y | 1176 |
| *Porphyromonas gingivalis* AJW4 (NZ_CP011996.1) | WP_053444417.1 | WP_043898408.1 | 11 | N | N | N | 1120 |
| *Porphyromonas gingivalis* (NZ_CP007756.1) | WP_039417390.1 | WP_021665928.1 | 5 | Y | Y | Y | 1120 |

TABLE 1-continued

Representative Type VI-B Effectors and Accessory Proteins

| Species (Genome Accession) | Cas13b Accession | Csx27/28 Accession | # Spacers | CRISPR-Cas? | Cas1? | Cas2? | Cas13b size (aa) |
|---|---|---|---|---|---|---|---|
| *Porphyromonas gingivalis* (NZ_LOEL01000001.1) | WP_061156470.1 | WP_021663076.1 | 5 | ? | ? | ? | 1120 |

The invention provides biomarkers for the identification, diagnosis and manipulation of cell properties, for use in a variety of diagnostic and/or therapeutic indications. Biomarkers in the context of the present invention encompasses, without limitation nucleic acids, together with their polymorphisms, mutations, variants, modifications, subunits, fragments, and other analytes or sample-derived measures.

Biomarkers are useful in methods of diagnosing, prognosing and/or staging cell proliferation and/or differentiation in a subject by detecting a first level of expression, activity and/or function of one or more biomarker and comparing the detected level to a control of level wherein a difference in the detected level and the control level indicates that the level of cell proliferation and/or differentiation in the subject.

These biomarkers are useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The present invention also may comprise a kit with a detection reagent that binds to one or more biomarkers.

Fragment

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of the peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., 40 consecutive amino acids, such as for example ≥50 consecutive amino acids, e.g., ≥60, ≥70, ≥80, ≥90, ≥100, ≥200, ≥300, ≥400, ≥500 or 600 consecutive amino acids of the corresponding full-length peptide, polypeptide, or protein.

The term "fragment" with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of the nucleic acid. For example, insofar not exceeding the length of the full-length nucleic acid, a fragment may include a sequence of 5 consecutive nucleotides, or 10 consecutive nucleotides, or ≥20 consecutive nucleotides, or ≥30 consecutive nucleotides, e.g., 40 consecutive nucleotides, such as for example 50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis. The phrase "gene or gene product signature" as intended throughout this specification refers to a set, group or collection of one or more, preferably two or more markers, such as genes or gene products, the expression status or profile of which is associated with or identifies a specific cell type, cell subtype, or cell state of a specific cell type or subtype. Such gene or gene product signatures can be used for example to indicate the presence of a specific cell type, cell subtype, or cell state of a specific cell type or subtype in a population of cells, and/or the overall cell type composition or status of an entire cell population. Such gene or gene product signatures may be indicative of cells within a population of cells in vivo. Preferably, a reference herein to a gene or gene product signature comprising or consisting of one or more genes or gene products from a discrete list of genes or gene products may denote that the genes or gene products said to be comprised by or constituting the signature are expressed in a specific cell type, cell subtype, or cell state of a specific cell type or subtype, i.e., that cells of the specific cell type, cell subtype, or cell state of the specific cell type or subtype are positive for the genes or gene products comprised by the signature.

Gene Signatures

Typically, a gene signature may comprise or consist of two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more, or 200 or more, or 300 or more, or 400 or more, or 500 or more genes or gene products. Where the present specification refers to a signature as comprising or consisting of one or more genes, the signature may comprise of consist of, by means of example and without limitation, one, or two or more, three or more, four or more, five or more, six or more, seven or more, eight or more, nine or more, ten or more, 15 or more, 20 or more, 25 or more, 30 or more, 35 or more, 40 or more, 45 or more, 50 or more, 60 or more, 70 or more, 80 or more, 90 or more, or 100 or more (provided that the recited number does not exceed the number of genes or gene products listed in the Table) or substantially all or all genes or gene products. In certain embodiments, the signature may comprise or consist of at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, at least 80%, or at least 90%, or at least 95%, e.g., 96%, 97%, 98%, 99%, or up to 100% (by number) of the genes or gene products, e.g., associated with a disorder or condition (rounded up or down as conventional to the closest integer).

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (be it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to further modulate respiratory epithelial cells. The signatures of the present invention may be discovered by analysis of expression profiles of single-cells within a population of cells from isolated samples (e.g. biopsy), thus allowing the discovery of novel cell subtypes or cell states that were previously invisible or unrecognized.

The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular phenotype of an respiratory epithelial cell, respiratory epithelial stem cell, respiratory immune cell, or sweat gland cell. Induction or suppression of a particular signature may consequentially be associated with or causally drive a particular phenotype.

Various aspects and embodiments of the invention may involve analyzing gene signature(s), protein signature(s), and/or other genetic signature(s) based on single cell analyses (e.g. single cell RNA sequencing) or alternatively based on cell population analyses, as is defined herein elsewhere.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type.

Markers as taught herein or genes or gene products comprised by or constituting gene or gene product signatures as taught herein, or the gene or gene product signatures as taught herein, may display AUC (area under the receiver-operating curve (ROC) as well-established in the art) value of 0.70 or more, e.g., 0.75 or more, preferably 0.80 or more, more preferably 0.85 or more, even more preferably 0.90 or more, and still more preferably 0.95 or more, e.g., 0.96, 0.97, 0.98, 0.99, or 1.00. An AUC value of 1 implies that the marker, gene, gene product or signature is a perfect classifier for a given outcome (e.g., a cell type or cluster). An AUC value of 0.50 implies no predictive value for the outcome.

A marker, for example a gene or gene product, for example a peptide, polypeptide, protein, or nucleic acid, or a group of two or more markers, is "measured" in a biological sample (e.g., in or on a cell, cell population, tissue, organ, or organism, e.g., in a biological sample of a subject) when the presence or absence and/or quantity of the marker or the group of markers is detected or determined in the tested object, preferably substantially to the exclusion of other molecules and analytes, e.g., other genes or gene products.

Depending on factors that can be evaluated and decided on by a skilled person, such as inter alia the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to another value, such as relative to a reference value. Performing a relative comparison between first and second variables (e.g., first and second quantities) may but need not require determining first the absolute values of the first and second variables. For example, a measurement method may produce quantifiable readouts (such as, e.g., signal intensities) for the first and second variables, wherein the readouts are a function of the value of the variables, and wherein the readouts may be directly compared to produce a relative value for the first variable vs. the second variable, without the actual need to first convert the readouts to absolute values of the respective variables.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed for example as a percentage or fraction (by number) of cells comprised in the population that are positive for the marker, or as percentages or fractions (by number) of cells comprised in the population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of markers in a tested object (e.g., in or on a cell, cell population, tissue, organ, or organism, e.g., in a biological sample of a subject).

In certain examples, such methods may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other examples, such methods may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In further examples, such methods may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other examples, such methods may include chromatography methods. The term "chromatography" encompasses methods for separating substances, such as chemical or biological substances, e.g., markers, such as preferably peptides, polypeptides, or proteins, referred to as such and vastly available in the art. In a preferred approach, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between the mobile phase and the stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

Further techniques for separating, detecting and/or quantifying markers, such as preferably peptides, polypeptides, or proteins, may be used, optionally in conjunction with any of the above described analysis methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridisation-based analysis, microarray expression analysis, digital gene expression profiling (DGE), RNA-in-situ hybridisation (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single-molecule real time sequencing, true single-molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In particular, methods of Macosko et al. (Cell. 2015, vol. 161, 1202-1214) and Klein et al. (Cell. 2015, vol. 161, 1187-1201) are contemplated for the present invention.

Scaffold Compositions

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the lung cells can be isolated from the polymer prior to implantation or such that the scaffold degrades over time in a subject and does not require removal. Thus, in one embodiment, the scaffold provides a temporary structure for growth and/or delivery of human lung cells to a subject in need thereof. In some embodiments, the scaffold permits human cells to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamins; polysaccharides such as alginate, heparin; and other naturally occurring biodegradable polymers of sugar units. Alternately, combinations of the aforementioned polymers can be used.

PLA, PGA and PLA/PGA copolymers are particularly useful for forming biodegradable scaffolds. PLA polymers are usually prepared from the cyclic esters of lactic acids. Both L(+) and D(-) forms of lactic acid can be used to prepare the PLA polymers, as well as the optically inactive DL-lactic acid mixture of D(-) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments, the scaffold can include decellularized lung tissue. Methods for producing decellularized lung tissue are known in the art, see e.g., WO2011/005306. Briefly, the process of decellularization involves chemically stripping lung tissue of its cells and removing the cellular debris, which leaves behind the structure of the extracellular matrix. The extracellular matrix can then be repopulated with human lung progenitor cells as described herein, and optionally with other bioactive agents. Such decellularized scaffolds can be prepared from a portion of the subject's own lung and therefore the risk of rejection or allergic reaction in response to the repopulated and administered scaffold can be minimized.

In some embodiments it can be desirable to add bioactive molecules to the scaffold. A variety of bioactive molecules can be delivered using the matrices described herein. These are referred to generically herein as "factors" or "bioactive factors".

In one embodiment, the bioactive factors include growth factors. Examples of growth factors include platelet derived growth factor (PDGF), transforming growth factor alpha or beta (TGF), bone morphogenic protein 4 (BMP4), fibroblastic growth factor 7 (FGF7), fibroblast growth factor 10 (FGF10), epidermal growth factor (EGF/TGFoc), vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Treatment of Lung Disease

The methods and compositions provided herein relate to the generation and use of respiratory epithelial ionocytes. Accordingly, provided herein are methods for the treatment and prevention of a lung injury or a lung disease or disorder in a subject in need thereof. The methods described herein can be used to treat, ameliorate, prevent or slow the progression of a number of lung diseases or their symptoms, such as those resulting in pathological damage to lung or airway architecture and/or alveolar damage. The terms "respiratory disorder," "respiratory disease," "lung disease," "lung disorder," "pulmonary disease," and "pulmonary disorder," are used interchangeably herein and refer to any condition and/or disorder relating to respiration and/or the respiratory system, including the lungs, pleural cavity, bronchial tubes, trachea, upper respiratory tract, airways, or other components or structures of the airway system.

Such lung diseases include, but are not limited to, bronchopulmonary dysplasia (BPD), chronic obstructive pulmonary disease (COPD), cystic fibrosis, bronchiectasis, cor pulmonale, pneumonia, lung abscess, acute bronchitis, chronic bronchitis, emphysema, pneumonitis (e.g., hypersensitivity pneumonitis or pneumonitis associated with radiation exposure), alveolar lung diseases and interstitial lung diseases, environmental lung disease (e.g., associated with asbestos, fumes or gas exposure), aspiration pneumonia, pulmonary hemorrhage syndromes, amyloidosis, connective tissue diseases, systemic sclerosis, ankylosing spondylitis, pulmonary actinomycosis, pulmonary alveolar proteinosis, pulmonary anthrax, pulmonary edema, pulmonary embolus, pulmonary inflammation, pulmonary histiocytosis X, pulmonary hypertension, surfactant deficiencies, pulmonary hypoplasia, pulmonary neoplasia, pulmonary nocardiosis, pulmonary tuberculosis, pulmonary veno-occlusive disease, rheumatoid lung disease, sarcoidosis, post-pneumonectomy, Wegener's granulomatosis, allergic granulomatosis, granulomatous vasculitides, eosinophilia, asthma and airway hyperreactivity (AHR) (e.g., mild intermittent asthma, mild persistent asthma, moderate persistent asthma, severe persistent asthma, acute asthma, chronic asthma, atopic asthma, allergic asthma or idiosyncratic asthma), allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or respiratory syncytial virus (RSV) infection or an acute or chronic adult or pediatric respiratory distress syndrome (RDS) such as grade I, II, III or IV RDS or an RDS associated with, e.g., sepsis, pneumonia, reperfusion, atelectasis or chest trauma.

Chronic obstructive pulmonary diseases (COPDs) include those conditions where airflow obstruction is located at upper airways, intermediate-sized airways, bronchioles or parenchyma, which can be manifested as, or associated with, tracheal stenosis, tracheal right ventricular hypertrophy pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation.

The methods and compositions provided herein are also used for the treatment and prevention of an inflammatory lung disease in a subject in need thereof. In some embodiments of this aspect, the inflammatory lung disease is asthma, bronchitis, cystic fibrosis, infection (e.g., pneumonia or tuberculosis), emphysema, lung cancer, pulmonary hypertension, chronic obstructive pulmonary disease, idiopathic pulmonary fibrosis, α-1-anti-trypsin deficiency, or congestive heart failure.

As used herein, the terms "administering," "introducing" and "transplanting" are used interchangeably in the context of the placement of cells, e.g. ionocytes, as described herein into a subject, by a method or route which results in at least partial localization of the introduced cells at a desired site, such as a site of injury or repair, such that a desired effect(s) is produced. The cells e.g. ionocytes, or their precursor cells can be implanted directly to the respiratory airways, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of ionocytes is administered directly to the lungs of a patient suffering from cystic fibrosis by intratracheal administration. In other embodiments, ionocytes can be administered via an indirect systemic route of administration, such as an intraperitoneal or intravenous route.

When provided prophylactically, ionocytes described herein can be administered to a subject in advance of any symptom of a lung disorder, e.g., an asthma attack or to a premature infant. Accordingly, the prophylactic administration of a ionocytes population serves to prevent a lung disorder, as disclosed herein.

When provided therapeutically, ionocytes are provided at (or after) the onset of a symptom or indication of a lung disorder, e.g., upon the onset of cystic fibrosis.

In some embodiments of the aspects described herein, the ionocyte population being administered according to the methods described herein comprises allogeneic lung ionocyte cells obtained from one or more donors. As used herein, "allogeneic" refers to a lung progenitor cell or biological samples comprising ionocyte cells obtained from one or more different donors of the same species, where the genes at one or more loci are not identical. For example, a ionocyte cell population being administered to a subject can be derived from umbilical cord blood obtained from one more unrelated donor subjects, or from one or more non-identical siblings. In some embodiments, syngeneic ionocyte cell populations can be used, such as those obtained from genetically identical animals, or from identical twins. In other embodiments of this aspect, the ionocyte cells are autologous cells; that is, the ionocyte cells are obtained or isolated from a subject and administered to the same subject, i.e., the donor and recipient are the same.

In another aspect, the present invention provides a method of treating an inflammatory lung disease, by administering a precursor cell of ionocytes, wherein the precursor cell can be induced to differentiate into ionocyte in vivo.

Gene Modification

In one aspect, the present invention provides a method of modulating the expression and/or activity of one or more of the genes in ionocytes by CRISPR technology. In some embodiments, the one or more genes is FOXI1, FOXI2, ASCL3, V-Type Proton ATPase, CFTR, PPARG, Cochlin, and STAP1. In some embodiments, the one or more gene is in the Notch signaling pathway. In some embodiments, the one or more gene is Notch1, Notch2, Jag1, Dll1, Dll2, and Jag2.

Any one or more of the several successive molecular mechanisms involved in the expression of a given gene or polypeptide may be targeted by or may be used to target the ionocyte cell intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localisation of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalised polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell. Functional genomics can be used to modify cells for therapeutic purposes, and identify networks and pathways. For example, Graham et al ("Functional genomics identifies negative regulatory nodes controlling phagocyte oxidative burst," Nature Communications 6, Article number: 7838 (2015)) describes functional genetic screens to identify the phagocytic oxidative burst. With the rapid advancement of genomic technology, it is now possible to associate genetic variation with phenotypes of respiratory epithelial cells, respiratory epithelial stem cells, respiratory immune cells (preferably respiratory epithelial cells), or sweat gland cells at the population level. In particular, genome-wide association studies (GWAS) have implicated genetic loci associated with risk for IBD and allowed for inference of new biological processes that contribute to disease. These studies highlight innate defense mechanisms such as antibacterial autophagy, superoxide generation during oxidative burst and reactive nitrogen species produced by iNOS. However GWAS requires functional analysis to unlock new insights. For example, many risk loci are densely populated with coding genes, which complicates identification of causal genes. Even when fine mapping clearly identifies key genes, a majority have poorly defined functions in host immunity. Moreover, any given gene may have multiple functions depending on the cell type in which it is expressed as well as environmental cues. Such context-specific functions of regulatory genes are largely unexplored. Thus, human genetics offers an opportunity to leverage insight from large amounts of genetic variation within healthy and patient populations to interrogate mechanisms of immunity. Irrespective of their putative roles in disease pathology, genes within risk loci are likely to be highly enriched for genes controlling signalling pathways.

In some embodiments, the CRISPR-Cas system or another gene editing system may be used to alter the expression and/or activity of one or more of the genes disclosed herein. As is well known to a skilled person, the Crispr/Cas system can be used for gene editing. Genes can be edited, mutated, replaced, or knocked-out using this system. Crispr/Cas can also be used to modulate gene expression by using modified "dead" Cas proteins fused to transcriptional activational domains (see, e.g., Khatodia et al. Frontiers in Plant Science 2016 7: article 506 and Ma et al. FEBS Journal 2014 5186-5193 for recent reviews of Crispr technology). In other embodiments, gene editing may be performed using zinc-finger nucleases (ZFNs), transcription activator-like effector nucleases (TALENs), meganucleases, or nicking endonucleases.

With respect to general information on CRISPR-Cas Systems, components thereof, the DNA-binding protein is a (endo)nuclease or a variant thereof having altered or modified activity (i.e. a modified nuclease, as described herein elsewhere). In certain embodiments, the nuclease is a targeted or site-specific or homing nuclease or a variant thereof having altered or modified activity. In certain embodiments, the nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease.

In certain embodiments, the (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild-type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence-specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence-specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA-binding protein is a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type zincs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA-binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA-binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/051830), WO/2016/094867 (PCT/US2015/065385), WO/2016/094872 (PCT/US2015/065393), WO/2016/094874 (PCT/US2015/065396), WO/2016/106244 (PCT/US2015/067177)

Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13) 01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013); Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikk elson, T., Heckl, D., Ebert, B L., Root, D E., Doench, J G., Zhang, F. Science Dec. 12, 2013. [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell Feb. 27, 2014. 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol.* 2014 Apr. 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi:10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Preferred DNA-binding proteins are CRISPR/Cas enzymes or variants thereof. In certain embodiments, the CRISPR/Cas protein is a class 2 CRISPR/Cas protein. In certain embodiments, the CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using the short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In this context of the guide RNA this may include one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence. In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In certain embodiments, the guide RNA (capable of guiding Cas to a target locus) may comprise (1) a guide sequence capable of hybridizing to a target locus and (2) a tracr mate or direct repeat sequence (in 5' to 3' orientation, or alternatively in 3' to 5' orientation, depending on the type of Cas protein, as is known by the skilled person). In particular embodiments, the CRISPR/Cas protein is characterized in that it makes use of a guide RNA comprising a guide sequence capable of hybridizing to a target locus and a direct repeat sequence, and does not require a tracrRNA. In particular embodiments, where the CRISPR/Cas protein is characterized in that it makes use of a tracrRNA, the guide sequence, tracr mate, and tracr sequence may reside in a single RNA, i.e. an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR/Cas complex to the target sequence.

In particular embodiments, the DNA-binding protein is a catalytically active protein. In these embodiments, the formation of a nucleic acid-targeting complex (comprising a guide RNA hybridized to a target sequence results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

Accordingly, in particular embodiments, the DNA-binding protein has nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g. for Cas9, such as SaCas9 or SpCas9). In some embodiments, the cleavage may be staggered (e.g. for Cpf1), i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of the target polynucleotide thereby modifying the target polynucleotide, wherein the CRISPR complex comprises a CRISPR enzyme complexed with a guide sequence hybridized to a target sequence within the target polynucleotide, wherein the guide sequence is linked to a tracr mate sequence which in turn hybridizes to a tracr sequence. The skilled person will understand that other Cas proteins may be modified analogously.

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g. RuvC I, RuvC II, and RuvC III or the HNH domain of a Cas9 protein) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As used herein, the term "modified" Cas generally refers to a Cas protein having one or more modifications or mutations (including point mutations, truncations, insertions, deletions, chimeras, fusion proteins, etc.) compared to the wild-type Cas protein from which it is derived. By derived is meant that the derived enzyme is largely based, in the sense of having a high degree of sequence homology with, a wild-type enzyme, but that it has been mutated (modified) in some way as known in the art or as described herein.

As detailed above, in certain embodiments, the nuclease as referred to herein is modified. As used herein, the term "modified" refers to which may or may not have an altered functionality. By means of example, and in particular with reference to Cas proteins, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc., as well as chimeric nucleases (e.g. comprising domains from different orthologues or homologues) or fusion proteins. Fusion proteins may without limitation include for instance fusions with heterologous domains or functional domains (e.g. localization signals, catalytic domains, etc.). Accordingly, in certain embodiments, the modified nuclease may be used as a generic nucleic acid binding protein with fusion to or being operably linked to a functional domain. In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR/Cas system or complex preferably still has the capacity to interact with or bind to the polynucleic acid (e.g. in complex with the gRNA).

By means of further guidance and without limitation, in certain embodiments, the nuclease may be modified as detailed below. As already indicated, more than one of the indicated modifications may be combined. For instance, codon optimization may be combined with NLS or NES fusions, catalytically inactive nuclease modifications or nickase mutants may be combined with fusions to functional (heterologous) domains, etc.

In certain embodiments, the nuclease, and in particular the Cas proteins of prokaryotic origin, may be codon optimized for expression into a particular host (cell). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

In certain embodiments, the nuclease, in particular the Cas protein, may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268):84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and gRNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR/Cas complex). In certain embodiments, the mutations result in an altered PAM recognition, i.e. a different PAM may be (in addition or in the alternative) be recognized, compared to the unmodified Cas protein (see e.g. "Engineered CRISPR-Cas9 nucleases with altered PAM specificities", Kleinstiver et al. (2015), Nature, 523(7561):481-485, incorporated herein by reference in its entirety). Particularly preferred mutations include positively charged residues and/or (evolutionary) conserved residues, such as conserved positively charged residues, in order to enhance specificity. In certain embodiments, such residues may be mutated to uncharged residues, such as alanine.

In certain embodiments, the nuclease, in particular the Cas protein, may comprise one or more modifications resulting in a nuclease that has reduced or no catalytic activity, or alternatively (in case of nucleases that target double stranded nucleic acids) resulting in a nuclease that only cleaves one strand, i.e. a nickase. By means of further guidance, and without limitation, for example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As further guidance, where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA-binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein.

In certain embodiments, the nuclease is a split nuclease (see e.g. "A split-Cas9 architecture for inducible genome editing and transcription modulation", Zetsche et al. (2015), Nat Biotechnol. 33(2):139-42, incorporated herein by reference in its entirety). In a split nuclease, the activity (which may be a modified activity, as described herein elsewhere), relies on the two halves of the split nuclease to be joined, i.e. each half of the split nuclease does not possess the required activity, until joined. As further guidance, and without limitation, with specific reference to Cas9, a split Cas9 may result from splitting the Cas9 at any one of the following split points, according or with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099. Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9. Ideally, the split position should be located within a region or loop. Preferably, the split position occurs where an interruption of the amino acid sequence does not result in the partial or full destruction of a structural feature (e.g. alpha-helixes or beta-sheets). Unstructured regions (regions that did not show up in the crystal structure because these regions are not structured enough to be "frozen" in a crystal) are often preferred options. In certain embodiments, a functional domain may be provided on each of the split halves, thereby allowing the formation of homodimers or heterodimers. The functional domains may be (inducible) interact, thereby joining the split halves, and reconstituting (modified) nuclease activity. By means of example, an inducer energy source may inducibly allow dimerization of the split halves, through appropriate fusion partners. An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together. The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer. The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a deadCas9 which is essentially a DNA-binding protein with very little or no catalytic activity, due to typically two or more mutations in its catalytic domains as described herein further.

In certain embodiments, the nuclease may comprise one or more additional (heterologous) functional domains, i.e. the modified nuclease is a fusion protein comprising the nuclease itself and one or more additional domains, which may be fused C-terminally or N-terminally to the nuclease, or alternatively inserted at suitable and appropriate sited internally within the nuclease (preferably without perturbing its function, which may be an otherwise modified function, such as including reduced or absent catalytic activity, nickase activity, etc.). any type of functional domain may suitably be used, such as without limitation including functional domains having one or more of the following activities: (DNA or RNA) methyltransferase activity, methylase activity, demethylase activity, DNA hydroxylmethylase domain, histone acetylase domain, histone deacetylases domain, transcription or translation activation activity, transcription or translation repression activity, transcription or translation release factor activity, histone modification activity, nuclease activity, single-strand RNA cleavage activity, double-strand RNA cleavage activity, single-strand DNA cleavage activity, double-strand DNA cleavage activity, nucleic acid binding activity, a protein acetyltransferase, a protein deacetylase, a protein methyltransferase, a protein deaminase, a protein kinase, a protein phosphatase, transposase domain, integrase domain, recombinase domain, resolvase domain, invertase domain, protease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase, histone tail protease, HDACs, histone methyltransferases (HMTs), and histone acetyltransferase (HAT) inhibitors, as well as HDAC and HMT recruiting proteins, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains. In some embodiments, the functional domain is an epigenetic regulator; see, e.g., Zhang et al., U.S. Pat. No. 8,507,272 (incorporated herein by reference in its entirety). In some embodiments, the functional domain is a transcriptional activation domain, such as VP64, p65, MyoD1, HSF1, RTA, SET7/9 or a histone acetyltransferase. In some embodiments, the functional domain is a transcription repression domain, such as KRAB. In some embodiments, the transcription repression domain is SID, or concatemers of SID (eg SID4X), NuE, or NcoR. In some embodiments, the functional domain is an epigenetic modifying domain, such that an epigenetic modifying enzyme is provided. In some embodiments, the functional domain is an activation domain, which may be the P65 activation domain. In some embodiments, the functional domain comprises nuclease activity. In one such embodiment, the functional domain may comprise Fok1. Mention is made of U.S. Pat. Pub. 2014/0356959, U.S. Pat. Pub. 2014/0342456, U.S. Pat. Pub. 2015/0031132, and Mali, P. et al., 2013, Science 339(6121):823-6, doi: 10.1126/science.1232033, published online 3 Jan. 2013 and through the teachings herein the invention comprehends methods and materials of these documents applied in conjunction with the teachings herein. It is to be understood that also destabilization domains or localization domains as described herein elsewhere are encompassed by the generic term "functional domain". In certain embodiments, one or more functional domains are associated with the nuclease itself. In some embodiments, one or more functional domains are associated with an adaptor protein, for example as used with the modified guides of Konnerman et al. (Nature 517(7536): 583-588, 2015; incorporated herein by reference in its entirety), and hence form part of a Synergistic activator mediator (SAM) complex. The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains.

In certain embodiments, the nuclease, in particular the Cas protein, may comprise one or more modifications resulting in a destabilized nuclease when expressed in a host (cell). Such may be achieved by fusion of the nuclease with a destabilization domain (DD). Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, a temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398 all of which are incorporated herein by reference and may be employed in the practice of the invention in selected a DD to associate with a CRISPR enzyme in the practice of this invention. As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a D associated Cas being degraded. When a new DD is fused to a protein of interest, its instability is conferred to the protein of interest, resulting in the rapid degradation of the entire fusion protein. Peak activity for Cas is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. By means of example, and without limitation, in some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT. More than one (the same or different) DD may be present, and may be fused for instance C-terminally, or N-terminally, or even internally at suitable locations. Having two or more DDs which are heterologous may be advantageous as it would provide a greater level of degradation control.

In some embodiments, the fusion protein as described herein may comprise a linker between the nuclease and the fusion partner (e.g. functional domain). In some embodiments, the linker is a GlySer linker. Attachment of a functional domain or fusion protein can be via a linker, e.g., a flexible glycine-serine (GlyGlyGlySer) or (GGGS)3 or a rigid alpha-helical linker such as (Ala(GluAlaAlaAlaLys) Ala). Linkers such as (GGGGS)3 are preferably used herein to separate protein or peptide domains. (GGGGS)3 is preferable because it is a relatively long linker (15 amino acids). The glycine residues are the most flexible and the serine residues enhance the chance that the linker is on the outside of the protein. (GGGGS)6 (GGGGS)9 or (GGGGS)12 may preferably be used as alternatives. Other preferred alternatives are (GGGGS)1, (GGGGS)2, (GGGGS)4, (GGGGS)5, (GGGGS)7, (GGGGS)8, (GGGGS)10, or (GGGGS)11. Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 linker may be used here (or the 6, 9, or 12 repeat versions therefore) or the NLS of nucleoplasmin can be used as a linker between Cas9 and the functional domain.

In some embodiments, the nuclease is fused to one or more localization signals, such as nuclear localization sequences (NLSs), such as about or more than about 1, 2, 3, 4, 5, 6, 7, 8, 9, 10, or more NLSs. In some embodiments, the nuclease comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the nuclease comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV; the NLS from nucleoplasmin (e.g. the nucleoplasmin bipartite NLS with the sequence KRPAATKKAGQAKKKK); the c-myc NLS having the amino acid sequence PAAKRVKLD or RQRRNELKRSP; the hRNPA1 M9 NLS having the sequence NQSSNFGPMKGGNFGGRSSGPYGGGGQYFAK-PRNQGGY; the sequence RMRIZFKNKGKDTAEL-RRRRVEVSVELRKAKKDEQILKRRNV of the IBB domain from importin-alpha; the sequences VSRKRPRP and PPKKARED of the myoma T protein; the sequence POPKKKPL of human p5³; the sequence SALIKKKKK-MAP of mouse c-abl IV; the sequences DRLRR and PKQKKRK of the influenza virus NS1; the sequence RKLKKKIKKL of the Hepatitis virus delta antigen; the sequence REKKKFLKRR of the mouse Mx1 protein; the sequence KRKGDEVDGVDEVAKKKSKK of the human poly(ADP-ribose) polymerase; and the sequence RKCLQAGMNLEARKTKK of the steroid hormone receptors (human) glucocorticoid.

With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g. also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867 (PROTECTED GUIDE RNAS (PGRNAS); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

By means of further guidance, and without limitation, in certain embodiments, the gRNA is a dead gRNA (dgRNA), which are guide sequences which are modified in a manner which allows for formation of the CRISPR complex and successful binding to the target, while at the same time, not allowing for successful nuclease activity (i.e. without nuclease activity/without indel activity). These dead guides or dead guide sequences can be thought of as catalytically inactive or conformationally inactive with regard to nuclease activity. Several structural parameters allow for a proper framework to arrive at such dead guides. Dead guide sequences are shorter than respective guide sequences which result in active Cas-specific indel formation. Dead guides are 5%, 10%, 20%, 30%, 40%, 50%, shorter than respective guides directed to the same Cas protein leading to active Cas-specific indel formation. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

By means of further guidance, and without limitation, in certain embodiments, the gRNA is an escorted gRNA (egRNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The escorted Cpf1 CRISPR-Cas systems or complexes have a gRNA with a functional structure designed to improve gRNA structure, architecture, stability, genetic expression, or any combination thereof. Such a structure can include an aptamer. Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

By means of further guidance, and without limitation, in certain embodiments, the gRNA is a protected guide. Protected guides are designed to enhance the specificity of a Cas protein given individual guide RNAs through thermodynamic tuning of the binding specificity of the guide RNA to target nucleic acid. This is a general approach of introducing mismatches, elongation or truncation of the guide sequence to increase/decrease the number of complimentary bases vs. mismatched bases shared between a target and its potential off-target loci, in order to give thermodynamic advantage to targeted genomic loci over genomic off-targets. In certain embodiments, the guide sequence is modified by secondary structure to increase the specificity of the CRISPR-Cas system and whereby the secondary structure can protect against exonuclease activity and allow for 3' additions to the guide sequence. In certain embodiments, a "protector RNA" is hybridized to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target binding to the mismatched basepairs at the 3' end. In certain embodiments, additional sequences comprising an extended length may also be present.

Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20nt and Z is of length 1-30nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended. An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA-binding protein, and/or a guide RNA. In particular embodiments, the composition comprises a vector. In further particular embodiments, the vector comprises a polynucleotide encoding a gRNA. In particular embodiments, the vector comprises two or more guide RNAs. The two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

In certain embodiments, the modulating agent is an inhibitory nucleic acid molecule that causes the degradation of or inhibits the function, transcription, or translation of its target gene in a sequence-specific manner. Exemplary inhibitory nucleic acid molecules include aptamers, siRNA, artificial microRNA, interfering RNA or RNAi, dsRNA, ribozymes, antisense oligonucleotides, and DNA expression cassettes encoding said nucleic acid molecules.

In preferred embodiments, the inhibitory nucleic acid molecule decreases the level of an mRNA in a cell.

Preferably, the inhibitory nucleic acid molecule decreases the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the inhibitory nucleic acid molecule (e.g. a miRNA or RNA interference molecule). In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

In some embodiments, the nucleic acid molecule is an antisense oligonucleotide. Antisense oligonucleotides (AONs) generally inhibit their target by binding target mRNA and sterically blocking expression by obstructing the ribosome. AONs can also inhibit their target by binding target mRNA thus forming a DNA-RNA hybrid that can be a substance for RNase H.

In certain embodiments, a modulating agent may comprise (i) a DNA-binding portion configured to specifically bind to the endogenous gene and (ii) an effector domain mediating a biological activity.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments the effector domain may be a transcriptional inhibitor (i.e., a repressor domain), such as an mSin interaction domain (SID). SID4X domain or a Kruppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein. In certain embodiments, a modulating agent may comprise introducing one or more endogenous genes and/or one or more exogenous genes in expressible format into the immune cell, in accordance with the practice of transgenesis as taught elsewhere in this specification.

Pharmaceutically Acceptable Carriers

The methods of administering human cells to a subject as described herein involve the use of therapeutic compositions comprising ionocytes or their progenitor cells. The present disclosure also encompasses the administration of an ionocyte modulating agent to a subject. Preferably, the modulating agent is formulated as a pharmaceutical composition.

Therapeutic compositions contain a physiologically tolerable carrier together with the cell composition or modulating agent and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal and produce an acceptable level of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the ionocyte or their progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human lung progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a pharmaceutical composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration and Efficacy

Provided herein are methods for treating an inflammatory lung disease or a disease or condition associated with sweat gland disorder comprising administering ionocytes or their precursor cells thereof to a subject in need thereof. Provided herein are also methods for treating a disease or condition associated with sweat gland disorder comprising administering an ionocyte modulating agent to a subject in need thereof.

It is within the purview of a skilled person to determine suitable dosages and dosage regimes. The exact amount required will vary depending on factors such as the type of disease being treated.

The term "effective amount" as used herein refers to the amount of the active agent (e.g. ionocyte or modulating agent or a composition comprising an ionocyte or modulating agent) needed to alleviate at least one or more symptom of the disorder to be treated, and relates to a sufficient amount of a composition to provide the desired effect, e.g., treat a subject having smoking induced-injury or cystic fibrosis. The term "therapeutically effective amount" therefore refers to an amount of the active agent that is sufficient to promote a particular effect when administered to a typical subject, such as one who has or is at risk for a lung disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the lung tissue or sweat gland prior to administering the active agent according to the methods described herein. In some embodiments, the subject is first diagnosed as being at risk of developing disease or disorder prior to administering the active agent.

For use in the various aspects described herein, an effective amount of ionocyte cells, comprises at least $10^2$ ionocyte cells, at least $5 \times 10^2$ ionocyte cells, at least $10^3$ ionocyte cells, at least $5 \times 10^3$ ionocyte cells, at least $10^4$ ionocyte cells, at least $5 \times 10^4$ ionocyte cells, at least $10^5$ ionocyte cells, at least $2 \times 10^5$ ionocyte cells, at least $3 \times 10^5$ ionocyte cells, at least $4 \times 10^5$ ionocyte cells, at least $5 \times 10^5$ ionocyte cells, at least $6 \times 10^5$ ionocyte cells, at least $7 \times 10^5$ ionocyte cells, at least $8 \times 10^5$ ionocyte cells, at least $9 \times 10^5$ ionocyte cells, at least $1 \times 10^6$ ionocyte cells, at least $2 \times 10^6$ ionocyte cells, at least $3 \times 10^6$ ionocyte cells, at least $4 \times 10^6$ ionocyte cells, at least $5 \times 10^6$ ionocyte cells, at least $6 \times 10^6$ ionocyte cells, at least $7 \times 10^6$ ionocyte cells, at least $8 \times 10^6$ ionocyte cells, at least $9 \times 10^6$ ionocyte cells, or multiples thereof. The ionocyte cells can be derived from one or more donors, or can be obtained from an autologous source. In some embodiments of the aspects described herein, the ionocyte cells are expanded in culture prior to administration to a subject in need thereof.

Exemplary modes of administration for use in the methods described herein include, but are not limited to, injection, intrapulmonary (including intranasal and intratracheal) infusion, inhalation as an aerosol (including intranasal), and implantation (with or without a scaffold material). "Injection" includes, without limitation, intravenous, intramuscular, intraarterial, intradermal, intraperitoneal, transtracheal and subcutaneous. The phrases "parenteral administration" and "administered parenterally" as used herein, refer to modes of administration other than enteral and topical administration, usually by injection, and includes, without limitation, intravenous, intraperitoneal, intramuscular, intraarterial, intradermal, transtracheal, and subcutaneous administration.

In some embodiments, a therapeutically effective amount of the active agent is administered using intrapulmonary administration, such as an intranasal or intratracheal route. In some aspects of these methods, a therapeutically effective amount of the active agent is administered using a systemic route, such as an intraperitoneal or intravenous route. In other aspects of these methods, a therapeutically effective amount of the active agent is administered using both intrapulmonary and intraperitoneal administration. These methods are particularly aimed at therapeutic and prophylactic treatments of human subjects having, or at risk of having, a lung disease or disorder. The active agent described herein can be administered to a subject having any lung disease or disorder by any appropriate route which results in an effective treatment in the subject. In some embodiments of the aspects described herein, a subject having a lung disorder is first selected prior to administration of the active agent.

In some embodiments, an effective amount of the active agent is administered to a subject by intrapulmonary administration or delivery. As defined herein, "intrapulmonary" administration or delivery refers to all routes of administration whereby the active agent, is administered in a way that results in direct contact of the active agent with the airways of a subject, including, but not limited to, transtracheal, intratracheal, and intranasal administration. In some such embodiments, the cells are injected into the nasal passages or trachea. In some embodiments, the active agent is directly inhaled by a subject. In some embodiments, intrapulmonary delivery of the active agent includes administration methods whereby the active agent is administered to an intubated subject via a tube placed in the trachea or "tracheal intubation." Preferably, a ionocyte cell suspension is administered via tracheal intubation.

As used herein, "tracheal intubation" refers to the placement of a flexible tube, such as a plastic tube, into the trachea. The most common tracheal intubation, termed herein as "orotracheal intubation" is where, with the assistance of a laryngoscope, an endotracheal tube is passed through the mouth, larynx, and vocal cords, into the trachea. A bulb is then inflated near the distal tip of the tube to help secure it in place and protect the airway from blood, vomit, and secretions. In some embodiments, the active agent is administered to a subject having "nasotracheal intubation," which is defined as a tracheal intubation where a tube is passed through the nose, larynx, vocal cords, and trachea.

In some embodiments, an effective amount of ionocyte cells is administered to a subject by systemic administration, such as intravenous administration. The phrases "systemic administration," "administered systemically", "peripheral administration" and "administered peripherally" as used herein refer to the administration of active agent other than directly into a target site, tissue, or organ, such as the lung, such that it enters, instead, the subject's circulatory system and, thus, is subject to metabolism and other like processes.

In some embodiments of the aspects described herein, one or more routes of administration are used in a subject to achieve distinct effects. For example, ionocyte cells can be administered to a subject by both intratracheal and intraperitoneal administration routes for treating or repairing lung epithelium and for pulmonary vascular repair and regeneration respectively. In such embodiments, different effective amounts of the active agent can be used for each administration route. Where aerosol administration is to be used, nebulizer devices require formulations suitable for dispensing the particular composition. The choice of formulation will depend upon the specific composition used and the concentration of active agent (e.g. the number of ionocytes) to be administered; such formulations can be adjusted by the skilled practitioner. However, as an example, where the composition is ionocyte cells in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells.

Typically, each formulation for aerosol delivery via a nebulizer is specific to the type of device employed and can involve the use of an appropriate propellant material, in addition to the usual diluents, adjuvants and/or carriers useful in therapy.

Nasal delivery of protein or other agents in addition to the ionocyte cells or their precursor cells is also contemplated. Nasal delivery allows the passage of the protein or other agent to the blood stream directly after administering the therapeutic product to the nose, without the necessity for deposition of the product in the lung. Formulations for nasal delivery include those with dextran or cyclodextran.

In some embodiments, additional agents to aid in treatment of the subject can be administered before or following treatment with the active agent described herein.

The efficacy of treatment can be determined by the skilled clinician. However, a treatment is considered "effective treatment," as the term is used herein, if any one or all of the symptoms, or other clinically accepted symptoms or markers of inflammatory lung diseases are reduced, e.g., by at least 10% following treatment with a composition comprising human lung progenitor cells as described herein. Methods of measuring these indicators are known to those of skill in the art and/or described herein.

Indicators of inflammatory lung disease include functional indicators, e.g., measurement of lung capacity and function, and oxygen saturation (e.g., tissue oxygen saturation or systemic arterial oxygen saturation), as well as biochemical indicators.

Where necessary or desired, animal models of lung injury or lung disease can be used to gauge the effectiveness of a particular composition as described herein. As one example, the bleomycin-induced lung injury model of acute lung injury (ALI) can be used. Animal models of lung function are useful for monitoring bronchoconstriction, allergic response, late airway hyperresponsiveness in response to inhaled allergens, among other endpoints and can include, for example, head-out plethysmography or body-plethysmography models (see e.g., Hoymann, H G et al., *J Pharmacol Toxicol Methods* (2007) 55(1): 16-26). Exemplary animal models for asthma, including models of allergic asthma (e.g., acute and chronic allergic asthma), are known in the art. See e.g., Nials and Uddin. (2008) *Dis Model Mech* 1:213-220; Zosky and Sly (2007) *Clin Exp Allergy* 37(7): 973-88; and Kumar and Foster. (2002) *Am J Respir Cell Mol Biol*.

Screening Compounds

In one aspect, the present invention provides methods for identifying an agent comprising contacting an agent (e.g., a test compound or candidate agent) with a respiratory epithelial ionocyte or its progenitor cell. Such agents may be useful for treating defective respiratory epithelial ion transport in a subject or for treating an inflammatory lung disease. In one aspect, the present invention provides methods for identifying an agent comprising contacting an agent (e.g., a test compound or candidate agent) with a sweat gland ionocyte or its progenitor cell. Such agents may be useful for treating defective sweat gland ion transport or treating a disease or condition associated with sweat gland disorder.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™ AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 μM, about 0.1 μM to about 20 μM, about 0.1 μM to about 10 μM, or about 0.1 μM to about 5 μM.

The compound screening assay can be used in a high through-put screen. High throughput screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Preferably, the screening assays measure, either directly or indirectly, the effect of the test compounds on ionocyte proliferation. Test compounds that increase proliferation of respiratory epithelial ionocytes are useful for treating defective respiratory epithelial ion transport in a subject or for treating an inflammatory lung disease, while test compounds that increase proliferation of sweat gland ionocyte are useful for treating defective sweat gland ion transport or treating a disease or condition associated with sweat gland disorder.

Kit

The terms "kit" and "kit of parts" as used throughout this specification refer to a product containing components necessary for carrying out the specified methods (e.g., methods for detecting, quantifying or isolating ionocytes, and method of treating inflammatory lung disease or a disease or condition associated with sweat gland according to the present invention, packed so as to allow their transport and storage.

In one aspect, the present invention provides a kit for treating or diagnosing an inflammatory lung disease, comprising a composition comprising an respiratory epithelial ionocyte and/or an ionocyte modulating agent (preferably an agonist of FOXI1, FOXI2, ASCL3, V-Type Proton ATPases, CFTR, PPARG, Cochlin, and STAP1 expression and/or activity). In another aspect, the present invention provides a kit for treating or diagnosing a disease or condition associated with sweat gland disorders, comprising an ionocyte isolated from sweat gland cells. cells and/or an ionocyte modulating agent (preferably an agonist of FOXI1, FOXI2, ASCL3, V-Type Proton ATPases, CFTR, PPARG, Cochlin, and STAP1 expression and/or activity).

In another aspect, the present invention provides a kit for identifying or screening a candidate agent for treating an inflammatory lung disease, the kit comprising: a respiratory epithelial ionocyte cell, one or more agents for detecting ionocyte specific cell surface markers, and instructions therefor.

In another aspect, the present invention provides a kit for generating respiratory epithelial ionocyte, comprising lung stem cells, an agent that induces lung stem cell differentiation into ionocyte, optionally, a cell culture medium, one or more agents for detecting ionocyte specific marker, and instruction for using the kit.

Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively.

Typically, kits and kit of parts are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridisation probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris(hydroxymethyl)-aminomethane) buffers or maleate buffers, or mixtures thereof), enzymes (such as for example but without limitation thermostable DNA polymerase), detectable labels, detection reagents, and control formulations (positive and/or negative), useful in the specified methods. Typically, the kits and kit of parts may also include instructions for use thereof, such as on a printed insert or on a computer readable medium. The terms may be used interchangeably with the term "article of manufacture", which broadly encompasses any man-made tangible structural product, when used in the present context.

In certain embodiments, the kit of parts or article of manufacture may comprise a microfluidic system.

In some embodiments, the kit of the present invention also comprises an instruction. The instruction can be descriptive, instructional, marketing or other material that relates to the methods described herein and/or the use of a compound(s) described herein for the methods described herein. The informational material of the kits is not limited in its form.

In one embodiment, the informational material can include instructions to administer an ionocyte cell or its precursor cell or a modulating agent as described herein in a suitable manner to effect treatment of in inflammatory lung disease, e.g., in a suitable dose, dosage form, or mode of administration (e.g., a dose, dosage form, or mode of administration described herein). Alternatively, the informational material can include instructions for screening a candidate agent for treating a lung disease or disorder.

In some embodiments, the composition of the kit can include other ingredients, such as a solvent or buffer, a stabilizer, a preservative, and/or an additional agent, e.g., for treating a condition or disorder described herein. Alternatively, the other ingredients can be included in the kit, but in different compositions or containers than a cell or signaling pathway or differentiation pathway modulating compound described herein.

The kit can include a component for the detection of a marker for ionocytes or their precursor cells. In addition, the kit can include one or more antibodies that bind a cell marker, or primers for an RT-PCR or PCR reaction, e.g., a semi-quantitative or quantitative RT-PCR or PCR reaction. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

Although the present invention and its advantages have been described in detail, it should be understood that various changes, substitutions and alterations can be made herein without departing from the spirit and scope of the invention as defined in the appended claims.

EXAMPLES

Example 1: Materials and Methods

Cell Isolation.

Murine respiratory epithelial cells are isolated and rinsed in cold PBS. The tissue is opened longitudinally and sliced into small fragments roughly 0.2 cm long. The tissue is incubated in 20 mM EDTA in PBS on ice for 90 min, while shaking every 30 min. The tissue is then shaken vigorously and the supernatant is collected as fraction 1 in a new conical tube. The tissue is incubated in fresh EDTA-PBS and a new fraction is collected every 30 min. Fractions are collected until the supernatant consisted almost entirely of respiratory epithelial cells. The final fraction (enriched for crypts) is washed twice in PBS, centrifuged at 300 g for 3 min, and dissociated with TrypLE express (Invitrogen) for 1 min at 37° C. The single cell suspension is then passed through a 40 µm filter and stained for FACS sorting for single cell RNA-seq by either platform (below).

FAE Isolation

Epithelial cells are isolated by extracting small sections (0.5 cm) from the respiratory pathway of mice with induced ionocytes. Ionocytes are harvested and single GFP$^+$ or GFP$^-$ cells are FACS sorted for single cell RNA-seq by either platform (below).

Cell Sorting

For SMART-Seq2 experiments, a FACS machine (Astrios) is used to sort a single cell into each well of a 96-well PCR plate containing 5 µl of TCL buffer with 1% 2-mercaptoethanol. The cells are stained for negative and positive gene expression. A population control of 200 cells is sorted into one well and a no-cell control is sorted into another well. After sorting, the plate is sealed tightly with a Microseal F and centrifuged at 800 g for 1 min. The plate is immediately frozen on dry ice and kept at −80° C. until ready for the lysate cleanup. Bulk population cells are sorted into an Eppendorf tube containing 100 µl solution of TCL with 1% 2-mercaptoethanol and stored at −80° C.

For 10×, cells are sorted with the same parameters as described for SMART-Seq2, but are sorted into an Eppendorf containing 50 µl of 0.4% BSA-PBS and stored on ice until proceeding to the GemCode Single Cell Platform.

SMART-Seq2

Single cells: Single cell sequencing libraries are prepared using a modified SMART-Seq2 protocol as previously reported (Picelli et al., 2014). Briefly, RNA lysate cleanup is preformed using RNAClean XP beads (Agencourt) followed by reverse transcription with Maxima Reverse Transcriptase (Life Technologies) and whole transcription amplification (WTA) with KAPA HotStart HIFI 2× ReadyMix (Kapa Biosystems) for 21 cycles. WTA products are purified with Ampure XP beads (Beckman Coulter), quantified with Qubit dsDNA HS Assay Kit (ThermoFisher), and assessed with a high sensitivity DNA chip (Agilent). RNA-seq libraries are constructed from purified WTA products using Nextera XT DNA Library Preparation Kit (Illumina). On each plate, the population and no-cell controls are processed using the same method as the single cells. The libraries are sequenced on an Illumina Nextseq 500.

Bulk: Bulk population samples are processed by extracting RNA with RNeasy Plus Micro Kit (Qiagen) per the manufacturer's recommendations, and then proceeding with the modified SMART-Seq 2 protocol as described above.

Droplet Single Cell RNA-Seq

More than 20,000 individual cells are processed through the GemCode Single Cell Platform using the GemCode Gel Bead, Chip and Library Kits (10× Genomics, Pleasanton, CA), following the manufacturer's protocol. Briefly, an input of 6,000 cells is added to each channel of a chip with a recovery rate of 1,500 cells. The cells are then partitioned into Gel Beads in Emulsion (GEMs) in the GemCode instrument, where cell lysis and barcoded reverse transcription of RNA occurred, followed by amplification, shearing and 5' adaptor and sample index attachment. Libraries are sequenced on an Illumina Nextseq 500.

Immunofluorescence and In Situ Hybridization

Immunofluorescence Staining of respiratory tissue samples is conducted as described (Biton et al., 2011). Briefly, tissues are fixed for 14 hours in formalin, embedded in paraffin and cut into 5 µm thick sections. Sections are deparaffinized with standard techniques, incubated with primary antibodies overnight at 4° C. and then with secondary antibodies at RT for 30 min. Slides are mounted with Slowfade Mountant+DAPI (Life Technologies, S36964) and sealed.

In situ Hybridization RNAScope Multiplex Fluorescent Kit (Advanced Cell Diagnostics) is used per manufacturer's recommendations with the following alterations. Target Retrieval boiling time is adjusted to 12 minutes and incubation with Protease IV at 40° C. is adjusted to 8 minutes rather than 15 min. Slides are mounted with Slowfade Mountant+DAPI (Life Technologies, S36964) and sealed.

Combined immunofluorescence and in situ hybridization staining is implemented by first performing FISH. After Amp 4, tissue sections are washed in washing buffer, incubated in primary antibodies overnight at 4° C., washed in 1×TBST 3 times and then incubated in secondary antibodies for 30 min at RT. Slides are mounted with Slowfade Mountant+DAPI (Life Technologies, S36964) and sealed.

Image analysis. Images of tissue sections are taken with a confocal microscope Fluorview FV1200 using Kalman and sequential laser emission to reduce noise and signal overlap. Scale bar is added to each picture using the confocal software FV10-ASW 3.1 Viewer. Images are overlaid and visualized using Image J software. To quantify respiratory epithelial cells, the combined IFA and smFISH is used. Antibodies and probes are used to assess proliferation and total stem cell counts, respectively, based on ionocyte markers. The presence of markers is evaluated, where a cell is determined positive for each marker if spots are within the cell borders.

Analysis

Pre-Processing of Droplet scRNA-Seq Data

Demultiplexing, alignment to the mm10 transcriptome and UMI-collapsing are performed using the Cellranger toolkit (version 1.0.1) provided by 10× Genomics. For each cell, this study quantifies the number of genes for which at least one read is mapped, and then excludes all cells with either fewer than 800 detected genes. Expression values $E_{i,j}$ for gene i in cell j are calculated by dividing UMI count values for gene i by the sum of the UMI counts in cell j, to normalize for differences in coverage, and then multiplying by 10,000 to create TPM-like values, and finally calculating $\log_2(TPM+1)$ values. Batch correction is performed using ComBat as implemented in the R package sva (Leek et al., 2012), using the default parametric adjustment mode. The output is a corrected expression matrix, which is used as input to further analysis.

Selection of variable genes is performed by fitting a generalized linear model to the relationship between the squared co-efficient of variation (CV) and the mean expression level in log/log space, and selecting genes that significantly deviated (P<0.05) from the fitted curve, as previously described (Brennecke et al., 2013).

Pre-Processing of SMART-Seq2 Single-Cell RNA-Seq Data

BAM files are converted to merged, demultiplexed FASTQs using the Illumina provided Bcl2Fastq software package v2.17.1.14. Paired-end reads are mapped to the UCSC hg19 human transcriptome using Bowtie (Langmead et al., 2009) with parameters "-q--phred33-quals-n 1-e 99999999-1 25-I1-X 2000-a-m 15-S-p 6", which allows alignment of sequences with one mismatch. Expression levels of genes are quantified as using transcript-per-million (TPM) values calculated by RSEM (Li and Dewey, 2011) v1.2.3 in paired-end mode. For each cell, this study quantifies the number of genes for which at least one read is mapped, and then excludes all cells with either fewer than 3,000 detected genes or a transcriptome-mapping of less than 40%. This study then identifies highly variable genes as described above.

Dimensionality Reduction Using PCA and tSNE

This study restricted the expression matrix to the subsets of variable genes and high quality cells noted above, and values are centred and scaled before input to PCA, which is implemented using the R function 'prcomp' from the 'stats' package for the SMART-seq2 dataset. For the droplet dataset, this study used a randomized approximation to PCA, implemented using the 'rpca' function from the 'rsvd' R package, with the parameter k set to 100. This low-rank approximation is used as it is several orders of magnitude faster to compute for very wide matrices. After PCA, significant PCs are identified using the permutation test described in (Buja and Eyuboglu, 1992), implemented using the 'permutationPA' function from the 'jackstraw' R package.

For visualization, the dimensionality of the datasets are further reduced using the 'Barnes-hut' approximate version of the t-distributed stochastic neighbor embedding (tSNE) (van der Maaten, 2014; van der Maaten and Hinton, 2008). This is implemented using the 'Rtsne' function from the 'Rtsne' R package using 20,000 iterations and a perplexity setting that ranged from 10 to 30 depending on the size of the dataset.

Identifying Cell Differentiation Trajectories Using Diffusion Maps

Prior to running diffusion-map dimensionality reduction this study selected highly variable genes in the data as follows. This study first fits a null model for baseline cell-cell gene expression variability in the data based on a power-law relationship between coefficient of variation (CV) and the mean of the UMI-counts of all the expressed genes, similar to Zeisel et al., 2015. Next, this study calculates for each gene the difference between the value of its observed CV and that expected by the null model ($CV_{diff}$). The histogram of $CV_{diff}$ exhibits a "fat tail". This study calculates the mean p and standard deviation 6 of this distribution and uncovers genes that are used for further analysis.

This study performs dimensionality reduction using the diffusion map approach (Coifman et al., 2005). Briefly, a cell-cell transition matrix is computed using the Gaussian kernel where the kernel width is adjusted to the local neighborhood of each cell, following (Haghverdi et al., 2015). This matrix is converted to a Markovian matrix after normalization. The right eigenvectors $v_i$ (i=0, 1, 2, 3, ... ) of this matrix are computed and sorted in the order of decreasing eigenvalues $\lambda_i$ (i=0, 1, 2, 3, ... ) after excluding the top eigenvector $v_0$, corresponding to $\lambda_0=1$ (which reflects the normalization constraint of the Markovian matrix). The remaining eigenvectors $v_i$ (i=1, 2 ... ) define the diffusion map embedding and are referred to as diffusion components ($DC_k$ (k=1, 2, ... )).

This study restricts the expression matrix to the subsets of variable genes and high quality cells, and values are centered and scaled before input to PCA, which is implemented using the R function 'prcomp' from the 'stats' package for the SMART-seq2 dataset. For the droplet-based datasets (10×), this study uses a randomized approximation to PCA, implemented using the 'rpca' function from the 'rsvd' R package, with the parameter k set to 100. This low-rank approximation is used as it is several orders of magnitude faster to compute for very wide matrices. After PCA, significant PCs are identified using a permutation test based on and implemented using the 'permutationPA' function from the 'jackStraw' R package.

t-distributed stochastic neighbor embedding (tSNE) maps are generated using the 'Barnes-Hut' approximate version of the tSNE algorithm, implemented in the R package 'Rtsne'. Scores from the first n PCs are used as the input to tSNE, where n is determined for each datasets using the significance test described above.

Removing Contaminating Cells and Doublets

Although cells are sorted prior to sequencing using EpCAM, a small number of contaminating cells are observed in the 10λ dataset. These cells are removed by an initial round of unsupervised clustering (density-based clustering of the tSNE map using 'dbscan' (Ester et al., 1996) from the R package 'fpc') as they form an extremely distinct cluster. In the case of the SMART-Seq2 dataset, several cells are outliers in terms of library complexity, which could possibly correspond to more than one individual cell per sequencing library or 'doublets'. These cells are then removed by calculating the top quantile 1% of the distribution of genes detected per cell and removing any cells in this quantile.

kNN-Graph Based Clustering

To cluster single cells by their expression, this study uses unsupervised clustering approach, based on the Infomap graph-clustering algorithm (Rosvall and Bergstrom, 2008), following approaches recently described for single cell CyTOF data (Levine et al., 2015) and scRNA-seq (Shekhar et al., 2016). Briefly, this study constructs a k nearest-neighbor graph on the data using, for each pair of cells, the distance between the scores of significant PCs as the metric. The parameter k is chosen in a manner roughly consistent with the size of the dataset. The nearest neighbor graph is computed using the function 'nng' from the R package 'cccd'. The k-NN graph is then used as the input to Infomap (Rosvall and Bergstrom, 2008), implemented using the 'infomap.community' function from the 'igraph' R package.

Detected clusters are mapped to cell-types or intermediate states using known markers for respiratory epithelial cell subtypes.

Defining Cell Type Signatures

To identify maximally specific genes, this study runs differential expression tests between each pair of clusters, for all possible pairwise comparisons. Then, for a given cluster, putative signature genes are filtered using the maximum FDR Q-value and ranked by the minimum $\log_2$ fold change across all pairwise comparisons. Cell-type signature genes are obtained using a maximum FDR of 0.05 and a minimum $\log_2$fc of 0.5. In the case of signature genes for subtypes within cell-types, the top 25 genes are used, ranked by minimum $\log_2$ fold change. Differential expression tests are carried out using the Mann-Whitney U-test (also known as the Wilcoxon rank-sum test) implemented using the R function 'wilcox.test'. Multiple hypothesis testing correction is performed by controlling the false discovery rate (Benjamini and Hochberg, 1995) using the R function p.adjust.

Scoring Cells Using Signature Gene Sets

To obtain a score for a specific set of n genes in a given cell, a 'background' gene set is defined to control for differences in sequencing coverage and library complexity between cells in a manner similar to Kowalczyk et al., 2015. The background gene set is selected to be similar to the genes of interest in terms of expression level. Specifically, the 10n nearest neighbors in the 2-D space defined by mean expression and detection frequency across all cells are selected. The signature score for that cell is then defined as the mean expression of the n signature genes in that cell, minus the mean expression of the 10n background genes in that cell.

Cell-Type Specific TFs, GPCRs and LRRs

A list of all genes identified as acting as transcription factors in mice is obtained from AnimalTFDB (Zhang et al., 2012), downloaded from: bioguo.org/AnimalTFDB/BrowseAllTF.php?spe=Mus_musculus. The set of G-protein coupled receptors (GPCRs) is obtained from the UniProt database, downloaded from: .uniprot.org/uniprot/?query=family%3A%22g+protein+coupled+receptor%22+AND+organism%3A%22Mouse+%5B10090%5D%22+AND+reviewed%3Ayes&sort=score. Functional annotations for each protein are obtained from the British Pharmacological Society (BPS) and the International Union of Basic and Clinical Pharmacology (IUPHAR) data, downloaded from:

http://www.guidetopharmacology.org/GRAC/GPCRListForward?class=A. The list of leucine-rich repeat proteins (LRRs) is taken from (Ng et al., 2011). To map from human to mouse gene names, human and mouse orthologs are downloaded from Ensembl (latest release 86, http://www.ensembl.org/biomart/martview), and human and mouse gene synonyms from NCBI (ftp://ftp.ncbi.nlm.nih.gov/gene/DATA/GENE_INFO/Mammalia/). For each human LRR gene, all human synonyms are mapped to the orthologous gene in mouse using the ortholog list, and mouse gene names are mapped to those in the single-cell data using the synonym list.

Cell-type specific TFs, GPCRs and LRRs are then identified by intersecting the list of genes specific to each cell type with the lists of TFs, GPCRs and LRRs defined above. Cell-type specific genes are defined using the SMART-Seq2 dataset, as those with a minimum $\log_2$ fold change of 0 and a maximum FDR of 0.5, retaining a maximum of 10 genes per cell type. In addition, a more extensive panel of cell-type specific GPCRs is identified by selecting a more lenient threshold. This is achieved by comparing each cell-type to all other cells, instead of the pairwise comparisons described in the previous section, and selecting all GPCR genes differentially expressed (FDR<0.001).

Defining a Gene Signature for Respiratory Stem Cells and Ionocytes

Genes specific to the subset of stem cells and/or ionocytes are defined using by running differential expression tests (all differential expression tests are performed using the Mann-Whitney U-test) between each pair of clusters defined on high coverage single cells, for all possible pairwise comparisons. Then putative signature genes are filtered using the maximum FDR Q-value and ranked by the minimum $\log_2$ fold change of means across all pairwise comparisons. An initial list of stem cell marker genes and ionocyte marker genes is thus obtained using a maximum FDR of 0.05 and a minimum $\log_2$fc of 0.5 (an exemplary signature includes genes from one or more of FOXI1, FOXI2, ASCL3, V-Type Proton ATPases, CFTR, PPARG, Cochlin, and STAP1). To obtain a more robust expression signature, genes are ranked by co-expression across the set of stem cells and ionocytes, measured by mean Spearman's rank correlation. Selecting genes above a threshold of 0.1 results in a set of genes.

GO Analysis

GO analysis is performed using the 'goseq' R package (Young et al., 2010), using significantly differentially expressed genes (FDR<0.05) as target genes, and all genes expressed with $\log_2$ (TPM+1)>3 in at least 10 cells as background.

Example 2A: Comprehensive Single-Cell Atlas of the Respiratory Epithelial Cells During Homeostasis and Inflammation As the gene expression program of a given cell closely reflects both its identity and function (Heinz et al., 2015), a systematic atlas of single-cell RNA profiles can help address many questions about discrete epithelial types in the respiratory tract, their networks and molecular processes, and the response of individual cells to stimuli, such as pathogenic insult. Most previous studies have examined the gene expression profiles of respiratory epithelial cells, but relied on known markers to purify cell populations, which may isolate either a mixed population if marker expression is promiscuous, or a subset of a larger group if overly specific. They may further fail to detect rare cellular populations or intermediate, transient states on a continuum.

This study uses scRNA-seq to chart a comprehensive atlas of respiratory epithelial cells. This study identifies gene signatures, key transcription factors (TFs) and specific GPCRs for each of the respiratory epithelial differentiated cell types, and traced their differentiation from stem cells. This study identifies and characterizes cellular heterogeneity within specific cell-types, and validated individual genes and signatures in situ. This study fnids a transcriptional signature distinguishing different respiratory cell types, including ionocytes. Finally, this study demonstrates how these cell types and states change dynamically as the respiratory system adapts to inflammation by distinct classes of inflammation-inducing agents. The comprehensive, high resolution atlas better defines the composition of the respiratory epithelial cells, highlights novel key molecules, TFs and GPCRs that can impact respiratory function and shows how changes in respiratory epithelial cell composition can play a key role in maintaining homeostasis in response to pathogens.

Example 2B: A Single-Cell ATLAS Identifies all Known Populations of Epithelial Cells in the Respiratory Epithelium This study profiles many individual cells. Initially, this study uses droplet-based massively-parallel single cell RNA-Seq (Zheng et al., 2016) to transcriptionally profile epithelial cells from the respiratory tract of mice.

Unsupervised clustering of the data partitions the cells into multiple groups. First, this study builds a k-nearest neighbor graph on a low-dimensional representation of the cellular expression data using principal component analysis (PCA), and partitions this graph into multiple discrete clusters using the Infomap algorithm (Rosvall and Bergstrom, 2008; Shekhar et al., 2016), each comprising transcriptionally similar cells. The clusters, each of which contains cells from all replicate experiments, are visualized using tSNE (Amir el at., 2013; Shekhar et al., 2016; van der Maaten and Hinton, 2008a).

This study labels the multiple clusters post hoc based on the expression of signatures of known marker genes, showing that each is associated with a distinct cell type or state. This study scores proliferating cells with a cell-cycle signature that this study previously developed from single-cell profiles to distinguish between dividing stem or progenitor cells and fully differentiated, post-mitotic cells.

This study validates the atlas by independently profiling single epithelial cells that are sorted by FACS followed by an established full-length scRNA-seq protocol (Picelli et al., 2014). This study profiles many single cells, filters isolated cells and lower quality cells, and retains a high-quality subset of single cells for analysis, with high reproducibility. The measured cell profiles have much higher coverage in terms of reads/cell and genes/cell.

Example 2C: Distinct Cell Types are Characterized by Specific Signatures, TFs and Receptors Relying on the high congruence between the two approaches, this study defines high-confidence consensus expression signatures for each cell type, highlighting known markers (corroborating the labels) and novel ones suggesting specific functions. Next, leveraging the higher sensitivity of the plate-based, full-length scRNA-Seq data, this study also identifies maximally specific TFs, GPCRs and leucine-rich repeat (LRR) proteins for each of the major cell types.

Example 2D: Distinct Regulators are Associated with the Proliferation-Differentiation The largest components of variation (PC-1 and PC-2) between single cells in the atlas reflect the processes of proliferation and differentiation in the respiratory epithelium. This study obtains sets of marker genes distinguishing various lineages. This study then is confirms at the protein level, observing a strong enrichment for ionocytes in expressing an ionocyte gene signature.

Focusing on the abundant population of ionocytes, this study uses diffusion maps (Coifman et al., 2005) to place them in a pseudo-temporal order. Several recent studies (Bendall et al., 2014; Trapnell et al., 2014) have shown that cellular differentiation and fate determination can be modeled as a dynamic process on a high-dimensional manifold, which can be inspected by ordering cells—sampled simultaneously from an ongoing asynchronous process—in pseudo-time. In the case, the diffusion components highlight a relationship between stem-like, progenitor, and ionocyte cells. Finally, this study identifies TFs with specific expression patterns in different regions of the diffusion map, associating regulators with early ionocyte lineage commitment.

Example 2E: Recalibration of Cell Proportions and Cell States in Response to Inflammation Whether respiratory epithelial cells tolerate or elicit a response to specific inflammation inducing agents plays a role in maintaining respiratory cell homeostasis. Because the epithelial cells of the respiratory tract are generated in an ongoing, continuous and rapid process of differentiation from stem cells throughout life, it is likely that following induction of inflammation (e.g., due to infection with a pathogen), there are changes both in the relative composition of respiratory epithelial cell types and in the internal state of each type, as well as in global expression changes common to all types.

This study investigates the respiratory epithelial cell response to an inflammation-inducing agent. This study profiles individual respiratory epithelial cells two days and ten days after exposure to an inflammation-inducing agent, as well as cells from control mice using droplet 3' scRNA-Seq and an additional cells with the deeper, full-length scRNA-Seq, which this study uses to obtain high-confidence 'consensus' differentially expressed genes for all comparisons in this experiment.

Within each cell type, this study also identifies cell-type specific changes in functional cell states in response to an inflammation-inducing agent. For example, there is a strong increase in the expression of some peptides and pro-inflammatory apolipoproteins.

Finally, analyzing respiratory epithelial cells during exposure to an inflammation-inducing agent finds distinct recalibration markers. Differential expression testing of the cells from exposed vs. control mice produce a set of up-regulated genes and a set of down-regulated genes (FDR<0.05, Mann-Whitney U-test) that are enriched with inflammatory response molecules.

The respiratory epithelium is a diverse epithelial tissue, composed of subtypes that are specialized to perform several crucial functions. This study dissects this complex tissue into its different components using massively parallel scRNA-Seq, creating the first comprehensive single-cell 'atlas' of the mouse respiratory epithelium, and revealing even further diversity than is previously appreciated. Using unsupervised computational analyses, this study identified and characterized the transcriptomes of the major differentiated epithelial cell-types, including ionocytes. In addition, this study also obtains specific gene signatures for respiratory stem cells and various precursor cells. For each major cell-type this study obtains cell-specific markers, TFs and GPCRs and high-confidence 'consensus' signatures from two complementary scRNA-seq methods (3' and full-length).

Example 3: Identification of Cellular States of Respiratory Stem Cells

To study respiratory stem cells, high-coverage single-cell RNA-Seq (scRNA-seq) profiles from respiratory epithelial cells using full-length scRNA-Seq are collected. Using unsupervised clustering (k-nearest neighbor (k-NN) graph-based clustering) of the cells, stem cells are identified, along with clusters corresponding to ionocytes.

Further unsupervised clustering of the respiratory stem cells partition them into distinct subgroups associated with distinct cell cycle signatures. First, principal component analysis (PCA) of the respiratory stem cells show that genes with high loadings on the first component (PC1) are enriched with cell cycle genes. Furthermore, comparing the expression of G1/S-phase specific genes and G2/M-specific genes for the cells in each cluster, one cluster consists primarily with cells in G1/S and a second spans several phases of the cell cycle including G2/M. A data-driven stem-cell signature from the single-cell profiles is determined by comparing all the stem cells (all groups together) vs. the non-stem cells in the data, revealing a gradient of stemness between the groups.

Next, the association of the signature genes with distinct cell proliferation rates is confirmed by double staining with single-molecule fluorescence in situ hybridization (smFISH) of the canonical proliferation marker mKi67 together with other common respiratory stem cell markers.

Example 4: Respiratory Epithelium Atlas Analysis of Human Biopsies Distinguishes Inflammatory Conditions from Normal Based on the aforementioned observations in murine models, studies are conducted with human tissue. A biopsy is obtained from a human patient with an inflammatory respiratory disorder. A separate biopsy is obtained from a patient control, i.e. without inflammatory disease. The biopsies are processed as before, on the basis of expression patterns, to identify cell types. The data shows differentiation trajectories being affected by the inflammatory disease. The data also demonstrates how respiratory epithelial atlas analysis can be performed to identify disease, and the nature and extent of the pathology. Such analysis is useful to direct treatment and monitor treatment and disease progression.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Example 5: Identify Ionocytes from Airway Cell Sample

The airway epithelium of the mouse and the majority of the human airway epithelium is comprised of four major cell types: basal stem cells abutting the basement membrane, secretory detoxifying Clara cells, ciliated cells that propel mucous out of the respiratory tree, and goblet cells that respond to injury or inflammation and secrete the mucous. In mice, Clara cells are the predominant cell type in the tracheo-bronchial and bronchiolar epithelium of the conducting airways. In humans, Clara cells only reside in the bronchiolar epithelium while the predominant cell type of the conducting airways are the ciliated cells.

Figure 2:
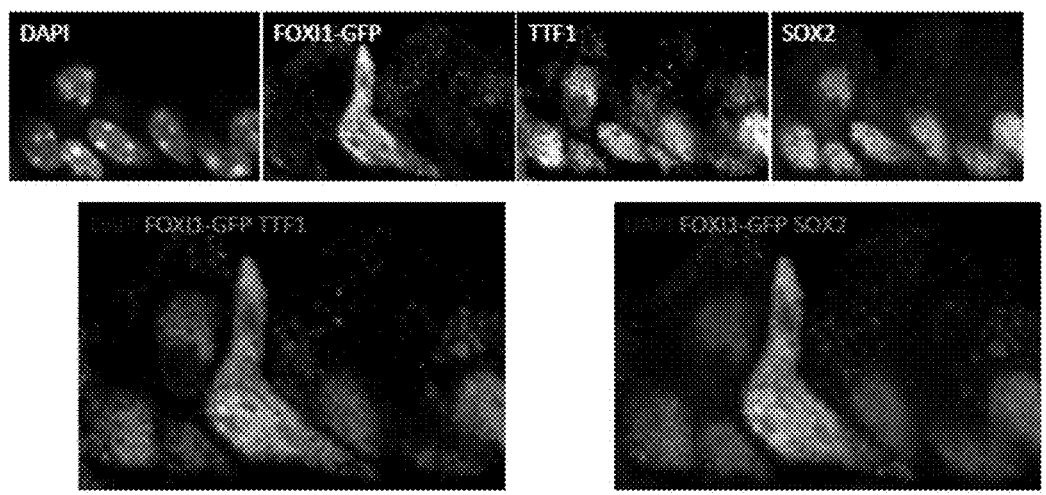
FIG. 2 shows the ionocytes are positive for Canonical Airway markers TTF1 and SOX2. The same ionocyte is co-stained with FOXI1-GFP (green) and TTF1 (pink), and with FOXI1-GFP (green) and SOX2 (pink).
Figure 3:
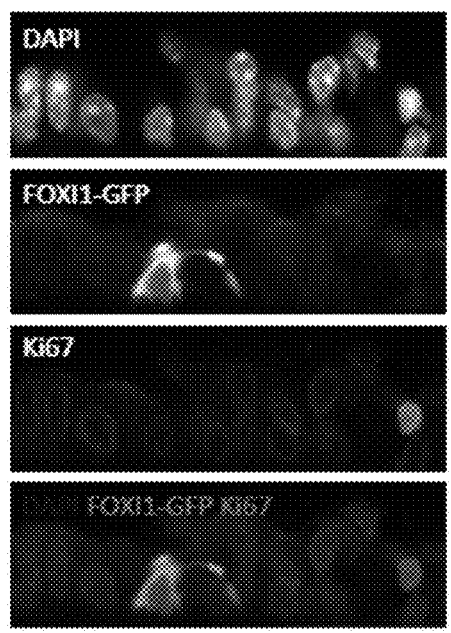
FIG. 3 shows some ionocytes are not proliferative upon Ki67 expression. The same ionocyte is co-stained with FOXI1-GFP (green) and Ki67 (pink).
Figure 4:
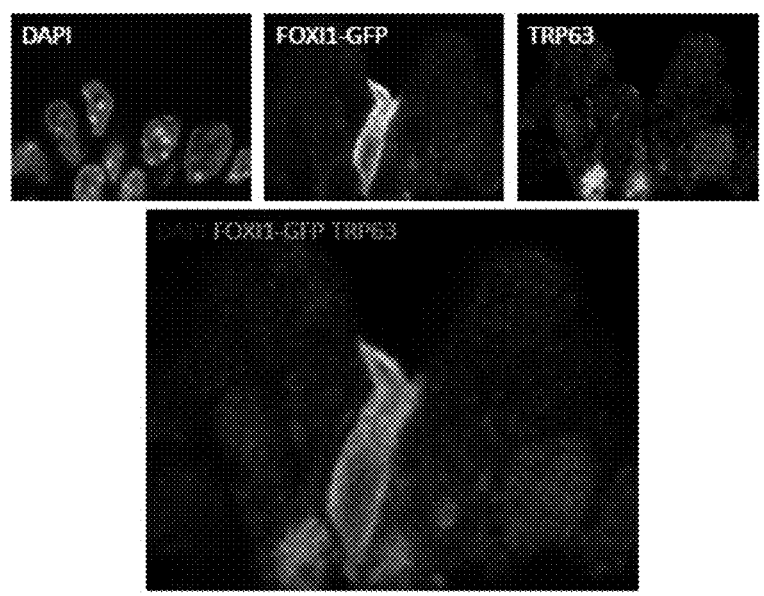
FIG. 4 shows some ionocytes that are mostly p63 negative. The same ionocyte is co-stained with FOXI1-GFP (green) and TRP63 (pink).
Figure 5:
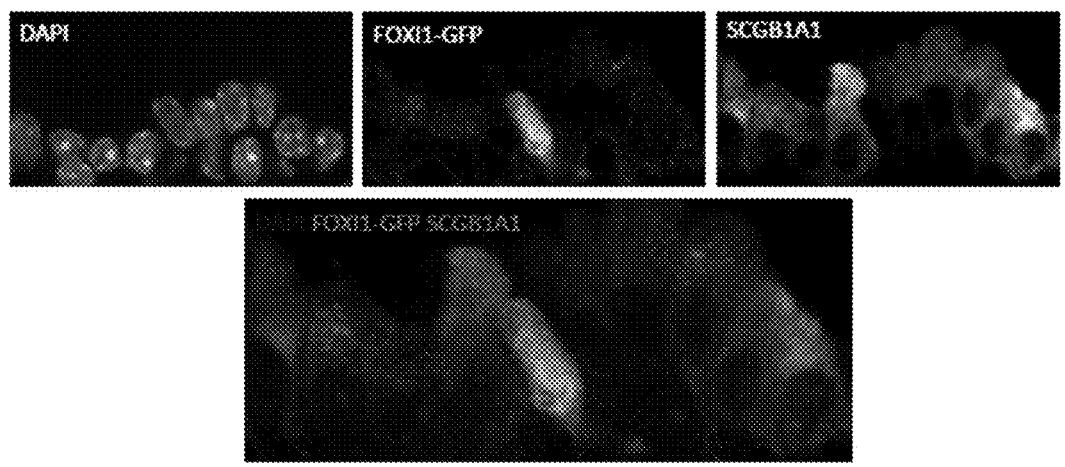
FIG. 5 shows some ionocytes that are SCGB1A1 negative. The same ionocyte is co-stained with FOXI1-GFP (green) and SCGB1A1 (pink).
Figure 6:
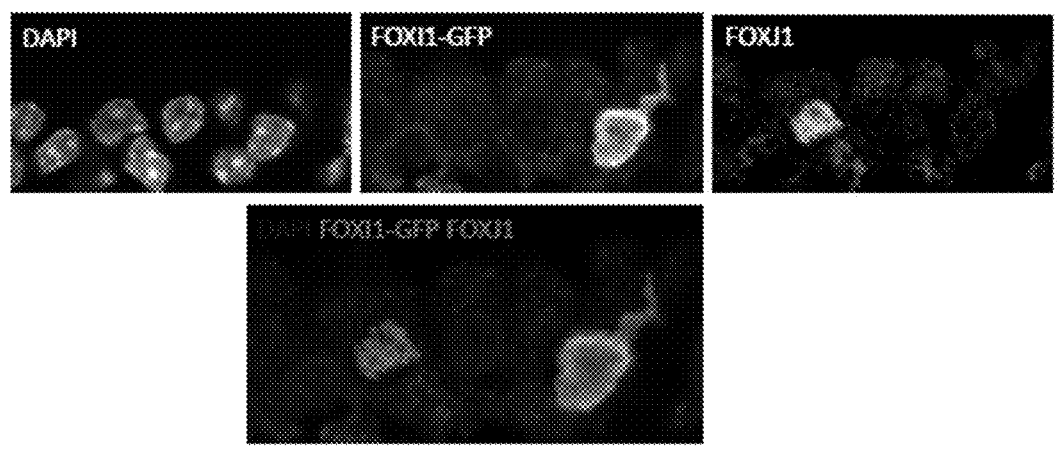
FIG. 6 shows some ionocytes are FOXJ1 negative. The same ionocyte is co-stained with FOXI1-GFP (green) and FOXJ1 (pink).
Figure 7:
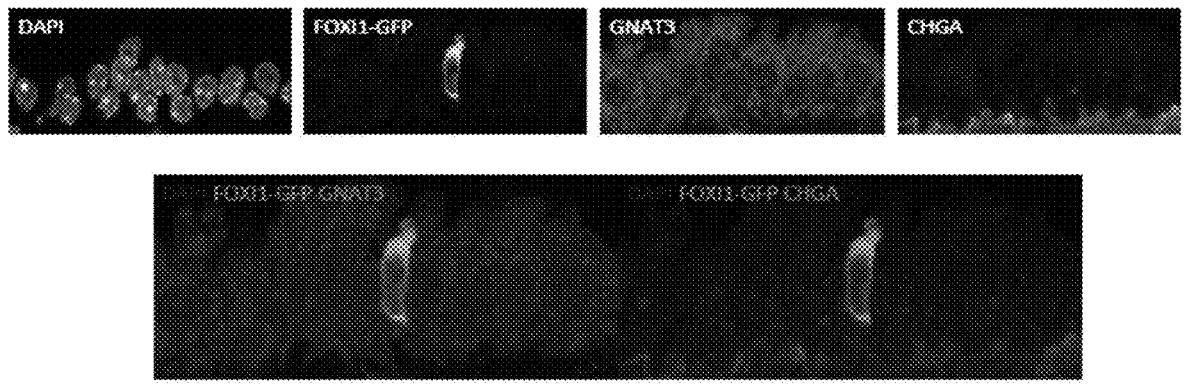
FIG. 7 shows some ionocytes are CHGA and GNAT3 (αGUS) negative. The same ionocyte is co-stained with FOXI1-GFP (green) and GNAT3 (pink), and with FOXI1-GFP (green) and CHGA (pink).

Using single cell RNA sequencing and clustering, the present inventors identified ionocytes in the airway epithelium using FOXI1 and CFTR as cell markers. The respiratory epithelial ionocytes have lineage from basal stem cells, and were found in the human bronchus. It was also found that in addition to FOXI1 and CFTR (FIGS. 1 and 12-15), other genes including FOXI2, ASCL3, V-Type Proton ATPase, PPARG, Cochlin and STAP2 are upregulated in ionocytes. It was further confirmed that Notch1, Notch2, Jag1, Dll1, Dll2 and Jag2 are the effectors in ionocyte specification. Exemplary ionocytes were also shown to be positive for canonical airway markers TTF1 and SOX2 (FIG. 2). FIG. 3 shows that under some conditions ionocytes are not proliferative upon Ki67 expression. Other exemplary ionocytes were negative for p63 (FIG. 4), SCGB1A1 (FIG. 5), FOXJ1 (FIG. 6), CHGA (FIG. 7), and GNAT3 (FIG. 7).

Figure 8:
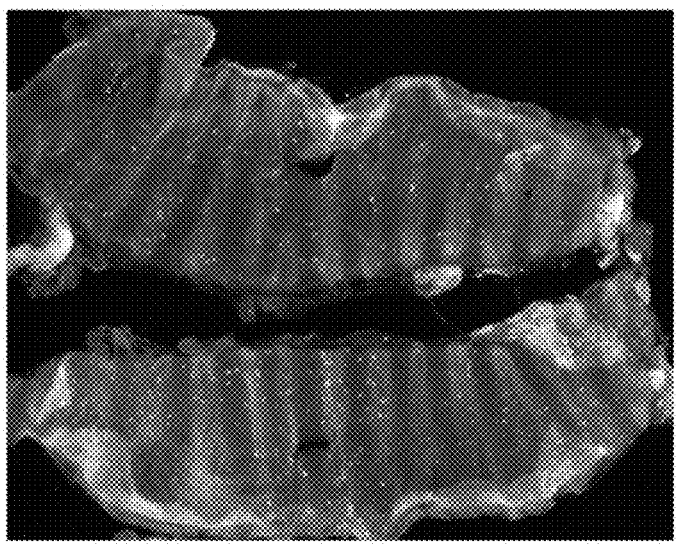
FIG. 8 shows the abundance and localization of ionocytes in the trachea.
Figure 9:
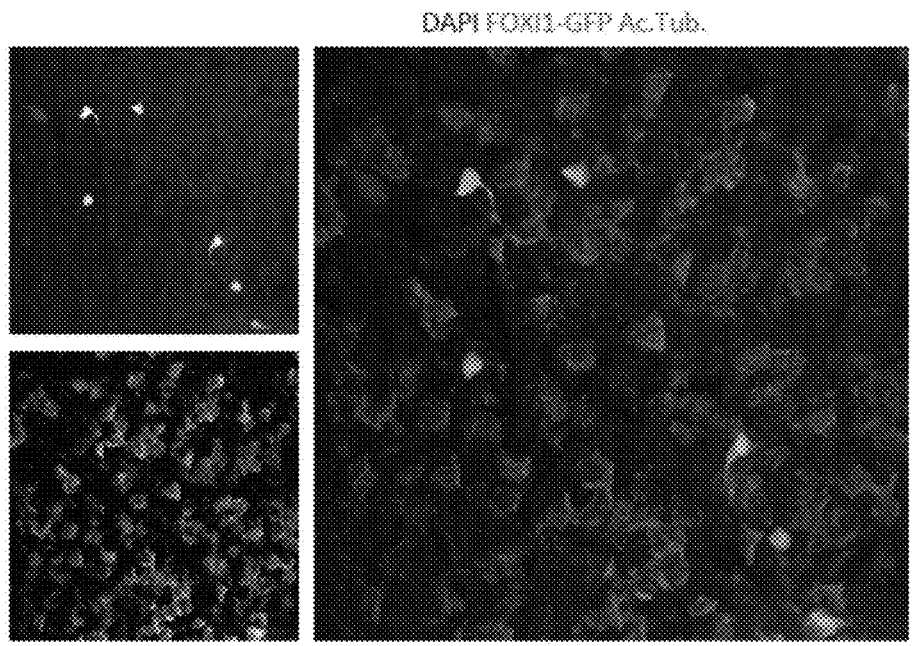
FIG. 9 shows the abundance and localization of ionocytes by co-staining with FOXI1-GFP (green) and Ac.Tub (pink).
Figure 10:
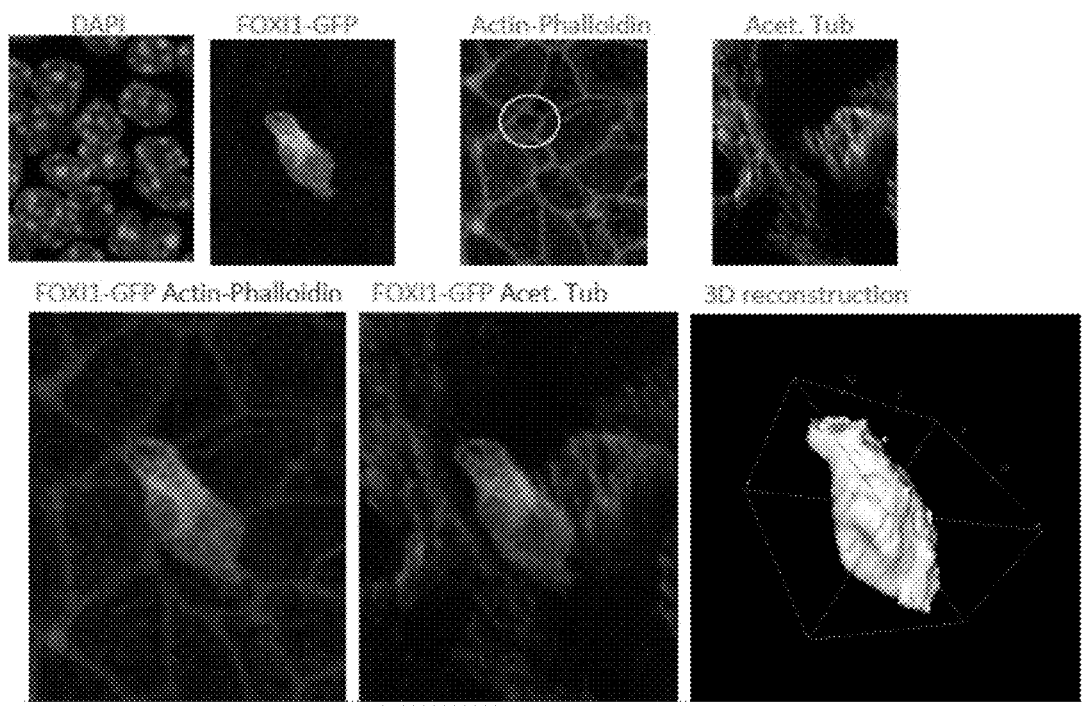
FIG. 10 shows ionocyte morphologies by co-staining the ionocyte with FOXI1-GFP (green) and Actin-Phalloidin (pink), with FOXI1-GFP (green) and Acet. Tub (pink), and by 3D-reconstruction.
Figure 11:
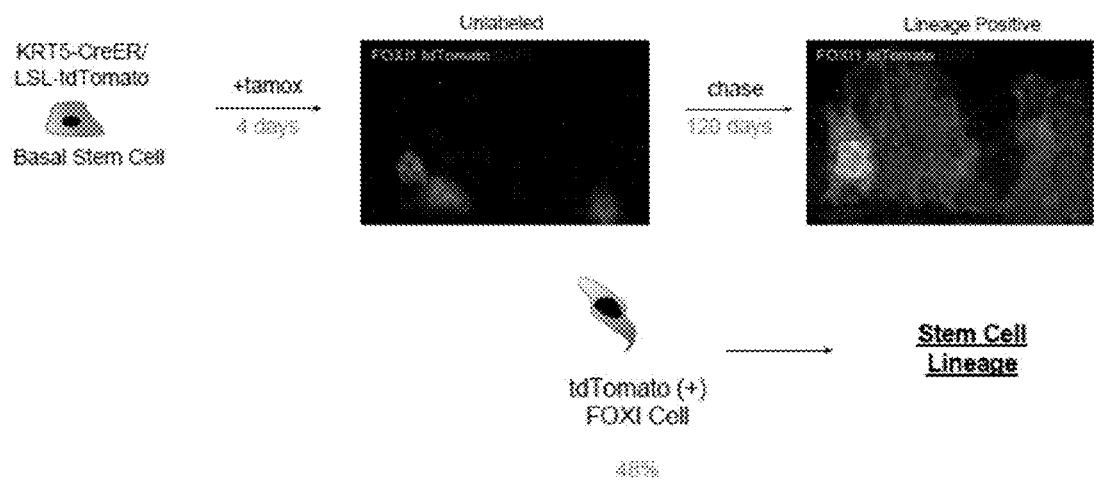
FIG. 11 shows the development lineage of ionocytes from basal stem cells.
Figure 12:
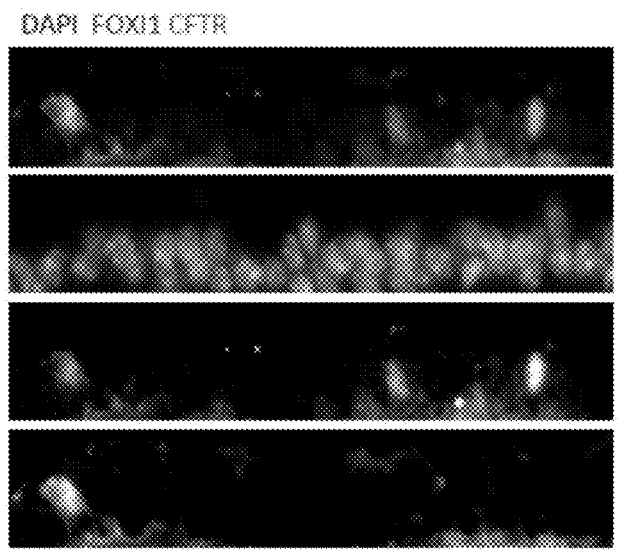
FIG. 12 shows ionocytes expressing CFTR by co-staining with FOXI1-GFP (green) and CFT1 (pink).
Figure 13:
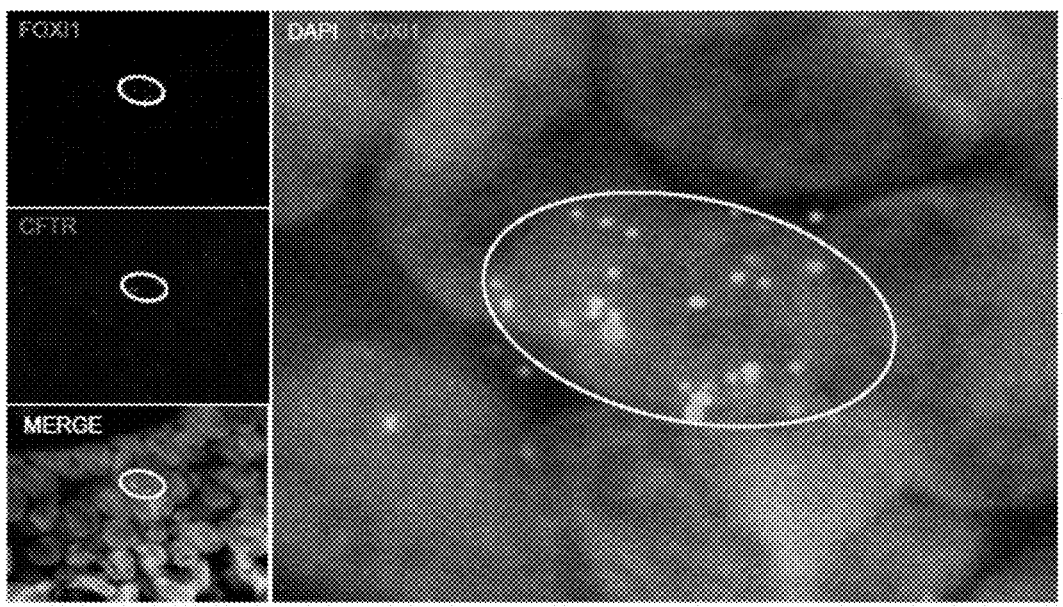
FIG. 13 shows that ionocytes exist in human bronchus by co-staining with FOXI1 (green) and CFTR (pink).
Figure 14A:
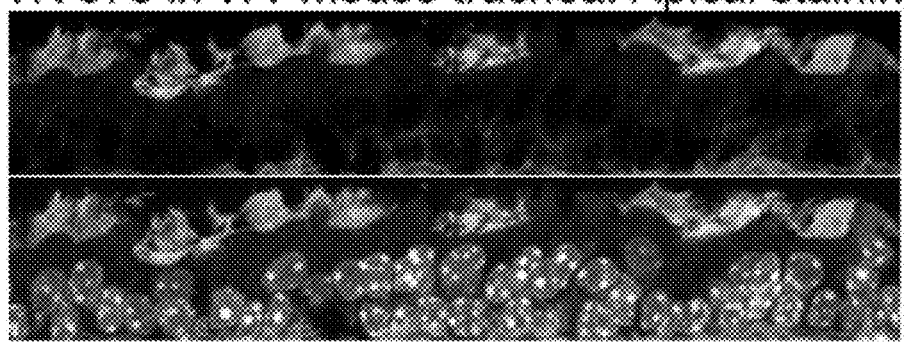
FIG. 14 shows CFTR expression in wild-type mouse trachea (FIG. 14A) and knock-out mouse trachea (FIG. 14B) by apical staining.
Figure 14B:
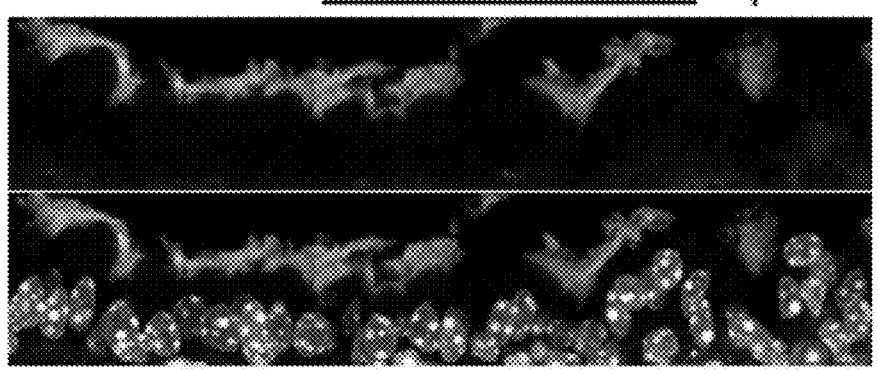
Figure 15:
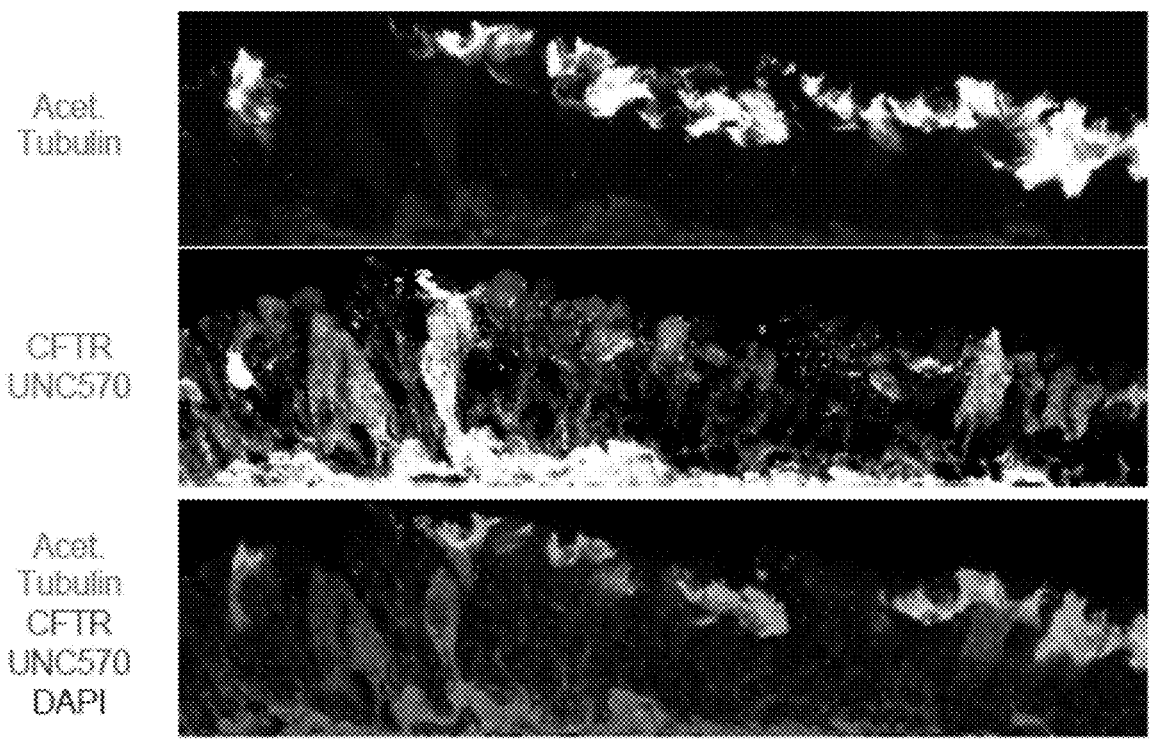
FIG. 15 shows CFTR expression in wild-type mouse trachea by cellular staining.

Other experiments showed that ionocytes can be localized to various regions of the gastrointestinal tract, such as the trachea (FIG. 8), and they can develop from basal stem cells (FIG. 11). Abundance and morphology of ionocytes in the respiratory tract are shown in FIGS. 9-10.

The ionocyte cell is functionally characterized by electrophysiology studies. In particular, transepithelial electrical potential and a series of current activation are applied, and the activated membrane conductance is measured. The specific type of ion channel can be determined by this study.

Cell surface markers are further identified, and which can be used to isolate ionocytes, for example by fluorescence activated cell sorting. An Exemplary procedure is summarized below:

Cells are prepared as a single cell at approximately $1\times10^7$ cells/ml suspended in ice cold PBS with 10% FBS (Invitrogen, Carlsbad, CA, USA) and 1% sodium azide (Sigma, St. Louis, MO, USA) just prior to indirect immunofluorescence staining for surface markers, and are counted using a hemocytometer to determine total cell number. For each marker, 100 μl of cell suspension is added to a 1.5 ml centrifuge tube. 2 μg/ml of each primary antibody (e.g. ms IgG anti-CD34 and rb IgG anti-CD 105, Abcam, Cambridge, MA, USA) in 3% BSA/PBS is added to the suspension. The cells are incubated for 30 min at 4° C. in the dark. Cells are then washed thrice by centrifugation at 200 g for 5 min and resuspend again in ice-cold PBS. The fluorescently labeled secondary antibody is prepared in 3% BSA/PBS at the indicated concentration (e.g. 1 g/ml of AlexaFluor 488-labeled donkey anti-mouse IgG and 2 g/ml AlexaFluor 568-labeled donkey anti-rabbit IgG, Invitrogen) and incubate for 30 min at 4° C. The cells are washed three times in PBS by centrifugation at 200 g for 5 min and resuspended in ice cold 3% BSA/PBS with 1% sodium azide and stored in the dark for sorting. The isolated ionocytes are cultured under aseptic, mammalian cell culture condition in appropriate media.

The inventors have demonstrated for the first time that ionocytes exist in the respiratory tract and can be characterized using markers. The identification and isolation of ionocytes provides new therapeutic strategies for treating inflammatory lung disease.

Example 6: Treatment of Inflammatory Lung Disease

Isolated ionocytes from EXAMPLE 5 are combined with a scaffold and implanted into the lung or airway of a patient who has been diagnosed with inflammatory lung disease, for example, cystic fibrosis. A pharmaceutically effective amount of the ionocytes is used. A control group of patients are implanted with scaffold only. Analysis is conducted to compare the treated group with the control group in terms of their disease progression. One way of assessing disease progression in inflammatory lung disease patient is by change in lung function.

For example, the primary efficacy endpoint is measured by FEV1 (L), from baseline to Week 24 end point. Secondary efficacy endpoints include the following: time to first pulmonary exacerbation during the 24-week placebo-controlled treatment period; incidence of pulmonary exacerbations during the 24-week placebo-controlled treatment period; number of pulmonary exacerbations/time at risk (incidence density) during the 24-week placebo-controlled treatment period; change in lung function, as measured by FEV1 (L) from baseline to Weeks 4 and 12, and FVC (L) and FEF 25%-75% (L/sec) from baseline to Weeks 4, 12, 24, and the end point. Other secondary efficacy endpoints include incidence of IV antibiotic use during the 24-week placebo-controlled treatment period; number of days of IV antibiotic use during the 24-week placebo-controlled treatment period; incidence of new use of antipseudomonal antibiotics during the 24-week placebo-controlled treatment period; incidence of hospitalizations/ER visits for a respiratory-related complaint during the 24-week placebo-controlled treatment period; number of days spent in the hospital for a respiratory-related complaint during the 24-week placebo-controlled treatment period; changes from baseline to Weeks 12 and 24 in Health-related Quality of Life and the Feeling Thermometer; and changes in utility assessment from baseline to Weeks 12 and 24 as measured by the Health Utilities Index; number of days lost from work or school during the 24-week placebo-controlled treatment period; and responses at Week 24 to the Patient Questionnaire.

Example 7: Treatment of Inflammatory Lung Disease with a Modulating Agent of Ionocyte Gene therapy is used to increase FOXI1 expression in the respiratory epithelium of a patient who has been diagnosed with inflammatory lung disease.

A derivative of human adenovirus serotype 5 (described in Smith, et al., (1997) Circulation 96:1899-1905) is used as the source of viral DNA backbone vector. Specifically, the vector contains a deletion of base pairs 355 to 3325 to eliminate E1a and E1b functions, a deletion of base pairs 3325 to 4021 to eliminate protein IX function and a deletion of base pairs 28592 to 30470 to eliminate E3 functions. See Wills, et al. (1994) Human Gene Therapy 5:1079-1088. A cDNA encoding human FOXI1 is isolated from a FOXI1 Human cDNA Clone plasmid (e.g., plasmid NM 144769 obtainable from OriGene Rockville, MD). The FOXI1 cDNA is inserted into recombinant adenoviruses using standard cloning methods to generate the FOXI1 viral vector.

The FOXI1 viral vector is administered to a patient who has been diagnosed with inflammatory lung disease, for example, cystic fibrosis. A pharmaceutically effective amount of the FOXI1 viral vector is administered by means of aerosol delivery. A control group of patients are treated with a placebo aerosol formulation. Analysis is conducted to compare the treated group with the control group in terms of their disease progression as described in EXAMPLE 6.

Example 8: Treatment of Inflammatory Lung Disease by Reprogramming Cells to Ionocyte Induced pluripotent stem cells are generated from a patient who has been diagnosed with inflammatory lung disease as described in Takahashi, K. et al. Induction of pluripotent stem cells from adult human fibroblasts by defined factors. Cell 131, 861-872 (2007). Briefly, dermal fibroblasts are obtained from the patient and are transduced with retroviruses expressing Oct3/4, Sox2, Klf4, and c-Myc. After approximately 4 weeks in culture, hES cell-like colonies are picked and mechanically disaggregated to obtain human iPSCs. The iPSCs are subsequently differentiated into patient specific airway epithelial cells as described in Wong et al. Nat Biotechnol. 2012 September; 30(9): 876-882 using a step-wise differentiation protocol and air-liquid interface conditions to promote differentiation. Ionocytes are identified and isolated from the differentiated cells using FACS analysis as described in EXAMPLE 5.

Isolated patient-derived ionocytes are combined with a scaffold as described in EXAMPLE 6 and implanted into the lung or airway of the patient. A control group of patients are implanted with the scaffold only. Analysis is conducted to compare the treated group with the control group in terms of their disease progression as described in EXAMPLE 6.

Example 9: Generating Ionocytes In Vitro from Human Primary Bronchial Epithelial Cells Using Air-Liquid-Interface (ALI) Culture Platform Human primary bronchial epithelial cells (PBEC) were cultured in a microfluidic culture system that maintains a dynamic air-liquid interface (ALI). The microfluidic culture system consists of 5 separate chambers that each houses a conventional Transwell®Blume et al., *PLoS One* 10(10): e0139872. Human primary bronchial epithelial cells were obtained by epithelial brushing using fiberoptic bronchoscopy from subjects selected from a volunteer database without any chronic airway diseases. All procedures were approved by the Southampton and South West Hampshire Research Ethics Committee and were undertaken following written informed consent. Filter supports with fully differentiated PBECs were inserted into the microfluidic culture system and perfused with basal medium at a flow rate of 30 μL/hr. As a static culture control, filter supports with fully differentiated PBECs were cultured in standard cell culture wells containing 500 μL of basal medium Procedures for culturing primary bronchial epithelial cells is described in Ghil et al., *Part Fibre. Toxicol.* (2013) 10:25. Specifically, human primary bronchial epithelial cells were expanded to passage-3 in bronchial epithelial growth medium (BEGM; Clonetics, San Diego, CA), plated on collagen-coated filters with a 0.4-micron pore size (Trans-CLR, Costar, Cambridge, MA) at a density of 1×105 cells/filter and inserted into 12 well culture plates (Ross A J, et al., *Am. J. Respir. Cell Mol. Biol.* (2007) 37:169-185 and Ghio A J et al., *Am. J. Physiol.* (1998) 274:L728-736). Cells were maintained in a 1:1 mixture of BEBM and Dulbecco's Modified Eagles Medium (DMEM) with high glucose, growth supplements, bovine pituitary extracts, bovine serum albumin, and nystatin. Fresh medium (0.5 mL in the apical chamber and 1.0 mL in the basal chamber) was provided every 48 hours. In those cells grown at ALI, the apical medium was removed (day 0). Submerged cells were continued with 0.5 mL in the apical chamber. With confluence of the cells, retinoic acid was added to the media to promote differentiation in cells grown both at ALI; submerged cells also received this supplement. The cells were maintained for 21 days allowing those grown at ALI to differentiate into ionocytes. Fresh medium was provided every 48 hours (1.0 mL in the basal chamber for those grown at ALT and 0.5 mL and 1.0 mL in the apical and basal chambers for those grown submerged).

Immunofluorescence staining: After fixation with 4% paraformaldehyde, cells were permeabilised with 0.1% Triton X-100, blocked with 1% BSA in PBS and stained with fluorescent-conjugated mouse anti-human COCH antibody. Subsequently, cells were washed extensively and mounted on slides using ProLong Gold antifade reagent with DAPI (Life technologies). Z-stacks were taken using LSM 6000 microscope (Leica Microsystems, Wetzlar, Germany). After deconvolution using Leica Application Suite software z-projections were performed using ImageJ software.

Figure 16:
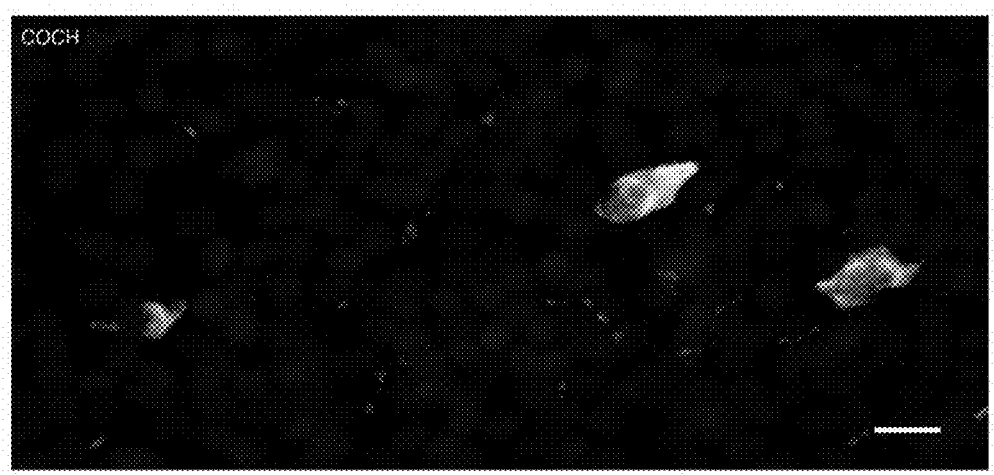
FIG. 16 shows ionocytes is generated in vitro from human primary bronchial epithelial cells using Air-Liquid-Interface culture platform. Ionocyte is stained with COCH (yellow).

As shown by immunofluorescence staining with COCH (FIG. 16), a marker for ionocytes, the differentiated human primary bronchial epithelial cells contain ionocytes. Therefore, ionocytes can be generated in vitro from human primary bronchial epithelial cells using Air-Liquid-Interface (ALI) culture platform.

Example 10: An Atlas of the Airway Epithelial Hierarchy Reveals CFTR-Expressing Ionocytes Introduction The airways are responsible for conducting oxygen from the atmosphere to the distal gas-exchanging alveoli, and are the locus of major diseases including asthma, COPD, and cystic fibrosis. The cells of epithelium include basal stem cells, secretory club cells, and ciliated cells that sweep debris out of the airway (Rock, J. R. et al. Basal cells as stem cells of the mouse trachea and human airway epithelium. *Proc. Natl. Acad. Sci. U.S.A.* 106, 12771-12775 (2009)). Rare cell types such as neuroendocrine (NE), goblet, and tuft cells have only recently been investigated, and their functions remain poorly understood. Diseases of the airway occur at distinct sites along the respiratory tree. Such localized disease presentations have been attributed to physical factors governing the deposition of inhaled particulates, toxins, smoke and allergens to particular regions of the airway (Nunn's Applied Respiratory Physiology—8th Edition. Available at: https://www.elsevier.com/books/nunns-applied-respiratory-physiology/lumb/978-0-7020-6295-7. (Accessed: 5 Apr. 2018)). An open question is whether disease heterogeneity is similarly a reflection of intrinsic cellular heterogeneity along the airway tree. Single-cell RNA-seq (scRNA-seq) opens the way to address these questions. Early scRNA-seq studies such as LungMAP (Ardini-Poleske, M. E. et al. LungMAP: The Molecular Atlas of Lung Development Program. *Am. J. Physiol. Lung Cell. Mol. Physiol.* 313, L733-L740 (2017)). have demonstrated the ability to probe epithelial cell-type diversity and lineage hierarchy (Treutlein, B. et al. Reconstructing lineage hierarchies of the distal lung epithelium using single-cell RNA-seq. *Nature* 509, 371-375 (2014)). in the developing lung. Here, Applicants combined massively-parallel single-cell RNA-seq and in vivo lineage tracing to study the cellular composition and hierarchy of the adult murine tracheal airway epithelium. Applicants now demonstrate that a finer comprehensive taxonomy of the cellular composition of this airway epithelium and its developmental hierarchies identifies new cell types, new developmental paths, and reframes the understanding of both cystic fibrosis, a prototypical Mendelian disease, and a complex multigenic disease like asthma.

Results

A single-cell census reveals new disease-associated cell types

Figure 17A:
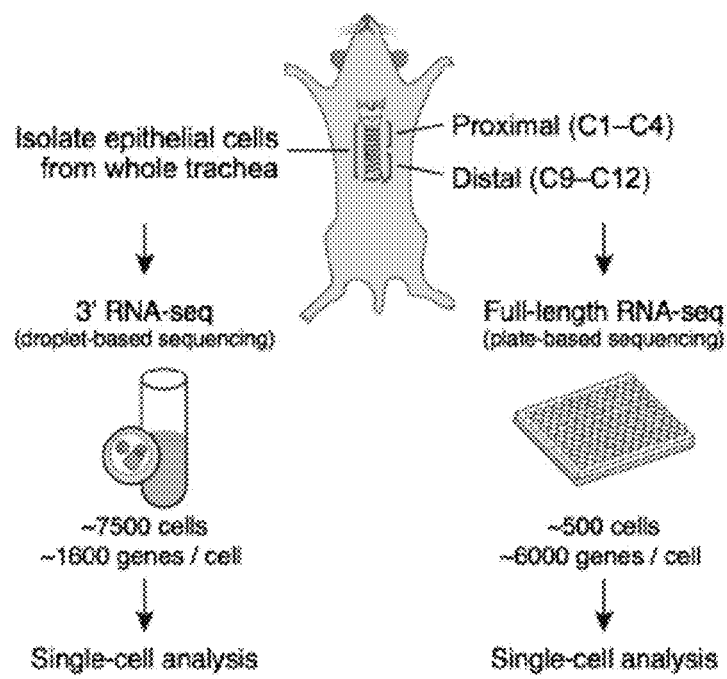
FIGS. 17A-17E show a single-cell expression atlas of tracheal epithelial cells. A. Schematic overview. Two complementary scRNA-seq methods used to create an atlas of the mouse tracheal epithelium. B. Cell type clusters. t-distributed stochastic nearest-neighbor embedding (tSNE) visualization of 7,193 3' scRNA-seq profiles. Single cells (points) are colored by their assignment to clusters (Methods; tSNE plot used for visualization only) and annotated post hoc (legend). Dashed circle: ionocyte cluster. C. Cell type clusters. Left: Pearson correlation coefficients (r, color bar) between every pair of 7,193 cells (rows and columns) ordered by cluster assignment (color bar, rows and columns). Inset (right): zoom of 288 cells from the rare types (black border on left). D. Gene signatures. Relative expression level (row-wise Z-score of $\log_2(TPM+1)$ expression values, color bar) of cell-type specific genes (rows) in each epithelial cell (columns). Large clusters (basal, club) are down-sampled to 500 cells. E. Cluster-specific transcription factors (TFs). Mean relative expression (row-wise Z-score of mean $\log_2(TPM+1)$, color bar) of the top TFs (rows) that are enriched (FDR<0.01, likelihood-ratio test) in cells (columns) of each cluster.
Figure 23A:
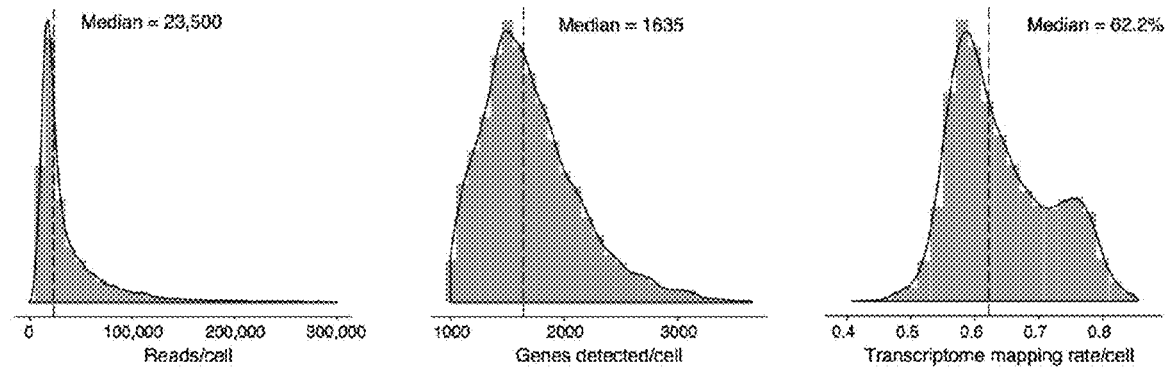
FIGS. 23A-23D show identifying tracheal epithelial cell types in 3' scRNA-seq. A. Quality metrics for the initial droplet-based 3' scRNA-seq data. Distributions (y axis) of the number of reads per cell (x-axis, left), the number of the genes detected with non-zero transcript counts per cell (x-axis, center), and the fraction of reads mapping to the mm10 transcriptome per cell (x-axis, right). Dashed and blue lines: median value and kernel density estimate, respectively. B. Cell type clusters are composed of cells from multiple biological replicates. Fraction of cells in each cluster that originate from a given biological replicate (color legend, bottom right, n=6 mice); post hoc annotation and number of cells are indicated above each pie chart. All biological replicates contribute to all clusters (except for WT mouse 1 which did not contain any of the very rare ionocytes), and no significant batch effect was observed. C. Reproducibility between biological replicates. Average gene expression values (log₂(TPM+1), x and y axes) across all cells of two representative 3' scRNA-seq replicate experiments (Pearson correlation coefficient, top left), blue shading: gene (point) density. D. Post hoc cluster interpretation based on the expression of known cell type markers[4]. tSNE of 7,193 scRNA-seq profiles (points), colored by cluster assignment (Methods, top left) or by the expression (log₂(TPM+1), color bar) of a single marker genes or the mean expression of several marker genes[4] for a particular cell type.

Applicants initially profiled 7,491 high quality individual airway EpCAM$^+$ epithelial cells from the tracheas of either C57BL/6 wild-type mice (n=4) or FOXJ1-GFP ciliated cell reporter mice (n=2; Methods), using two complementary single-cell approaches: massively parallel droplet-based 3' scRNA-seq (k=7,193 cells) and deeper, full-length scRNA-seq (k-301 cells) (FIG. 17A, Methods, FIG. 23A,C).

Figure 23B:
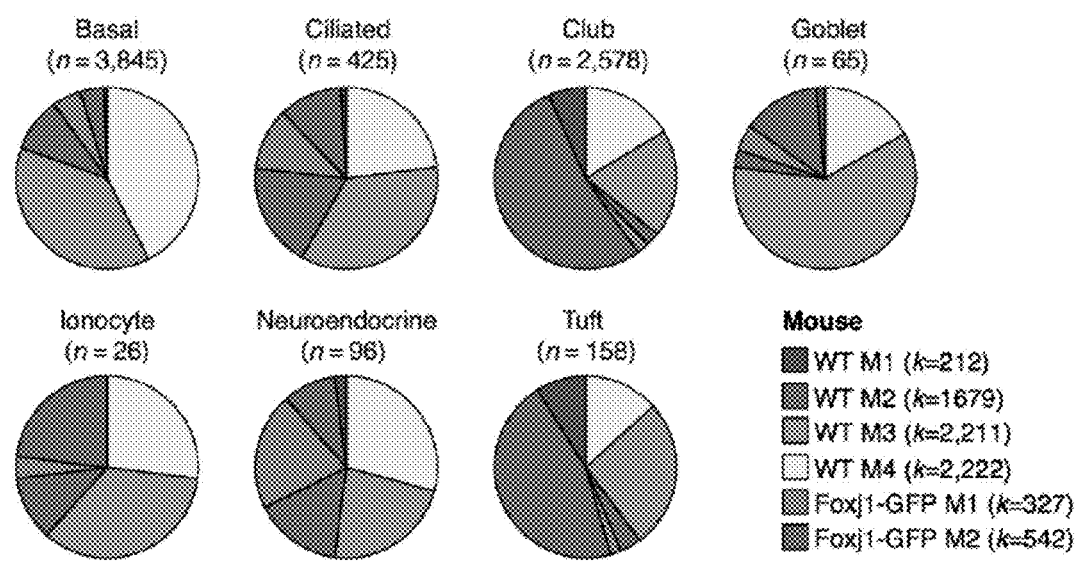
Figure 23C:
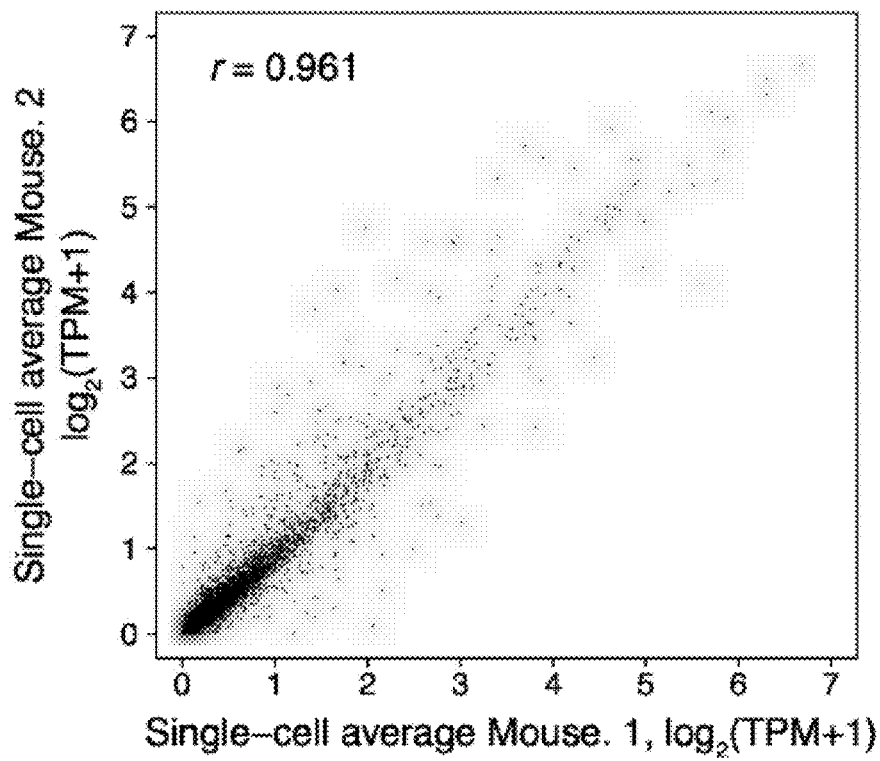
Figure 23D:
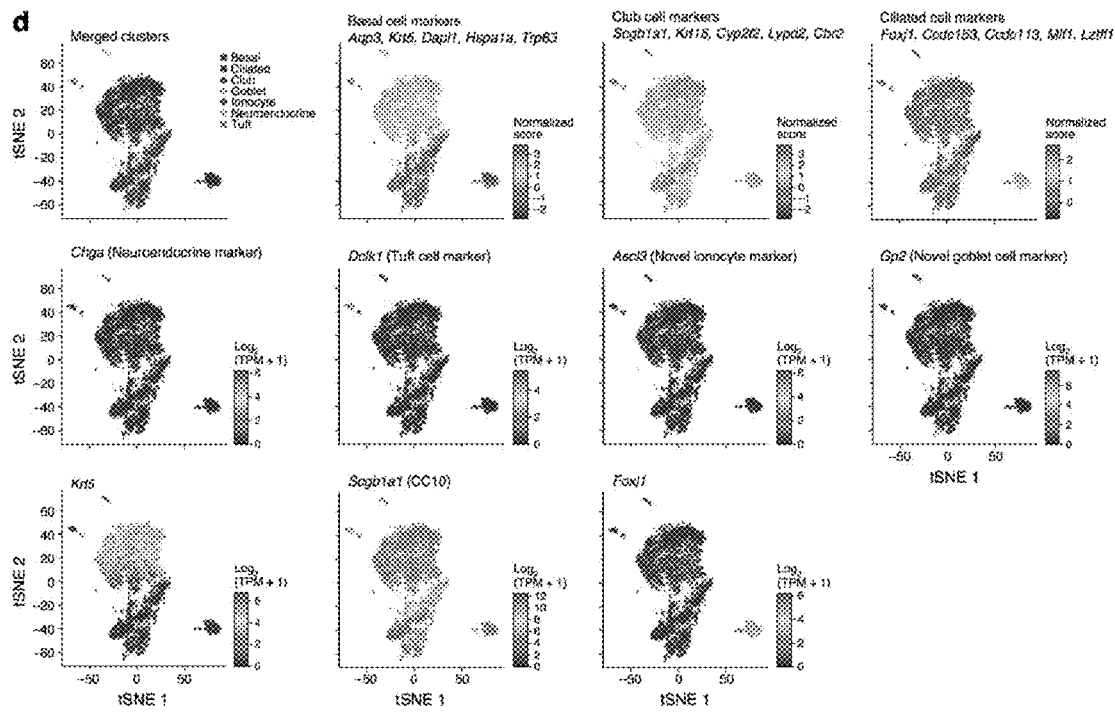
Figure 24A:
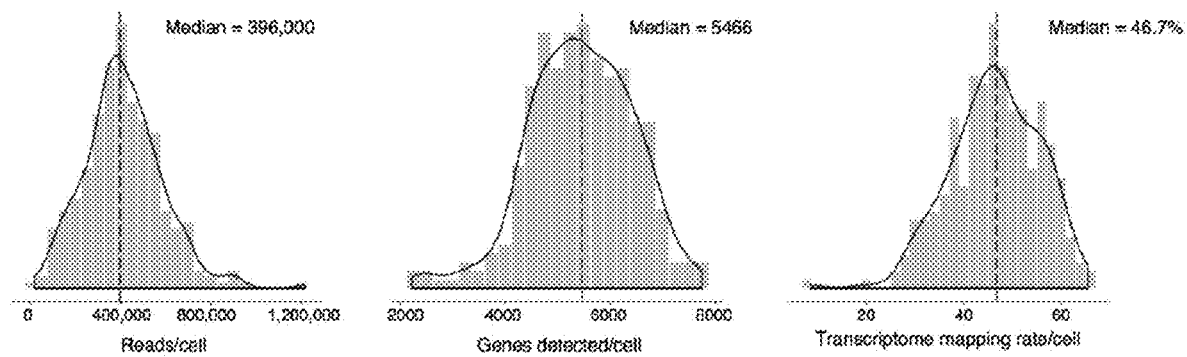
FIGS. 24A-24D show identifying tracheal epithelial cell types in full-length scRNA-seq. A. Quality metrics for full-length, plate-based scRNA-seq data. Distributions (y axis) of the number of reads per cell (x-axis, left), the number of the genes detected with non-zero transcript counts per cell (x-axis, center), and the fraction of reads mapping to the mm10 transcriptome per cell (x-axis, right). B,C. High reproducibility between plate-based scRNA-seq data from biological replicates of tracheal epithelial cells. Average expression values (x and y axes; log₂(TPM+1)) in two representative full-length scRNA-seq replicate experiments (left panel, x and y axes) and in the average of a full-length scRNA-seq dataset (right panel, x axis) and a population control (right panel, y axis) for cells extracted from proximal (B) and distal (C) mouse trachea. Blue shading: density of genes (points); r—Pearson correlation coefficient. D. Post hoc cluster annotation by the expression of known cell-type markers. tSNE of 301 scRNA-seq profiles (points) colored by region of origin (top left panel), cluster assignment (top second panel, Methods), or, for the remaining plots, the expression level (log₂(TPM+1), color bar) of a single marker genes or the mean expression of several marker genes[4] for a particular cell type. All clusters are populated by cells from both proximal and distal epithelium except rare NE cells, which were only detected in proximal experiments (top left panel).
Figure 24B:
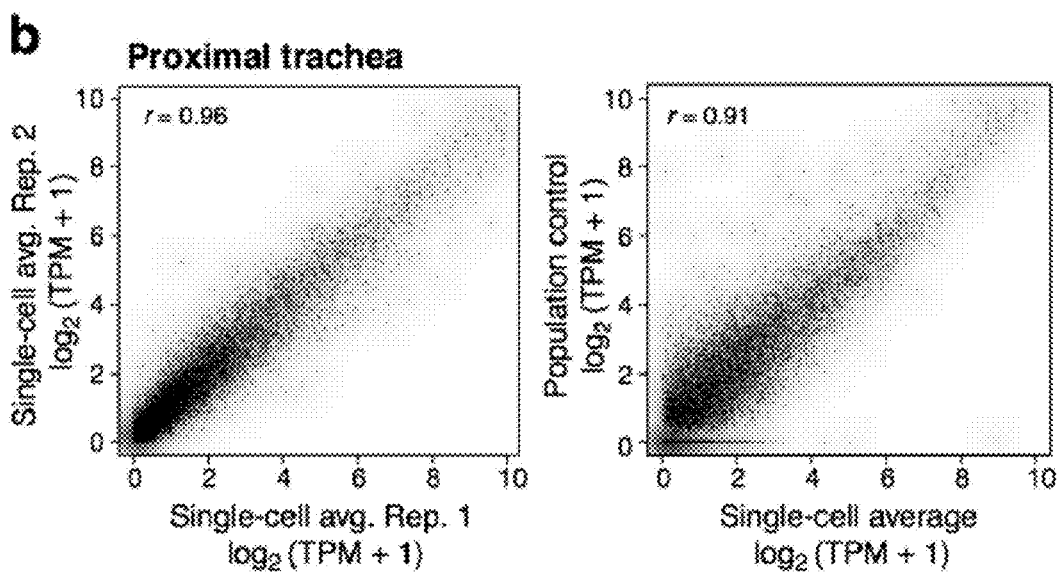
Figure 24C:
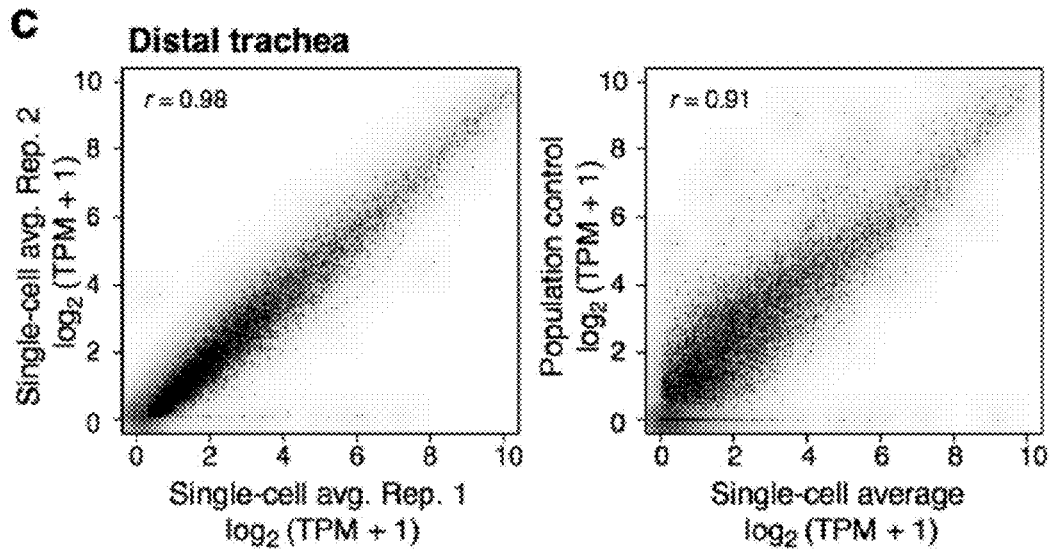
Figure 24D:
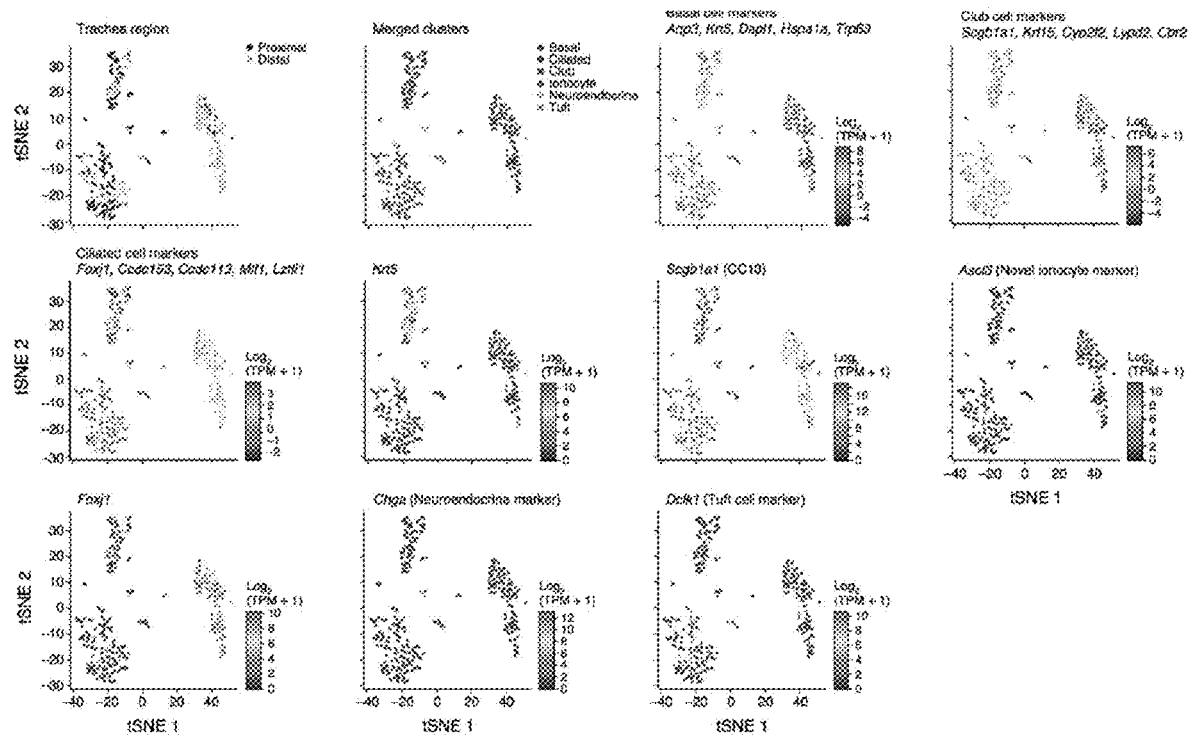
Figure 25A:
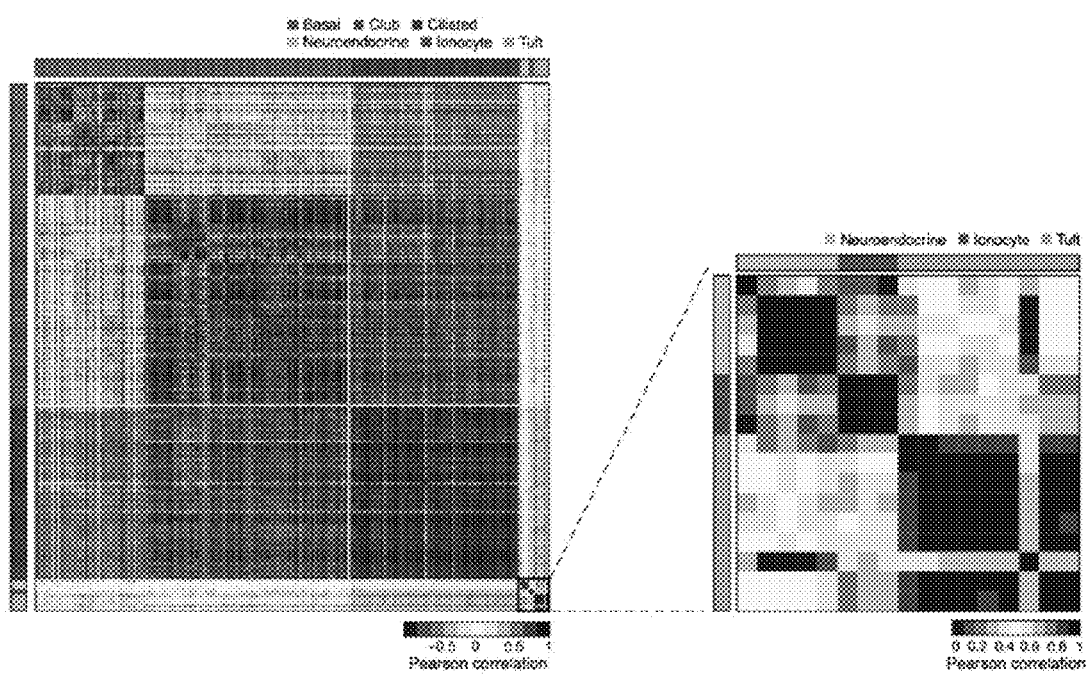

Applicants partitioned the cells into seven distinct clusters (Shekhar, K. et al. Comprehensive Classification of Retinal Bipolar Neurons by Single-Cell Transcriptomics. *Cell* 166, 1308-1323.e30 (2016); Rosvall, M. & Bergstrom, C. T. Maps of random walks on complex networks reveal community structure. *Proc. Natl. Acad. Sci. U.S.A.* 105, 1118-1123 (2008)) (FIG. 17B-D, Methods), annotated post-hoc by the expression of known marker genes (FIG. 23D). Each cluster mapped one-to-one with a distinct cell type: three known major cell types (basal, club, and ciliated), three known rare cell types (tuft, NE, and goblet cells), and one additional cluster (FIG. 17B), whose expression signature was distinct from any known airway epithelial cell type, suggesting that this may be a previously unrecognized population. Applicants termed this cell type the pulmonary ionocyte, because of a conserved expression pattern with ionocytes, specialized cells that function to regulate ion transport and pH in freshwater fish skin and gill epithelia, *Xenopus* skin, and the mammalian kidney and epididymis. All clusters contained cells from all mice (n=6, FIG. 23b), except for the goblet cell cluster (five of six mice) and the unannotated cluster of exceedingly rare (0.31%) cells (four of six mice). Applicants validated the assignment of each cell type cluster with high quality full-length scRNA-Seq (Picelli, S. et al. Full-length RNA-seq from single cells using Smart-seq2. *Nat. Protoc.* 9, 171-181 (2014)) of 301 EpCAM$^+$CD45$^-$ epithelial cells from tracheas of C57BL/6 wild-type mice (n=3; FIGS. 24 and 25A,B) obtained from either proximal (cartilage 1-4) or distal (cartilage 9-12) tracheal segments (FIG. 17A, FIG. 24D, top left). Applicants did not detect a distinct goblet cell cluster in this small dataset, consistent with their low frequency (0.85% of epithelial cells, FIGS. 24D and 25A,B).

Figure 17B:
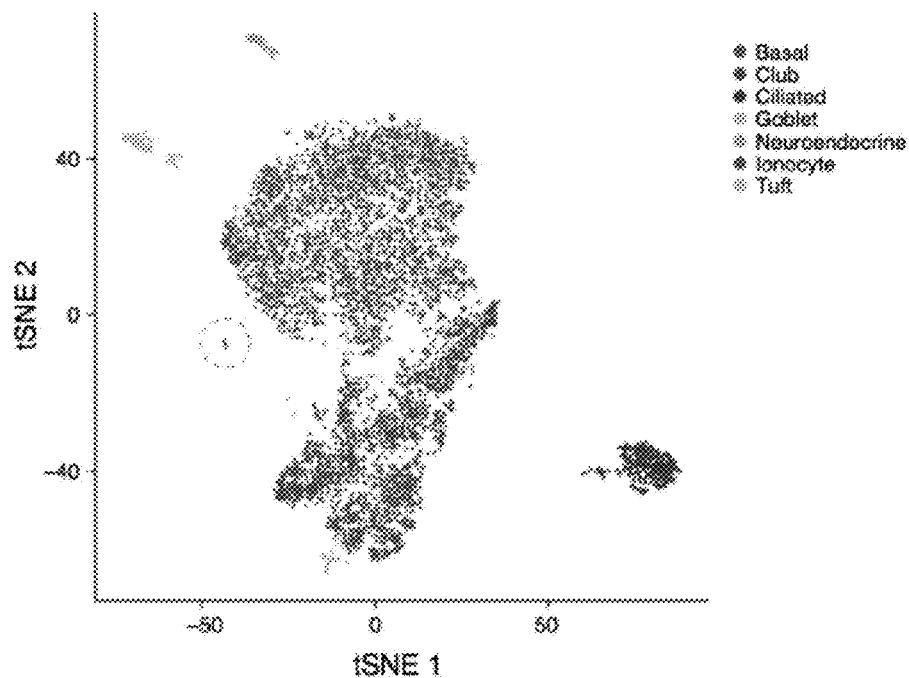
Figure 17C:
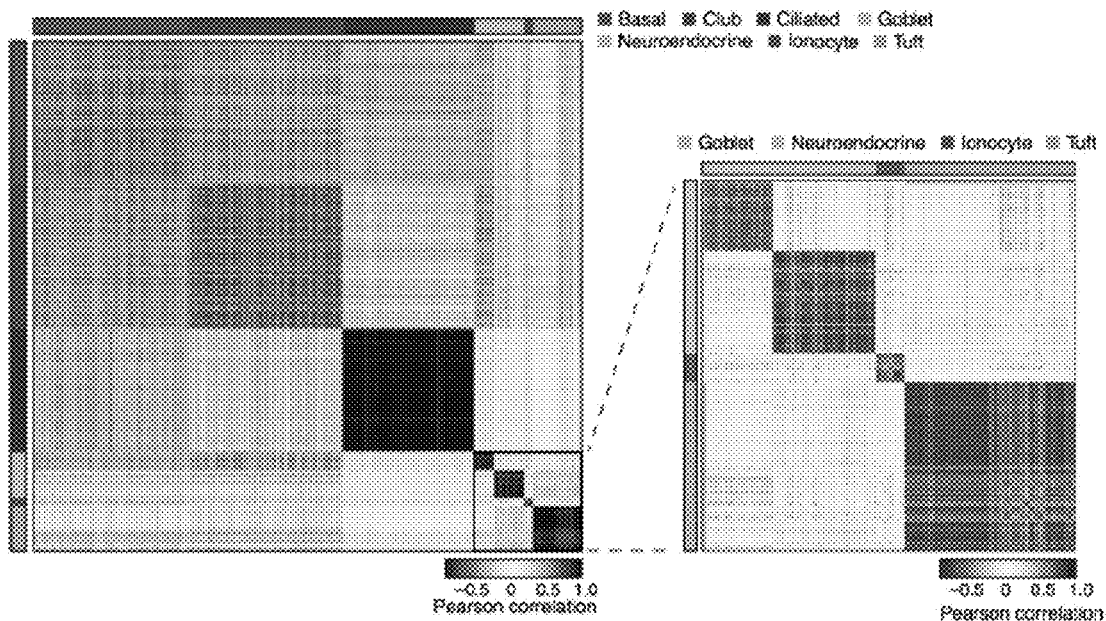
Figure 17D:
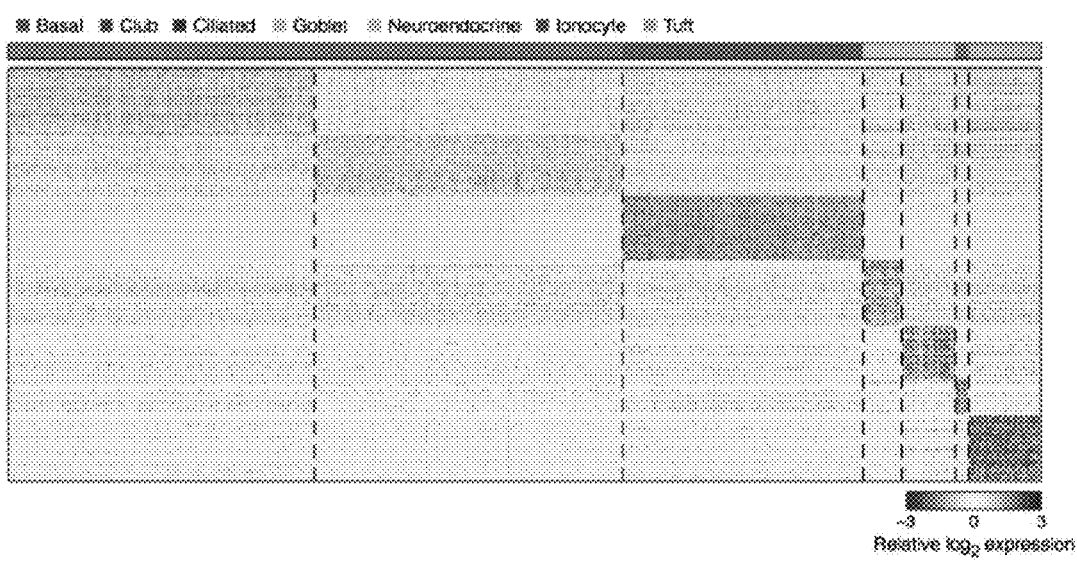
Figure 17E:
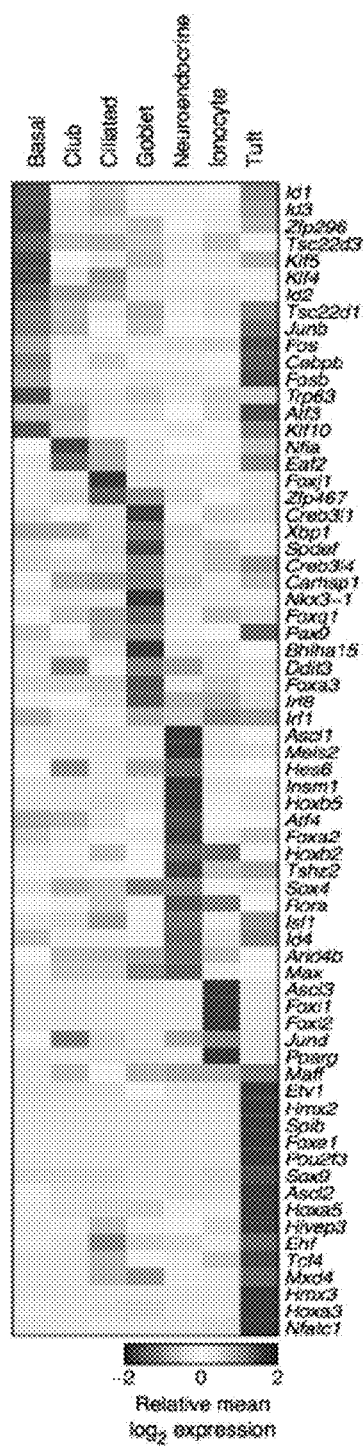
Figure 25B:
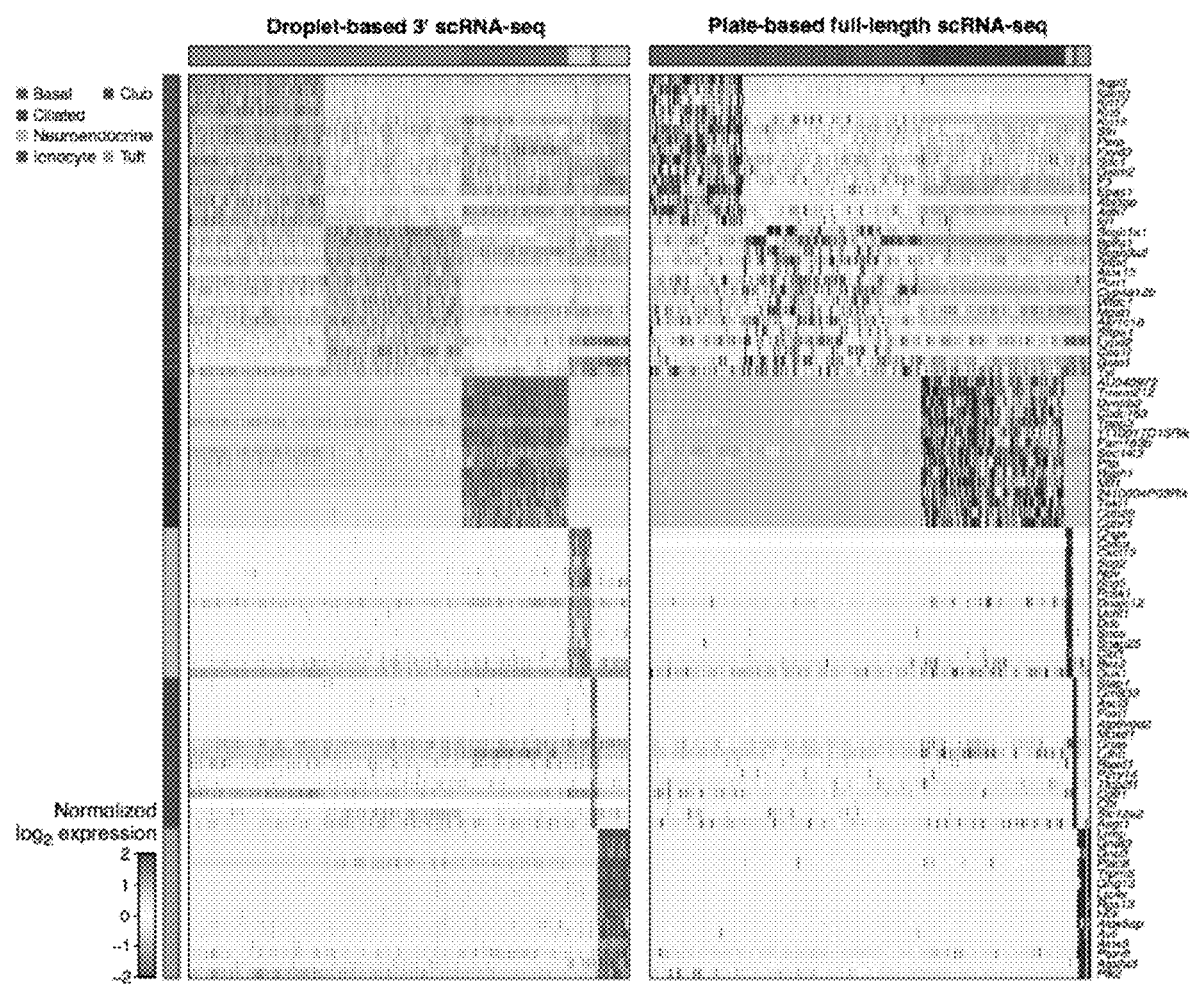

Applicants associated novel functions with rare cell types and highlighted new cell-type specific transcription factors (TFs) by defining cell-type specific expression signatures that are congruent between the two datasets (FDR<0.01, likelihood-ratio test, FIG. 17D,E, FIG. 25B). Basal cell-type specific TFs (FIG. 17E) included the canonical TF Trp63, as well as Klf4, Klf5, and Klf10, a family known to regulate proliferation and differentiation in epithelia (Ghaleb, A. M. et al. Krüppel-like factors 4 and 5: the yin and yang regulators of cellular proliferation. *Cell Res.* 15, 92-96 (2005)). In club cells, Applicants identify Nfia and Eaf2, which are the first TFs specifically associated with this cell type. Nfia is associated with the regulation of Notch signaling, which is required for club cell identity and maintenance (Pardo-Saganta, A. et al. Parent stem cells can serve as niches for their daughter cells. *Nature* 523, 597-601 (2015)). Ascl1, Ascl2, and Ascl3, which are also associated with Notch signaling (Sriuranpong, V. et al. Notch signaling induces rapid degradation of achaete-scute homolog 1. *Mol. Cell. Biol.* 22, 3129-3139 (2002); Moriyama, M. et al. Multiple roles of Notch signaling in the regulation of epidermal development. *Dev. Cell* 14, 594-604 (2008)), are specifically enriched the rare NE, tuft, and ionocyte cells, respectively (FDR<0.0001, likelihood-ratio test). Tuft cells also expressed the known intestinal tuft cell TF Pou2f3 (Gerbe, F. et al. Intestinal epithelial tuft cells initiate type 2 mucosal immunity to helminth parasites. *Nature* 529, 226-230 (2016)) along with novel TFs Foxe1 and Etv1. Ionocytes were marked by the expression of Foxi1 (Quigley, I. K., Stubbs, J. L. & Kintner, C. Specification of ion transport cells in the *Xenopus* larval skin. *Dev. Camb. Engl.* 138, 705-714 (2011)), whose ortholog is associated with ionocytes in *Xenopus*, as well as Foxi2. Finally, goblet cells specifically express the known goblet cell regulator Spdef; as well as Foxq1, which is essential for mucin gene expression and granule content in gastric epithelia (Verzi, M. P., Khan, A. H., Ito, S. & Shivdasani, R. A. Transcription factor foxq1 controls mucin gene expression and granule content in mouse stomach surface mucous cells. *Gastroenterology* 135, 591-600 (2008)).

Figure 25C:
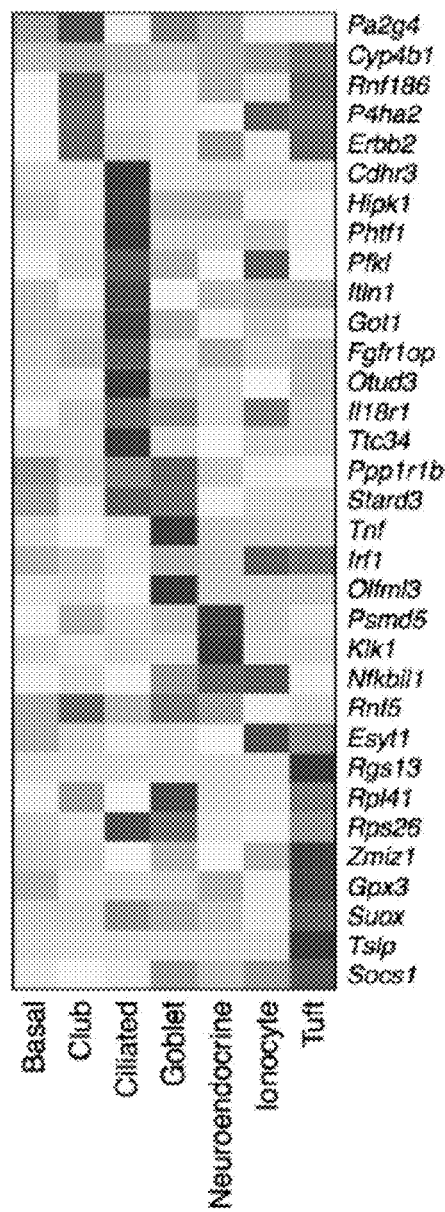

Some cell-type specific signature genes have previously been identified as risk genes in Genome-Wide Association Studies (GWAS) of asthma (Methods, FIG. 25C-E). For example, the asthma-associated genes Cdhr3 and Rgs13 (Li, M. J. et al. GWASdb v2: an update database for human genetic variants identified by genome-wide association studies. *Nucleic Acids Res.* 44, D869-876 (2016)) are specifically expressed in ciliated and tuft cells, respectively (FIG. 25C-E). Cdhr3 encodes a rhinovirus receptor and is associated with severe childhood asthma exacerbations (Bønnelykke, K. et al. A genome-wide association study identifies CDHR3 as a susceptibility locus for early childhood asthma with severe exacerbations. *Nat. Genet.* 46, 51-55 (2014), Bochkov, Y. A. et al. Cadherin-related family member 3, a childhood asthma susceptibility gene product, mediates rhinovirus C binding and replication. *Proc. Natl. Acad. Sci. U.S.A.* 112, 5485-5490 (2015)), suggesting that exacerbations may be precipitated by rhinovirus infection of ciliated cells. Rgs13 was associated with asthma and IgE-mediated mast cell degranulation (Bansal, G., Xie, Z., Rao, S., Nocka, K. H. & Druey. K. M. Suppression of immunoglobulin E-mediated allergic responses by regulator of G protein signaling 13. *Nat. Immunol.* 9, 73-80 (2008)); its specific expression in tuft cells (FIG. 25C-E), which play an immunomodulatory role in the intestines (Gerbe (2016); Von Moltke, J., Ji, M., Liang, H.-E. & Locksley, R. M. Tuft-cell-derived IL-25 regulates an intestinal ILC2-epithelial response circuit. *Nature* 529, 221-225 (2016); Howitt, M. R. et al. Tuft cells, taste-chemosensory cells, orchestrate parasite type 2 immunity in the gut. *Science* 351, 1329-1333 (2016)), suggests that they may also participate in driving asthmatic inflammation.

Figure 18A:
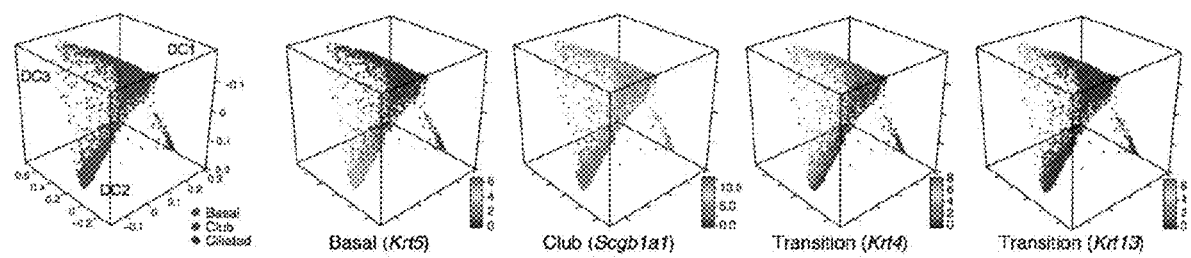
FIGS. 18A-18I show Krt13$^+$ club cell progenitors exhibit rapid turnover and are found in hillocks. A-B. Alternative putative developmental paths to club cells. Diffusion map embedding of 6,905 cells inferred to differentiate from basal (blue) to club (green) to ciliated (red) cells (Methods), colored by either cluster assignment (left) or expression ($\text{Log}_2(TPM+1)$, color bar) of specific genes (all other panels). B. Cell fate trajectories. Schematic of the number of individual cells associated with each cell fate trajectory (Methods). C-F. Krt13$^-$ cells occur in hillock structures. c. Whole-mount stain of Krt13 (magenta) and ciliated cell marker Acetylated tubulin (AcTub) shows the distribution of hillocks (which lack ciliated cells) throughout the trachea. D. Immunofluorescence stainings of Krt13 (green) and either basal (Trp63$^+$, solid white line top panel), suprabasal (Trp63$^+$, dashed white line top panel) or luminal (Scgb1a1$^+$, solid white line, bottom panel) markers (magenta, both panels), showing distinct strata of basal Trp63$^+$Krt13$^+$ cells and luminal Scgb1a1$^+$Krt13$^+$ cells. E. Hillocks are proliferative. Co-stain of EdU (magenta) and Krt13 (green). F. A schematic of hillocks within pseudostratified ciliated epithelium. G-I. Proximal vs. distal specific club cell expression. Relative expression level (row-wise Z-score, color bar) for genes (rows) enriched in proximal and distal tracheal club cells (FDR<0.05, likelihood-ratio test) in the full-length scRNA-seq data. H,I. Mucous metaplasia in distally-derived epithelia. H. Muc5ac (goblet cell stain) and AcTub (ciliated cell stain) levels in cultured epithelia from proximal (top) or distal (bottom) trachea stimulated with recombinant IL-13 (rIL-13, 25 ng/mL, right) vs. control (left). I. Goblet cell quantification (ln(Muc5ac$^+$/GFP$^+$ ciliated cells, y-axis) in Foxj1-GFP mice (n=6, dots) in each of four conditions in (H) (x-axis). p<0.01, *p<0.001, Tukey's HSD test, black bars: mean, error bars: 95% CI.
Figure 18B:
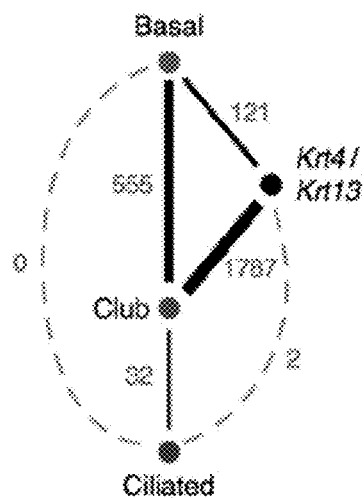
Figure 18C:
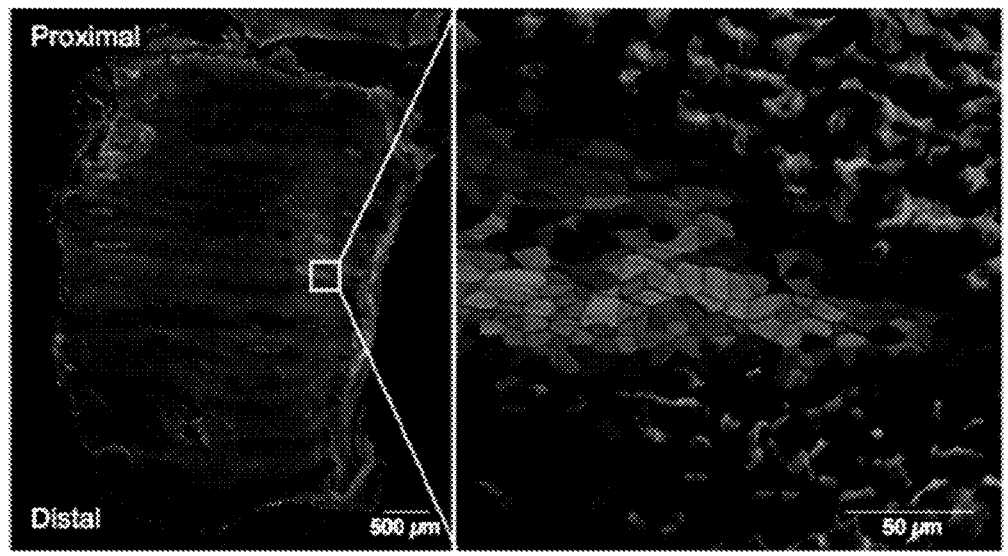
Figure 18D:
Figure 18D:
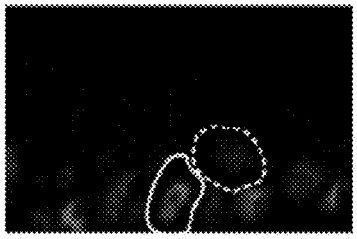
Figure 18D:
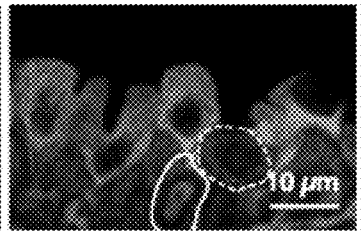
Figure 18D:
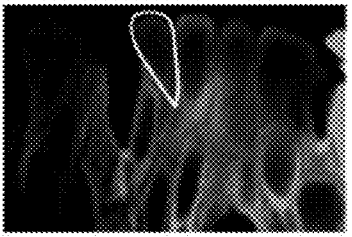
Figure 18D:
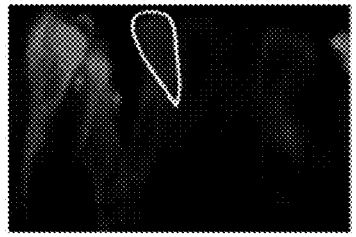
Figure 18D:
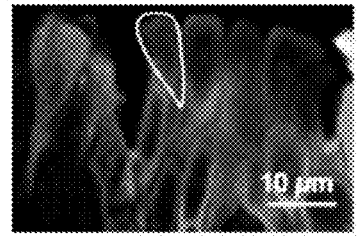
Figure 18E:
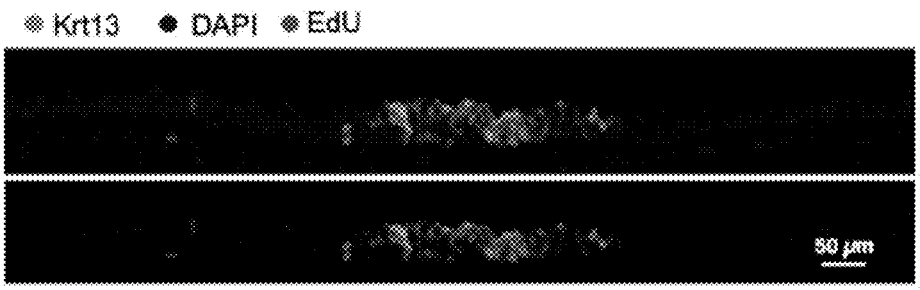
Figure 18F:
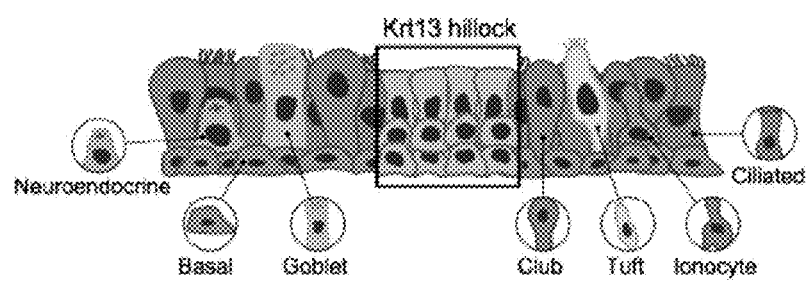
Figure 18G:
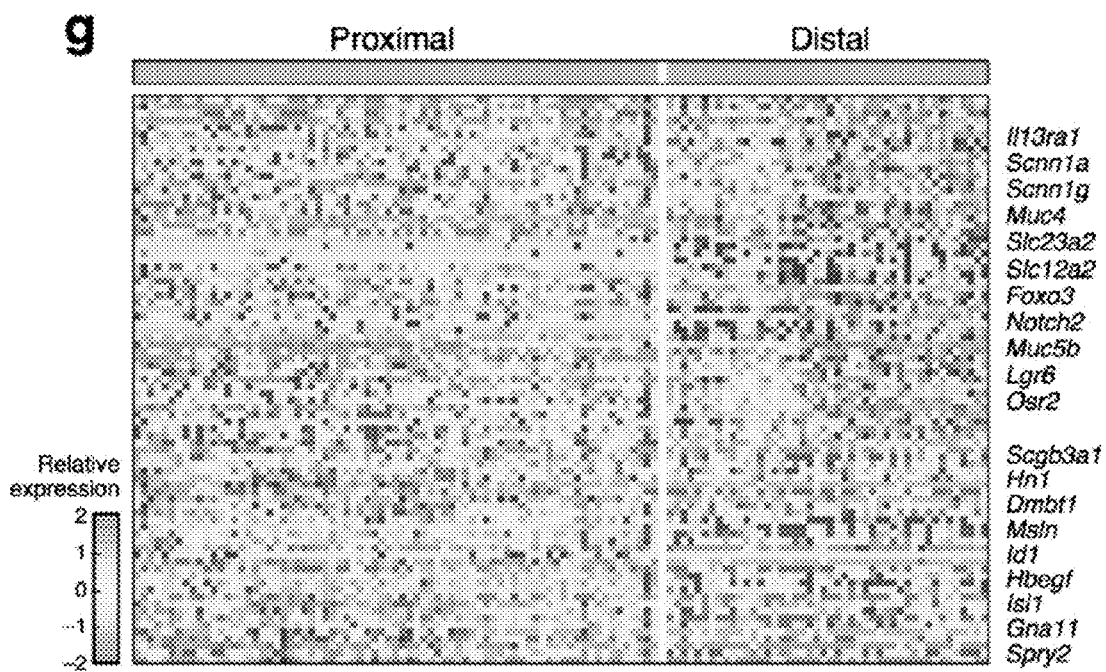
Figure 18H:
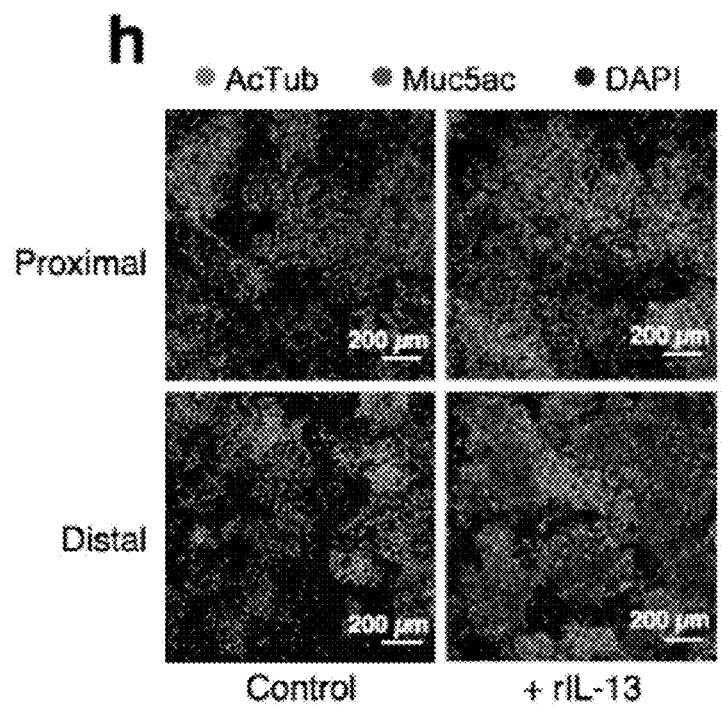
Figure 18I:
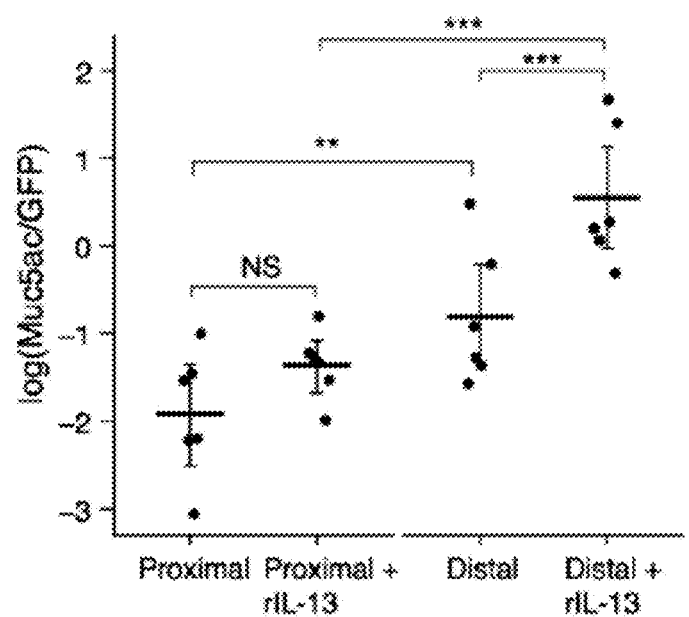

Some cell-type specific expression programs also vary along the proximodistal axis of the airway tree, mirroring the distribution of airway pathologies. In mouse, mucous metaplasia (an excess of mucus-producing goblet cells) occurs more prominently in the distal versus proximal trachea, and is the identifying epithelial pathology of asthma (Warburton, D. et al. The molecular basis of lung morphogenesis. *Mech. Dev.* 92, 55-81 (2000)). Notch signaling is required for this mucous metaplasia in mouse models (Danahay, H. et al. Notch2 is required for inflammatory cytokine-driven goblet cell metaplasia in the lung. *Cell Rep.* 10, 239-252 (2015)). Applicants found that 105 genes are differentially expressed (FDR<0.05, Mann-Whitney U-test) between club cells of the proximal versus distal trachea (FIG. 18G). In particular, Muc5b (Roy, M. G. et al. Muc5b is required for airway defence. *Nature* 505, 412-416 (2014); Chen, Y., Zhao, Y. H. & Wu, R. In silico cloning of mouse Muc5b gene and upregulation of its expression in mouse asthma model. *Am. J. Respir. Crit. Care Med.* 164, 1059-1066 (2001)), Notch2, and Il13ra1 (Munitz, A., Brandt, E. B., Mingler, M., Finkelman, F. D. & Rothenberg, M. E. Distinct roles for IL-13 and IL-4 via IL-13 receptor alpha1 and the type II IL-4 receptor in asthma pathogenesis. *Proc. Natl. Acad. Sci. U.S.A.* 105, 7240-7245 (2008)), are all more prevalent in distal club cells, and all play known roles in mucous metaplasia. Indeed, when Applicants induced mucous metaplasia using recombinant murine IL-13 (rIL-13) in cultured proximal and distal airway epithelium, Applicants found a much higher induction of goblet cell differentiation in the distal epithelium, consistent with the increased expression of Il13ra1 in distal club cells (FIG. 18H,I, p<0.001, likelihood-ratio test).

A Novel Cell Population Organized in "Hillocks"

Cellular differentiation during adult tissue homeostasis in the trachea is an ongoing, asynchronous process. Applicants inferred trajectories of cell differentiation from pseudo-ordered putative transitional cells between the three common cell types (FIG. 18A,B FIGS. 26 and 27) using diffusion maps (Trapnell, C. et al. The dynamics and regulators of cell fate decisions are revealed by pseudotemporal ordering of single cells. *Nat. Biotechnol.* 32, 381-386 (2014); Bendall, S. C. et al. Single-cell trajectory detection uncovers progression and regulatory coordination in human B cell development. *Cell* 157, 714-725 (2014)). Applicants predicted which cells are in transition using curve fitting (Methods) and characterized gene programs and TFs that vary coherently along these trajectories (p<0.001, permutation test, Methods, Extended Data FIG. 5). For example, the expression of the novel club cell TF Nfia diminished while the ciliated cell TF Foxj1 increased along the inferred trajectory from club to ciliated cells (Extended Data FIG. 5h).

Figure 26A:
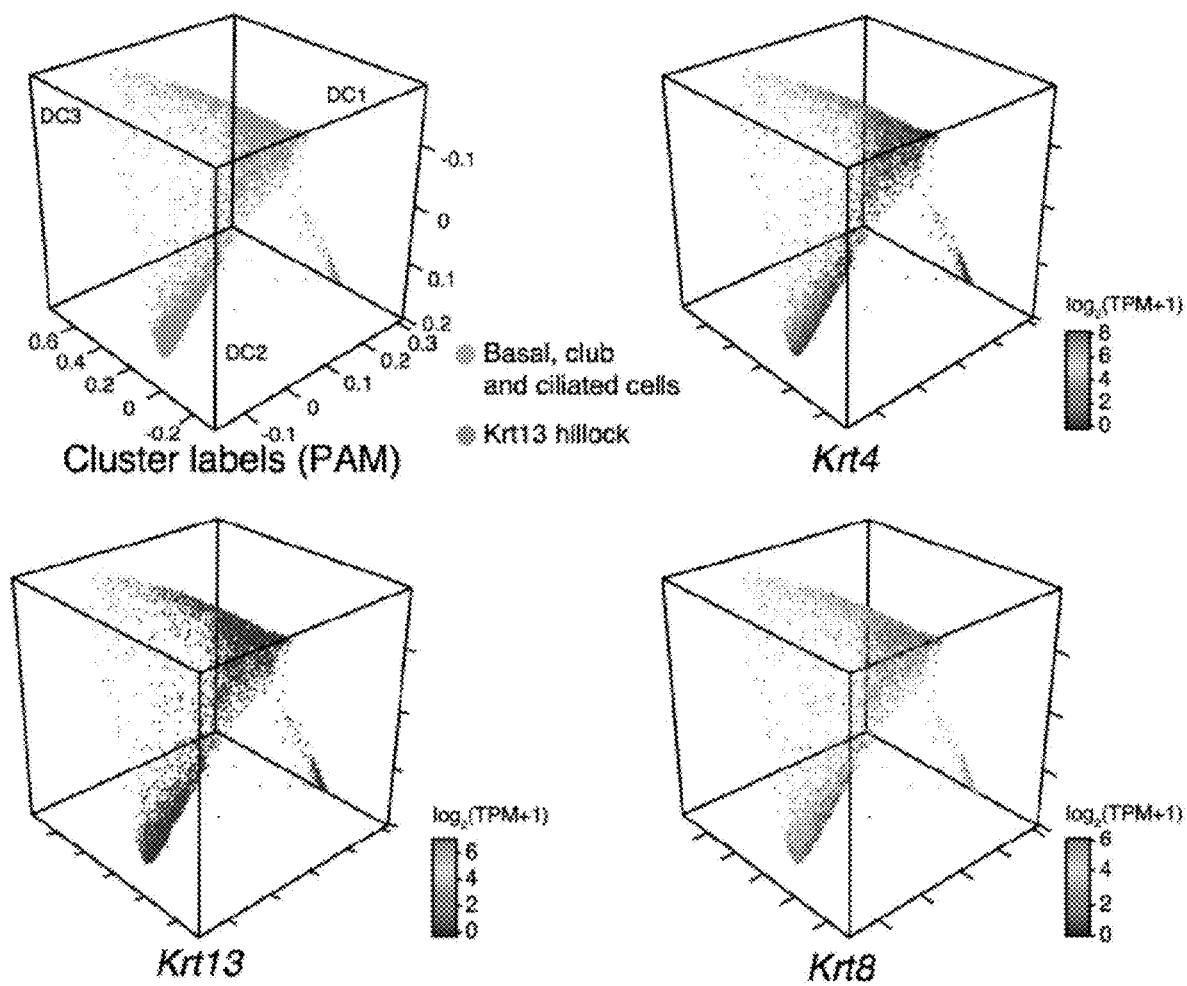
FIGS. 26A-26E show Krt13$^+$ progenitors express a unique set of markers distinct from mature club cells. A. Krt8 does not distinguish pseudostratified club cell development from hillock-associated club cell development. Diffusion map embedding of 6,905 cells (as in FIG. 18A) colored either by their Krt13$^+$ hillock membership (top left: green), or by expression ($\text{Log}_2$(TPM+1), color bar) of specific genes (all other panels). B. Hillocks are more proliferative. Fraction of EdU$^+$ epithelial cells (%, y-axis; representative image in FIG. 18E) in hillocks and non-hillock areas (x axis). ***p<0.001, likelihood-ratio test, black bar: mean, error bars: 95% CI. c. Krt13$^+$ hillock cells are turned over rapidly. Fraction of Krt13$^+$ cells that are club cell lineage labeled (%, y axis) at day 5 (10.2%, 95% CI [0.07, 0.16]) and its dilution at day 80 (5.2%, 95% CI [0.03, 0.08]). Error bars: 95% confidence interval, n=3 mice (dots). *p<0.05, likelihood-ratio test. D,E. Genes and processes associated with Krt13$^+$ cells. D. The differential expression (x axis, $\log_2$(fold-change)) and its associated significance (y axis, $\log_{10}$(FDR)) for each gene (dot) that is differentially expressed in Krt13$^+$ cells (identified using clustering in diffusion map space, Methods) as compared to all cells (FDR<0.05, likelihood-ratio test). Color code: cell type with highest expression (green: genes whose highest expression is in Krt13$^+$ cells). Dots show all the genes differentially expressed (FDR<0.05) between Krt13$^+$ hillock cells and other cells. Those genes with absolute effect sizes greater than $\log_2$(fold-change)>1 are marked with large points, while others are identified as small points (grey). E. Krt13$^+$ cell type-enriched pathways. Representative MSigDB[78] gene sets (rows) that are significantly enriched (x axis and color bar, $-\log_{10}$(FDR), hypergeometric test) in Krt13$^+$ cells.
Figure 26B:
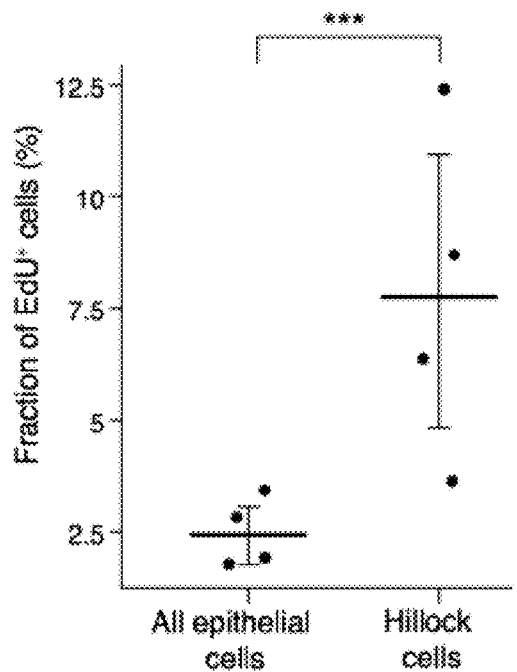
Figure 26C:
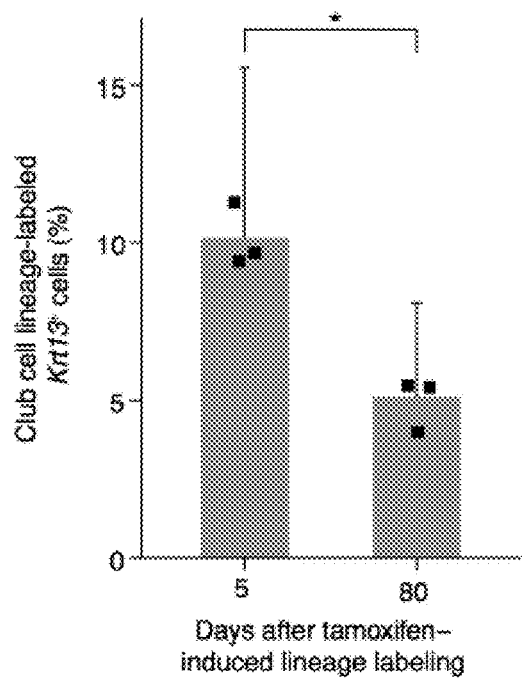

Surprisingly, the diffusion map revealed not only the canonical lineage path wherein basal cells produce club cells directly (DC1 and 2, k=555 cells, FIG. 18A,B), but also another path by which basal cells transition into club cells. This path was populated by novel transitional cells demarcated by the unique expression of Krt13 and Krt4 (FDR< $10^{-5}$, likelihood-ratio test), two characteristic markers of squamous epithelia (DC2 and 3, k=1,908 cells, FIG. 18A,B). Conversely, Krt8, a prior marker of basal to luminal cell differentiation (Watson, J. K. et al. Clonal Dynamics Reveal Two Distinct Populations of Basal Cells in Slow-Turnover Airway Epithelium. *Cell Rep.* 12, 90-101 (2015)), is broadly expressed, and does not uniquely identify the novel cells (FIG. 26A, bottom right). Applicants did not detect any cells on a direct trajectory from basal to ciliated (FIG. 18A,B), supporting previous reports that club cells are the primary source of ciliated cells during homeostasis.

Remarkably, the majority of $Krt13^+$ cells are confined to discrete structures comprised of contiguous groups of stratified cells with cuboidal morphology. Unlike the majority of the pseudostratified epithelium, these structures possess no ciliated cells (FIG. 18C). $Scgb1a1^+Krt13^+$ club cells are located at the luminal surface (FIG. 18D,F). Additionally, there are scattered rare $Krt13^+$ cells throughout the epithelium (data not shown). $Trp63^+Krt13^+$ cells are located in both the basal and intermediate strata of the structures, appearing as multiple layers of $Trp63^+$ cells. This pattern of layered $Trp63^+$ cells is not seen outside of the $Krt13^+$ regions. Applicants term these small mounds of distinct presumptive progenitors and their $Krt13^+$ club cell progeny "hillocks". The graded decrease of Trp63 expression and the graded increase of Scgb1a1 expression in cells along the basal to luminal axis of the hillock parallel the transition of $Krt13^+$ basal cells into $Krt13^+$ club cells, as predicted by the pseudo-ordering analysis (FIG. 18A).

To examine turnover in these unique progenitors, Applicants administered the thymidine analog 5-ethynyl-2'-deoxyuridine (EdU) to wild-type mice to label proliferating cells (Methods). The distribution of replicating cells varied across hillocks. In aggregate, Applicants found that 7.7% (95% CI [4.8%, 10.5%]) of $Krt13^-$ cells were $EdU^+$ vs. 2.4% (95% CI [1.8%, 3.1%]) of $Krt13^-$ cells in the neighboring pseudostratified epithelium (FIG. 26B, p<0.0001, likelihood-ratio test, n=4 mice). Thus, the topologically distinct hillocks represent discrete zones of unique cells that replicate faster than the adjoining pseudostratified epithelium (FIG. 18E,F).

Although club cells are known to dedifferentiate into stem cells following basal cell injury (Tata, P. R. et al. Dedifferentiation of committed epithelial cells into stem cells in vivo. *Nature* 503, 218-223 (2013)), Applicants did not find evidence of appreciable club cell dedifferentiation in hillocks under homeostatic conditions. Applicants generated an Scgb1a1-CreER/LSL-tdTomato mouse strain to label hillock club cells and their progeny. After 8 weeks of homeostatic turnover, the hillock club cell lineage label was actually diluted from an initial 10.17% of all $Krt13^+$ club cells to only 5.12% of $Krt13^+$ club cells (FIG. 26B), consistent with ongoing cell turnover rather than dedifferentiation. This supports a model in which $Trp63^+Krt13^+$ hillock progenitor cells rapidly produce hillock club cells that are then lost.

Figure 26D:
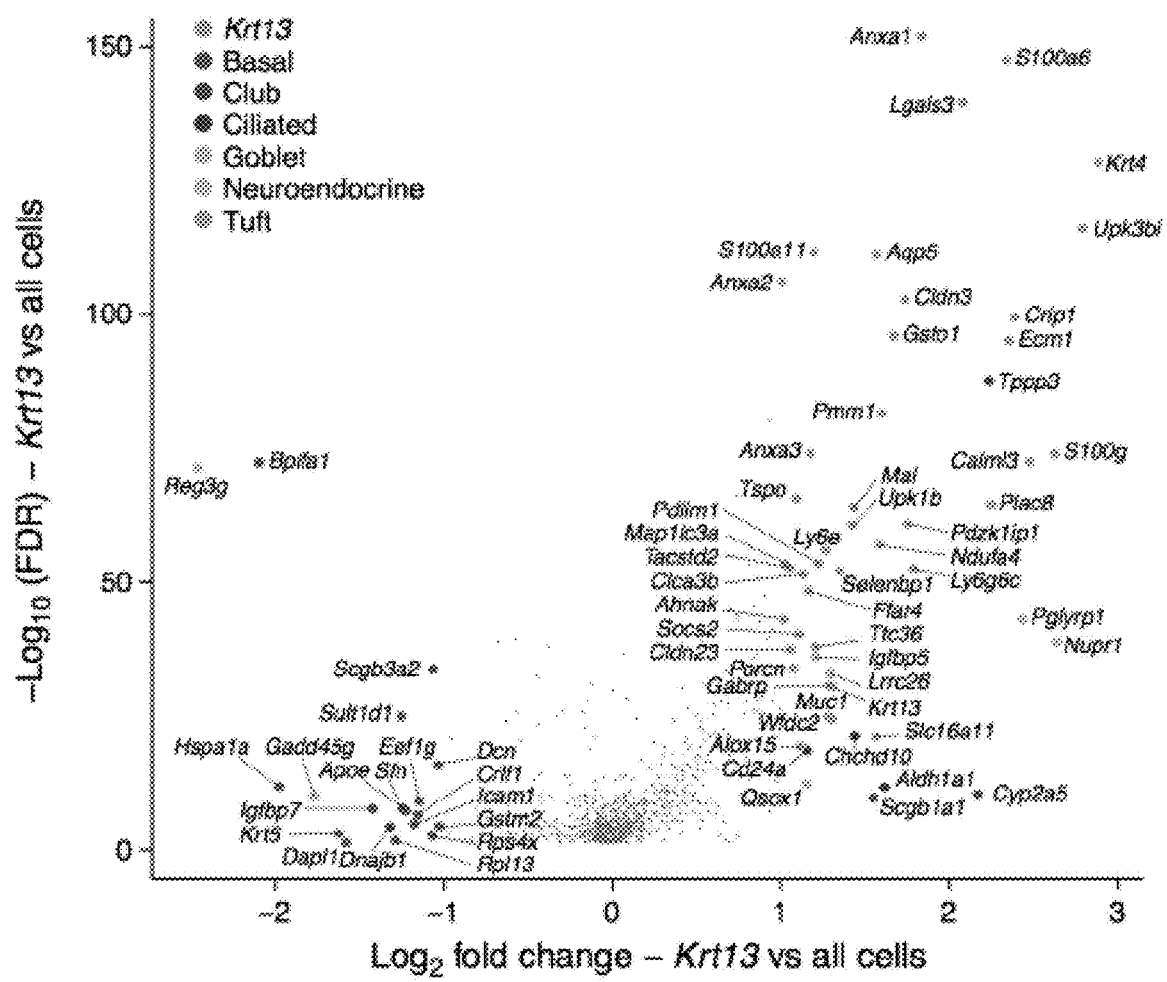
Figure 26E:
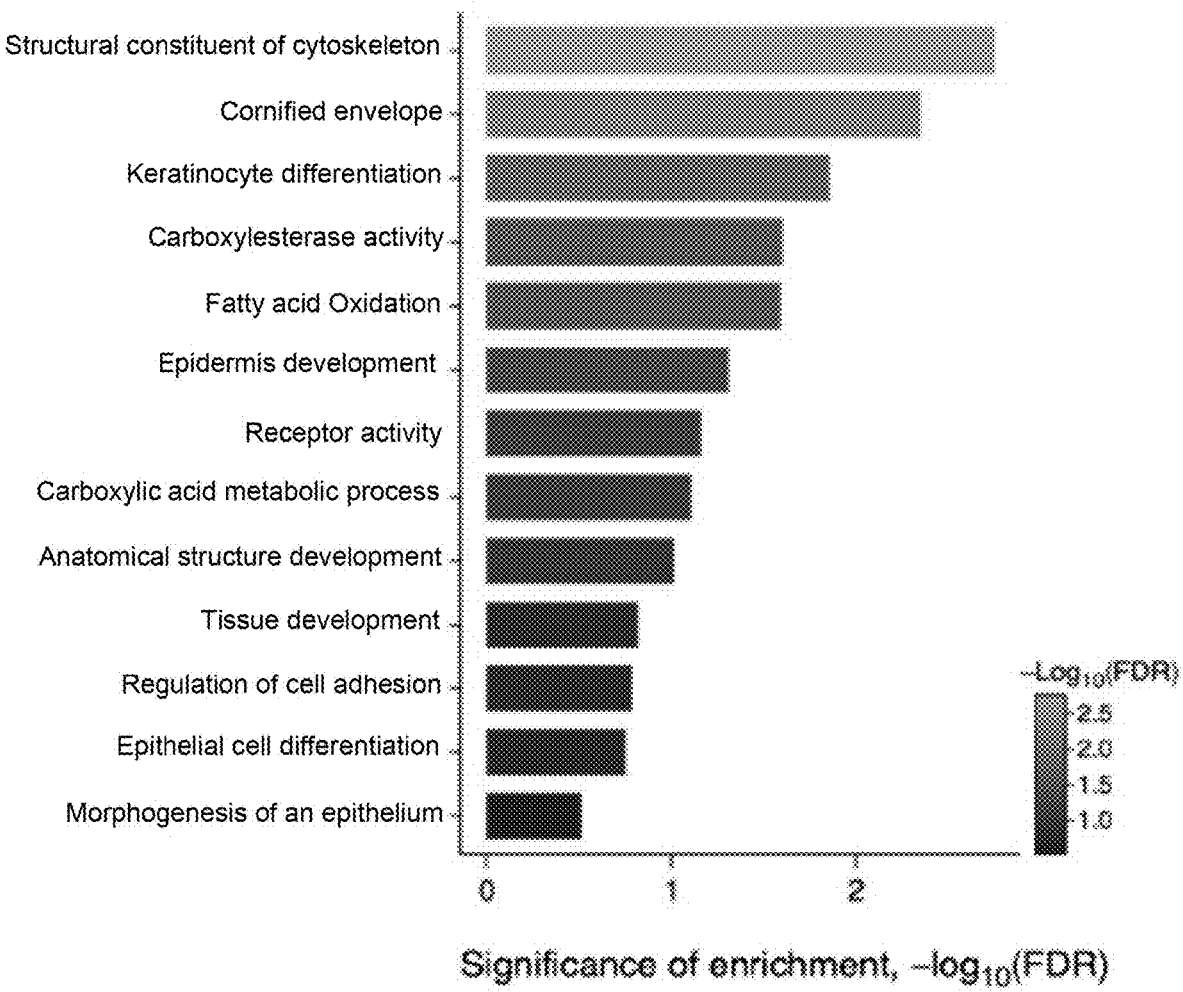

$Krt13^+$ hillock cells express unique gene modules associated with immunomodulation, squamous differentiation, and barrier function (FIG. 26D, E). Genes involved in squamous differentiation and the regulation of cellular adhesion and differentiation in squamous epithelia (Chan, I. The role of extracellular matrix protein 1 in human skin. *Clin. Exp. Dermatol.* 29, 52-56 (2004); Sakaguchi, M. & Huh, N. S100A11, a dual growth regulator of epidermal keratinocytes. *Amino Acids* 41, 797-807 (2011); Troy, T.-C., Arabzadeh, A., Yerlikaya, S. & Turksen, K. Claudin immunolocalization in neonatal mouse epithelial tissues. *Cell Tissue Res.* 330, 381-388 (2007)) include Ecm1, S100a11, and Cldn3 (FIG. 26D). Immune modulatory genes with asthma related functions (D'Acquisto, F. et al. Annexin-1 modulates T-cell activation and differentiation. *Blood* 109, 1095-1102 (2007); Ng, F. S. P. et al. Annexin-1-deficient mice exhibit spontaneous airway hyperresponsiveness and exacerbated allergen-specific antibody responses in a mouse model of asthma. *Clin. Exp. Allergy J. Br. Soc. Allergy Clin. Immunol.* 41, 1793-1803 (2011); Zuberi, R. I. et al. Critical role for galectin-3 in airway inflammation and bronchial hyperresponsiveness in a murine model of asthma. *Am. J. Pathol.* 165, 2045-2053 (2004)) include Anxa1 and Lgals3 (FDR<$10^{-10}$ likelihood-ratio test). Overall, hillocks have attributes that normally would be predicted to play a role in regenerating epithelium: rapid turnover to replace damaged cells, squamous differentiation to enhance barrier function, and immunomodulation.

High Resolution Lineage Tracing Incorporating Cellular Dynamics with Pulse-Seq

During homeostatic turnover, basal stem cells self-renew and generate club cell progenitors, which in turn generate terminally differentiated ciliated cells (Rawlins, E. L. et al. The role of Scgb1a1+ Clara cells in the long-term maintenance and repair of lung airway, but not alveolar, epithelium. *Cell Stem Cell* 4, 525-534 (2009)). However, the source of rare cells is unknown. The tuft cell lineage hierarchy has not been directly assessed in the airway epithelium, but it has been suggested that Gnat3$^+$ tuft cells in the trachea are static because they do not appreciably label with BrdU pulses (Saunders, C. J., Reynolds, S. D. & Finger, T. E. Chemosensory brush cells of the trachea. A stable population in a dynamic epithelium. *Am. J. Respir. Cell Mol. Biol.* 49, 190-196 (2013)). Moreover, although prior lineage tracing has shown that Pgp9.5$^+$ NE cells are derived from basal cells during a 6 month lineage trace, no specific progenitor cell was identified as the immediate parent of mature NE cells.

Figure 19A:
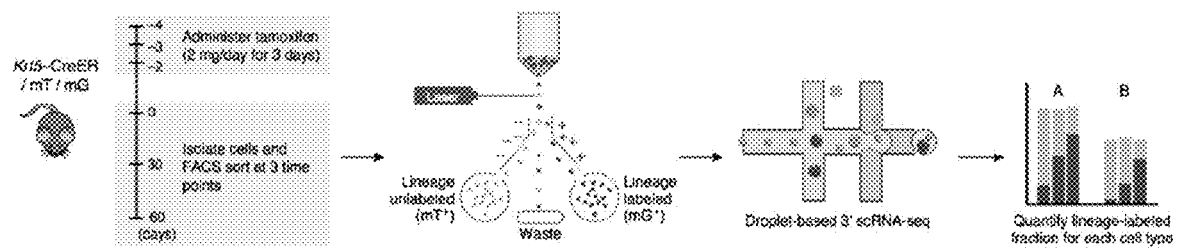
FIGS. 19A-19G show Pulse-Seq reveals novel lineage paths and records cell dynamics with single-cell resolution. A. Pulse-Seq. Tmx: tamoxifen, mT: tdTomato, mG: mGFP. B-C. Cell type clusters and lineage labeling. tSNE visualization of 66,265 scRNA-seq profiles from Pulse-Seq. Cells colored by assignment to clusters (b, Methods), or by the presence of a lineage label (c). D. Lineage tracing of each tracheal epithelial cell type. Estimated fraction (%, y-axis, Methods) of cells of each type that are positive for the fluorescent lineage label (by FACS) from n=3 mice per time point (x-axis). Points: individual mice. *p<0.1, *p<0.05, p<0.01, *p<0.001, likelihood-ratio test (Methods), error bars: 95% CI. E. Ciliated and goblet cells are produced later than club and rare epithelial cell types. Estimated daily rate of new lineage labeled cells (%, y-axis, Methods, FIG. 28C) for each type (x-axis). *p<0.05, p<0.01, rank test (Methods), error bars: 95% CI. F. Conventional lineage trace of Gnat3$^+$ tuft cells confirms they are generated by basal cells. Left: Representative images and basal cell lineage labeling quantification (bar plot, right) of Gnat3$^+$ tuft cells at Day 4 (0%, n=2 mice, dots) and Day 30 (22.9%, 95% CI [0.17, 0.30], n=3 mice) post-labeling. Dashed white lines: unlabeled tuft cells; solid white lines: labeled tuft cells. *p<0.001, likelihood-ratio test. Error bars: 95% CI. G. Cell types, lineage, and cellular dynamics inferred using Pulse-Seq.
Figure 19B:
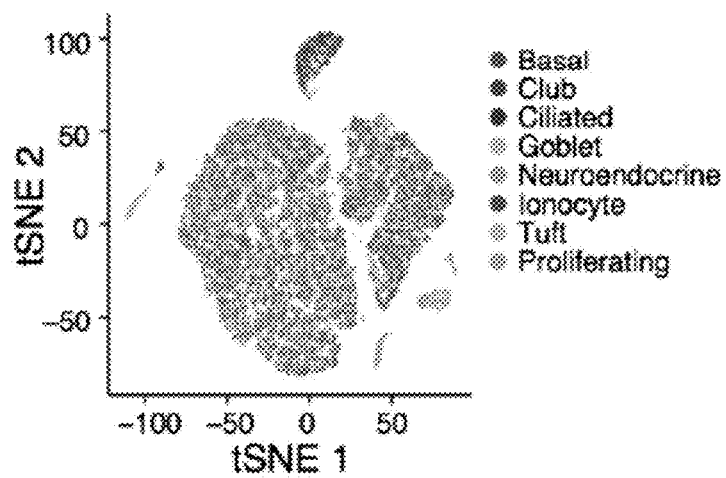
Figure 19C:
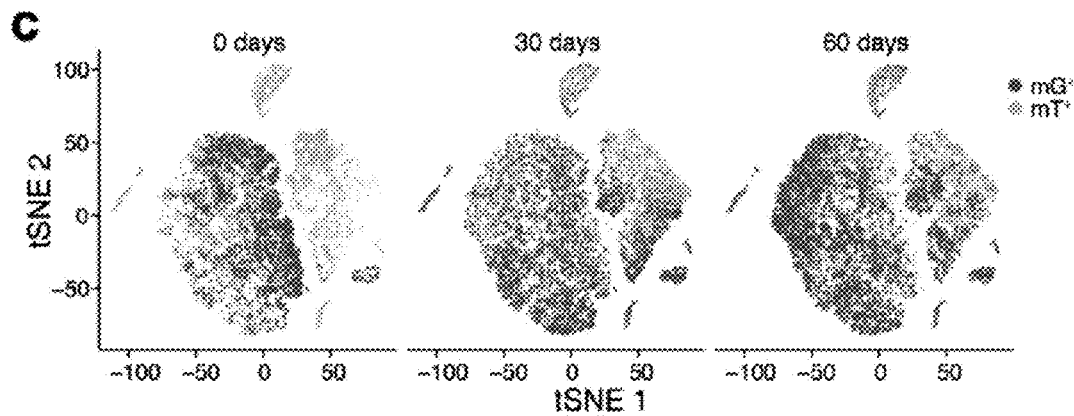
Figure 28A:
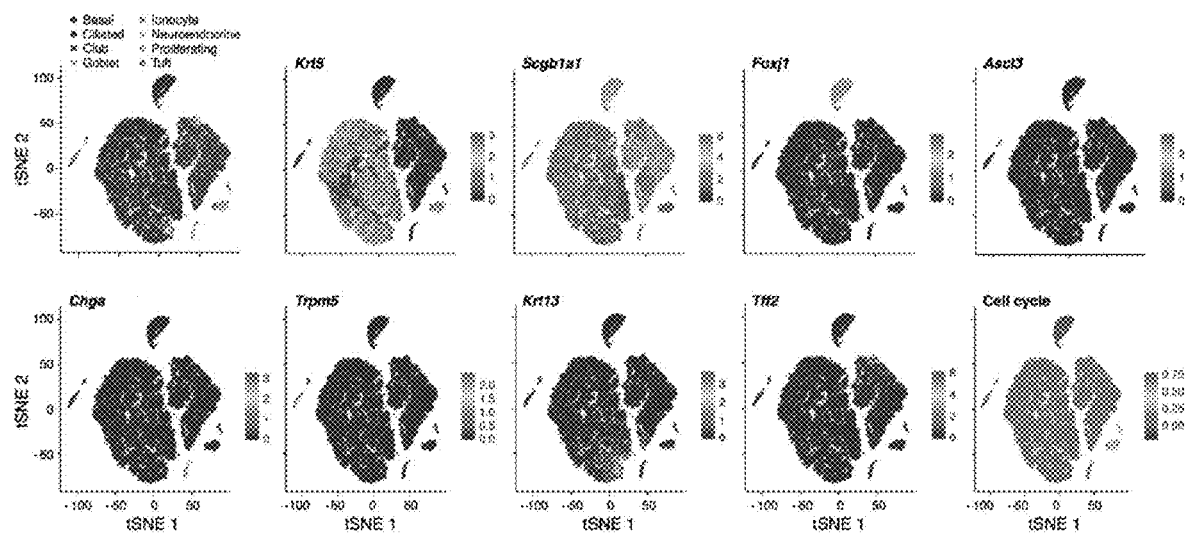
FIGS. 28A-28F show lineage tracing using Pulse-Seq. A. Post hoc cluster annotation by known cell type markers[4]. tSNE of 66,265 scRNA-seq profiles (points) from Pulse-Seq, colored by the expression ($\log_2$(TPM+1), color bar) of single marker genes for a particular cell type or cell-cycle score[79] (bottom right) B. Labeled fraction of basal cells is unchanged during Pulse-Seq time course, as expected. Estimated fraction (%, y-axis, Methods) of cells of each type that are positive for the fluorescent lineage label (by FACS) in each of n=3 mice (points) per time point (x axis). NS: p>0.1, likelihood-ratio test (Methods), error bars: 95% CI. C. Pulse-Seq lineage-labeled fraction of various cell populations over time. Linear quantile regression fits (trendline, Methods) to the fraction of lineage-labeled cells of each type (n=3 mice per time point, dots, y-axis) as a function of the number of days post tamoxifen-induced labeling (x-axis). β: estimated regression coefficient, interpreted as daily rate of new lineage-labeled cells, p: p-value for the significance of the relationship, Wald test (Methods). As expected, goblet and ciliated cells are labeled more slowly than club cells (FIG. 19E). D-F. Conventional Scgb1a1 (CC10) lineage trace of rare epithelial types shows minimal contribution to rare cell lineages. Fraction of Scb1a1 labeled (club cell trace) cells (y axis, %) of Gnat3$^+$ tuft cells (D) at day 4 (0.6%, 95% CI [0.00, 0.04]) and day 30 (6.3%, 95% CI [0.04, 0.11]), Foxi1-GFP$^+$ ionocytes at day 30 (2.9%, 95% CI [0.01, 0.11]) (E), and Chga$^-$ neuroendocrine (NE) cells at day 4 (2.5%, 95% CI [0.01, 0.08]) and day 30 (2.6%, 95% CI [0.01, 0.08]) (F) after club cell lineage labeling. **p<0.01, likelihood-ratio test. Error bars: 95% confidence interval. Each time point cell type combination has at least n=2 mice.

Applicants developed a novel assay, Pulse-Seq, to monitor the generation of rare tuft cells, NE cells, and ionocytes (FIG. 19A). Pulse-Seq combines scRNA-seq and in vivo genetic lineage tracing of stem cells so that labeling of all their progeny can be monitored over a time course in the steady-state tracheal epithelium. Applicants crossed a basal cell-specific tamoxifen-inducible CreER driver to a reporter strain such that lineage-labeled basal stem cells and their subsequently labeled progeny will express membrane-localized eGFP (mG), while non-lineage-labeled cells will express membrane-localized tdTomato (mT) (Krt5-CreER/LSL-mT/mG) (Methods). Following tamoxifen-induced basal cell labeling, Applicants profiled 66,265 high quality labeled (mG$^+$) and unlabeled (mT$^+$) cells by scRNA-seq at day 0, 30, and 60 of homeostatic turnover (Methods; n=9 mice, 3 per time point). Applicants identified groups of cells corresponding to each of the seven epithelial cell types (Methods) and an additional group of proliferating cells, predominantly basal (FIG. 19B and FIG. 28A). For each subset, Applicants directly calculated the fraction of lineage-labeled cells at each time point (FIG. 19C,D). Applicants then used quantile regression to estimate the daily rate of change of this fraction, thereby estimating new cell generation (or the fraction of each cell-type that is produced from basal cells each day) (Methods, FIG. 19E, FIG. 28C). Confirming the specificity of the basal cell trace, at time point 0, 64.2% of the cells in the basal cluster are labeled, all non-basal cells were labeled at less than 3.3%, including less than 1.8% of the goblet, tuft, NE, and ionocyte cells (n=3 mice, FIG. 19C,D).

Figure 19D:
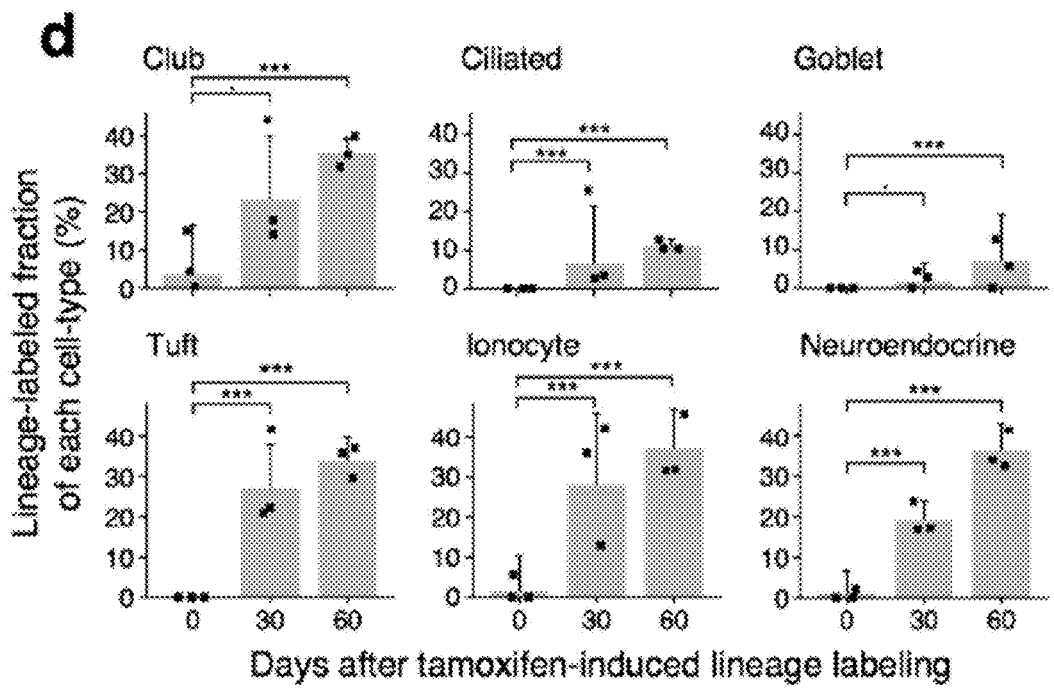
Figure 28B:
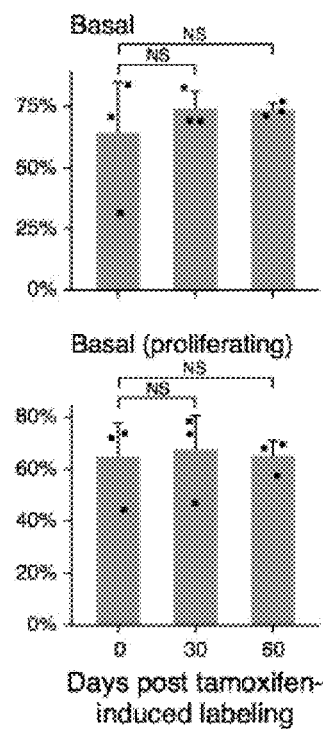
Figure 28C:
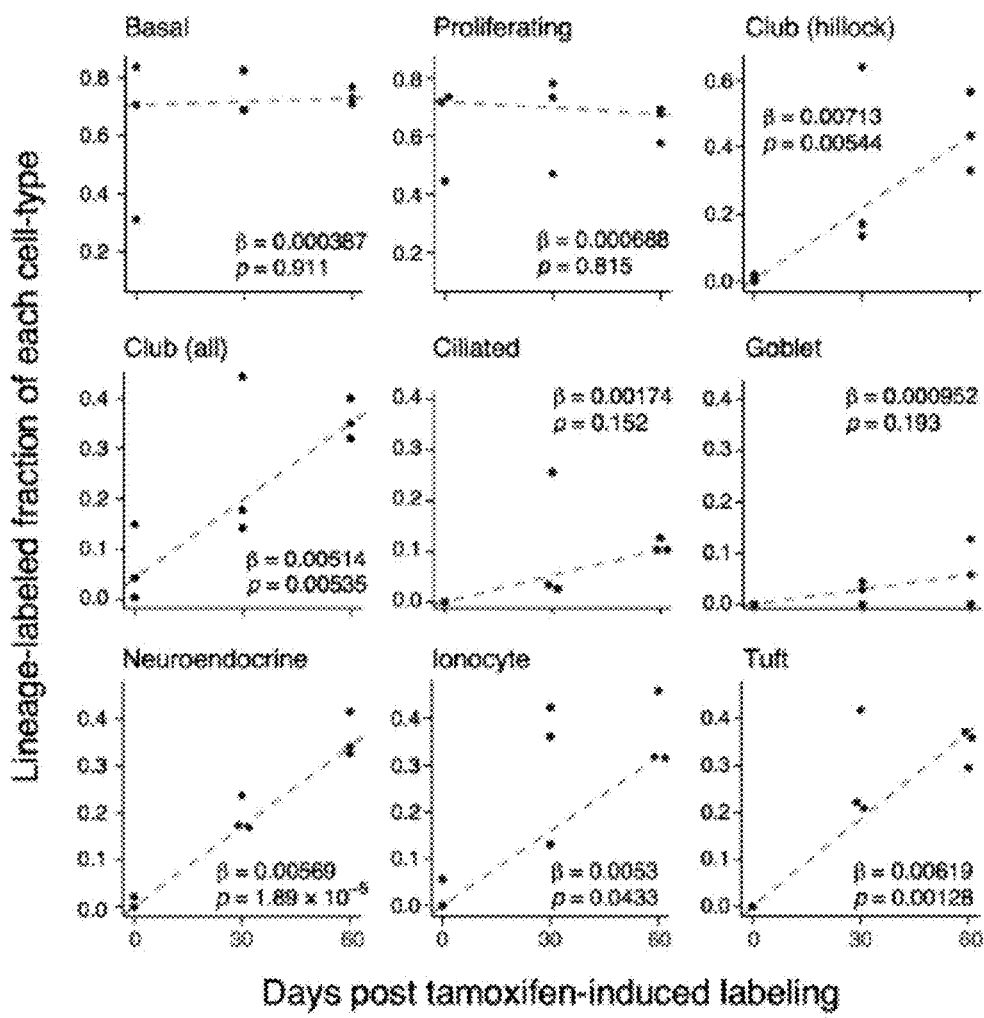

Cells that are not direct basal cell progeny would be expected to be labeled at low frequencies at early time points relative to those that arise directly. Indeed, in prior basal stem cell lineage traces, club cells were labeled earlier than ciliated cells. Subsequent club cell lineage traces confirmed that ciliated cells are produced from club cells in the steady-state epithelium, underscoring why basal cell lineage traces appear late in the ciliated cell population. Using Pulse-Seq, Applicants showed that the fraction of labeled basal cells did not significantly change over the time course, consistent with the behavior of a self-renewing cell population (FIG. 28B). However, the fractions of labeled tuft, NE and ionocyte cells were substantially increased at day 30 and had further risen at day 60 (FIG. 19D). These rates are consistent with the club cell population at day 30 and 60 (FIG. 19D,E), suggesting that the rare cells are similarly immediate descendants of basal cells.

Figure 19E:
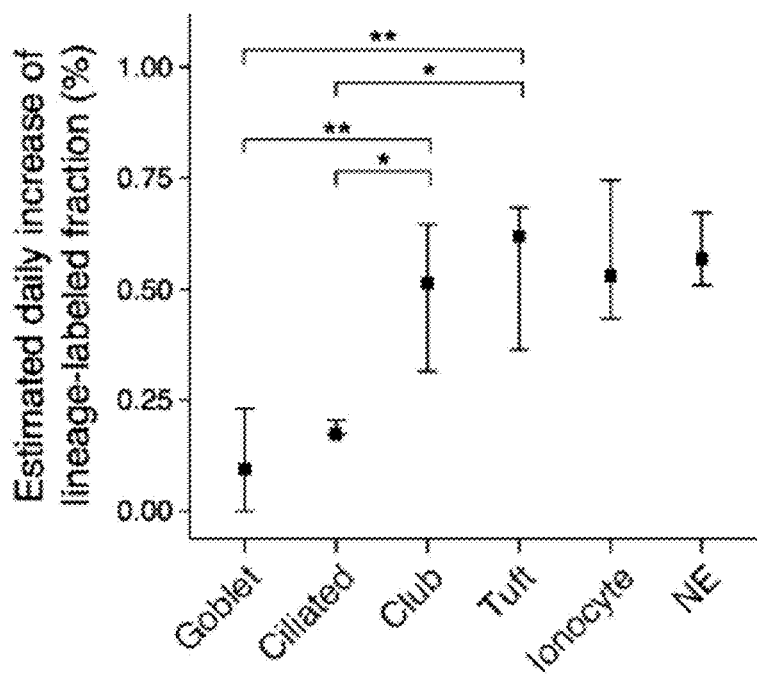
Figure 19F:
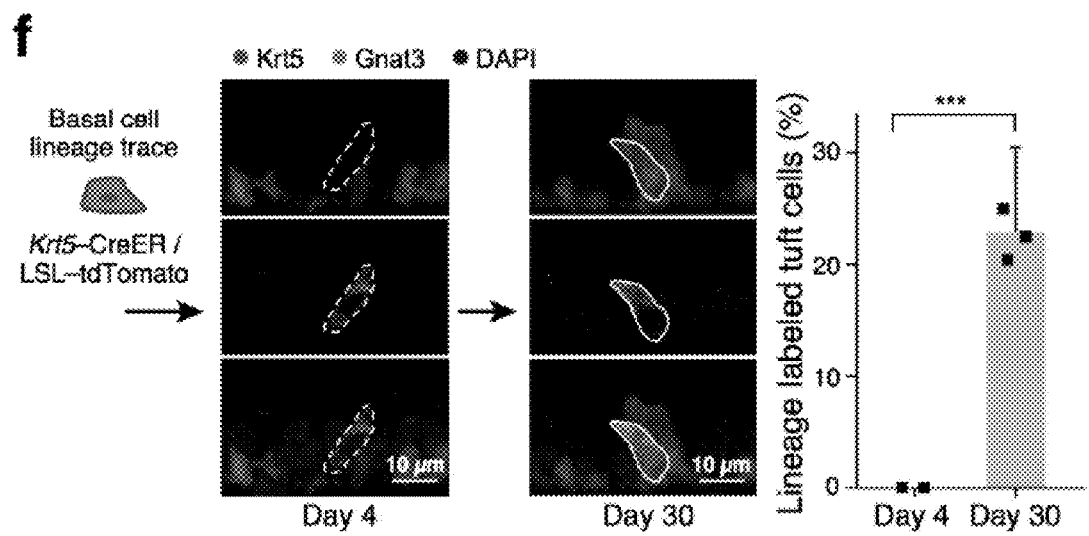
Figure 19G:
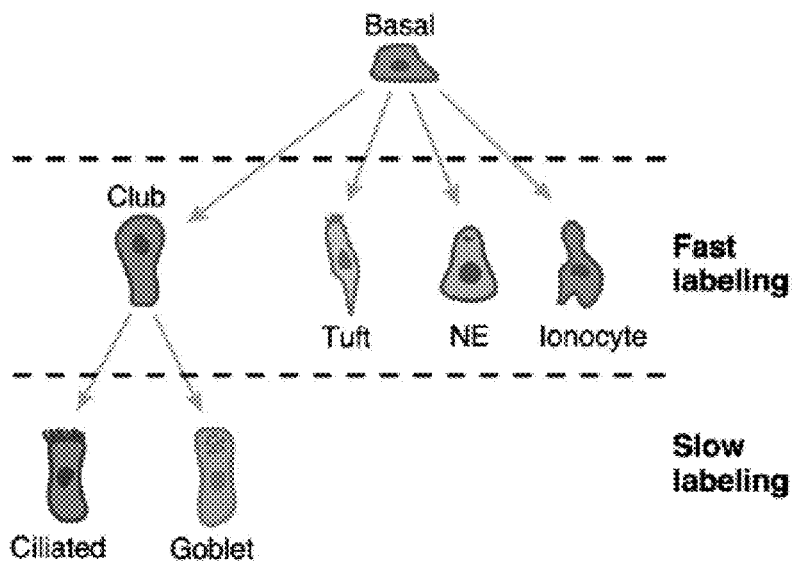
Figure 28D:
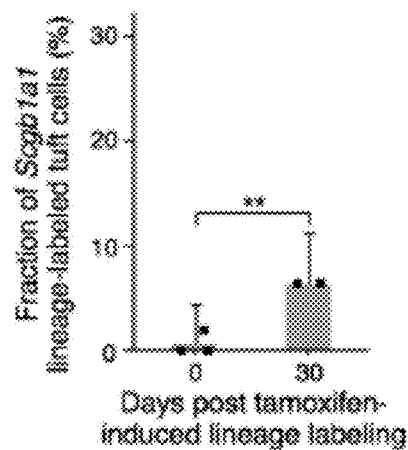
Figure 28E:
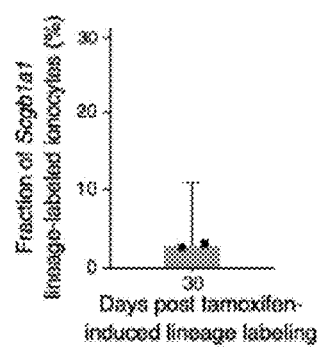
Figure 28F:
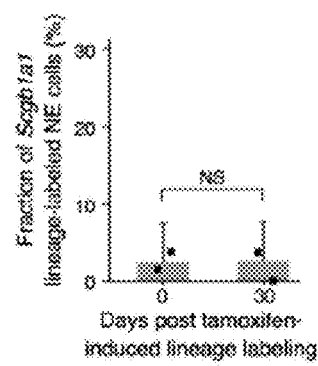

Applicants validated the result that basal cells are the direct parents of tuft cells using conventional in vivo lineage tracing of both basal and club cells separately along with subsequent in situ detection of tuft cells. Over a 30-day basal cell lineage trace (with Krt5-CreER/LSL-tdTomato mice), the proportion of lineage-labeled tuft cells dramatically increased (FIG. 19F), whereas club cell lineage tracing (with Scgb1a1-CreER/LSL-tdTomato mice) labeled only a modest fraction of Gnat3$^+$ tuft cells (FIG. 28D). Thus, basal cells are the predominant source of tuft cells (FIG. 19G), while club cells may provide a minor pathway of their differentiation. Applicants similarly verify that club cells do not substantially contribute to the ionocyte or NE cell populations following club cell lineage tracing (less than 3% labeling of each, FIG. 28E,F). While the fraction of labeled goblet and ciliated cells increased over time (p<0.05 in both cases, likelihood-ratio test), fewer cells were labeled by day 30 than for other cell types (FIG. 19D), and the rate of appearance of label within goblet cells was as low as that for ciliated cells (FIG. 19E). This is consistent with a model in which goblet cells are produced from club cells (FIG. 19G).

Figure 29A:
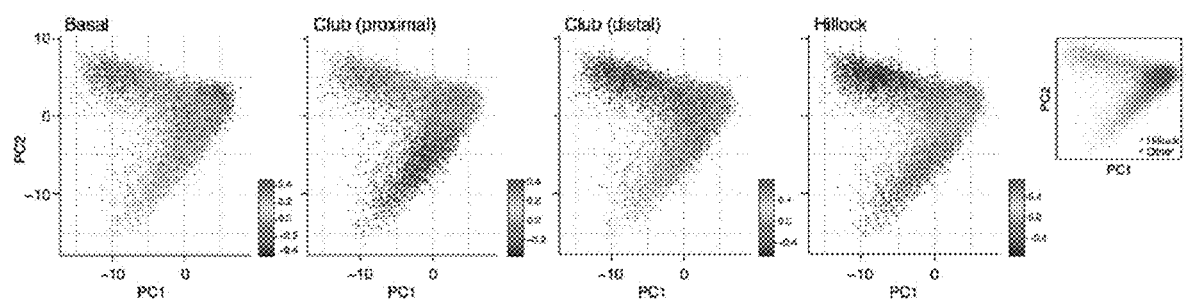
FIGS. 29A-29E show club cell heterogeneity and lineage tracing hillock-associated club cells using Pulse-Seq. A,B. PC-1 and PC-2 are associated with basal to club differentiation and both proximodistal heterogeneity and hillock gene modules respectively. A. PC-1 (x-axis) vs. PC-2 (y-axis) for a PCA of 17,700 scRNA-seq profiles of club cells (points) in the Pulse-Seq dataset, colored by signature scores (color legends, Methods) for basal (left), proximal club cells (center left), distal club cells (center right), the Krt13$^+$/Krt4$^+$ hillock (right), or their cluster assignment (inset, right). B. Bar plots show the extent (normalized enrichment score, y-axis, Methods) and significance of association of PC-1 (left) and PC-2 (right) for gene sets associated with different airway epithelial types (x-axis), or gene modules associated with proximodistal heterogeneity (FIG. 18G). Heatmaps shows the relative expression level (row-wise Z-score of $\log_2$(TPM+1) expression values, color bar) of the 20 genes (rows) with the highest and lowest loadings on PC-1 (left) and PC-2 (right) in each club cell (columns, down-sampled to 1,000 cells for visualization only). NS p>0.05, *p<0.05, p<0.01, *p<0.001, permutation test (Methods). C. Lineage tracing of hillock-associated cells. Estimated fraction (%, y-axis, Methods) of cells of each type that are positive for the fluorescent lineage label (by FACS) from n=3 mice (points) per time point (x axis). *p<0.001, likelihood-ratio test (Methods), error bars: 95% CI. D. Hillock-associated club cells are produced at a greater rate than all club cells. Estimated rate (%, y-axis) based on the slope of quantile regression fits (Methods) to the fraction of lineage-labeled cells of each type (x-axis). p<0.01, rank test (Methods), error bars: 95% CI. E. Schematic of the more rapid turnover of basal to club cells inside (top) and outside (bottom) hillocks.
Figure 29B:
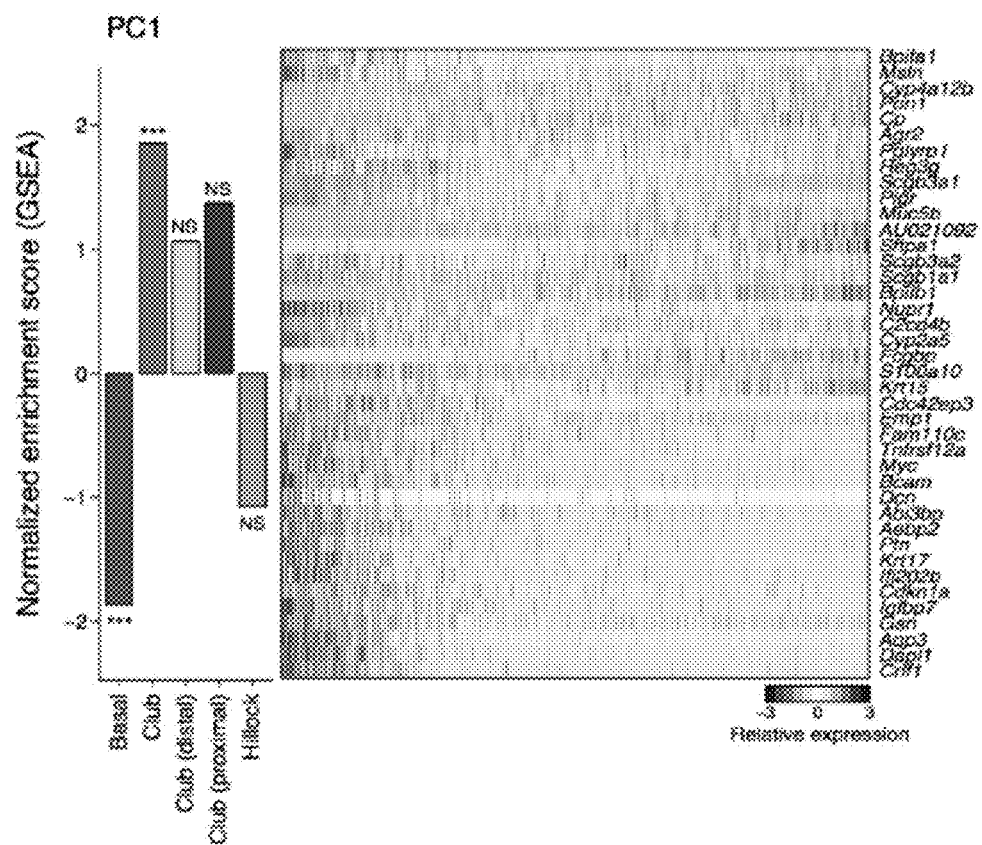
Figure 29C:
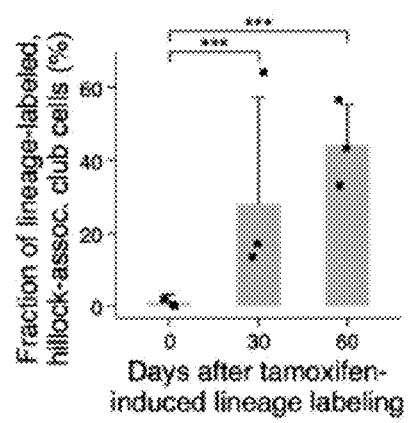
Figure 29D:
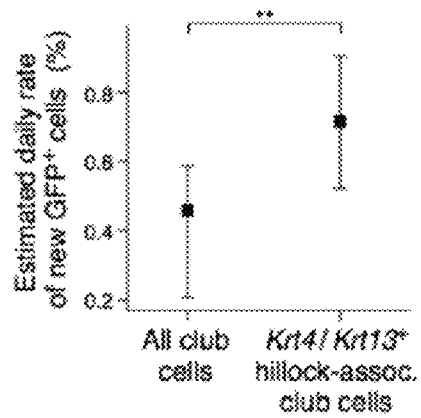
Figure 29E:
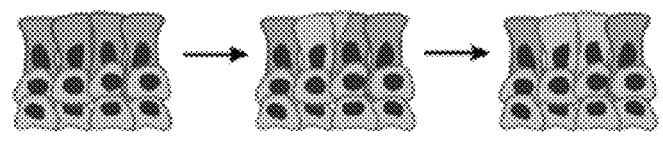
Figure 29E:
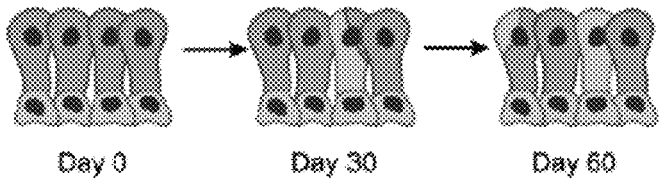

Finally, Applicants investigated the lineage of hillock-associated club cells identified by clustering of club cells (FIG. 29A,B, Methods). The fraction of labeled hillock-specific club cells increased more rapidly than the fraction of total labeled club cells (p<0.01, rank test, FIG. 29C-E) (compare FIG. 19E and FIG. 29D). This is consistent with the frequent EdU labeling observed within hillocks (FIG. 18E).

Distinct Types of Tuft and Goblet Cells

Applicants next tested if each of the rare cell populations (tuft, NE, goblet, ionocytes) are comprised of distinct subsets, by re-clustering the cells of each rare cell type from both droplet-based datasets combined (FIG. 17B and FIG. 19B, n=15 mice). The 892 tuft cells and 468 goblet cells each partitioned into three clusters, whereas neither the 276 ionocytes nor the 726 NE cells further partitioned, as the latter do in the intestine.

Figure 30A:
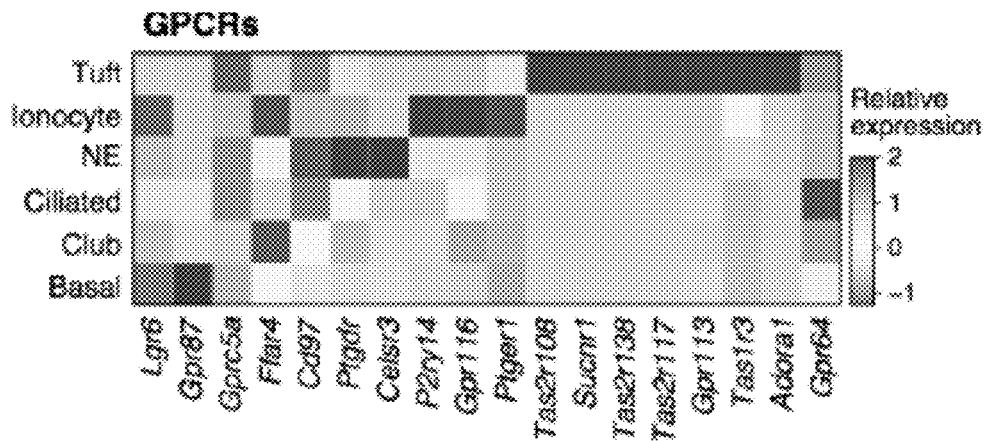
FIGS. 30A-30I show heterogeneity of rare tracheal epithelial cell types. A. Cell type-enriched GPCRs. Relative expression (Z-score of mean $\log_2$(TPM+1), color bar) of the GPCRs (columns) that are most enriched (FDR<0.001, likelihood-ratio test) in the cells of each trachea epithelial cell type (rows) based on full-length scRNA-seq data. B. Tuft cell-specific expression of Type I and Type II taste receptors. Expression level (mean $\log_2$(TPM+1), color bar) of tuft-cell enriched (FDR<0.05, likelihood-ratio test) taste receptor genes (columns) in each trachea epithelial cell type (rows, labeled as in E) based on full-length scRNA-seq data. C. Tuft cell-specific expression of the Type-2 immunity-associated alarmins Il25 and Tslp. Mean expression level (y-axis, $\log_2$(TPM+1)), of Il-25 (left) and Tslp (right) in each cell type (x axis). ***FDR<$10^{-10}$, likelihood-ratio test. D. Morphological features of tuft cells. Immunofluorescence staining of the tuft-cell marker Gnat3 (yellow) along with DAPI (blue). Arrowhead: "tuft", arrows: cytoplasmic extension. E-F. Mature and immature subsets are identified using marker gene expression. The distribution of expression of scores (y-axis, using top 20 marker genes, Methods) for tuft (E) goblet (F), basal and club cells (label on top) in each cell subset (x axis) (basal and club cells downsampled to 1,000 cells). *p<0.05, ***p<0.001, Mann-Whitney U-test. G-H. Gene signatures for goblet-1 and goblet-2 subsets. The distribution (g) and relative expression level (H, row-wise Z-scores, color bar) of marker genes that distinguish ($log_2$ fold-change>0.1, FDR<0.001, likelihood-ratio test) cells in the goblet-1 and goblet-2 sub-clusters (color bar, top and left) from the combined 3' scRNA-seq datasets. I. Immunofluorescence staining of the goblet-1 marker Tff2 (magenta), the known goblet cell marker Muc5ac (green), and DAPI (blue). Solid white line: boundary of a goblet-1 cell.
Figure 30B:
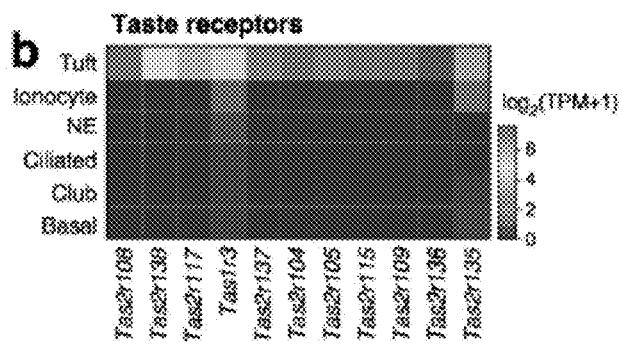

The entire tuft cell population expressed a greater number of specific GPCRs than any other cell type (FDR<0.001 likelihood-ratio test, FIG. 30A), suggestive of a sensory specialization. These included Adoral (involved in the regulation of respiratory rate in response to hypoxia (Heitzmann, D. et al. The in vivo respiratory phenotype of the adenosine A1 receptor knockout mouse. *Respir. Physiol. Neurobiol.* 222, 16-28 (2016))), Gpr64 (mediation of fluid exchange in the epididymis (Davies, B. et al. Targeted deletion of the epididymal receptor HE6 results in fluid dysregulation and male infertility. *Mol. Cell. Biol.* 24, 8642-8648 (2004))), and the taste receptor cell transducer Gpr113 (Lopez Jimenez, N. D. et al. Two novel genes, Gpr113, which encodes a family 2 G-protein-coupled receptor, and Treg1, are selectively expressed in taste receptor cells. *Genomics* 85, 472-482 (2005))). They also express the alarmins Il25 and Tslp (FDR<$10^{-10}$, FIG. 30C), possibly linking their sensory function to the initiation of type-2 immunity in the airway, paralleling the gut. Tuft cells possess unique lateral cytoplasmic extensions that traverse several cell diameters (FIG. 30D), perhaps extending their chemosensory span.

Applicants found one cluster of immature tuft cells and two clusters of mature tuft cells (FIG. 30E), which Applicants term tuft-1 and tuft-2 (FIG. 20). Cells in both the tuft-1 and tuft-2 clusters express the known tuft cell marker Trpm5, while the immature cells display low Trpm5 expression (FIG. 20A). The tuft-1 subset expresses genes that suggest a more prominent chemosensory function: elements of the taste transduction pathway (Gnb3, Gng13, Atp1b1, Fxyd6 (Shindo, Y. et al. FXYD6, a Na,K-ATPase regulator, is expressed in type II taste cells. *Biosci. Biotechnol. Biochem.* 75, 1061-1066 (2011)), many type II taste receptors including those implicated in airway sensing of gram-negative bacterial infection (Tas2R38) (Adappa, N. D. et al. Genetics of the taste receptor T2R38 correlates with chronic rhinosinusitis necessitating surgical intervention. *Int. Forum Allergy Rhinol.* 3, 184-187 (2013); Lee, R. J. et al. T2R38 taste receptor polymorphisms underlie susceptibility to upper respiratory infection. *J. Clin. Invest.* 122, 4145-4159 (2012)) and regulation of breathing (Tas2R105, Tas2R108) (Yoon, S.-Y. et al. Association between Polymorphisms in Bitter Taste Receptor Genes and Clinical Features in Korean Asthmatics. *Respir. Int. Rev. Thorac. Dis.* 91, 141-150 (2016); Krasteva, G. et al. Cholinergic chemosensory cells in the trachea regulate breathing. *Proc. Natl. Acad. Sci. U.S.A.* 108, 9478-9483 (2011); Krasteva, G., Canning, B. J., Papadakis, T. & Kummer, W. Cholinergic brush cells in the trachea mediate respiratory responses to quorum sensing molecules. *Life Sci.* 91, 992-996 (2012)), and the type I taste receptor Tas1r3 (FIG. 20F). Conversely, tuft-2 cells are associated with expression of inflammation, asthma and allergy-related genes (FIG. 20B-D,F) including Mgst3 and Alox5ap, both which are necessary for leukotriene biosynthesis (Jakobsson, P. J., Mancini, J. A., Riendeau, D. & Ford-Hutchinson, A. W. Identification and characterization of a novel microsomal enzyme with glutathione-dependent transferase and peroxidase activities. *J. Biol. Chem.* 272, 22934-22939 (1997); Dixon, R. A. et al. Requirement of a 5-lipoxygenase-activating protein for leukotriene synthesis. *Nature* 343, 282-284 (1990)) (FDR<0.05, hypergeometric test, FIG. 20B-D). They are also enriched, as in the gut, for the immune-cell associated Ptprc (CD45, FDR<0.1). Interestingly canonical tuft cell lineage TFs are specifically associated with the respective subsets, such as Pou2f3 (tuft-1) and Gfi1b, Spib, Sox9 (tuft-2, FDR<0.01, FIG. 20G).

Figure 20A:
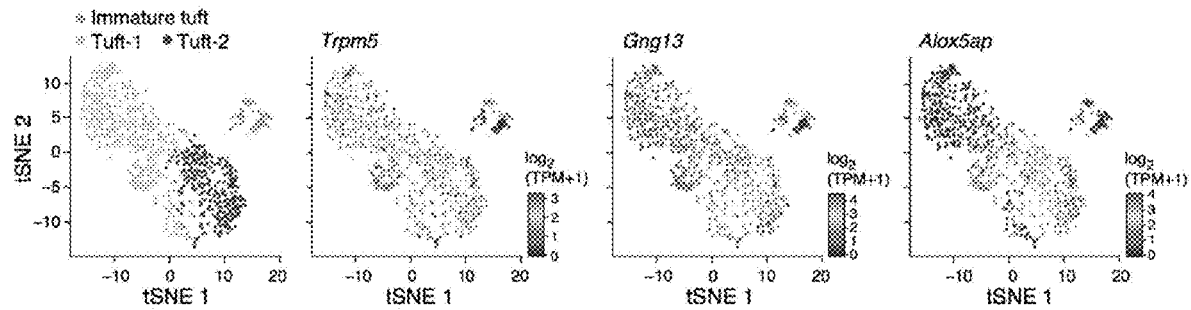
FIGS. 20A-20H show Tuft and goblet cell subtypes display unique functional gene expression programs. A. Tuft-1 and tuft-2 sub-clusters. tSNE visualization of 892 tuft cells (points) colored either by their cluster assignment (left, color legend), or by the expression level ($\log_2(TPM+1)$, color bar, remaining panels) of marker genes for mature tuft cells (Trpm5), tuft-1 (Gng13), tuft-2 (Alox5ap) subsets. B-D. Gene signatures for tuft-1 and tuft-2 subsets. B. Distribution of expression levels (y-axis, $\log_2(TPM+1)$) of the top markers for each subset (x-axis). NS: FDR>0.05, **FDR<10$^{10}$, likelihood-ratio test. C. Relative expression level (row-wise Z-scores, color bar) of genes (rows) differentially expressed (FDR<0.25, likelihood-ratio test) in tuft cells (columns) of each sub-cluster (color bar, top). D. Validation of tuft-1 and tuft-2 markers in vivo. Immunofluorescence staining of expression of the respective tuft-1 and tuft-2 cell markers Gng13 (green) and Alox5ap (magenta) by distinct tuft cells (solid white lines), along with pan-tuft marker Trpm5 (blue) and DAPI (grey). E. Tuft-1 and tuft-2 subtypes are each generated from basal cell parents. Estimated fraction (%, y-axis, Methods) of cells of each type that are positive for the basal-cell lineage label (by FACS) from n=3 mice (points) per time point (x-axis) in the Pulse-Seq experiment. *p<0.001, likelihood-ratio test (Methods), error bars: 95% CI. F-G. Tuft-1 and tuft-2 respectively express chemosensory and inflammatory gene modules. Differential expression between tuft subtypes for all genes (f, left), those involved in leukotriene synthesis (f, center left), taste transduction (f, right), and transcription factors (g). Labeled genes are differently expressed in the tuft cell subsets (FDR<0.01, likelihood-ratio test). H. Validation of goblet cell subtype markers. Immunofluorescence staining of the goblet-1 (Tff2, magenta) and goblet-2 Lipf (green) markers along with DAPI (blue) in distinct cells (solid white lines).
Figure 20B:
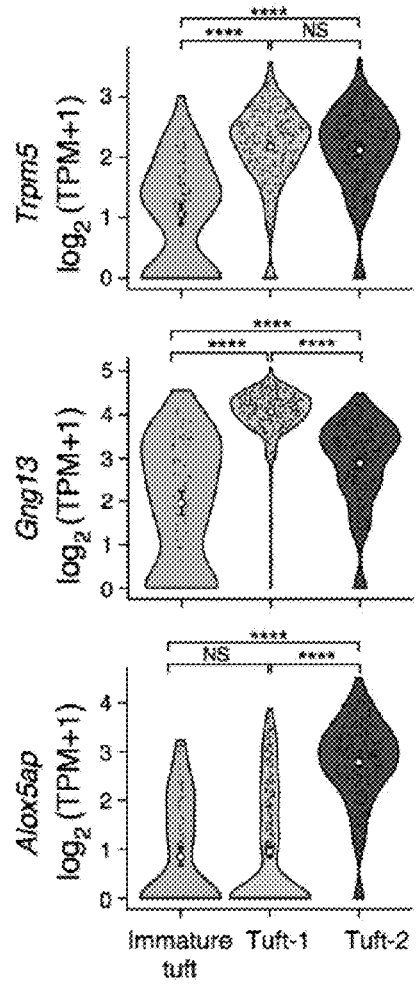
Figure 20C:
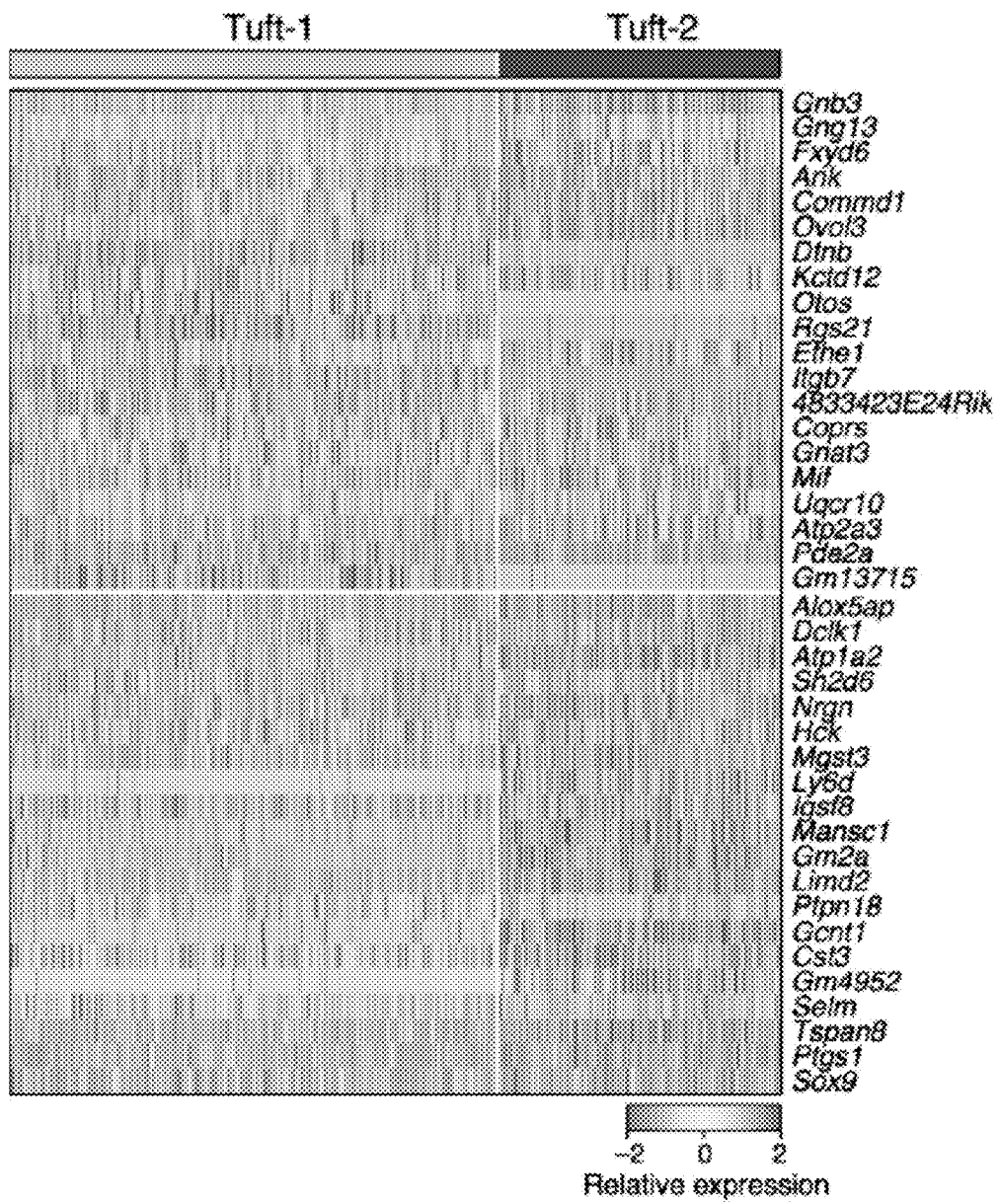
Figure 20D:
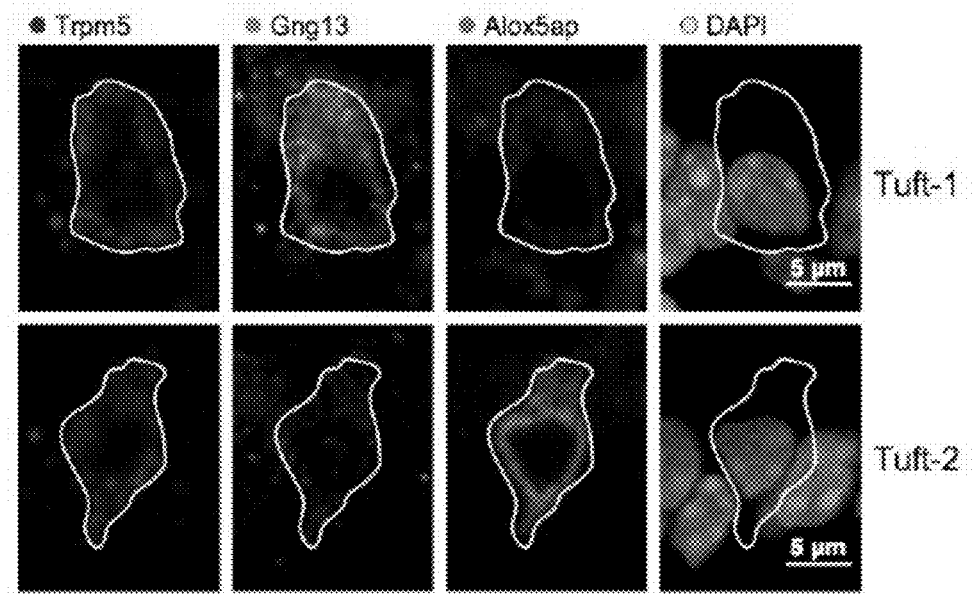
Figure 20E:
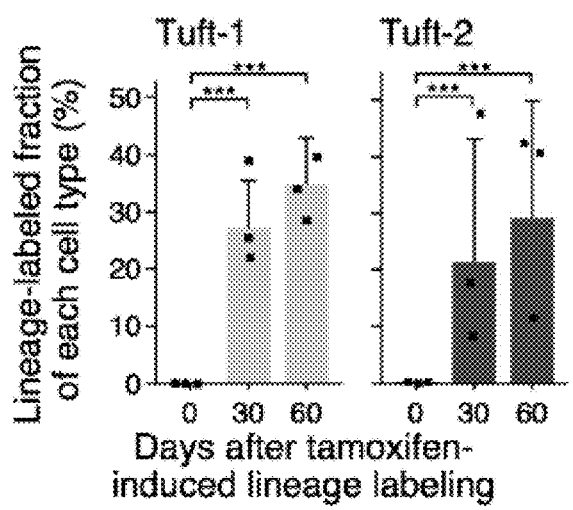
Figure 20F:
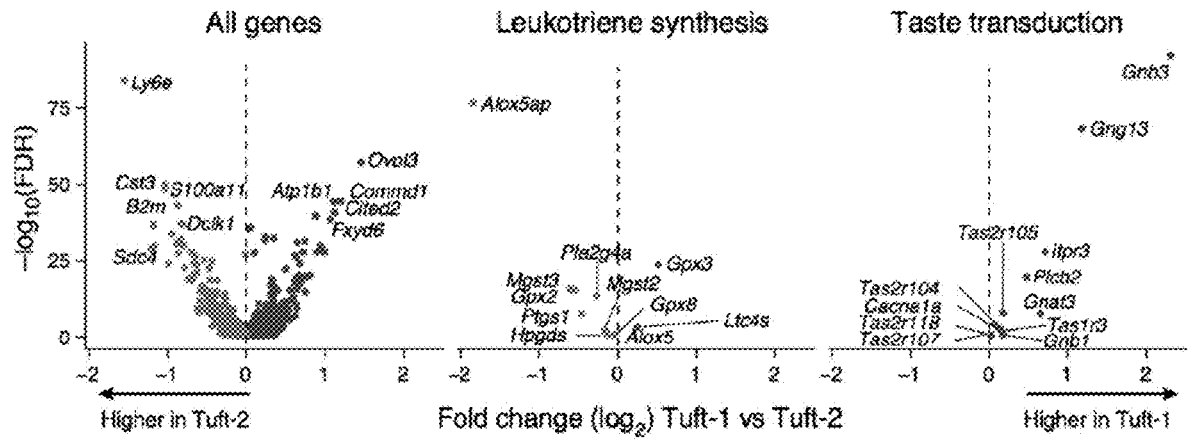
Figure 20G:
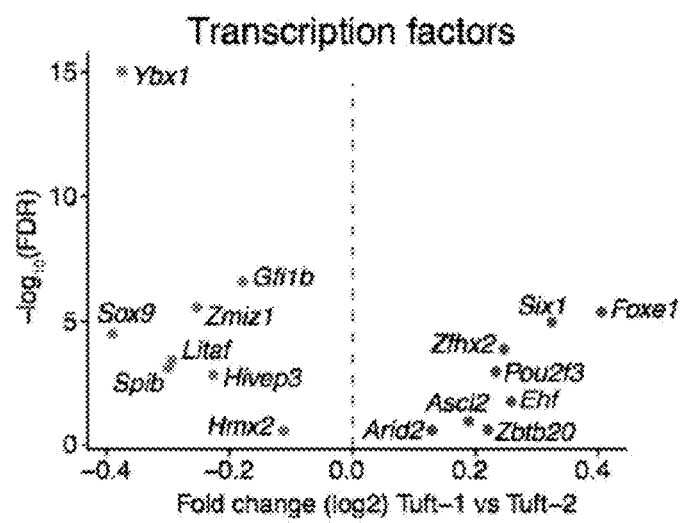
Figure 20H:
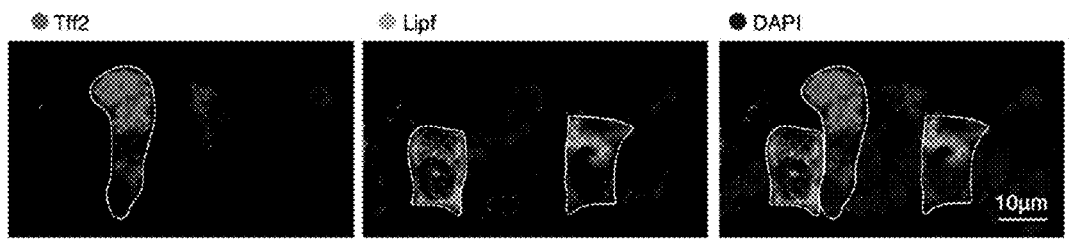
Figure 30C:
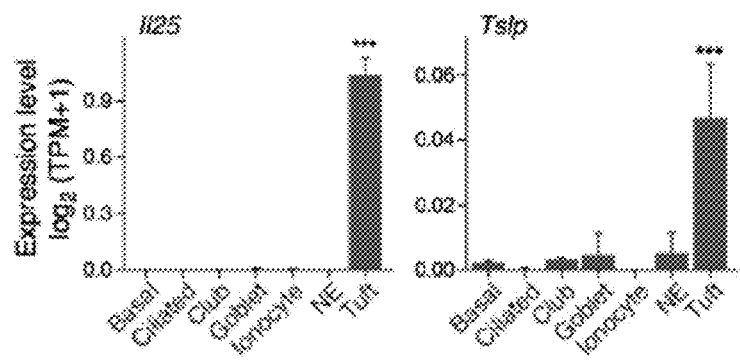
Figure 30D:
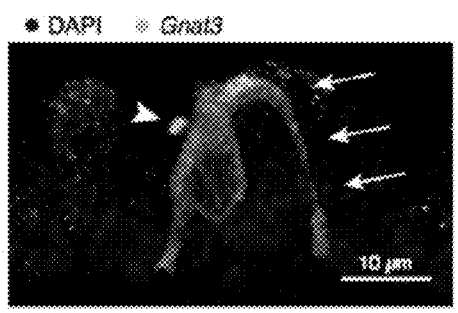
Figure 30E:
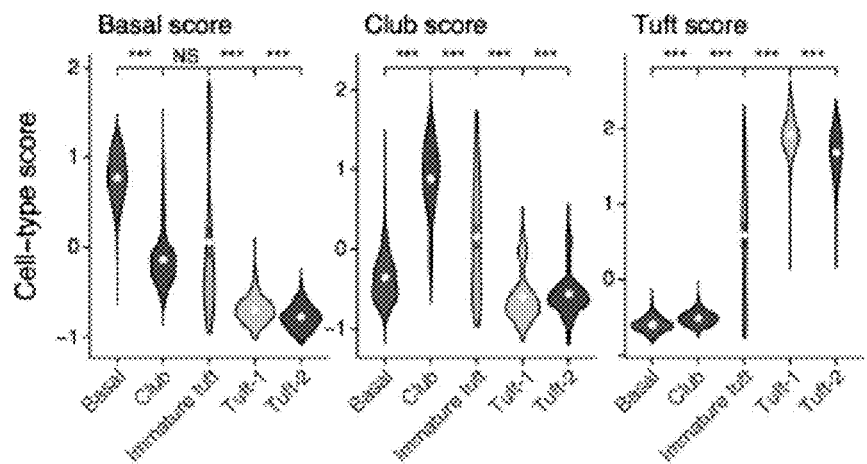
Figure 30F:
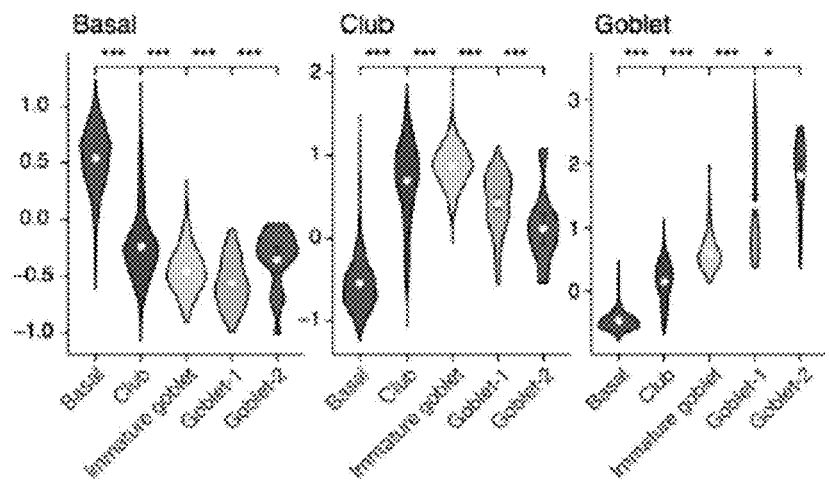
Figure 30G:
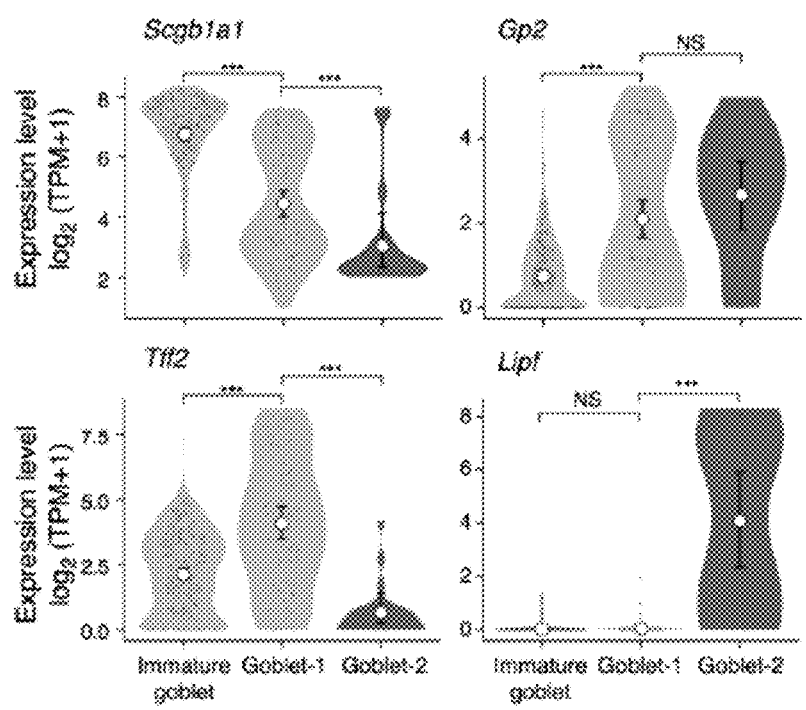
Figure 30H:
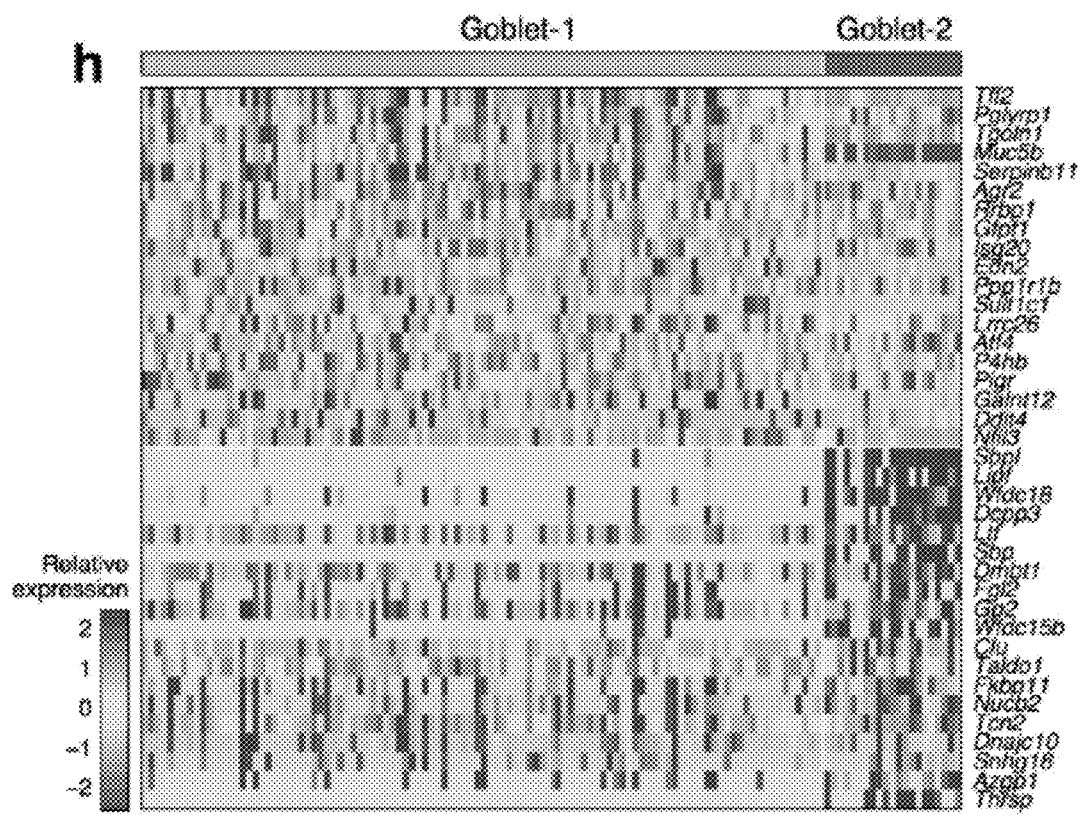
Figure 30I:

Goblet cells also partitioned into one putative immature cell subset and two mature cell subsets, goblet-1 and goblet-2 (FIG. 20H and FIG. 30F-I). The most highly enriched marker across the entire goblet cell cluster was Gp2 (FIG. 17D, FIG. 23D), an M cell-specific marker in the intestinal epithelium, which binds pathogenic enterobacteria and initiates a mucosal immune response (Hase, K. et al. Uptake through glycoprotein 2 of FimH(+) bacteria by M cells initiates mucosal immune response. *Nature* 462, 226-230 (2009)). Goblet-1 cells are enriched for the expression of genes encoding key mucosal proteins (e.g., Tff1, Tff2, Muc5b, FDR<0.001, likelihood-ratio test, FIGS. 30G-I) and regulators of mucus secretion (e.g., Lman11, P2rx4[50-52], FDR<0.1, likelihood-ratio test). Applicants validated co-expression of Tff2 and Muc5ac in goblet-1 cells by antibody staining (FIG. 30I). Goblet-2 cells are distinguished by higher expression of Dcpp1, Dcpp2, and Dcpp3 (FIG. 30H), orthologs of the lectin-like secreted protein ZG16B (Mullins, J. J. et al. Identification of a human ortholog of the mouse Depp gene locus, encoding a novel member of the CSP-1/Dcpp salivary protein family. *Physiol. Genomics* 28, 129-140 (2006)), which physically aggregates bacteria (Bergstrom, J. H. et al. Gram-positive bacteria are held at a distance in the colon mucus by the lectin-like protein ZG16. *Proc. Natl. Acad. Sci. U.S.A.* 113, 13833-13838 (2016)) and of Lipf a secreted gastric lipase that hydrolyses triglycerides (FIG. 20H and FIG. 30G,H). Applicants validated that Tff2 and Lipf are unique markers of the goblet-1 and goblet-2 cells, respectively (FIG. 20H).

The Foxi1$^+$ pulmonary ionocyte expresses CFTR in mouse and human

Figure 31A:
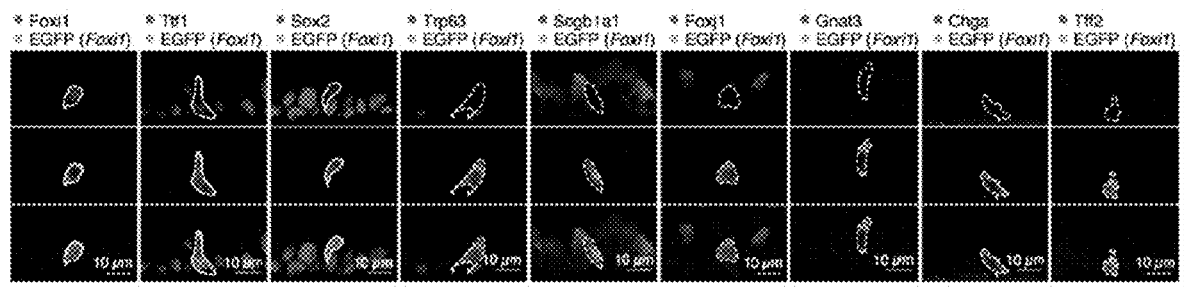
FIGS. 31A-31H show ionocyte characterization. A. Immunofluorescent characterization of ionocytes. Ionocytes visualized with EGFP(Foxi1) mouse. EGFP appropriately marks Foxi1 antibody-positive cells (left panel, solid white line). EGFP$^+$ cells express canonical airway markers Ttfl (Nkx2-1) and Sox2 (solid white lines). EGFP(Foxi1)$^+$ cells do not label with basal (Trp63), club (Scgb1a1), ciliated (Foxj1), tuft (Gnat3), neuroendocrine (NE) (Chga), or goblet (Tff2) cell markers (dashed white lines). B. Ionocytes are sparsely distributed in the surface epithelium. Representative whole mount confocal image of ionocytes EGFP(Foxi1) and ciliated cells (AcTub). C. GFP(Foxi1)$^+$ ionocytes extend cytoplasmic appendages (arrows). D. Immunofluorescent labeling of GFP(Foxi1)$^+$ cells in the submucosal gland. Dotted line separates surface epithelium (SA) from submucosal gland (SMG). E. Ascl3-KO moderately decreases ionocyte TFs and Cftr in ALI cultured epithelia. Expression quantification (ΔΔCT, y-axis) of ionocyte (Cftr: −0.82 ΔΔCT, 95% CI [±0.20], Foxi1: −0.75 ΔΔCT, 95% CI [0.28], Ascl3: −10.28 ΔΔCT, 95% CI [±1.85]) and basal (Trp63), club (Scgb1a1), or ciliated (Foxj1) markers (x-axis) in hetero- and homozygous KO (color legend) are normalized to wild-type littermates. The mean of independent probes (p1 and p2) was used for Cftr. n=10 and 5 hetero- and homozygous KO, respectively and n=4 wild-type mice. *p<0.05, **p<0.01, Dunn's Method, error bars: 95% CI. F. Increased depth of airway surface liquid (ASL) in Foxi1-KO ALI culture compared to WT. Representative OCT image of ASL. Red bar: airway surface liquid and mucous layer depth. Scale bar (white): 10 μm. G,H. Increased forskolin $ΔI_{eq}$ in heterozygous and KO epithelia. $ΔI_{eq}$ (y axis) in ALI cultures of wild type (WT), heterozygous (HET) and Foxi1 knock-out (KO) mice (n=5 WT, n=4 HET, n=6 KO, dots) that were characterized for their forskolin-inducible equivalent currents (G, $I_{eq}$) and for currents sensitive to CFTR$_{inh}$-172 (H). The inhibitor-sensitive $ΔI_{eq}$s reported may be somewhat underestimating the true inhibitor-sensitive current, since not for all filters the inhibitor response reached a steady plateau on the time scale of the experiment.
Figure 31B:
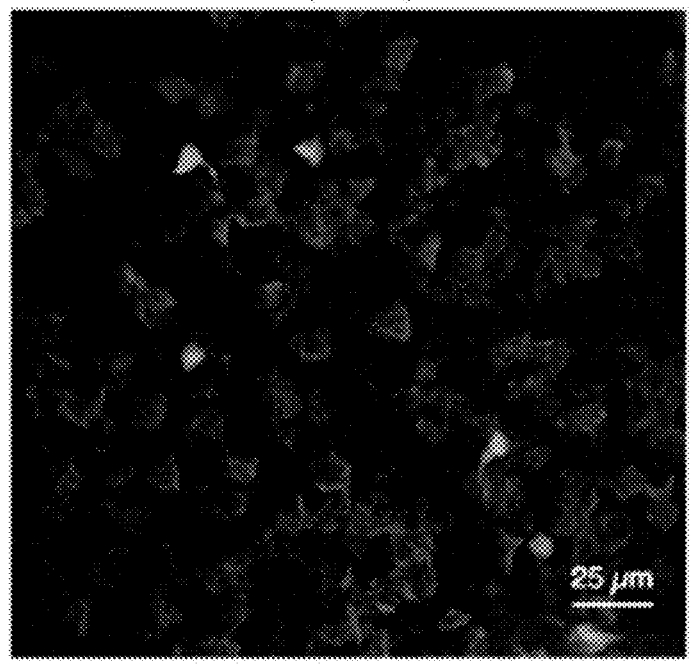

Foxi1$^+$ ionocytes are a new cell population, observed as a cluster of 26 cells in the initial dataset, and confirmed independently as a 276 cell cluster in the larger Pulse-Seq dataset. Applicants validated the presence of ionocytes using a transgenic Foxi1-GFP reporter mouse strain (Bergström, J. H. et al. Gram-positive bacteria are held at a distance in the colon mucus by the lectin-like protein ZG16. *Proc. Natl. Acad. Sci. U.S.A.* 113, 13833-13838 (2016)). Foxi1-GFP$^+$ cells co-labeled with anti-Foxi1 antibody, confirming the fidelity of the reporter line (FIG. 31A, left column). Ionocytes are labeled by the canonical airway markers Sox2 and Ttf1 (Nkx2-1) but are not labeled by the cell-type specific markers of any of the known airway epithelial cell types, confirming their distinct identity (FIG. 31A). Cell counting in three formalin-fixed whole-mounted tracheas (FIG. 31B, Methods), showed 1,038±501 ionocytes per trachea on average (~1% of all epithelial cells in the mouse trachea; compared to 0.36-0.42% detection by scRNA-seq).

Based on their expression signature, pulmonary ionocytes resemble evolutionarily conserved V-ATPase-rich ionocytes in other organisms, where Foxi1 orthologs specify cell identity and regulate V-ATPase expression. In the multiciliated skin of *Xenopus*, ionocytes are specified by Foxi1. Foxi3a and Foxi3b identify mitochondria-rich skin ionocytes in zebrafish (Esaki, M. et al. Mechanism of development of ionocytes rich in vacuolar-type H(+)-ATPase in the skin of zebrafish larvae. *Dev. Biol.* 329, 116-129 (2009)). Mammalian Foxi1 regulates V-ATPase in specialized cells of the inner ear, kidney, and epididymis that regulate ion transport and fluid pH (Vidarsson, H. et al. The forkhead transcription factor Foxi1 is a master regulator of vacuolar H-ATPase proton pump subunits in the inner ear, kidney and epididymis. *PloS One* 4, e4471 (2009); Overdier, D. G., Ye, H., Peterson, R. S., Clevidence, D. E. & Costa, R. H. The winged helix transcriptional activator HFH-3 is expressed in the distal tubules of embryonic and adult mouse kidney. *J. Biol. Chem.* 272, 13725-13730 (1997)). Pulmonary ionocytes are similarly enriched in the expression of V-ATPase subunits Atp6v1c2 and Atp6v0d2 (FDR<0.0005, likelihood-ratio test, FIG. 21B top row, FIG. 27B) and are uniquely marked by an anti-ATP6v0d2 antibody (FIG. 27B, top row).

Figure 31C:
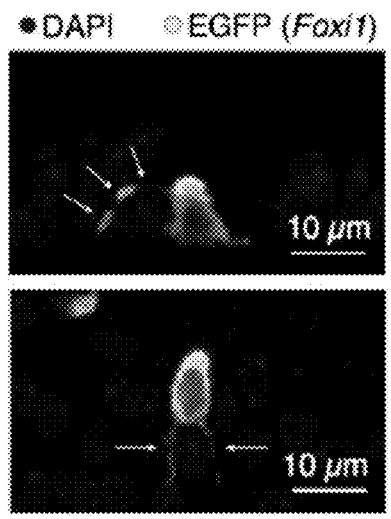

Like tuft cells (FIG. 30D) and zebrafish ionocytes (Jonz, M. G. & Nurse, C. A. Epithelial mitochondria-rich cells and associated innervation in adult and developing zebrafish. *J. Comp. Neurol.* 497, 817-832 (2006)), pulmonary ionocytes extend lateral processes some 10 μm-20 μm away from their cell bodies, contacting several additional epithelial cells beyond their immediate neighbors, as well as the basement membrane (FIG. 31C). Applicants speculate these processes may be involved in chemosensation and cell-to-cell communication.

Figure 21A:
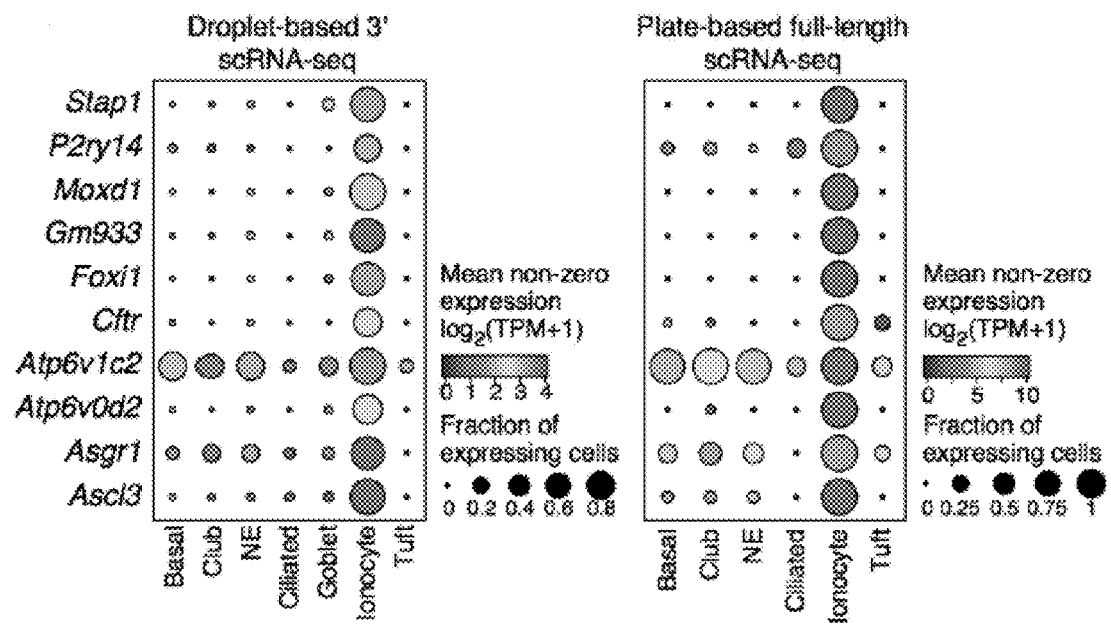
FIGS. 21A-21K show the pulmonary ionocyte is a novel mouse and human airway epithelial cell type that specifically expresses CFTR. A. Mouse ionocyte markers. Expression level (mean $\log_2(TPM+1)$, color bar) of ionocyte markers (columns, FDR<0.05 in both 3' and full-length scRNA-seq datasets, likelihood-ratio test) in the 3' scRNA-seq dataset of each airway epithelial cell type (rows). Dot size: proportion of cells with non-zero expression. Color intensity: mean expression in those cells with non-zero expression. B. Ionocytes specifically express V-ATPase and Cftr. Immunofluorescent co-labeling of EGFP (Foxi1+) ionocytes and a V-ATPase subunit (Atp6v0d2, top left, solid white line) and Cftr (bottom left, solid white line). C. tSNE visualization colored by expression level of ionocyte markers Foxi1 (left) and Cftr (right) across all 66,265 trachea epithelial cells from the Pulse-Seq experiment and in the subset of 276 ionocytes (inset). D. qRT-PCR confirms ionocyte enrichment of Cftr relative to ciliated cells and EpCAM⁻ populations. Expression (ΔΔCT, y-axis) of ionocyte (Cftr, Foxi1) and ciliated cell (Foxj1) markers (x-axis) detected using qRT-PCR of prospectively isolated populations of ionocytes and ciliated cells from Foxi1-(n=4, dots) and Foxj1-GFP mice (n=3), respectively. All values normalized relative to EpCAM+ populations from wild-type mice (n=6; 7.30 ΔΔCT, 95% CI [±0.66]), ***p<0.001, Dunn's Method, error bars: 95% CI. E. Foxi1-KO displays loss of expression of ionocyte TFs and Cftr in ALI cultured epithelia. Expression (ΔΔCT, y-axis) of ionocyte (Cftr: −2.77 ΔΔCT, 95% CI [±0.28], Foxi1: −9.46 ΔΔCT, 95% CI [13.32], Ascl3: −4.77 ΔΔCT, 95% CI [10.57]) and basal (Trp63), club (Scgb1a1), or ciliated (Foxj1) markers (x-axis) in hetero- and homozygous KO (color legend), normalized to wild-type littermates. The mean of independent probes (p1 and p2) was used for Cftr. Heterozygous KO: n=4; homozygous KO: n=6, wild type: 11=8, *p<0.05, p<0.01, Dunn's Method, error bars: 95% CI. F. Ionocyte depletion via Foxi1-KO disrupts mucosal homeostasis in ALI cultured epithelia. Effective viscosity (cP, left) and ciliary beat frequency (Hz, right) from optical coherence tomography (OCT) in homozygous Foxi1-KO (n=9, dots) vs. wild-type littermates (x-axis, n=3 mice). *p<0.001, ****p<0.0001, Mann-Whitney U-test. G-H. Foxi1 transcriptional activation (Foxi1-TA) in ferret increases Cftr expression and chloride transport. G. qRT-PCR expression quantification (ΔΔCT, y-axis) of ionocyte markers (x-axis) in ferret Foxi1-TA ALI (n=4) normalized to mock transfection (Cftr: −1.39 ΔΔCT, 95% CI [±0.44], Foxi1: −5.37 ΔΔCT, 95% CI [±0.91], Methods), error bars: 95% CI. H. Foxi1 activation in ferret cell cultures results in a CFTR inhibitor-sensitive short-circuit current ($\Delta I_{sc}$). Representative trace of short-circuit current ($I_{sc}$, y-axis) tracings from Foxi1-TA ferret ALI after sgRNA reverse transfection (n=4, light blue) vs. mock transfection (n=4, black). I. Ionocytes are sparsely distributed in human bronchial epithelium. In situ hybridization shows cells co-labeled for Foxi1 and Cftr (20 double Z probe pairs spanning 960 nucleotides including the only documented CFTR splice site). J-K. Human pulmonary ionocytes are the major source of Cftr in the bronchial epithelium. J. tSNE of 765 human pulmonary ionocytes (red points) identified using clustering of 78,217 3' droplet scRNA-seq profiles (grey points) from human bronchial epithelium (n=1 patient). K. Difference in fraction of cells in which transcript is detected (x axis) and log₂ fold-change (y-axis) between human ionocytes and all other bronchial epithelial cells. All labeled genes are differentially expressed (log₂ fold-change>0.25 and FDR<<10⁻¹⁰, Mann-Whitney U-test). Red: consensus ionocyte markers in mouse (log₂ fold-change>0.25, FDR<10⁻⁵, likelihood-ratio test) and human.
Figure 21B:
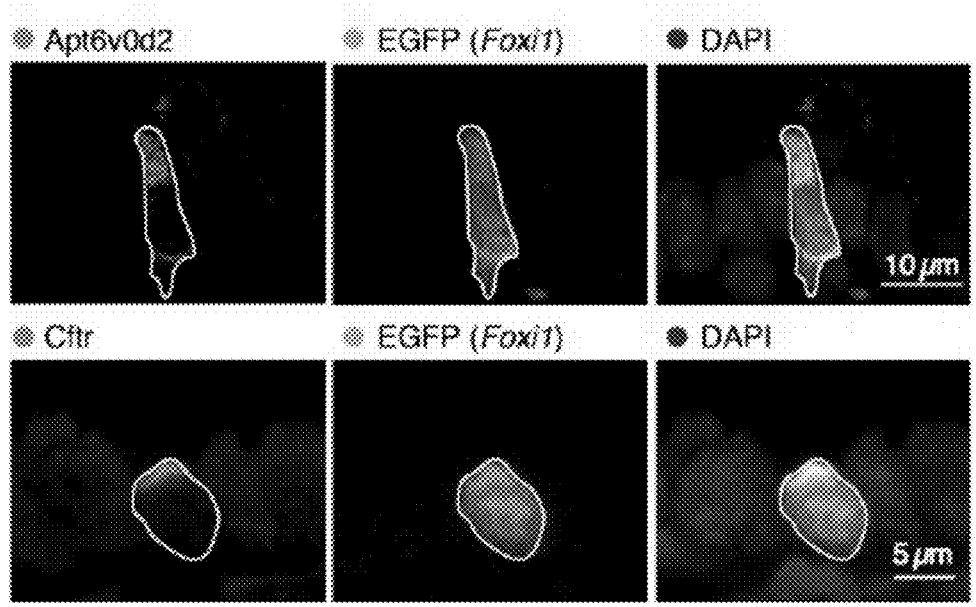
Figure 21C:
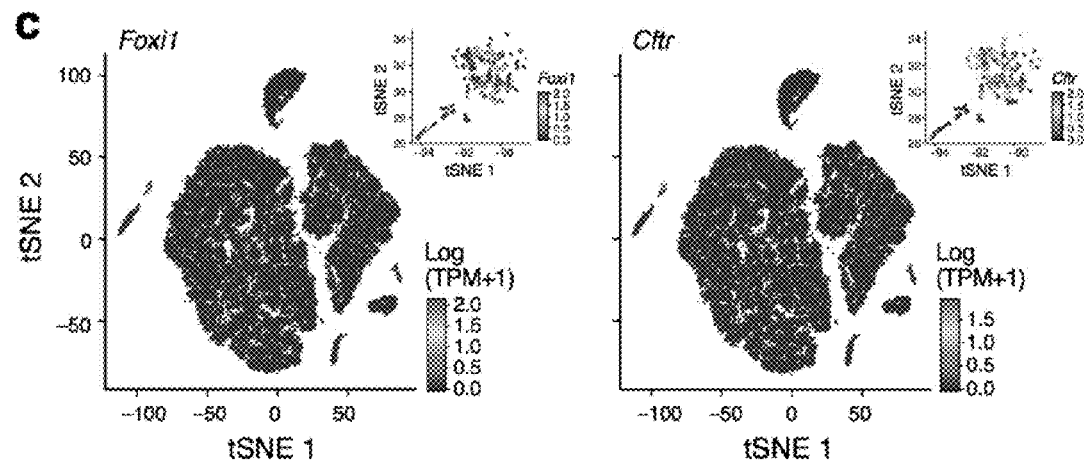
Figure 21D:
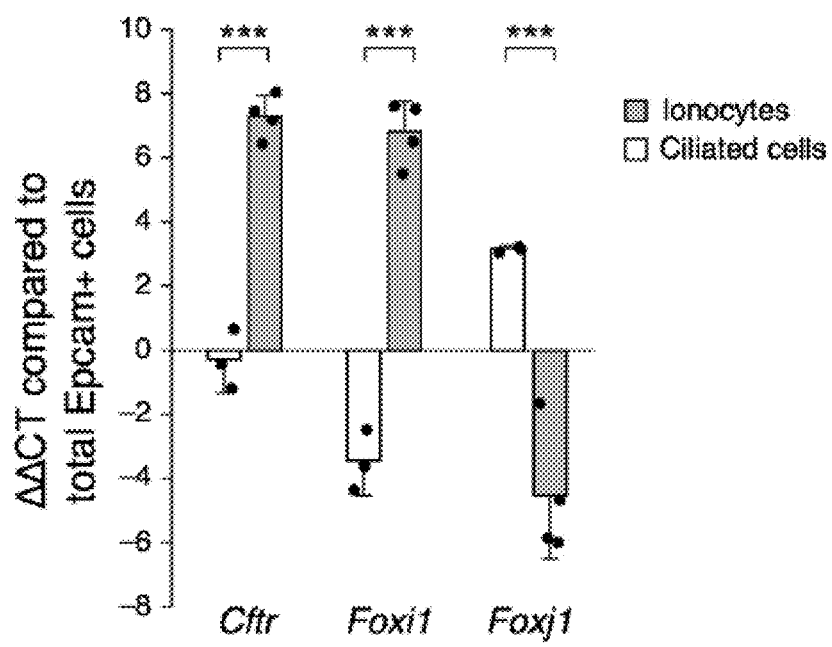

Strikingly, the pulmonary ionocyte is specifically enriched for the expression of cystic fibrosis transmembrane conductance regulator (Cftr) mRNA (FDR<0.005 and FDR<$10^{-10}$ in the initial and Pulse-Seq dataset respectively, likelihood-ratio test, FIG. 21A,C, FIG. 25B), accounting, on average, for 55% of detected Cftr transcripts across all single cells profiled from the mouse tracheal epithelium, despite the fact that ionocytes comprise, on average, only 0.39% of the cells analyzed. Applicants confirmed the specific enrichment of Cftr in ionocytes by qRT-PCR of prospectively isolated populations of primary ionocytes (Foxi1-GFP) vs. ciliated cells (Foxj1-GFP) or bulk EpCAM$^+$ epithelial cells (FIG. 21D), and at the protein level by Cftr staining of Foxi1-GFP$^-$ cells in situ (FIG. 21B, bottom row).

Figure 31D:
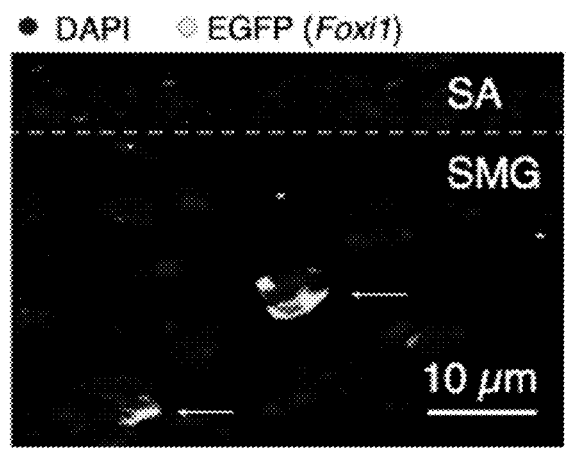

Of note, Foxi1-GFP$^+$ cells are detected in murine submucosal glands (FIG. 31D), which are implicated in the pathogenesis of cystic fibrosis (Hoegger, M. J. et al. Impaired mucus detachment disrupts mucociliary transport in a piglet model of cystic fibrosis. *Science* 345, 818-822 (2014)) and have the highest levels of CFTR expression in human airways (Engelhardt, J. F. et al. Submucosal glands are the predominant site of CFTR expression in the human bronchus. *Nat. Genet.* 2, 240-248 (1992)). Ionocytes also specifically express Cochlin (Coch), a secreted protein that promotes antibacterial innate immunity against *Pseudomonas aeruginosa* and *Staphylococcus aureus*, the two most prominent pathogens in CF lung disease (Py, B. F. et al. Cochlin produced by follicular dendritic cells promotes antibacterial innate immunity. *Immunity* 38, 1063-1072 (2013)). Deletion of Foxi1 in the mouse results in defective acidification of the epididymal lumen and male infertility (Blomqvist, S. R., Vidarsson, H., Söder, O. & Enerbäck, S. Epididymal expression of the forkhead transcription factor Foxi1 is required for male fertility. *EMBO J.* 25, 4131-4141 (2006)), resembling the reduced fertility phenotype observed clinically in CF.

Figure 21E:
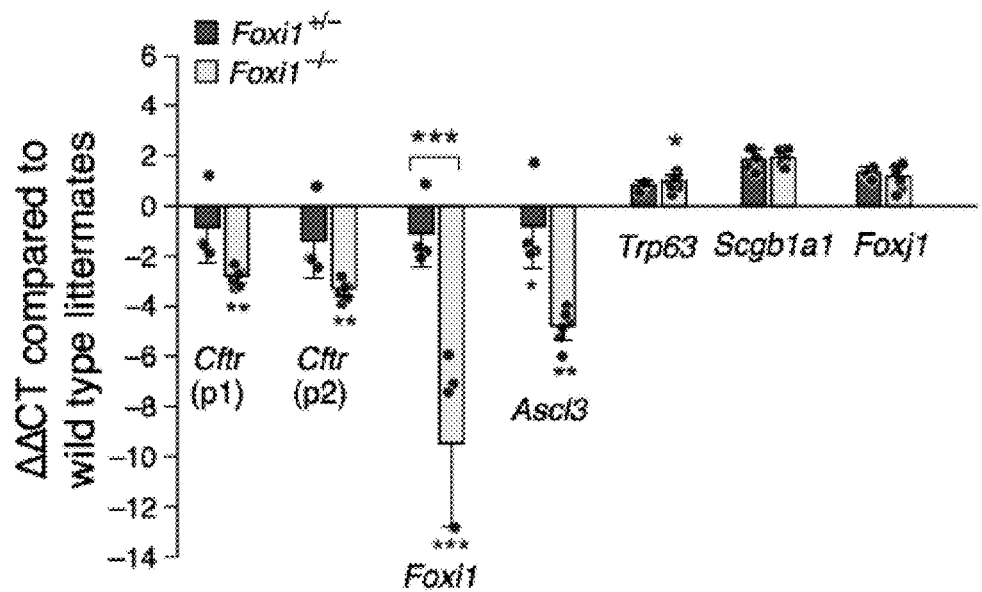
Figure 31E:
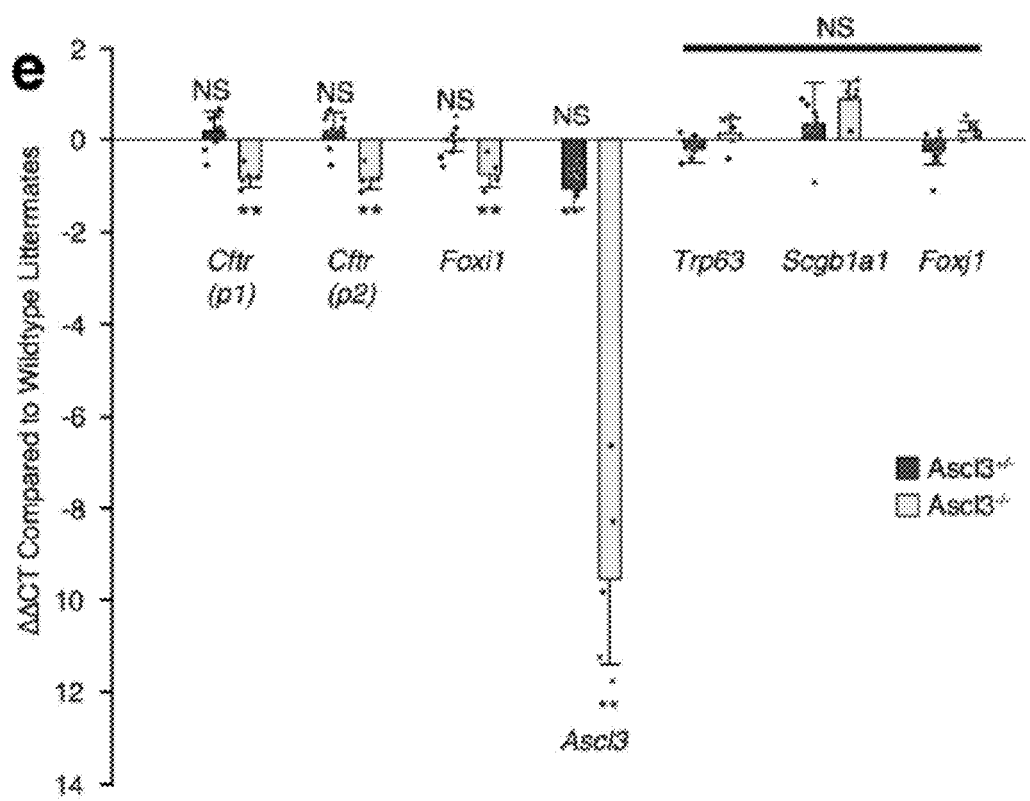

Analysis of epithelial cells derived from Foxi1 knockout (Foxi1-KO) mice shows that Foxi1 is required for the expression of the ionocyte TF Ascl3, and the majority of Cftr expression (FIG. 21E). Thus, loss of Foxi1 causes either loss of the ionocyte itself or a significant alteration in its transcriptional state. In contrast, epithelial cells derived from the Ascl3 knockout mouse displayed only moderately reduced Foxi1 and Cftr expression (FIG. 31E).

Ionocytes Regulate Epithelial Surface Physiology

Figure 21F:
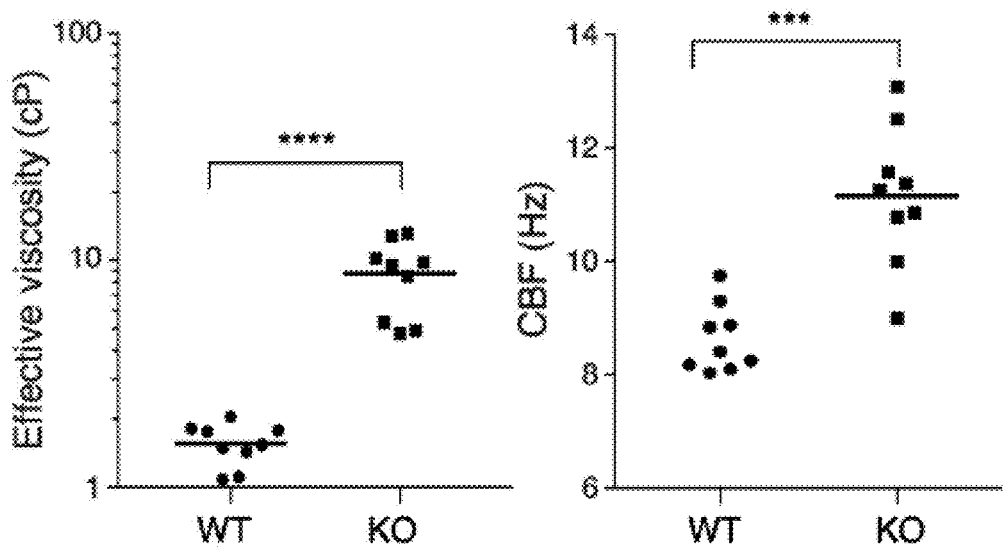
Figure 31F:
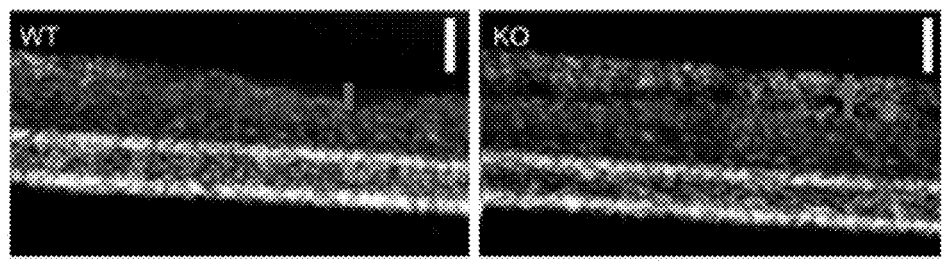
Figure 32A:
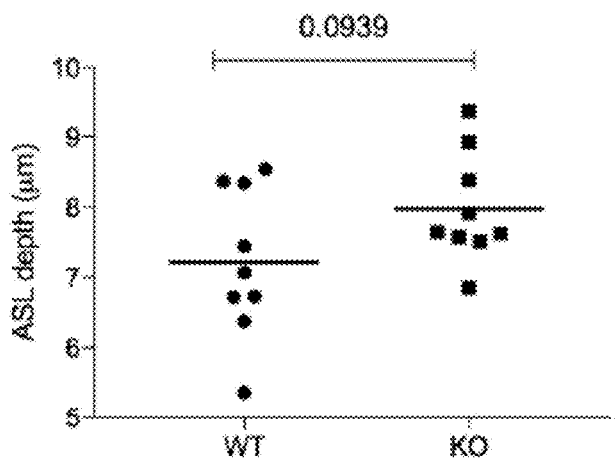
FIGS. 32A-32C show ionocyte characterization. A,B. Ionocyte depletion or disruption via Foxi1-KO disrupts mucosal homeostasis in ALI cultured epithelia. ASL depth determined via OCT (A) and pH (B) in homozygous Foxi1-KO (n=9, dots) vs. wild-type littermates (x-axis, n=3 mice). p values: Mann-Whitney U-test. c. Foxi1-TA results in increased Cftr short-circuit current ($ΔI_{sc}$, y-axis) in ferret ALI vs. mock transfected controls (Methods). n=5, *p<0.05, t-test, error bars: 95% CI.
Figure 32B:
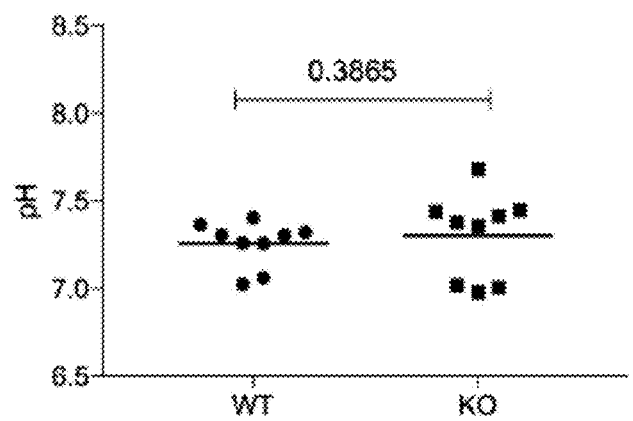

Both the amount and viscosity of mucus in the airway surface liquid (ASL) is tightly regulated and this process is necessary for effective mucociliary clearance of debris and pathogens and is disturbed in diseases such as CF (Birket, S. E. et al. A functional anatomic defect of the cystic fibrosis airway. *Am. J. Respir. Crit. Care Med.* 190, 421-432 (2014); Birket, S. E. et al. Development of an airway mucus defect in the cystic fibrosis rat. *JCI Insight* 3, (2018)). Several functional assays show that the loss of Foxi1 in mouse airway epithelium alters physiologic parameters that govern mucus clearance. Applicants assessed ASL depth, mucus viscosity, and ciliary beat frequency in the murine airway epithelium of Foxi1-KO with live imaging by micro-optical coherence tomography (μOCT) and particle-tracking microrheology (Liu, L. et al. Method for quantitative study of airway functional microanatomy using micro-optical coherence tomography. *PloS One* 8, e54473 (2013)) (Methods). Strikingly, Foxi1-KO epithelia had increased optical density of airway mucus (FIG. 31F) and increased effective viscosity compared to wild-type littermates (1.56+/−0.3 cP WT, 8.78+/−3.2 KO, p<0.0001 Mann Whitney U-test, FIG. 21F, left). Though modest in magnitude, these results are consistent with the increased mucus viscosity seen in animal models of cystic fibrosis (Tang, X. X. et al. Acidic pH increases airway surface liquid viscosity in cystic fibrosis. *J. Clin. Invest.* 126, 879-891 (2016)). Indeed, the changes in mucus viscosity are in line with those observed in primary human bronchial epithelial cells of CF patients as compared to normal individuals (Birket, S. E. et al. Combination therapy with cystic fibrosis transmembrane conductance regulator modulators augment the airway functional microanatomy. *Am. J. Physiol. Lung Cell. Mol. Physiol.* 310, L928-939 (2016)). Ciliary beat frequency (CBF) significantly increased in the Foxi1-KO epithelium (FIG. 21F, right, 8.54+/−0.8 and 11.16+/−1.2 Hz in WT and KO, p<0.001, Mann Whitney U-test), consistent with mechanical feedback elicited by increased airway mucus viscosity (Liu, L. et al. An autoregulatory mechanism governing mucociliary transport is sensitive to mucus load. *Am. J. Respir. Cell Mol. Biol.* 51, 485-493 (2014)). In this model, as mechanical load increases, CBF increases until a failure threshold is reached. As with murine Cftr knockout models, neither depth (FIG. 32A) nor pH (FIG. 32B) of the ASL was significantly altered in Foxi1-KO epithelial cultures (Methods). In Cftr knockout models this lack of alteration in pH is attributed to low expression of Na$^-$/K$^+$ adenosine triphosphatase (Shah, V. S. et al. Airway acidification initiates host defense abnormalities in cystic fibrosis mice. *Science* 351, 503-507 (2016)) and ASL depth is preserved through high compensatory upregulation of CaCC expression (Tarran, R. et al. Regulation of murine airway surface liquid volume by CFTR and Ca2+-activated Cl− conductances. *J. Gen. Physiol.* 120, 407-418 (2002)), as is also observed in murine Cftr$^{-/-}$ excised trachea.

Figure 31G:
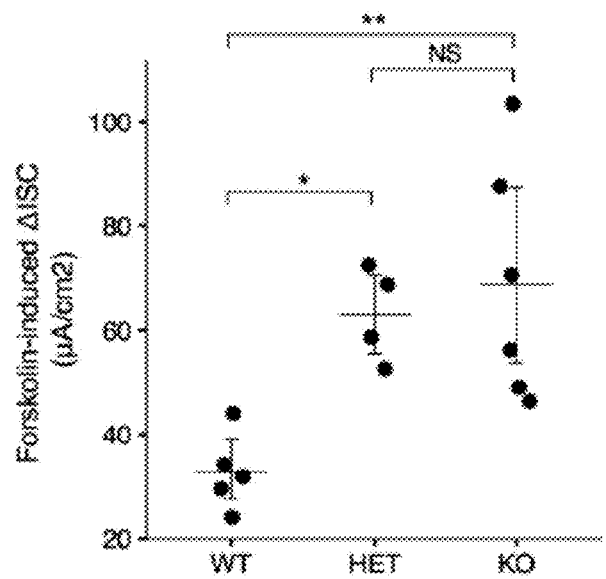
Figure 31H:
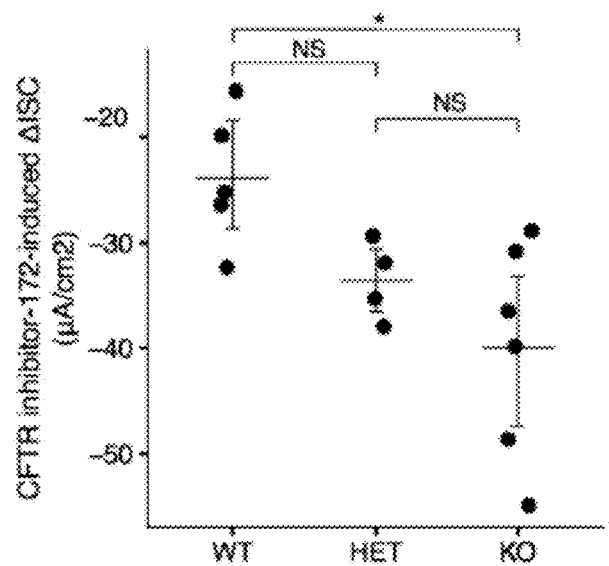

Applicants also tested whether Foxi1-KO epithelia display abnormal forskolin-induced and CFTR inhibitor (CFTR$_{inh}$-172)-blocked equivalent currents ($\Delta I_{eq}$) in measurements with the transepithelial current clamp system (Mou, H. et al. Dual SMAD Signaling Inhibition Enables Long-Term Expansion of Diverse Epithelial Basal Cells. *Cell Stem Cell* 19, 217-231 (2016)) (Methods). Paradoxically, Foxi1-KO mouse epithelium displayed increases in CFTR$_{inh}$-172-sensitive forskolin-induced currents under asymmetrical chloride (FIG. 31G,H). The reason for increased chloride currents in the setting of reduced Cftr expression of Foxi1-KO epithelium remains unclear, although cross-talk between cAMP and Ca$^{2+}$ pathways in mouse airways has been suggested to be partially responsible for a compensatory activation of forskolin-inducible currents in CF mouse airway epithelia (Grubb, B. R., Paradiso, A. M. & Boucher, R. C. Anomalies in ion transport in CF mouse tracheal epithelium. *Am. J. Physiol.* 267, C293-300 (1994)). The relevance of these findings and whether other non-ionocyte cell types contribute to Cftr currents in mouse airway epithelia in the setting of Foxi1 loss remain to be determined.

Figure 21G:
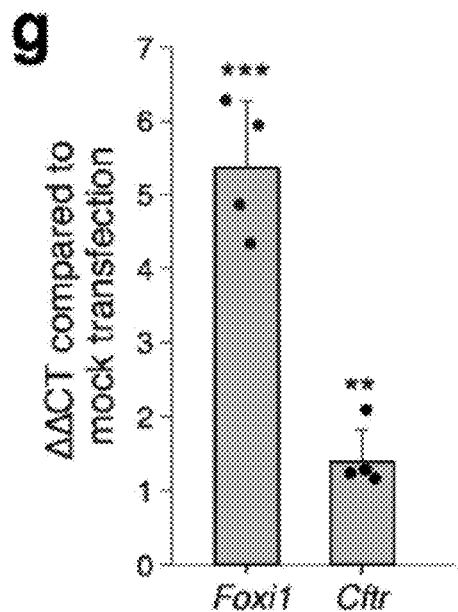
Figure 21H:
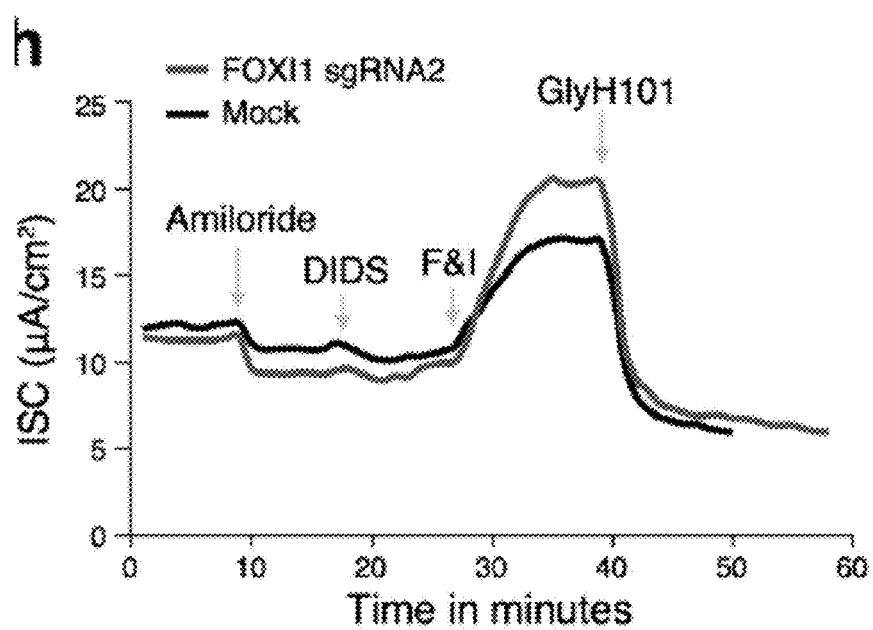
Figure 32C:
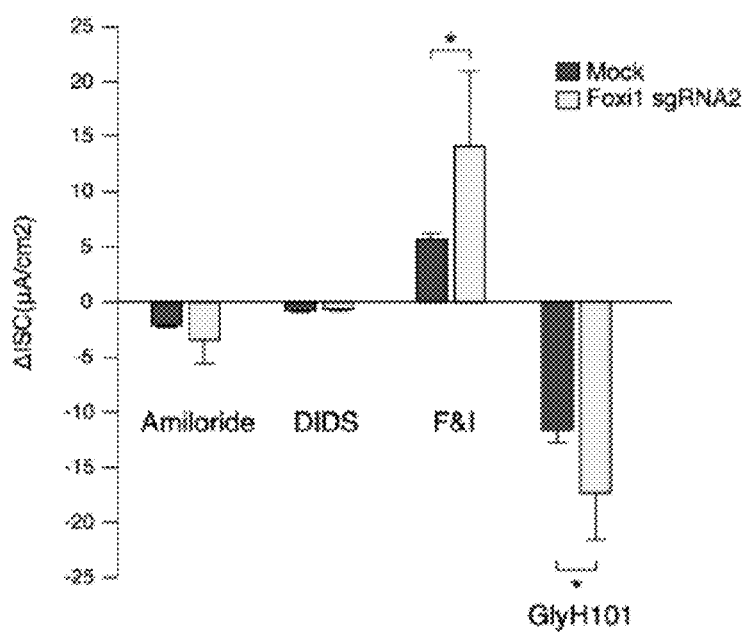

Since the ferret represents a more faithful model of human cystic fibrosis (Sun, X. et al. Lung phenotype of juvenile and adult cystic fibrosis transmembrane conductance regulator-knockout ferrets. *Am. J. Respir. Cell Mol. Biol.* 50, 502-512 (2014); Sun, X. et al. Disease phenotype of a ferret CFTR-knockout model of cystic fibrosis. *J. Clin. Invest.* 120, 3149-3160 (2010)), Applicants investigated the role of Foxi1 in regulating CFTR. CRISPR/dCas9VP64/p65-mediated transcriptional activation of Foxi1 increased airway epithelial expression of Cftr and other ionocyte genes as assessed by qRT-PCR (Methods, FIG. 21G). Importantly, Applicants found that ferret epithelial cultures subjected to Foxi1 transcriptional activation displayed significantly increased forskolin-induced $\Delta I_{sc}$ and CFTR (GlyH101) inhibitor $\Delta I_{sc}$ relative to mock-transfected controls (FIG. 21H, FIG. 32C). Thus, Foxi1 regulates CFTR expression and function in ferret airway epithelium.

The pulmonary ionocyte is the predominant CFTR expressing cell in human airways

Figure 21I:
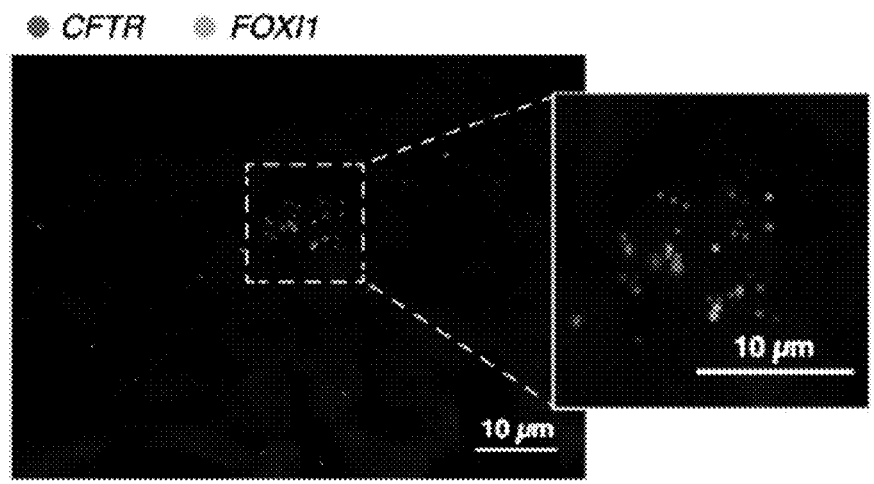
Figure 21J:
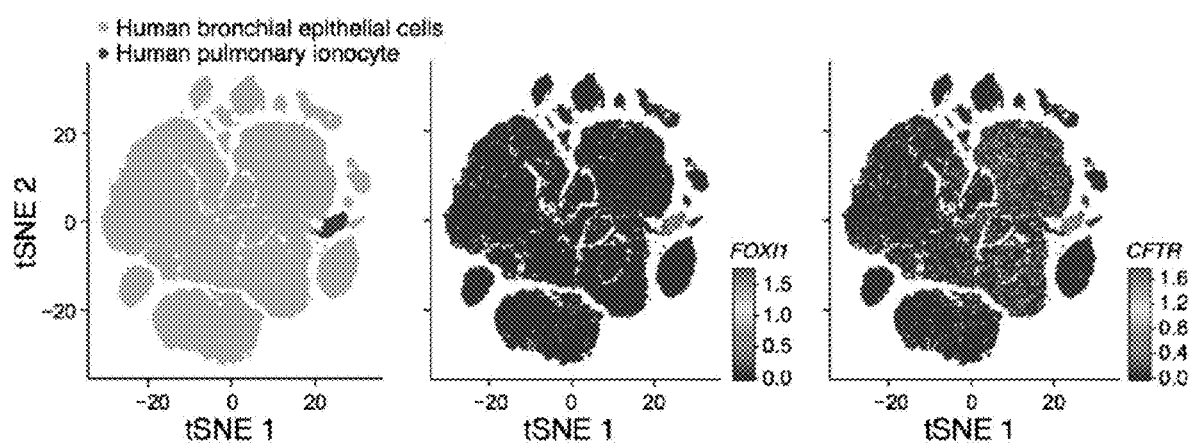
Figure 21K:
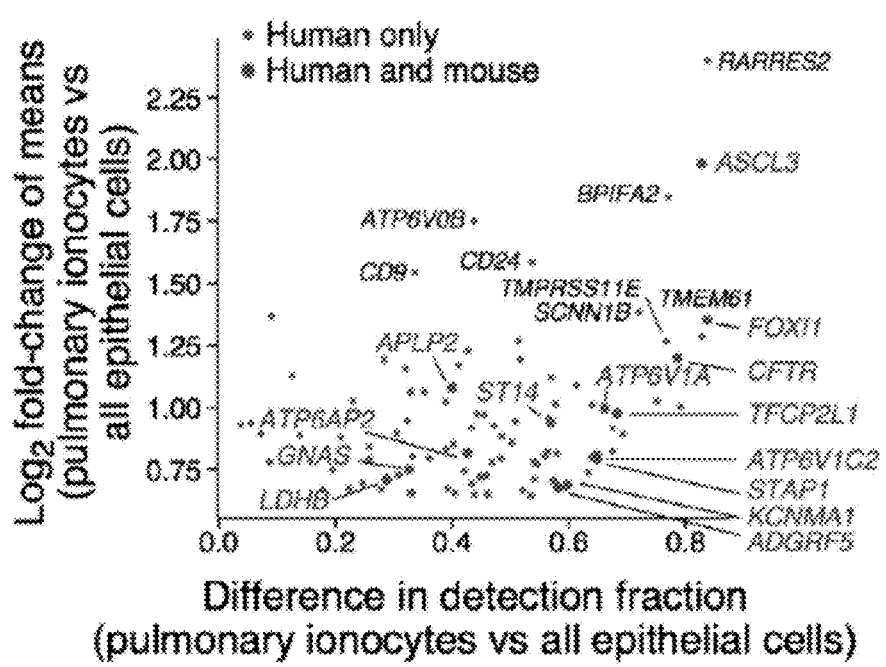

Human pulmonary ionocytes are the major source of CFTR in the airway epithelium as assessed by scRNA-Seq of healthy human lung from transplant material (FIG. 21J,K) and by RNA fluorescent in situ hybridization (RNA-FISH, Methods) of FOXI1 and CFTR in human bronchial airway epithelium (FIG. 21I). Among 78,217 cells from 5 regions along the airways of human lung (AT, AW, JR, AR, MS, JW et al, unpublished data), 765 ionocytes are detected by unsupervised clustering (FIG. 21J, left), with specific expression of FOXI1, ASCL3 and CFTR (FDR<$10^{-10}$, likelihood-ratio test, FIG. 21J, K), and a 14 gene cross-species consensus signature (FDR<$10^{-5}$, FIG. 21K). Ionocytes are detected at approximately the same fraction (0.5-1.5%) along the proximodistal axis from the carina to the secondary bronchus. As in mouse, FOXI1 expression is specific to ionocytes (FIG. 21J, middle), and CFTR is highly expressed in those cells (FIG. 21K, middle). Applicants do note however, that much lower expression is detected in a modest portion of some club and basal cells (FIG. 21J, right). In an accompanying manuscript, FOXI1 transcriptional activation in human airway epithelial cultures results in increased ionocyte differentiation. Additionally, numbers of human ionocytes correlated with forskolin-induced CFTR (inh)-172 inhibitable short-circuit currents (Wingert et al., accompanying manuscript).

Taken together, these results identify the ionocyte as a novel rare airway epithelial cell type with unique morphology, expression profile, and role in regulating airway epithelial surface physiology. Though the loss of pulmonary ionocytes alters physiologic parameters that are also aberrant in cystic fibrosis, defining the role of the ionocyte in cystic fibrosis or any other airways disease requires future study.

Discussion

Figure 22:
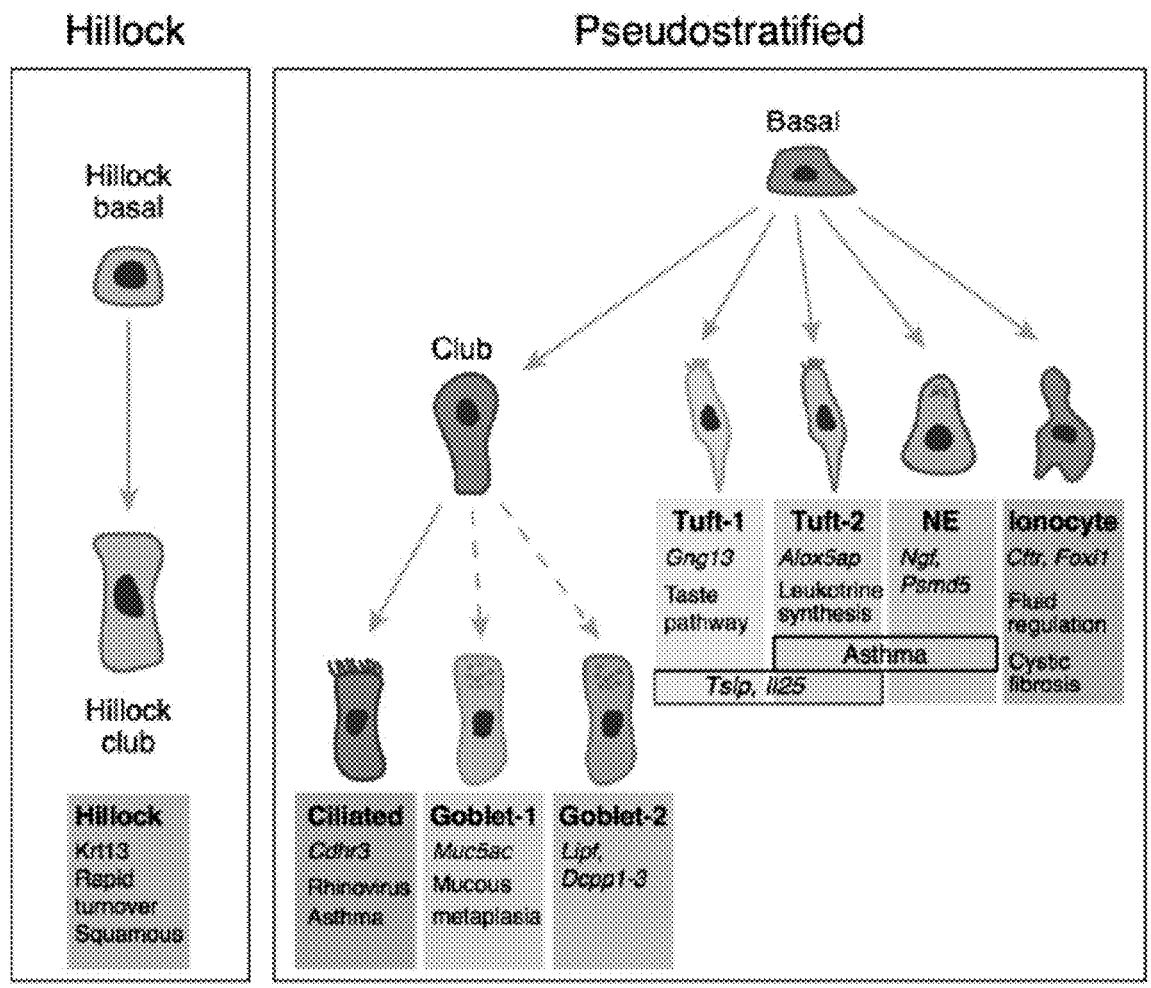
FIG. 22 shows a new lineage hierarchy of the airway epithelium reframes our understanding of the cellular basis of airways disease. Specific cells are associated with novel cell-type markers and disease-relevant genes.

Applicants combined scRNA-seq and genetic lineage tracing to generate a revised hierarchy of the murine tracheal epithelium that includes a new cell type, the ionocyte, new subclasses of tuft and goblet cells, new transitional cells, a new structure (hillocks). Applicants also show that the basal cell is the direct parent cell of club, tuft, NE, and ionocyte cells (FIG. 22). An accompanying manuscript, using related but distinct models and computational approaches including murine tracheal regeneration models, identified similar cell types including the pulmonary ionocyte (Wingert et al., accompanying manuscript). The use of Pulse-Seq allowed Applicants to assess differentiation dynamics across multiple cell types and subtypes in a complex new lineage tree in a single internally controlled experiment. Surprisingly, Applicants show that ionocytes, NE cells, and tuft cells appear at approximately the same rate as club cells. Within hillocks, cells appear even more rapidly and are associated with squamous, barrier, and immunomodulatory features. However, their actual function and origin is mysterious.

Have Applicants catalogued the full range of biologically relevant epithelial cell types? Statistical modeling (Haber, A. L. et al. A single-cell survey of the small intestinal epithelium. *Nature* 551, 333-339 (2017)) suggests that with 66,000 cells Applicants should have detected any discrete cell type that comprises more than 0.035% of the total cell population with 99% confidence. As a caveat, the model assumes that one recovers cells in their correct in vivo proportions, but Applicants note some cell populations may require special dissociation conditions. Importantly, injury and disease are likely to induce plasticity, thereby revealing new lineage paths. Indeed, cell states may change with disease and cell types not evident in the homeostatic epithelium may make an appearance.

The cell census allows one to reconstruct a hypothetical new cellular narrative of lung disease (FIG. 22). Disease genes associated with common diseases with complex genetic architecture, such as asthma, or with rare Mendelian genes, such as CF, can now be associated with particular cell types and subtypes. Generating comprehensive cell atlases of the healthy and diseased human lung and airways are a critical next step (Regev, A. et al. Science Forum: The Human Cell Atlas. *eLife* 6, e27041 (2017)). Lineage relationships, cell types, and cell type functionality may all be different in mouse and human. Indeed, Applicants focused on the murine trachea and even here Applicants have shown functional variation along this short anatomic span. As the human respiratory tree is so large, it will be important to sample single cells along its length.

Materials and Methods

Experimental Methods

Mouse models. The MGH Subcommittee on Research Animal Care approved animal protocols in accordance with NIH guidelines. Krt5-creER (Van Keymeulen, A. et al. Distinct stem cells contribute to mammary gland development and maintenance. *Nature* 479, 189-193 (2011)) and Scgb1a1-creER mice were described previously. Foxi1-eGFP mice were purchased from GENSAT. C57BL/6J mice (stock no. 000664), LSL-mT/mG mice (mouse stock no. 007676), and LSL-tdTomato (stock no. 007914), Ascl3-EGFP-Cre mice (stock no. 021794), and Foxi1-KO mice (stock no. 024173) were purchased from the Jackson Laboratory. To label basal cells and secretory cells for in vivo lineage traces, Applicants administered tamoxifen by intraperitoneal injection (3 mg per 20 g body weight) three times every 48 hours to induce the Cre-mediated excision of a stop codon and subsequent expression of tdTomato. For Pulse-Seq experiments Applicants administered tamoxifen by intraperitoneal injection (2 mg per 20 g body weight) three times every 24 hours to induce the Cre-mediated excision of a stop codon and subsequent expression GFP. To label proliferating cells, Applicants administered 5-ethynyl-2'-deoxyuridine (EdU) per 25 g mouse by intraperitoneal injection (2 mg per 20 g body weight). 6-12-week-old mice were used for all experiments. Male C57BL/6 mice were used for the full length and initial 3' scRNA-seq experiments. Both male and female mice were used for lineage tracing and 'Pulse-Seq' experiments. Applicants used three mice for each lineage time point.

Immunofluorescence, microscopy and cell counting. Tracheae were dissected and fixed in 4% PFA for 2 h at 4° C. followed by two washes in PBS, and then embedded in OCT. Cryosections (6 μm) were treated for epitope retrieval with 10 mM citrate buffer at 95° C. for 10-15 minutes, permeabilized with 0.1% Triton X-100 in PBS, blocked in 1% BSA for 30 min at room temperature (27° C.), incubated with primary antibodies for 1 hour at room temperature, washed, incubated with appropriate secondary antibodies diluted in blocking buffer for 1 h at room temperature, washed and counterstained with DAPI.

In the case of whole mount trachea stains, tracheas were longitudinally re-sectioned along the posterior membrane, permeabilized with 0.3% Triton X-100 in PBS, blocked in 0.3% BSA and 0.3% Triton X-100 for 120 min at 37° C. on an orbital shaker, incubated with primary antibodies for 12 hours at 37° C. (again on an orbital shaker), washed in 0.3% Triton X-100 in PBS, incubated with appropriate secondary antibodies diluted in blocking buffer for 1 h at 37° C. temperature, washed in 0.3% Triton X-100 in PBS and counterstained with Hoechst 33342. They were then mounted on a slide between two magnets to ensure flat imaging surface.

The following primary antibodies were used: rabbit anti-Atp6v0d2 (1/300; pa5-44359, Thermo), goat anti-CC10 (aka Scgb1a1, 1:500; SC-9772, Santa Cruz), rabbit anti-CFTR (1:100; ACL-006, Alomone), mouse anti-Chromogranin A (1/500; sc-393941, Santa Cruz), rat anti-Cochlin (1/500; MABF267, Millipore), goat anti-FLAP (aka Alox5ap, 1:500; NB300-891, Novus), goat anti-Foxi1 (1:250; ab20454, Abcam), chicken anti-GFP (1:500; GFP-1020, Aves Labs), rabbit anti-Gnat3 (1/300; sc-395, Santa Cruz), rabbit anti-Gng13 (1:500; ab126562, Abcam), rabbit anti-Krt13 (1/500; ab92551, Abcam), goat anti-Krt13 (1/500; ab79279, Abcam), goat anti-Lipf (1:100; MBS421137, mybiosource.com), mouse anti-Muc5ac (1/500; mal-38223, Thermo), mouse anti-Muc5ac (1/500; mal-38223, Thermo), mouse anti-p63 (1:250; gtx102425, GeneTex), rabbit anti-Tff2 (1/500; 13681-1-AP, ProteinTech), rabbit anti-Trpm5 (1:500; ACC-045, Alomone), mouse anti-tubulin, acetylated (1:100; T6793, Sigma). All secondary antibodies were Alexa Fluor conjugates (488, 594 and 647) and used at 1:500 dilution (Life Technologies).

EdU was stained in fixed sections alongside the above antibody stains as previously described (Salic, A. & Mitchison, T. J. A chemical method for fast and sensitive detection of DNA synthesis in vivo. *Proc. Natd. Acad. Sci. U.S.A.* 105, 2415-2420 (2008)).

Confocal images for both slides and whole mount tracheas were obtained with an Olympus FV10i confocal laser-scanning microscope with a 60× oil objective. Cells were manually counted based on immunofluorescence staining of markers for each of the respective cell types. Cartilage rings (1 to 12) were used as reference points in all the tracheal samples to count specific cell types on the basis of immunostaining. Serial sections were stained for the antibodies tested and randomly selected slides were used for cell counting.

Cell dissociation and FACS. Airway epithelial cells from trachea were dissociated using papain solution. For whole trachea sorting, longitudinal halves of the trachea were cut into five pieces and incubated in papain dissociation solution and incubated at 37° C. for 2 h. For proximal-distal cell sorting, proximal (cartilage 1-4) and distal (cartilage 9-12) trachea regions were dissected and dissociated by papain independently. After incubation, dissociated tissues were passed through a cell strainer and centrifuged and pelleted at 500 g for 5 min. Cell pellets were dispersed and incubated with Ovo-mucoid protease inhibitor (Worthington biochemical Corporation, cat. no. LK003182) to inactivate residual papain activity by incubating on a rocker at 4° C. for 20 min. Cells were then pelleted and stained with EpCAM-PECy7 (1:50; 25-5791-80, eBioscience) and CD45, CD81, or basis of GFP expression for 30 min in 2.5% FBS in PBS on ice. After washing, cells were sorted by fluorescence (antibody staining and/or GFP) on a BD FACS Aria (BD Biosciences) using FACS Diva software and analysis was performed using FlowJo (version 10) software.

For plate-based scRNA-seq, single cells were sorted into each well of a 96-well PCR plate containing 5 μl of TCL buffer with 1% 2-mercaptoethanol. In addition, a population control of 200 cells was sorted into one well and a no-cell control was sorted into another well. After sorting, the plate was sealed with a Microseal F, centrifuged at 800 g for 1 minute and immediately frozen on dry ice. Plates were stored at −80° C. until lysate cleanup.

For droplet-based scRNA-seq, cells were sorted into an Eppendorf tube containing 50 μl of 0.4% BSA-PBS and stored on ice until proceeding to the GemCode Single Cell Platform.

Plate-based scRNA-seq. Single cells were processed using a modified SMART-Seq2 protocol as previously described (Treutlein (2014)). Briefly, RNAClean XP beads (Agencourt) were used for RNA lysate cleanup, followed by reverse transcription using Maxima Reverse Transcriptase (Life Technologies), whole transcription amplification (WTA) with KAPA HotStart HIFI 2× ReadyMix (Kapa Biosystems) for 21 cycles and purification using AMPure XP beads (Agencourt). WTA products were quantified with Qubit dsDNA HS Assay Kit (ThermoFisher), visualized with high sensitivity DNA Analysis Kit (Agilent) and libraries were constructed using Nextera XT DNA Library Preparation Kit (Illumina). Population and no-cell controls were processed with the same methods as singe cells. Libraries were sequenced on an Illumina NextSeq 500.

Droplet-based scRNA-seq. Single cells were processed through the GemCode Single Cell Platform per manufacturer's recommendations using the GemCode Gel Bead, Chip and Library Kits (10× Genomics, Pleasanton, CA). Briefly, single cells were partitioned into Gel Beads in Emulsion (GEMs) in the GemCode instrument with cell lysis and barcoded reverse transcription of RNA, followed by amplification, shearing and 5' adaptor and sample index attachment. An input of 6,000 single cells was added to each channel with a recovery rate of roughly 1,500 cells. Libraries were sequenced on an Illumina Nextseq 500.

qRT-PCR. FACS isolated cells were sorted into 150 μl TRIzol LS (ThermoFisher Scientific), while ALI culture membranes were submerged in 300 μl of standard TRIzol solution (ThermoFisher Scientific). A standard chloroform extraction was performed followed by an RNeasy column-based RNA purification (Qiagen) according to manufacturer's instructions. 1 μg (when possible, otherwise 100 ng) of RNA was converted to cDNA using SuperScript VILO kit with additional ezDNase treatment according to manufacturer's instructions (ThermoFisher Scientific). qRT-PCR was performed using 0.5 μl of cDNA, predesigned TaqMan probes, and TaqMan Fast Advanced Master Mix (ThermoFisher Scientific), assayed on a LightCycler 480 in 384 well format (Roche). Assays were run in parallel with the loading controls Hprt and Ubc, previously validated to remain constant in the tested assay conditions. Subsequent experiments using ferret epithelial cells were performed using the same methodology.

Single-molecule fluorescence in situ hybridization (smFISH). Intact primary human bronchus was obtained through the New England Organ Bank. Segments of bronchus were flash frozen by immersion in liquid nitrogen and embedded in OCT and 4 uM sections were collected. RNAScope Multiplex Fluorescent Kit (Advanced Cell Diagnostics) was used per manufacturer's recommendations, and confocal imaging was carried out as described above.

Transwell cultures. Cells were cultured and expanded in complete SAGM (small airway epithelial cell growth medium; Lonza, CC-3118) containing TGF-β/BMP4/WNT antagonist cocktails and 5 μM Rock inhibitor Y-27632 (Selleckbio, S1049). To initiate air-liquid interface (ALI) cultures, airway basal stem cells were dissociated from mouse tracheas and seeded onto transwell membranes. After reaching confluence, media was removed from the upper chamber. Mucociliary differentiation was performed with PneumaCult-ALI Medium (StemCell, 05001). Differentiation of airway basal stem cells on an air-liquid interface was followed by directly visualizing beating cilia in real time after 10-14 days.

Once air-liquid cultures were fully differentiated, as indicated by beating cilia, treatment cultures were supplemented with 10 ng/mL of recombinant murine IL-13 (Peprotechstock diluted in water and used fresh) diluted in PneumaCult-ALI Medium, while control cultures received an equal volume of water for 72 hours. After treatment, whole ALI wells were fixed in 4% PFA, immunostained in whole mount using the same buffers and imaged with a confocal microscope as described above.

Airway surface physiologic parameters. Epithelia derived from Foxi1-KO mice (wild-type, heterozygous knockout, and homozygous knockout genotypes) were grown as ALI cultures in transwells as described above and μOCT, particle-tracking microrheology, airway surface pH measurements, and equivalent current ($I_{eq}$) assays were used to characterize their physiological parameters as described below.

μOCT methodologies have been used as previously described (Birket et al. (2014); Liu et al. (2013); Liu, L. et al. An autoregulatory mechanism governing mucociliary transport is sensitive to mucus load. *Am. J. Respir. Cell Mol. Biol.* 51, 485-493 (2014)). Briefly, Airway Surface Liquid (ASL) depth and ciliary beat frequency (CBF) were directly assessed via cross-sectional images of the airway epithelium with high resolution (<1 μM) and high acquisition speed (20,480 Hz line rate resulting in 40 frames/s at 512 line/frame). Quantitative analysis of images was performed in ImageJ (Schneider, C. A., Rasband, W. S. & Eliceiri, K. W. NIH Image to ImageJ: 25 years of image analysis. *Nat. Methods* 9, 671-675 (2012)). To establish CBF, custom code in Matlab (Mathworks, Natick, MA) was used to quantify Fourier analysis of the reflectance of beating cilia. ASL depth was characterized directly by geometric measurement of the respective layers.

Particle-tracking microrheology was used to measure mucous viscosity following the methods detailed in Birket et al. (Birket, S. E. et al. Combination therapy with cystic fibrosis transmembrane conductance regulator modulators augment the airway functional microanatomy. *Am. J Physiol. Lung Cell. Mol. Physiol.* 310, L928-939 (2016)).

Airway surface pH was measured by use of a small probe as described in Birket et al. (Birket, S. E. et al. Development of an airway mucus defect in the cystic fibrosis rat. *JCI Insight* 3, (2018)).

Equivalent current ($I_{eq}$) assay on mouse ALI was carried out as described in Mou et al.[72] with these changes: benzamil was used at 20 uM and CFTR activation was done only with 10 uM forskolin.

Transcriptional activation of Foxi1 in ferret basal cell cultures. Lentivirus production and transduction. HEK 293T cells were cultured in 10% FBS, 1% penicillin/streptomycin DMEM. Cells were seeded at ~30% confluency, and then were transfected the next day at ~90% confluency. For each flask, 22 μg of plasmid containing the vector of pLent-dCas9-VP64 Blast or pLent-MS2-p65-HSF1 Hygromycin, 16 μg of psPAX2, and 7 μg pMD2 (VSV-G) were transfected using calcium phosphate buffer. The next day after transfection, culture medium was removed and replaced with 2% FBS-DMEM medium and incubated for 24 h. Lentivirus supernatant was harvested 48 h after transfection, and the supernatant was centrifuged at 5000 rpm for 5 min. Lentivirus was filtered with a 0.45 μm PVDF filter, concentrated by Lenti X concentrator (Takara), aliquoted and stored at 80° C. Ferret basal cells were cultured in Pneumacult-Ex with medium supplemented with Pneumacult-Ex and supplemented with hydrocortisone and 1% penicillin/streptomycin and passaged at a 1:5 ratio. Cells were incubated with lentivirus for 24 h in growth media. At 72 h selection was initiated (10 μg/mL Blasticidin, 50 μg/mL Hygromycin). Selection was performed for 14 days for Hygromycin and Blasticidin with media changes every 24 h (Konermann, S. et al. Genome-scale transcriptional activation by an engineered CRISPR-Cas9 complex. *Nature* 517, 583-588 (2015)).

To generate sgRNA for transcriptional activation of Foxi1 in ferret cells, gBlocks were synthesized from IDT and included all components necessary for small guide (sg)RNA production, namely: T7 promoter, Foxi1 target specific sequence, guide RNA scaffold, MS2 binding loop and termination signal. gBlocks were PCR amplified and gel purified. PCR products were used as the template for in vitro transcription using MEGAshortscript T7 kit (Ambion). All sgRNAs were purified using MegaClear Kit (Ambion) and eluted in RNase-free water.

Foxi1 sgRNA was reverse transfected using Lipofectamine RNAiMAX Transfection Reagent (Life Science) into ferret basal cells that stably expresses dCas9-VP64 fusion protein and MS2-p65-HSF1 fusion protein. For the 0.33-cm² ALI inserts, (1 μg) sgRNA and Lipofectamine RNAiMAX was diluted in 50 μl of Opti-MEM. The solution was gently mixed, dispensed into insert and incubated for 20-30 min at room temperature. Next, 300,000 cells were suspended in 150 μl pneumacult-Ex plus medium and incubated for 24 h at 37° C. in a 5% $CO_2$ incubator.

Short circuit current measurements of CFTR-mediated chloride transport in ferret. Polarized ferret basal cells with activated Foxi1 expression as well as matched mock transfection controls (without DNA) were grown in ALI, and after three weeks short-circuit current ($I_{sc}$) measurements were performed as previously described (Yan, Z. et al. Optimization of Recombinant Adeno-Associated Virus-Mediated Expression for Large Transgenes, Using a Synthetic Promoter and Tandem Array Enhancers. *Hum. Gene Ther.* 26, 334-346 (2015)). The basolateral chamber was filled with high-chloride HEPES-buffered Ringer's solution (135 mM NaCl, 1.2 mM $CaCl_2$, 1.2 mM $MgCl_2$, 2.4 mM $KH_2PO_4$, 0.2 mM $K_2HPO_4$, 5 mM HEPES, pH 7.4). The apical chamber received a low-chloride HEPES-buffered Ringer's solution containing a 135-mM sodium gluconate substitution for NaCl. Is was recorded using Acquire & Analyze software (Physiologic Instruments) after clamping the transepithelial voltage to zero. The following antagonists and agonists were sequentially added into the apical chamber: amiloride (100 μM) to block ENaC channels, apical DIDS (100 μM) to block calcium-activated chloride channels, forskolin (10 μM) and IBMX (100 μM) to activate CFTR, and GlyH101 (500 μM) to block CFTR.

Computational Methods

Pre-processing of 3' droplet-based scRNA-seq data. Demultiplexing, alignment to the mm10 transcriptome and UMI-collapsing were performed using the Cellranger toolkit (version 1.0.1, 10× Genomics). For each cell, Applicants quantified the number of genes for which at least one read was mapped, and then excluded all cells with fewer than 1,000 detected genes. Expression values $E_{i,j}$ for gene i in cell j were calculated by dividing UMI count values for gene i by the sum of the UMI counts in cell j, to normalize for differences in coverage, and then multiplying by 10,000 to create TPM-like values, and finally calculating $\log_2(TPM+1)$ values.

Selection of variable genes was performed by fitting a generalized linear model to the relationship between the squared co-efficient of variation (CV) and the mean expression level in log/log space, and selecting genes that significantly deviated ($p<0.05$) from the fitted curve, as previously described (Brennecke, P. et al. Accounting for technical noise in single-cell RNA-seq experiments. *Nat. Methods* 10, 1093-1095 (2013)).

Both prior knowledge and this data show that different cell types have dramatically differing abundances in the trachea. For example, 3,845 of the 7,193 cells (53.5%) in the droplet-based dataset were eventually identified as basal cells, while only 26 were ionocytes (0.4%). This makes conventional batch correction difficult, as, due to random sampling effects, some batches may have very few (or even zero) of the rarest cells (Extended Data FIG. 1b). To avoid this problem and simultaneously identify maximally discriminative genes, Applicants performed an initial round of clustering on the set of variable genes described above, and identified a set of 1,380 cell-type specific genes (FDR<0.01), with a minimum log 2 fold-change of 0.25. In addition, Applicants performed batch correction within each identified cluster, which contained only transcriptionally similar cells, ameliorating problems with differences in abundance. Batch correction was performed (only on these 1,380 genes) using ComBat (Johnson, W. E., Li, C. & Rabinovic, A. Adjusting batch effects in microarray expression data using empirical Bayes methods. *Biostat. Oxf. Engl.* 8, 118-127 (2007)) as implemented in the R package sva (Leek, J. T., Johnson, W. E., Parker, H. S., Jaffe, A. E. & Storey, J. D. The sva package for removing batch effects and other unwanted variation in high-throughput experiments. *Bioinforma. Oxf. Engl.* 28, 882-883 (2012)) using the default parametric adjustment mode. The output was a corrected expression matrix, which was used as input to further analysis.

Pre-processing of plate-based scRNA-seq data. BAM files were converted to merged, de-multiplexed FASTQs using the Illumina Bcl2Fastq software package v2.17.1.14. Paired-end reads were mapped to the UCSC mm10 mouse transcriptome using Bowtie (Langmead, B., Trapnell, C., Pop, M. & Salzberg, S. L. Ultrafast and memory-efficient alignment of short DNA sequences to the human genome. *Genome Biol.* 10, R25 (2009)) with parameters "-q-- phred33-quals-n 1-e 99999999-1 25-I1-X 2000-a-m 15-S-p 6", which allows alignment of sequences with one mismatch. Expression levels of genes were quantified as transcript-per-million (TPM) values by RSEM (Li, B. & Dewey, C. N. RSEM: accurate transcript quantification from RNA-Seq data with or without a reference genome. *BMC Bioinformatics* 12, 323 (2011)) v1.2.3 in paired-end mode. For each cell, Applicants determined the number of genes for which at least one read was mapped, and then excluded all cells with fewer than 2,000 detected genes. Applicants then identified highly variable genes as described above.

Dimensionality reduction by PCA and tSNE. Applicants restricted the expression matrix to the subsets of variable genes and high-quality cells noted above, and values were centered and scaled before input to PCA, which was implemented using the R function 'prcomp' from the 'stats' package for the plate-based dataset. For the droplet-based dataset, Applicants used a randomized approximation to PCA, implemented using the 'rpca' function from the 'rsvd' R package, with the parameter k set to 100. This low-rank approximation is several orders of magnitude faster to compute for very wide matrices. After PCA, significant PCs were identified using a permutation test as previously described (Buja, A. & Eyuboglu, N. Remarks on Parallel Analysis. *Multivar. Behav. Res.* 27, 509-540 (1992)), implemented using the 'permutationPA' function from the 'jackstraw' R package. Because of the presence of extremely rare cells in the droplet-based dataset (as described above), Applicants used scores from 10 significant PCs using scaled data, and 7 significant PCs using unscaled data. Only scores from these significant PCs were used as the input to further analysis.

For visualization purposes only (and not for clustering), dimensionality was further reduced using the Barnes-Hut approximate version of the t-distributed stochastic neighbor embedding (tSNE) (Van Der Maaten, L. Accelerating t-SNE Using Tree-based Algorithms. *J Mach Learn Res* 15, 3221-3245 (2014); Maaten, L. van der & Hinton, G. Visualizing Data using t-SNE. *J. Mach. Learn. Res.* 9, 2579-2605 (2008)). This was implemented using the 'Rtsne' function from the 'Rtsne' R package using 20,000 iterations and a perplexity setting of 10 and 75 for plate- and droplet-based respectively. Scores from the first n PCs were used as the input to tSNE, where n was 11 and 12 for plate- and droplet-based data, respectively, determined using the permutation test described above.

Excluding immune, mesenchymal cells and suspected doublets. Although cells were sorted using EpCAM prior to scRNA-seq, 1,873 contaminating cells were observed in the initial droplet dataset, and were comprised of: 91 endothelial cells expressing Egfl7, Sh3gl3 and Esam, 229 macrophages expressing MHCII (H2-Abl, H2-Aa, Cd74), C1qa, and Cd68, and 1,553 fibroblasts expressing high levels of collagens (Col1a1, Col1a2, and Col3a1). Each of these cell populations was identified by an initial round of unsupervised clustering (density-based clustering of the tSNE map using 'dbscan' (Gong et al. (2003)) from the R package 'fpc') as they formed extremely distinct clusters, and then removed. In the case of the Pulse-Seq dataset, the initial clustering step removed a total of 532 dendritic cells identified by high expression of Ptprc and Cd83. In addition, 20 other cells were outliers in terms of library complexity, which could possibly correspond to more than one individual cell per sequencing library, or 'doublets'. As a conservative precaution, Applicants removed these 20 possible doublet cells with over 3,700 genes detected per cell.

kNN-graph based clustering. To cluster single cells by their expression profiles, Applicants used unsupervised clustering, based on the Infomap community-detection algorithm[6], following approaches recently described for single-cell CyTOF data (Levine, J. H. et al. Data-Driven Phenotypic Dissection of AML Reveals Progenitor-like Cells that Correlate with Prognosis. *Cell* 162, 184-197 (2015)) and scRNA-seq (Shekhar et al. (2016)). Applicants constructed a k nearest-neighbor (k-NN) graph using, for each pair of cells, the Euclidean distance between the scores of significant PCs as the metric.

The number k of nearest neighbors was chosen in a manner roughly consistent with the size of the dataset, and set to 25 and 150 for plate- and droplet-based data respectively. For sub-clustering of rare cell subsets, Applicants used k=100, 50, 50 and 20 for tuft cells, neuroendocrine cells, ionocytes and goblet cells respectively. The k-NN graph was computed using the function 'nng' from the R package 'cccd' and was then used as the input to Infomap (Rosvall et al., (2008)), implemented using the 'infomap.community' function from the 'igraph' R package.

Detected clusters were mapped to cell-types using known markers for tracheal epithelial subsets. In particular, because of the large proportion of basal and club cells, multiple clusters expressed high levels of markers for these two types. Accordingly, Applicants merged nine clusters expressing the basal gene score above a median $\log_2(TPM+1)>0$, and seven clusters expressing the club gene score above median $\log_2(TPM+)>1$. Calculation of a ciliated cell gene score showed only a single cluster with non-zero median expression, so no further merging was performed. This resulted in seven clusters, each corresponding 1 to 1 with a known airway epithelial cell type, with the exception of the ionocyte cluster, which Applicants show represents a novel subset.

Rare cells (tuft, neuroendocrine, ionocyte and goblet) were sub-clustered to examine possible heterogeneity of mature types (FIG. 20 and FIG. 30). In each case, cells annotated as each type from the initial 3' droplet-based dataset (FIG. 17B and FIG. 23D) were combined with the corresponding cells from the Pulse-Seq dataset (FIG. 19B and FIG. 28A) before sub-clustering. In the case of goblet cells, sub-clustering the combined 468 goblet cells (k=20, above) partitioned the data into 7 groups, two of which expressed the novel goblet cell marker Gp2 (FIG. 17D) at high levels (median $\log_2(TPM+1)>1$). These two groups were annotated as mature goblet-1 and goblet-2 cells (FIG. 30F-J), while the five groups were merged and annotated as immature goblet cells.

Differential expression and cell-type signatures. To identify maximally specific genes for cell-types, Applicants performed differential expression tests between each pair of clusters for all possible pairwise comparisons. Then, for a given cluster, putative signature genes were filtered using the maximum FDR Q-value and ranked by the minimum $\log_2$ fold-change (across the comparisons). This is a stringent criterion because the minimum fold-change and maximum Q-value represent the weakest effect-size across all pairwise comparisons. Cell-type signature genes for the initial droplet based scRNA-seq data (FIG. 17c) were obtained using a maximum FDR of 0.05 and a minimum $\log_2$ fold-change of 0.5.

Where less cells were available, as is the case of full-length plate-based scRNA-seq data (FIG. 25B) or for sub-types within cell-types (FIG. 19C, FIG. 30C), a combined p-value across the pairwise tests for enrichment was computed using Fisher's method (a more lenient criterion) and a maximum FDR Q-value of 0.001 was used, along with a cutoff of minimum $\log_2$ fold-change of 0.1 for tuft and goblet cell subsets (FIG. 19C, FIG. 30C). Larger clusters (basal, club, ciliated cells) were down-sampled to 1,000 cells for the pairwise comparisons. Marker genes were ranked by minimum $\log_2$ fold-change. Differential expression tests were carried out using a two part 'hurdle' model to control for both technical quality and mouse-to-mouse variation. This was implemented using the R package MAST (Birket et al. (2014)), and p-values for differential expression were computed using the likelihood-ratio test. Multiple hypothesis testing correction was performed by controlling the false discovery rate (Birket et al. (2018)) using the R function 'p.adjust'.

Assigning cell-type specific TFs, GPCRs and genes associated with asthma. A list of all genes annotated as transcription factors in mice was obtained from AnimalTFDB (Zhang, H.-M. et al. AnimalTFDB: a comprehensive animal transcription factor database. *Nucleic Acids Res.* 40, D144-149 (2012)), downloaded from:
  www.bioguo.org/AnimalTFDB/
    BrowseAllTF.php?spe=Mus_musculus.

The set of G-protein coupled receptors (GPCRs) was obtained from the UniProt database, downloaded from:
  www.uniprot.org/uniprot/?query=family%3A%22g+protein+coupled+receptor%22+AND+organism%3A%22Mouse+%5B10090%5D%22+AND+reviewed%3Ayes&sort=score. To map from human to mouse gene names, human and mouse orthologs were downloaded from Ensembl latest release 86 at:
  www.ensembl.org/biomart/martview, and human and mouse gene synonyms from: NCBI (ftp.ncbi.nlm.nih.gov/gene/DATA/GENE_INFO/Mammalia/).

Cell-type enriched TFs and GPCRs were then identified by intersecting the list of genes enriched in to each cell type with the lists of TFs and GPCRs defined above. Cell-type enriched TFs (FIG. 17E) and GPCRs (FIG. 30A) were defined using the 3' droplet-based and full-length plate-based datasets, respectively, as those with a minimum $\log_2$ fold-change of 0.1 and a maximum FDR of 0.001, retaining a maximum of 10 genes per cell type in FIG. 17E.

Gene set or pathway enrichment analysis. GO analysis of enriched pathways in Krt13[+] hillocks (FIG. 25D) was performed using the 'goseq' R package (*fgsea: Fast Gene Set Enrichment Analysis*. (Computer Technologies Laboratory, 2018)), using significantly differentially expressed genes (FDR<0.05) as target genes, and all genes expressed with $\log_2(TPM+1)>3$ in at least 10 cells as background. For pathway and gene sets, Applicants used a version of MSigDB (Liberzon, A. et al. Molecular signatures database (MSigDB) 3.0. *Bioinforma. Oxf. Engl.* 27, 1739-1740 (2011)) with mouse orthologs, downloaded from: bioinf: wehi.edu.au/software/MSigDB/. Association of principal components with cell-types (FIG. 29A,b) was computed using the Gene Set Enrichment Analysis (GSEA) algorithm (fgsea: *Fast Gene Set Enrichment Analysis*. (Computer Technologies Laboratory, 2018) implemented using the 'fgsea' package in R. Genes that are involved in leukotriene biosynthesis and taste transduction pathways (FIG. 20F and FIG. 30B) were identified using KEGG and GO pathways. Specifically, genes in KEGG pathway 00590 (arachidonic acid metabolism) or GO terms 0019370 (leukotriene biosynthetic process) or 0061737 (leukotriene signaling pathway) were annotated as leukotriene synthesis-associated, while genes in KEGG pathway 04742 (taste transduction) were annotated as taste transduction-associated.

Statistical analysis of proximodistal mucous metaplasia. For the analysis in FIG. 18H,I, the extent of goblet cell hyperplasia was assessed using counts of Muc5ac[+] goblet cells, normalized to counts of GFP⁺ ciliated cells. To quantify differences in the count values between the samples in different conditions (n=6, Foxj1-GFP mice), Applicants fit a negative binomial regression using the 'glm.nb' function from the 'MASS' package in R. Pairwise comparisons between means for each condition were computed using post hoc tests and p-values were adjusted for multiple comparisons using Tukey's HSD, implemented using the function 'pairs' from the 'emeans' package in R.

Lineage inference using diffusion maps. Applicants restricted the analysis to the 6,848 cells in basal, club or ciliated cell clusters (95.2% of the 7,193 cells in the initial droplet dataset), since it was unlikely that rare cells (e.g., NE, tuft, goblet, and ionocyte cells) in transitional states will be sufficiently densely sampled. Next, Applicants selected highly variable genes among these three cell subsets as described above, and performed dimensionality reduction using the diffusion map approach (Coifman, R. R. et al. Geometric diffusions as a tool for harmonic analysis and structure definition of data: multiscale methods. *Proc. Natl. Acad. Sci. U.S.A.* 102, 7432-7437 (2005)). Briefly, a cell-cell transition matrix was computed using the Gaussian kernel where the kernel width was adjusted to the local neighborhood of each cell, following the approach of Haghverdi et al. (Haghverdi, L., Buettner, F. & Theis, F. J. Diffusion maps for high-dimensional single-cell analysis of differentiation data. *Bioinforma. Oxf. Engl.* 31, 2989-2998 (2015)). This matrix was converted to a Markovian matrix after normalization. The right eigenvectors $v_i$ (i=0, 1, 2, 3, . . . ) of this matrix were computed and sorted in the order of decreasing eigenvalues $\lambda_i$ (i=0, 1, 2, 3, . . . ), after excluding the top eigenvector $v_0$, corresponding to $\lambda_0=1$ (which reflects the normalization constraint of the Markovian matrix). The remaining eigenvectors $v_i$ (i=1, 2 . . . ) define the diffusion map embedding and are referred to as diffusion components ($DC_k$ (k=1, 2, . . . )). Applicants noticed a spectral gap between the $\lambda_3$ and the $\lambda_4$, and hence retained $DC_1$-$DC_3$ for further analysis.

To extract the edges of this manifold, along which cells transition between states (FIG. 2a), Applicants fit a convex hull using the 'convhulln' from the 'geometry' R package. To identify edge-associated cells, any cell within d<0.1 of an edge of the convex hull (where d is the Euclidean distance in diffusion-space) is assigned to that edge.

To identify cells associated with the Krt4⁺Krt13⁺ population, Applicants used unsupervised Partitioning Around Medoids (PAM) clustering of the cells in diffusion-space with the parameter k-4. Edge-association of genes (or TFs) was computed as the autocorrelation (lag=25), implemented using the 'acf' function from the 'stats' R package. Empirical p-values for each edge-associated gene were assessed using a permutation test (1,000 bootstrap iterations), using the autocorrelation value as the test statistic.

Figure 27:
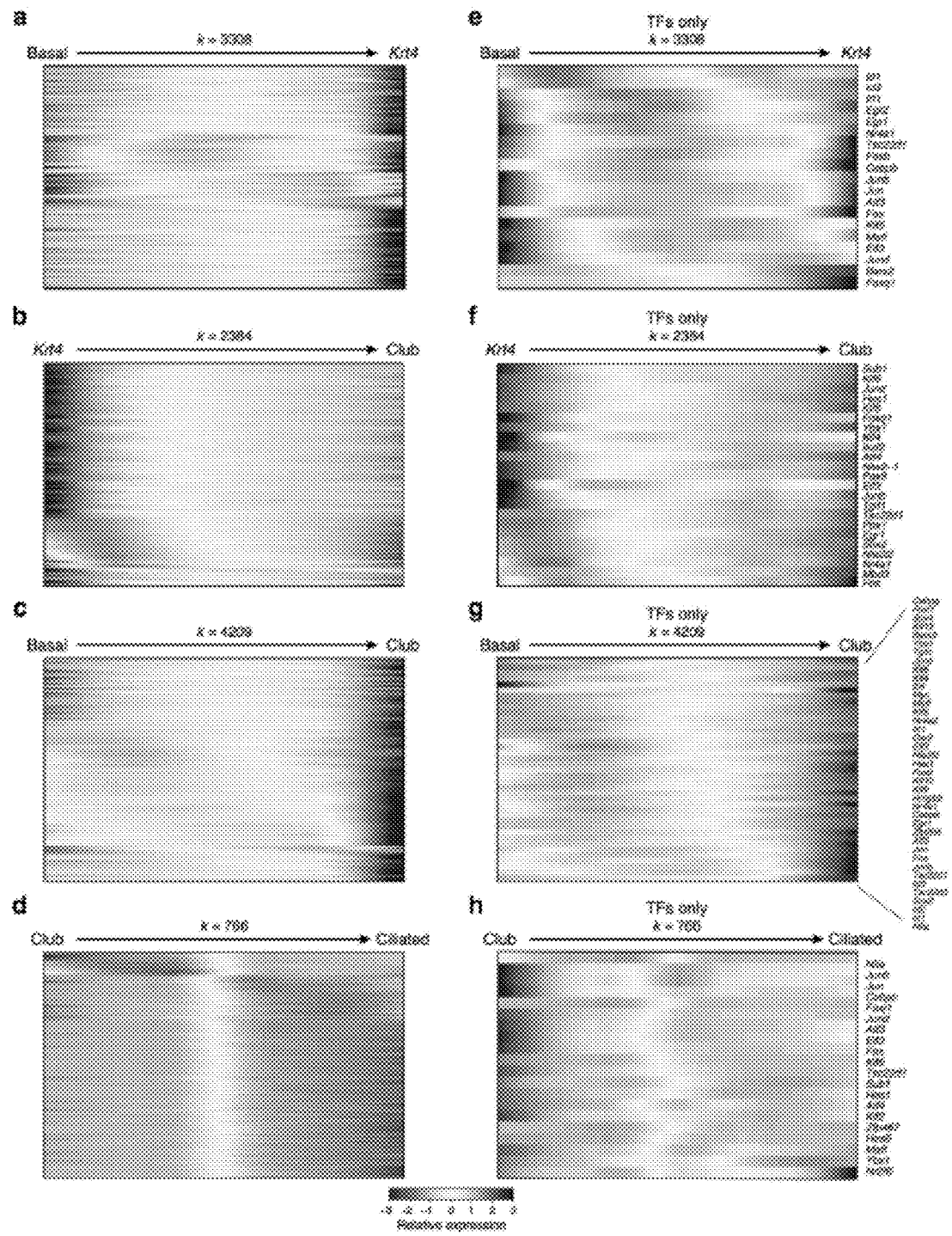
FIG. 27 shows genes associated with cell fate transitions. Relative mean expression (loess-smoothed row-wise Z-score of mean $\log_2$(TPM+1), color bar at bottom) of significantly (p<0.001, permutation test) varying genes (a-d) and TFs (e-h) (rows) across subsets of 6,905 (columns) basal, club and ciliated cells. Cells are pseudotemporally ordered (x axis, all plots) using diffusion maps (FIG. 24A). Each cell was assigned to a cell fate transition if it was within d<0.1 of an edge of the convex hull of all points (where d is the Euclidean distance in diffusion-space) is assigned to that edge (Methods).

Genes were placed in pseudotemporal order by splitting the interval into 30 bins from 'early' to 'late', and assigning each gene the bin with the highest mean expression. These data were smoothed using loess regression and then visualized as heatmaps (FIG. 27).

Pulse-Seq data analysis. For the much larger Pulse-Seq dataset (~66,700 cells), Applicants used a very similar, but more scalable, analysis pipeline, with the following modifications. Alignment and UMI collapsing was performing using the Cellranger toolkit (version 1.3.1, 10× Genomics). $Log_2(TPM+1)$ expression values were computed using Rcpp-based function in the R package 'Seurat' (v2.2). Applicants also used an improved method of identifying variable genes. Rather than fitting the mean-$CV^2$ relationship, a logistic regression was fit to the cellular detection fraction (often referred to as a), using the total number of UMIs per cell as a predictor. Outliers from this curve are genes that are expressed in a lower fraction of cells than would be expected given the total number of UMIs mapping to that gene, i.e., cell-type or state specific genes. Applicants used a threshold of deviance<−0.25, producing a set of 708 variable genes. Applicants restricted the expression matrix to this subset of variable genes and values were centered and scaled—while 'regressing out'(Buettner, F. et al. Computational analysis of cell-to-cell heterogeneity in single-cell RNA-sequencing data reveals hidden subpopulations of cells. *Nat. Biotechnol.* 33, 155-160 (2015)) technical factors (number of genes detected per cell, number of UMIs detected per cell and cell-cycle score) using the 'ScaleData' function before input to PCA, implemented using 'RunPCA' in Seurat. After PCA, significant PCs were identified using the knee in the scree plot, which identified 10 significant PCs. Only scores from these significant PCs were used as the input to nearest-neighbor based clustering and tSNE, implemented using the 'FindClusters' (resolution parameter r=1) and 'RunTSNE' (perplexity p=25) methods respectively from the 'Seurat' package.

Once again due to their abundance, the populous basal, club and ciliated cells were spread across several clusters, which were merged using the strategy described above: 19 clusters expressing the basal score above mean $log_2(TPM+1)>0$, 12 expressing the club score above mean $log_2(TPM+1)>-0.1$, and 2 clusters expressing the ciliated signature above were merged to construct the basal, club and ciliated subsets, respectively. Goblet cells were not immediately associated with a specific cluster, however, cluster 13 (one of those merged into the club cluster) expressed significantly elevated levels of goblet markers Tff2 and Gp2 ($p<10^{-10}$, likelihood-ratio test). Sub-clustering this population (resolution parameter r=1) revealed 6 clusters, of which two expressed the goblet score constructed using the top 25 goblet cell marker genes above mean $log_2(TPM+1)>1$, which were merged and annotated as goblet cells. To identify the Krt4⁺/Krt13⁺ hillock-associated club cells, the remaining 17,700 club cells were re-clustered (resolution parameter r=0.2) into 5 clusters, of which one expressed much higher levels ($p<10^{-10}$ in all cases) of Krt4, Krt13 and a hillock score constructed using the top 25 hillock marker genes, this cluster was annotated as 'hillock-associated club cells'.

Estimating lineage-labeled fraction for Pulse-Seq and conventional lineage tracing. For any given sample (here, mouse) the certainty in the estimate of the proportion of labeled cells increases with the number of cells obtained; the more cells, the higher the precision of the estimate. Estimating the overall fraction of labeled cells (from conventional lineage tracing; FIG. 19F and FIGS. 26 and 28, or Pulse-seq lineage tracing FIG. 19 and FIG. 28) based on the individual estimates from each mouse is analogous to performing a meta-analysis of several studies, each of which measures a population proportion; studies with greater power (higher n) carry more information, and should influence the overall estimate more, while low n studies provide less information and should not have as much influence. Generalized linear mixed models (GLMM) provide a framework to obtain an overall estimate in this manner (Pujana, M. A. et al. Network modeling links breast cancer susceptibility and centrosome dysfunction. *Nat. Genet.* 39, 1338-1349 (2007)). Accordingly, Applicants implemented a fixed effects logistic regression model to compute the overall estimate and 95% confidence interval using the function 'metaprop' from the R package 'meta'(Stijnen, T., Hamza, T. H. & Ozdemir, P. Random effects meta-analysis of event outcome in the framework of the generalized linear mixed model with applications in sparse data. *Stat. Med.* 29, 3046-3067 (2010)).

Testing for difference in labeled fraction for Pulse-Seq and conventional lineage tracing. To assess the significance of changes in the labeled fraction of cells in different conditions, Applicants used a negative binomial regression model of the counts of cells at each time point, controlling for variability amongst biological (mouse) replicates. For each cell-type, Applicants model the number of lineage-labeled cells detected in each analyzed mouse as a random count variable using a negative binomial distribution. The frequency of detection is modeled by using the natural log of the total number of cells of that type profiled in a given mouse as an offset. The time point of each mouse (0, 30 or 60 days post tamoxifen) is provided as a covariate. The negative binomial model was fit using the R command 'glm.nb' from the 'MASS' package. The p-value for the significance of the change in labeled fraction size between time points was assessed using a likelihood-ratio test, computing using the R function 'anova'.

Estimating turnover rate using quantile regression. Given the relatively few samples (n=9 mice) with which to model the rate of new lineage-labeled cells, Applicants used the more robust quantile regression (Koenker, R. & Hallock, K. F. Quantile Regression. *J. Econ. Perspect.* 15, 143-156 (2001)), which models the conditional median (rather than the conditional mean, as captured by least-squares linear regression, which can be sensitive to outliers). The fraction of labeled cells in each mouse was modeled as a function of days post tamoxifen (FIG. 28C) using the function 'rq' from the R package 'quantReg'. Significance of association between increasing labeled fraction and time were computing using Wald tests implemented with the 'summary.rq' function, while tests comparing the slopes of fits were conducted using 'anova.rq'.

Statistical analysis of qRT-PCR data. $\Delta\Delta CT$ values were generated by normalization to the average of loading controls Hprt and Ubc, followed by comparison to wild-type samples. Statistical analysis was performed at the $\Delta CT$ stage. For single comparisons, all datasets passed the Shapiro-Wilk normality test, which was followed by a post-hoc two-tailed t-test. For multiple comparisons, all datasets passed the Shapiro-Wilk normality test for equal variance. Data was then tested by two-way ANOVA, with sex as the second level of variance. In a few certain cases, sex trended towards significance, however, not enough to justify separate analysis. Post hoc multiple comparisons to the control group were performed using Dunn's Method. In the single case of Foxi1 KO (FIG. 21E), two heterozygous samples were identified as outliers and removed using a standard implementation of DBscan clustering using the full dataset of all genes assayed using qRT-PCR. These two samples exhibited gene expression closer to full Foxi1 knockouts and were removed from consideration. In all cases, error bars represent the calculated 95% CI, and *$p<0.05$, $p<0.01$, *$p<0.001$.

Data Availability. All data is deposited in GEO (GSE103354) and in the Single Cell Portal (portals.broadinstitute.org/single_cell/study/trachea-epithelium).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method for increasing expression of CFTR in epithelial ionocytes, the method comprising delivering in vivo to a subject in need thereof one or more modulating agents comprising an adenovirus viral vector (AAV) comprising a polynucleotide sequence encoding FOXI1, wherein delivery of the polynucleotide sequence encoding FOXI1 increases the expression of FOXI1 and CFTR in the epithelial ionocytes.

2. The method of claim 1, wherein the subject suffers from an inflammatory lung disease.

3. The method of claim 2, wherein the inflammatory lung disease is asthma, bronchitis, cystic fibrosis, infection, emphysema, lung cancer, pulmonary hypertension, chronic obstructive pulmonary disease, idiopathic pulmonary fibrosis, or α-1-anti-trypsin deficiency.

4. The method of claim 2, wherein the inflammatory lung disease is cystic fibrosis.

5. The method of claim 1, wherein the AAV is an AAV5 viral vector.

6. The method of claim 1, wherein the viral vector is administered as an aerosol.

7. The method of claim 5, wherein the vector comprises a deletion of base pairs 355 to 3325 to eliminate E1a and E1b functions, a deletion of base pairs 3325 to 4021 to eliminate protein IX function, and a deletion of base pairs 28592 to 30470 to eliminate E3 functions.

8. The method of claim 1, wherein the polynucleotide sequence encoding FOXI1 comprises set forth in NCBI Reference Sequence NM_144769.

* * * * *

SEQUENCE LISTING

```
<160> NUMBER OF SEQ ID NOS: 31

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 1

Gly Gly Gly Ser Gly Gly Gly Ser Gly Gly Gly Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Ala Glu Ala Ala Ala Lys Ala
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide
```

```
<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 4

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 5
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 5

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 6
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 6

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser
    50                  55                  60

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Gly Ser
1               5

<210> SEQ ID NO 8
<211> LENGTH: 10
<212> TYPE: PRT
```

```
<213> ORGANISM: Artificial Sequence
<220> FEATURE:
<223> OTHER INFORMATION: Synthetic Peptide

<400> SEQUENCE: 8

Gly Gly Gly Gly Ser Gly Gly Gly Gly Ser
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 9

Gly Gly Gly Gly Ser Gly Gly Gly Gly Ser Gly Gly Gly Gly Ser Gly
1               5                   10                  15

Gly Gly Gly Ser
            20

<210> SEQ ID NO 10
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 11
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 11

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 12
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 13
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 13

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser
    50

<210> SEQ ID NO 14
<211> LENGTH: 55
<212> TYPE: PRT
<213> ORGANISM: Artificial Sequence
<220> FEATURE:
<223> OTHER INFORMATION: Synthetic Peptide

<400> SEQUENCE: 14

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Gly Ser
    50                  55

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Pro Lys Lys Lys Arg Lys Val
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 16

Lys Arg Pro Ala Ala Thr Lys Lys Ala Gly Gln Ala Lys Lys Lys Lys
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

```
Pro Ala Ala Lys Arg Val Lys Leu Asp
1               5
```

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 18

```
Arg Gln Arg Arg Asn Glu Leu Lys Arg Ser Pro
1               5                   10
```

<210> SEQ ID NO 19
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 19

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35
```

<210> SEQ ID NO 20
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 20

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40
```

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 21

```
Val Ser Arg Lys Arg Pro Arg Pro
1               5
```

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 22

```
Pro Pro Lys Lys Ala Arg Glu Asp
```

```
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 23

Pro Gln Pro Lys Lys Lys Pro Leu
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Ser Ala Leu Ile Lys Lys Lys Lys Lys Met Ala Pro
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Asp Arg Leu Arg Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 26

Pro Lys Gln Lys Lys Arg Lys
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Arg Lys Leu Lys Lys Lys Ile Lys Lys Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Arg Glu Lys Lys Lys Phe Leu Lys Arg Arg
1               5                   10
```

```
<210> SEQ ID NO 29
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 29

Lys Arg Lys Gly Asp Glu Val Asp Gly Val Asp Glu Val Ala Lys Lys
1               5                   10                  15

Lys Ser Lys Lys
            20

<210> SEQ ID NO 30
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 30

Arg Lys Cys Leu Gln Ala Gly Met Asn Leu Glu Ala Arg Lys Thr Lys
1               5                   10                  15

Lys

<210> SEQ ID NO 31
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 31

Gly Gly Gly Ser
1
```